US012797465B2

(12) United States Patent
Ang et al.

(10) Patent No.: US 12,797,465 B2
(45) Date of Patent: Nov. 17, 2026

(54) ENHANCED CHIMERIC ANTIGEN RECEPTORS AND USE THEREOF

(71) Applicant: BOARD OF REGENTS, THE UNIVERSITY OF TEXAS SYSTEM, Austin, TX (US)

(72) Inventors: Sonny Oon Ang, Houston, TX (US); Enli Liu, Houston, TX (US); Elizabeth Shpall, Houston, TX (US); Katy Rezvani, Houston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 18/750,233

(22) Filed: Jun. 21, 2024

(65) Prior Publication Data

US 2024/0336699 A1 Oct. 10, 2024

Related U.S. Application Data

(63) Continuation of application No. 17/233,157, filed on Apr. 16, 2021, now abandoned, which is a continuation of application No. 16/632,762, filed as application No. PCT/US2018/043779 on Jul. 25, 2018, now abandoned.

(60) Provisional application No. 62/536,934, filed on Jul. 25, 2017.

(51) Int. Cl.

| | |
|---|---|
| ***A61K 40/15*** | (2025.01) |
| ***A61K 35/17*** | (2025.01) |
| ***A61K 38/00*** | (2006.01) |
| ***A61K 39/00*** | (2006.01) |
| ***A61K 40/31*** | (2025.01) |
| ***A61K 40/42*** | (2025.01) |
| ***A61P 37/06*** | (2006.01) |
| ***C07K 14/54*** | (2006.01) |
| ***C07K 14/705*** | (2006.01) |
| ***C07K 14/71*** | (2006.01) |
| ***C07K 16/28*** | (2006.01) |
| ***C12N 5/0783*** | (2010.01) |
| ***C12N 15/52*** | (2006.01) |
| ***C12N 15/86*** | (2006.01) |

(52) U.S. Cl.

CPC .............. *A61K 40/15* (2025.01); *A61K 35/17* (2013.01); *A61K 40/31* (2025.01); *A61K 40/4211* (2025.01); *A61P 37/06* (2018.01); *C07K 14/5443* (2013.01); *C07K 14/70503* (2013.01); *C07K 14/7051* (2013.01); *C07K 14/70521* (2013.01); *C07K 14/71* (2013.01); *C07K 16/2803* (2013.01); *C07K 16/2863* (2013.01); *C07K 16/2896* (2013.01); *C12N 5/0646* (2013.01); *C12N 15/52* (2013.01); *C12N 15/86* (2013.01); *A61K 38/00* (2013.01); *A61K 2039/5156* (2013.01); *A61K 2039/5158* (2013.01); *A61K 2039/572* (2013.01); *A61K 2239/17* (2023.05); *A61K 2239/22* (2023.05); *A61K 2239/48* (2023.05); *C07K 2317/24* (2013.01); *C07K 2317/622* (2013.01); *C07K 2317/73* (2013.01); *C07K 2317/732* (2013.01); *C07K 2317/76* (2013.01); *C07K 2319/02* (2013.01); *C07K 2319/03* (2013.01); *C07K 2319/30* (2013.01); *C07K 2319/33* (2013.01)

(58) Field of Classification Search

None

See application file for complete search history.

(56) References Cited

U.S. PATENT DOCUMENTS

| | | | |
|---|---|---|---|
| 4,536,468 | A | 8/1985 | Yasui et al. |
| 4,981,784 | A | 1/1991 | Evans et al. |
| 5,164,897 | A | 11/1992 | Clark et al. |
| 5,171,671 | A | 12/1992 | Evans et al. |
| 5,342,929 | A | 8/1994 | Ernst et al. |
| 5,552,303 | A | 9/1996 | Grabstein et al. |
| 5,571,696 | A | 11/1996 | Evans et al. |
| 5,602,009 | A | 2/1997 | Evans et al. |
| 5,686,281 | A | 11/1997 | Roberts |
| 5,696,233 | A | 12/1997 | Evans et al. |
| 5,707,798 | A | 1/1998 | Brann |
| 5,723,329 | A | 3/1998 | Mangelsdorf et al. |
| 5,747,292 | A | 5/1998 | Greenberg et al. |
| 5,789,187 | A | 8/1998 | Ross et al. |
| 5,843,728 | A | 12/1998 | Seed et al. |
| 5,851,828 | A | 12/1998 | Seed et al. |
| 5,869,619 | A | 2/1999 | Studnicka |
| 5,906,936 | A | 5/1999 | Eshhar et al. |
| 5,912,132 | A | 6/1999 | Brann |
| 5,912,170 | A | 6/1999 | Seed et al. |

(Continued)

FOREIGN PATENT DOCUMENTS

| | | |
|---|---|---|
| CA | 2994751 | 2/2017 |
| CN | 103483453 | 1/2014 |

(Continued)

OTHER PUBLICATIONS

GenBank AAX36174.1 (Jul. 26, 2016).*

Hoyos et al., "Engineering CD19-specific T lymphocytes with interleukin-15 and a suicide gene to enhance their anti-lymphoma/leukemia effects and safety," Leukemia, 24.61170, 2010.

Karlsson, "CD19-targeting Car T cells for treatment of B cell malignancies: From bench to bedside," Dissertation, Acta Universitatis Upsaliensis Uppsala, 78 pages, 2014.

Office Communication issued in Australian Patent Application No. 2018306307, dated Jun. 21, 2024.

(Continued)

*Primary Examiner* — Tara L Martinez

(74) *Attorney, Agent, or Firm* — Norton Rose Fulbright US LLP

(57) ABSTRACT

Provided herein are chimeric antigen receptors (CARs) comprising a truncated EGFRvIII (Ev3) in the hinge region of the CAR and/or a humanized scFv. Further provided herein are immune cells expressing the CARs as well as methods of their use in the treatment of immune disorders.

13 Claims, 56 Drawing Sheets

Specification includes a Sequence Listing.

(56) References Cited

U.S. PATENT DOCUMENTS

| | | | |
|---|---|---|---|
| 5,912,172 | A | 6/1999 | Eshhar et al. |
| 5,981,195 | A | 11/1999 | Fuller et al. |
| 6,001,973 | A | 12/1999 | Strom et al. |
| 6,004,811 | A | 12/1999 | Seed et al. |
| 6,077,675 | A | 6/2000 | Stormann et al. |
| 6,083,751 | A | 7/2000 | Feldhaus et al. |
| 6,090,914 | A | 7/2000 | Linsley et al. |
| 6,103,521 | A | 8/2000 | Capon et al. |
| 6,120,669 | A | 9/2000 | Bradley |
| 6,146,631 | A | 11/2000 | Better et al. |
| 6,284,240 | B1 | 9/2001 | Seed et al. |
| 6,361,714 | B1 | 3/2002 | Iwabuchi et al. |
| 6,376,198 | B1 | 4/2002 | Kopin et al. |
| 6,392,013 | B1 | 5/2002 | Seed et al. |
| 6,410,014 | B1 | 6/2002 | Seed et al. |
| 6,410,319 | B1 | 6/2002 | Raubitschek et al. |
| 6,416,957 | B1 | 7/2002 | Evans et al. |
| 6,451,308 | B1 | 9/2002 | Strom et al. |
| 6,500,672 | B1 | 12/2002 | Sladek et al. |
| 6,509,016 | B1 | 1/2003 | Chatterjee et al. |
| 6,534,289 | B1 | 3/2003 | Fuller et al. |
| 6,607,879 | B1 | 8/2003 | Cocks et al. |
| 6,706,867 | B1 | 3/2004 | Lorenz |
| 6,747,665 | B1 | 6/2004 | Stoval, III et al. |
| 6,797,263 | B2 | 9/2004 | Strom et al. |
| 6,824,974 | B2 | 11/2004 | Pisharody et al. |
| 6,937,446 | B2 | 8/2005 | Kamiguchi et al. |
| 6,958,236 | B2 | 10/2005 | Pascal et al. |
| 6,998,476 | B2 | 2/2006 | Strom et al. |
| 7,001,733 | B1 | 2/2006 | Ferrick et al. |
| 7,041,467 | B2 | 5/2006 | Ferrick et al. |
| 7,049,136 | B2 | 5/2006 | Seed et al. |
| 7,052,906 | B1 | 5/2006 | Lawson et al. |
| 7,070,995 | B2 | 7/2006 | Jensen |
| 7,089,052 | B2 | 8/2006 | Kodama et al. |
| 7,094,599 | B2 | 8/2006 | Seed et al. |
| 7,105,644 | B2 | 9/2006 | Rosen et al. |
| 7,118,751 | B1 | 10/2006 | Ledbetter et al. |
| 7,135,603 | B2 | 11/2006 | Messenger |
| 7,196,164 | B2 | 3/2007 | Rosen et al. |
| 7,196,877 | B2 | 3/2007 | Yoshikawa et al. |
| 7,235,190 | B1 | 6/2007 | Wilcoxon et al. |
| 7,258,853 | B2 | 8/2007 | Strom et al. |
| 7,294,468 | B2 | 11/2007 | Bell et al. |
| 7,319,140 | B2 | 1/2008 | Bakker et al. |
| 7,320,787 | B2 | 1/2008 | Seed et al. |
| 7,332,574 | B2 | 2/2008 | Bakker et al. |
| 7,341,944 | B2 | 3/2008 | Harutyunyan |
| 7,347,995 | B2 | 3/2008 | Strom et al. |
| 7,354,762 | B2 | 4/2008 | Jensen |
| 7,379,278 | B2 | 5/2008 | Koui et al. |
| 7,446,179 | B2 | 11/2008 | Jensen et al. |
| 7,446,190 | B2 | 11/2008 | Sadelain et al. |
| 7,468,248 | B2 | 12/2008 | DeNise et al. |
| 7,485,600 | B2 | 2/2009 | Harutyunyan et al. |
| 7,514,537 | B2 | 4/2009 | Jensen |
| 7,569,664 | B2 | 8/2009 | Jakobsen et al. |
| 7,569,670 | B2 | 8/2009 | Novak et al. |
| 7,572,772 | B2 | 8/2009 | Linsley et al. |
| 7,579,439 | B2 | 8/2009 | Strom et al. |
| 7,628,986 | B2 | 12/2009 | Weber et al. |
| 7,629,171 | B2 | 12/2009 | Meagher et al. |
| 7,659,093 | B2 | 2/2010 | Bakker et al. |
| 7,700,728 | B2 | 4/2010 | Bates et al. |
| 7,723,111 | B2 | 5/2010 | Hwu et al. |
| 7,732,133 | B2 | 6/2010 | Yabuta et al. |
| 7,732,149 | B2 | 6/2010 | Kojima et al. |
| 7,736,644 | B2 | 6/2010 | Weber et al. |
| 7,741,465 | B1 | 6/2010 | Eshhar et al. |
| 7,834,152 | B2 | 11/2010 | Strom et al. |
| 7,919,086 | B2 | 4/2011 | Nakano et al. |
| 7,948,154 | B2 | 5/2011 | Ifuku et al. |
| 7,964,349 | B2 | 6/2011 | Bell et al. |
| 7,968,687 | B2 | 6/2011 | McDonagh et al. |
| 7,972,438 | B2 | 7/2011 | Fei et al. |
| 7,998,736 | B2 | 8/2011 | Morgan et al. |
| 8,008,029 | B2 | 8/2011 | Lefevre |
| 8,088,589 | B2 | 1/2012 | Muraca |
| 8,105,769 | B2 | 1/2012 | Bell et al. |
| 8,120,239 | B2 | 2/2012 | Cheon et al. |
| 8,124,084 | B2 | 2/2012 | Lefrancois et al. |
| 8,124,361 | B2 | 2/2012 | Slack et al. |
| 8,129,125 | B2 | 3/2012 | Muraca |
| 8,158,360 | B2 | 4/2012 | Heise et al. |
| 8,178,660 | B2 | 5/2012 | Weiner et al. |
| 8,263,375 | B2 | 9/2012 | Abassi et al. |
| 8,329,421 | B2 | 12/2012 | Powell et al. |
| 8,350,108 | B2 | 1/2013 | Cortright et al. |
| 8,367,882 | B2 | 2/2013 | Cortright et al. |
| 8,399,645 | B2 | 3/2013 | Campana et al. |
| 8,435,762 | B2 | 5/2013 | Sternson et al. |
| 8,450,112 | B2 | 5/2013 | Li et al. |
| 8,465,743 | B2 | 6/2013 | Rosenberg et al. |
| 8,465,916 | B2 | 6/2013 | Bell et al. |
| 8,535,672 | B2 | 9/2013 | Kaempfer et al. |
| 8,591,858 | B2 | 11/2013 | Harutyunyan et al. |
| 8,592,567 | B2 | 11/2013 | Weiner et al. |
| 8,679,492 | B2 | 3/2014 | Blein et al. |
| 8,710,186 | B2 | 4/2014 | Li et al. |
| 8,771,664 | B2 | 7/2014 | Berraondo Lopez et al. |
| 8,796,421 | B2 | 8/2014 | Li et al. |
| 8,802,374 | B2 | 8/2014 | Jensen |
| 8,822,196 | B2 | 9/2014 | Rosenberg et al. |
| 8,822,647 | B2 | 9/2014 | Jensen |
| 8,859,275 | B2 | 10/2014 | Notka et al. |
| 8,871,114 | B2 | 10/2014 | Miyagawa et al. |
| 8,871,191 | B2 | 10/2014 | Pavlakis et al. |
| 8,877,199 | B2 | 11/2014 | Rader et al. |
| 8,883,992 | B2 | 11/2014 | Damschroder et al. |
| 8,900,816 | B2 | 12/2014 | Schmittling et al. |
| 8,900,820 | B2 | 12/2014 | Muraca |
| 8,906,682 | B2 | 12/2014 | June et al. |
| 8,911,993 | B2 | 12/2014 | June et al. |
| 8,912,385 | B2 | 12/2014 | Meagher |
| 8,916,381 | B1 | 12/2014 | June et al. |
| 8,940,288 | B2 | 1/2015 | Lefrancois et al. |
| 8,975,071 | B1 | 3/2015 | June et al. |
| 9,035,036 | B2 | 5/2015 | Bell et al. |
| 9,040,669 | B2 | 5/2015 | Cheung et al. |
| 9,101,584 | B2 | 8/2015 | June et al. |
| 9,102,760 | B2 | 8/2015 | June et al. |
| 9,102,761 | B2 | 8/2015 | June et al. |
| 9,115,171 | B2 | 8/2015 | Ong et al. |
| 9,156,915 | B2 | 10/2015 | Waldman et al. |
| 9,163,258 | B2 | 10/2015 | Riddell et al. |
| 9,169,328 | B2 | 10/2015 | Spriggs et al. |
| 9,175,308 | B2 | 11/2015 | Shiku et al. |
| 9,181,527 | B2 | 11/2015 | Sentman |
| 9,187,732 | B2 | 11/2015 | Wolschek et al. |
| 9,212,104 | B2 | 12/2015 | Qiao et al. |
| 9,212,229 | B2 | 12/2015 | Schonfeld et al. |
| 9,220,728 | B2 | 12/2015 | Sadelain et al. |
| 9,233,125 | B2 | 1/2016 | Davila et al. |
| 9,266,960 | B2 | 2/2016 | Morgan et al. |
| 9,272,002 | B2 | 3/2016 | Powell, Jr. et al. |
| 9,273,283 | B2 | 3/2016 | Sentman |
| 9,315,585 | B2 | 4/2016 | Cheung et al. |
| 9,328,156 | B2 | 5/2016 | June et al. |
| 9,359,447 | B2 | 6/2016 | Feldman et al. |
| 9,365,630 | B2 | 6/2016 | Lefrancois et al. |
| 9,365,641 | B2 | 6/2016 | June et al. |
| 9,371,368 | B2 | 6/2016 | Lefrancois et al. |
| 9,393,268 | B2 | 7/2016 | Waldman et al. |
| 9,394,368 | B2 | 7/2016 | Brogdon et al. |
| 9,402,865 | B2 | 8/2016 | Powell et al. |
| 9,422,351 | B2 | 8/2016 | Scholler et al. |
| 9,422,360 | B2 | 8/2016 | Suo et al. |
| 9,446,105 | B2 | 9/2016 | Powell, Jr. |
| 9,447,194 | B2 | 9/2016 | Jensen |
| 9,453,075 | B2 | 9/2016 | Cheung et al. |
| 9,464,140 | B2 | 10/2016 | June et al. |
| 9,476,028 | B2 | 10/2016 | Karlsson-Parra et al. |
| 9,481,728 | B2 | 11/2016 | June et al. |
| 9,487,800 | B2 | 11/2016 | Schonfeld et al. |

(56) References Cited

U.S. PATENT DOCUMENTS 9,492,499 B2 11/2016 Jaynes et al.
9,493,740 B2 11/2016 Brenner et al.
9,499,629 B2 11/2016 June et al.
9,499,823 B2 11/2016 Lorenzo et al.
9,511,092 B2 12/2016 Campana et al.
9,518,119 B2 12/2016 Bergstein
9,518,123 B2 12/2016 June et al.
9,518,132 B2 12/2016 Li et al.
9,522,955 B2 12/2016 Rosenberg et al.
9,540,445 B2 1/2017 June et al.
9,562,087 B2 2/2017 Ring et al.
9,572,836 B2 2/2017 June et al.
9,572,837 B2 2/2017 Wu
9,573,988 B2 2/2017 Brogdon et al.
9,580,685 B2 2/2017 Jensen
9,587,020 B2 3/2017 Wu et al.
9,597,357 B2 3/2017 Gregory et al.
9,605,049 B2 3/2017 Campana et al.
9,617,336 B2 4/2017 Cojocaru et al.
9,623,049 B2 4/2017 Eshhar et al.
9,624,276 B2 4/2017 Young et al.
9,624,306 B2 4/2017 Morgan et al.
9,629,877 B2 4/2017 Cooper et al.
9,650,428 B2 5/2017 Sampath et al.
9,657,105 B2 5/2017 Forman et al.
9,663,763 B2 5/2017 Sentman
9,670,281 B2 6/2017 Lim et al.
9,677,136 B2 6/2017 Denise et al.
9,685,295 B2 6/2017 King et al.
9,688,740 B2 6/2017 Choi et al.
9,688,760 B2 6/2017 Kufer et al.
9,701,758 B2 7/2017 Cooper et al.
9,708,384 B2 7/2017 Scholler et al.
9,714,278 B2 7/2017 June et al.
9,725,492 B2 8/2017 Felber et al.
9,725,519 B2 8/2017 Masuko et al.
9,745,368 B2 8/2017 Milone et al.
9,765,142 B2 9/2017 Dimitrov et al.
9,765,342 B2 9/2017 Kochenderfer
9,777,061 B2 10/2017 Ebersbach et al.
9,783,591 B2 10/2017 June et al.
9,790,261 B2 10/2017 Felber et al.
9,790,278 B2 10/2017 Sentman et al.
9,790,282 B2 10/2017 Orentas et al.
9,809,581 B2 11/2017 Chen et al.
9,815,901 B2 11/2017 Brogdon et al.
9,815,908 B2 11/2017 Schonfeld et al.
9,821,011 B1 11/2017 Sentman
9,821,012 B2 11/2017 Wu et al.
9,822,340 B1 11/2017 Sentman
9,828,399 B2 11/2017 Tremblay et al.
9,828,435 B2 11/2017 Evans et al.
9,833,476 B2 12/2017 Zhang et al.
9,833,480 B2 12/2017 Junghans et al.
9,834,545 B2 12/2017 Chen et al.
9,834,590 B2 12/2017 Campana et al.
9,845,362 B2 12/2017 Mukherjee
9,855,297 B2 1/2018 Duchateau et al.
9,855,298 B2 1/2018 Bot et al.
9,856,176 B2 1/2018 Harris et al.
9,856,322 B2 1/2018 Campana et al.
9,856,497 B2 1/2018 Qi et al.
9,868,774 B2 1/2018 Orentas et al.
9,889,160 B2 2/2018 Jantz et al.
9,889,161 B2 2/2018 Jantz et al.
9,913,882 B2 3/2018 Slawin et al.
9,914,909 B2 3/2018 Brown et al.
9,920,132 B2 3/2018 Wels et al.
9,931,347 B2 4/2018 Cowley et al.
9,931,377 B2 4/2018 Pavlakis et al.
9,932,387 B2 4/2018 Lefrancois et al.
9,932,405 B2 4/2018 Xiao et al.
9,932,572 B2 4/2018 Spencer et al.
9,938,497 B2 4/2018 Sentman
9,944,702 B2 4/2018 Galetto
9,944,709 B2 4/2018 Galetto
9,944,931 B2 4/2018 Wucherpfennig et al.
9,950,010 B1 4/2018 Jantz et al.
9,950,011 B1 4/2018 Jantz et al.
9,951,118 B2 4/2018 Kitchen et al.
9,957,480 B2 5/2018 Sentman
9,963,497 B2 5/2018 Kaempfer et al.
9,969,790 B2 5/2018 Lefrancois et al.
9,987,308 B2 6/2018 Riddell et al.
10,011,658 B2 7/2018 Liu et al.
10,023,648 B2 7/2018 Hombach et al.
10,040,846 B2 8/2018 Frigault et al.
10,071,118 B2 9/2018 Katz et al.
10,072,078 B2 9/2018 Orentas et al.
10,117,897 B2 11/2018 Sadelain et al.
10,166,255 B2 1/2019 Moriarity et al.
10,351,612 B2 7/2019 Schonfeld et al.
10,406,177 B2 9/2019 Moriarity et al.
10,428,142 B2 * 10/2019 Jarjour ............... C07K 16/2896
2002/0102264 A1 8/2002 Cheung
2003/0148982 A1 8/2003 Brenner et al.
2004/0038886 A1 2/2004 Finney et al.
2005/0239141 A1 10/2005 Studnicka et al.
2006/0110360 A1 5/2006 Klingemann
2007/0071759 A1 3/2007 Shin et al.
2008/0050341 A1 2/2008 Morgan et al.
2010/0105136 A1 4/2010 Carter et al.
2011/0286980 A1 11/2011 Brenner
2012/0040452 A1 2/2012 Nishimura et al.
2012/0148552 A1 6/2012 Jensen
2013/0001376 A1 1/2013 Peled et al.
2013/0280221 A1 10/2013 Schonfeld et al.
2014/0044714 A1 2/2014 Ho et al.
2014/0255363 A1 9/2014 Metelitsa et al.
2014/0322216 A1 10/2014 Kaplan
2015/0368360 A1 12/2015 Liang et al.
2015/0376296 A1 12/2015 Fedorov et al.
2016/0046700 A1 2/2016 Foster et al.
2016/0145337 A1 5/2016 Galetto et al.
2016/0158285 A1 6/2016 Cooper et al.
2016/0207989 A1 7/2016 Short
2017/0008963 A1 1/2017 Brogdon et al.
2017/0067021 A1 3/2017 Moriarity et al.
2017/0081405 A1 3/2017 Adusumilli et al.
2017/0152480 A1 6/2017 Jensen
2017/0335281 A1 11/2017 Loew et al.
2018/0142035 A1 5/2018 Lobb et al.
2019/0046659 A1 2/2019 Wang et al.
2019/0345217 A1 11/2019 Ma et al.
2021/0230548 A1 7/2021 Daher et al.

FOREIGN PATENT DOCUMENTS

CN 106397593 2/2017
EP 2614151 7/2013
EP 2995682 3/2016
EP 3333192 6/2018
JP 2013-509879 3/2013
JP 2017-514471 A 6/2017
KR 10-2016- 0131026 11/2016
WO WO 1993/011794 6/1993
WO WO 2006/133398 12/2006
WO WO 2010/042189 4/2010
WO WO 2012/033885 3/2012
WO WO 2012/136231 11/2012
WO WO 2013/040371 3/2013
WO WO 2013/070468 5/2013
WO WO 2014/138314 9/2014
WO WO 2014/186469 11/2014
WO WO 2015/051247 4/2015
WO WO 2015/138460 9/2015
WO WO 2016/044811 3/2016
WO WO 2016/073755 5/2016
WO WO 2016/102965 6/2016
WO WO 2016/120220 8/2016
WO WO 2016/154055 9/2016
WO WO 2016/172606 10/2016
WO WO 2016/174405 11/2016
WO WO 2016/197108 12/2016

(56) References Cited

FOREIGN PATENT DOCUMENTS

| | | |
|---|---|---|
| WO | WO 2017/020812 | 2/2017 |
| WO | WO 2017/027843 | 2/2017 |
| WO | WO 2017/048902 | 3/2017 |
| WO | WO 2017/096329 | 6/2017 |
| WO | WO 2017/100861 | 6/2017 |
| WO | WO 2017/112877 | 6/2017 |
| WO | WO 2017/123556 | 7/2017 |
| WO | WO 2017/220704 | 12/2017 |
| WO | WO 2017/222593 | 12/2017 |
| WO | WO 2018/027155 | 2/2018 |
| WO | WO 2018/081470 | 5/2018 |
| WO | WO 2018/195339 | 10/2018 |
| WO | WO 2018/237022 | 12/2018 |
| WO | WO 2019/157130 | 8/2019 |
| WO | WO 2011/056894 | 5/2021 |

OTHER PUBLICATIONS

English translation of Office Communication issued in Japanese Patent Application No. 2023-117421, dated Mar. 11, 2025.
Agrawal et al., "14G2a anti-GD2 crossreactivity with the CD166 antigen," J Immunother., 1014-1015, Nov.-Dec. 2010;33(9).
Baev et al., "Distinct homeostatic requirements of CD4+ and CD4− subsets of Va24-invariant natural killer T cells in humans", Blood, vol. 104, No. 13 (2004), pp. 4150-4156.
Batra et al., "Armored Glypican-3-Specific CART Cells for the Immunotherapy of Hepatocellular Carcinoma", Molecular Therapy, vol. 26, No. 5, Suppl. 1, May 2018 (May 2018), p. 441.
Bendelac, et al., "The Biology of NKT Cells", Annu. Rev. Immunol., 25, (2007), pp. 297-336.
Bendelac et al., "CD1 Recognition by Mouse NK1+ T Lymphosytes", Science, 268, (1995), pp. 863-865.
Brocker and Karjalainen, "Signals through T Cell Receptor-z Chain Alone Are Insufficient to Prime Resting T Lymphocytes", J. Exp. Med., May 1, 1995, vol. 181, pp. 1653-1659, The Rockefeller University Press.
Brudno et al., "Toxicities of Chimeric antigen Receptor T Cells: Recognition and Management"; Blood 2016, Jun. 30; 127(26): 3321-3330.
Cartellieri et al., "Chimeric Antigen Receptor-Engineered T Cells for Immunotherapy of Cancer", Journal of Biomedicine and Biotechnology, vol. 21, No. 4, Jan. 1, 2010 (Jan. 1, 2010), pp. 427-13.
Chan et al., "Immunohistochemical Expression of Glypican-3 in Pediatric Tumors: An Analysis of 414 Cases", Pediatric and Developmental Pathology, 2013, vol. 16, pp. 272-277.
Chang et al., "Sustained expansion of NKT cells and antigen-specific T cells after injection of a-galactosyl-ceramide loaded mature dendritic cells in cancer patients", J. Exp. Med., vol. 201, No. 9, (2005), pp. 1503-1517.
Cheresh et al., "Biosynthesis and Expression of the Disialoganglioside GD2, a Relevant Target Antigen on Small Cell Lung Carcinoma for Monoclonal Antibody-mediated Cytolysis1", Cancer Research, vol. 46, Oct. 1, 1986 (Oct. 1, 1986), pp. 5112-5118.
Cohen et al., "Shared and distinct transcriptional programs underlie the hybrid nature of INKT cells", Nat Immunol., Jan. 2013; 14(1): 90-99.
Crowe et al., "Differential antitumor immunity mediated by NKT cell subsets in vivo", J. Exp. Med., vol. 202, No. 9, (2005), pp. 1279-1288.
Delconte et al., "CIS is a potent checkpoint in NK cell-mediated tumor immunity", Nature Immunology, vol. 17, No. 7, Jul. 2016, Nature America, Inc.
Dhodapkar, "Harnessing human CD1d restricted T cells for tumor immunity: progress and challenges", Front Biosci., 14, (2009), pp. 796-807.
Di Stasi et al., "Inducible Apoptosis as a Safety Switch for Adoptive Cell Therapy", N. Engl. J. Med., 365, (2011), pp. 1673-1683.
Dotti et al., "Design and development of therapies using chimeric antigen receptor- expressing T cells", Immunological Reviews, vol. 257, No. 1, Dec. 13, 2013 (Dec. 13, 2013), pp. 107-126.
Dotti et al., Fifteen Years of Gene Therapy Based on Chimeric Antigen Receptors: "Are We Nearly There Yet?", Human Gene Therapy, Nov. 2009, 20: 1229-1239.
Dotti et al., "Design and development of therapies using chimeric antigen receptorexpressing T cells," Immunol Rev. 2014;257(1): 107-126.
English translation of Office Action issued in Japanese Patent Application No. 2020- 503988, dated Jun. 23, 2022.
English translation of Office Communication issued in Korean Patent Application No. 10-2020-7005375, dated Mar. 14, 2024.
Exley et al., "Selective activation, expansion, and monitoring of human INKT cells with a monoclonal antibody specific for the TCR a-chain CDR3 loop", Eur. J. Immunol. 2008. 38: 1756-1766.
Fehniger et al., "Fatal Leukemia in Interleukin 15 Transgenic Mice Follows Early Expansions in Natural Killer and Memory Phenotype CD8+ T Cells", J. Exp. Med., vol. 193, No. 2, (2001), pp. 219-231.
Furukawa et al., "Biosignals modulated by tumor-associated carbohydrate antigens: novel targets for cancer therapy," Ann. N.Y. Acad. Sci. 1086: 185-198 (2006).
Gan et al., "The epidermal growth factor receptor variant III (EGFRvIII): where wild things are altered", The FEBS Journal, vol. 280, No. 21, Jul. 8, 2013 (Jul. 8, 2013), pp. 5350-5370.
Gao et al., "Development of T Cells Redirected to Glypican-3 for the Treatment of Hepatocellular Carcinoma," Clinical Cancer Research, vol. 20, No. 24, Dec 15, 2014 (Dec. 15, 2014), pp. 6418-6428.
Gao et al., "Supplementary Data: Development of T Cells Redirected to Glypican-3 for the Treatment of Hepatocellular Carcinoma," Clinical Cancer Research, Dec. 15, 2014 (Dec. 15, 2014), pp. 6418-6642, Figures Only—Retrieved from Internet: http://clincancerres.aacrjournals.org/content/20/24/6418.
Godfrey and Kronenberg, "Going both ways: immune regulation via CD1d-dependent NKT cells," Journal of Clinical Investigation, vol. 114, No. 10, Nov. 2004, pp. 1379-1388.
Godfrey et al., "Raising the NKT cell family," Nat Rev Immun, Mar. 2010, vol. 11, No. 3, pp. 197-206, Nature America, Inc.
Godfrey et al., "NTK cells: what's in a name?" Nature Reviews Immunology; Nature Publishing Group; 2004, vol. 4; 231-237.
Graef et al., "Serial transfer of single-cell-derived immunocompetence reveals sternness of CDS(+)central memory T cells," Immunity. 2014;41(1):116-126.
Heczey et al., "Invariant NKT cells with chimeric antigen receptor provide a novel platform for safe and effective cancer immunotherapy," BLOOD, Oct. 30, 2014, vol. 124, No. 18, pp. 2824-2833, The American Society of Hematology.
Heczey et al., "NKT cells as a novel platform for cancer immunotherapy with chimeric antigen receptors," The Journal of Immuno, the American Association of Immunologists, US, vol. 190, May 1, 2013 (May 1, 2013 ), p. P2038.
Hofflin et al., "Generation of COB+ T cells expressing two additional T-cell receptors (TETARs) for personalised melanoma therapy," Cancer Biology & Therapy, Jul. 15, 2015 (Jul. 15, 2015), vol. 16, Iss. 9, pp. 1323-1331.
Hsu et al., "Cytokine-independent growth and clonal expansion of a primary human CD8+ T-cell clone following retroviral transduction with the IL-15 gene," Blood, vol. 109, No. 12, (2007), pp. 5168-5177.
Huang et al., "Interleukin-armed chimeric antigen receptor-modified T cells for cancer immunotherapy," Gene Therapy, vol. 25, No. 3, Sep. 21, 2017 (Sep. 21, 2017), pp. 192-197, Nature Publishing Group, London, GB.
Imai et al., "Complement-Mediated Mechanisms in Anti-GD2 Monoclonal Antibody Therapy for Murine Metastatic Cancer". American Association for Cancer Research, 10562-10568, 2005.
International Search Report and Written Opinion issued in Application No. PCT/US16/28693, mailed Jul. 21, 2016.
Ishikawa et al., "A Phase I Study of a-Galactosylceramide (KRN7000)-Pulsed Dendritic Cells in Patients with Advanced and Recurrent Non-Small Cell Lung Cancer," Clin. Cancer Res., 11, (2005), pp. 1910-1917.
Johnson et al., "Rational development and characterization of humanized anti-EGFR variant III chimeric antigen receptor T cells for glioblastoma" Science Translational Medicine, Feb. 2015, vol. 7, No. 275.

(56) References Cited

OTHER PUBLICATIONS

Kalos and June, "Adoptive T cell transfer for cancer immunotherapy in the era of synthetic biology," Immunity 2013;39(1):49-60.
Kambayashi et al., Emergence of D8+ T Cells Expressing NI Cell Receptors in Influenza A virus-infected mice; The Journal of Immunology; 2000, 165: 4964-4969.
Kershaw et al., "A Phase I Study on Adoptive Immunotherapy Using Gene-Modified T cells for Ovarian Cancer," Clin. Cancer Res., 12, (2006), pp. 6106-6115.
Khor et al., "CISH and Susceptibility to Infectious Diseases," New England Journal of Medicine, Jun. 3, 2010 Jun. 3, 2010), vol. 362, No. 22, pp. 2092-2101.
Kim et al., "4-1BB Engagement Costimulates NKT Cell Activation and Exacerbates NKT Cell Ligand-Induced Airway Hyperresponsiveness and Inflammation," J. Immunol., 180, (2008), pp. 2062-2068.
KRONENBERGet al., "The unconventional lifestyle of NKT cells," Nat. Rev. Immunol., 2, (2002), pp. 557-568.
Kunii et al., "Combination therapy of in vitro-expanded natural killer T cells and a-galactosylceramide-pulsed antigen-presenting cells in patients with recurrent head and neck carcinoma," Cancer Sci., vol. 100, No. 6, (2009), pp. 1092-1098.
Lantz et al., "An Invariant T Cell Receptor a Chain Is Used by a Unique Subset of Major Histocompatibility Complex Class I-specific CD4+ and CD4-8-T Cells in Mice and Himans," J. Exp. Med., 180, (1994), pp. 1097-1106.
Lappas et al., "Adenosine A2A receptor activation reduces hepatic ischemia reperfusion injury by inhibiting CD1d-dependent NKT cell activation," J. Experimental Medicine, vol. 203, No. 12, Nov. 27, 2006, pp. 2639-2648, The Rockefeller University Press.
Levy et al., "Expression of glypican-3 in undifferentiated embryonal scarcoma and mesenchymal hamartoma of the liver," Human Patholoy (2012) 43, 695-791.
Li et al., "NKT Cell Activation Mediates Neutrophil IFN-g Production and Renal Ischemia-Reperfusion Injury," The Journal of Immunology, 2007, 178: 5899-5911.
Li et al., "Immunotherapy of Hepatocellular Carcinoma with T Cells Engineered to Express Glypican-3-Specific Chimeric Antigen Receptors," Molecular Therapy, vol. 23, No. Suppl. I, May 2015 (May 2015), pp. SI64-SI65.; and 18th Annual Meeting of the American-Society-of-Gene-and-Cell-Therapy (ASGCT); New Orleans, LA, USA; May 13-16, 2015.
Li et al., "In vitro validation of human glypican-3 specific chimeric antigen receptors for hepatocellular carcinoma," HEPATOLOGY, vol. 60, No. Suppl. 1, Sp. Iss. Sl, Oct. 2014, p. 870A, XP002780485; and 65th Annual Meeting of the American-Association-for-the-Study-of-Liver-Diseases; Boston, MA, USA; Nov. 7-11, 2014, ISSN: 0270-9139.
Li et al., "Validation of glypican-3-specific scFv isolated from paired display/secretory yeast display library," BMC Biotechnology, vol. 12, No. 1, May 7, 2012 (May 7, 2012), p. 23. Biomed Central Ltd., London, GB.
Liu et al., "IL-15 protects NKT cells from inhibition by tumor-associated macrophages and enhances antimetastatic activity," The Journal of Clinical Invesigation, vol. 122, No. 6, Jun. 2012, pp. 2221-2233.
Lo et al., "Anti-GD3 chimeric sFv-CD28/T-cell receptor zeta designer T cells for treatment of metastatic melanoma and other neuroectodermal tumors," Cancer Res. 2010; 16(10):2769-2780.
Louis et al., "Treatment of High-Risk Neuroblastoma with Adoptively Transferred T Lymphocytes Genetically Engineered to Recognize GD2," Biology of Blood and Marrow Transplantation, 15(2):26, 2009.
Macdonald, "NKT Cells In the Beginning . . . " Eur. J. Immunol. 2007. 37: S111-115, Wiley-VCH Verlag GmbH & Co. KGaA, Weinheim.
Maher et al., "Human T-lymphocyte cytotoxicity and proliferation directed by a single chimeric TCRz/CD28 receptor," Nat. Biotechol., 20, (2002), pp. 70-75.
Mantovani et al., "Cancer-related inflammation," NATURE, vol. 454:24, Jul. 2008, pp. 436-444, Macmillan Publishers Limited.
Matsuda et al., "Homeostasis of Val 4INKT cells," Nat. Immunol., vol. 3, No. 10, (2002), pp. 966-974.
Menger et al., "TALEN-mediated genetic inactivation of the glucocorticoid receptor in cytomegalovirus-specific T cells." Blood, 2015, 126(26):2781-2789. (Year: 2015).
Metelitsa et al., "Human NKT Cells Mediate Antitumor Cytotoxicity Directly by Recognizing Target Cell CD1d with Bound Ligand or Indirectly by Producing IL-2 to Activate NK Cells," Journal of Immunology, 2001; 167:3114-3122; The American Association of Immunologists, Inc.
Metelitsa "Anti-tumor potential of type-I NKT cells against CD1d-positive and CD1d-negative tumors in humans," Clinical Immunology (2011) 140, pp. 119-129.
Metelitsa et al., "Natural Killer T Cells Infiltrate Neuroblastomas Expressing the Chemokine CCL2," J. Exp. Med., vol. 199, No. 9, (2004), pp. 1213-1221.
Molling et al., "Low Levels of Circulating Invariant Natural Killer T Cells Predict Poor Clinical Outcome in Patients with Head and Neck Squamous Cell Carcinoma," J. Clin. Oncol., vol. 25, No. 7, (2007), pp. 862-868.
Motohashi et al., "A Phase I-II Study of a-Galactosylceramide-Pulsed IL-2/GM-CSF-Cultured Peripheral Blood Mononuclear Cells in Patients with Advanced and Recurrent Non-Small Cell Lung Cancer," J. Immunol., 182, (2009), pp. 2492-2501.
Mujoo et al., "Functional Properties and Effect on Growth Suppression of Human Neuroblastoma Tumors by Isotype Switch Variants of Monoclonal Antiganglioside GD2". American Association for Cancer Research, 2857-2861, 1989.
Nandagopal et al., "The critical role of IL-15-PI3K-mTOR pathway in natural killer cell effector functions," Frontiers in Immunology, Apr. 23, 2014 (Apr. 23, 2014), vol. 5, Art. 187, pp. 1-12.
Navid et al., "Anti-GD2 antibody therapy for GD2-expressing tumors," Curr Cancer Drug Targets. 2010; 10(2):200-209.
Nguyen et al., "Glypican-3-Specific Car Nkt Cells Armored with IL-15 Exhibit Potent and Sustained Anti-Tumor Activity against Hepatocellular Carcinoma," Molecular Therapy, vol. 26, No. 5, Suppl. 1, May 2018 (May 2018), p. 62.
Nieda et al., "Therapeutic activation of Va24+Vb11+ NKT cells in human subjects results in highly coordinated secondary activation of acquired and innate immunity," Blood, vol. 103, No. 2,(2004), pp. 383-389.
Peralbo et al., Invariant NKT and NKT-like lymphocytes: Two different T cell subsets that are differentially affectedby ageing; Science Direct, Experimental Gerontology 42; Dept. of Immunology, 2007; pp. 703-708.
Porcelli et al., "Analysis of T Cell Antigen Receptor (TCR) Expression by Human Peripheral Blood CD4-8-a/b T Cell Demonstrates Preferential Use of Several Vb genes and an Invariant TCR a Chain," J. Exp. Med., 178, (1993), pp. 1-16.
Porter et al., "Chimeric Antigen Receptor-Modified T Cells in Chronic Lymphoid Leukemia," N. Engl. J. Med. , 365(8), (2011), pp. 725-733.
Pule et al., "A chimeric T cell antigen receptor that augments cytokine release and supports clonal expansion of primary human T cells," Molecular Therapy vol. 12: 933-941 (2005).
Pule et al., "Virus-specific T cells engineered to coexpress tumor-specific receptors: persistence and antitumor activity in individuals with neuroblastoma," Nat. Med., 14(11), (2008), pp. 1264-1270.
Qian et al., "The novel anti-CD19 chimeric antigen receptors with humanized scFv (single-chain variable fragment) trigger leukemia cell killing," Cellular Immunology, vol. 304, Mar. 14, 2016 (Mar. 14, 2016), pp. 49-54, Academic Press, San Diego, CA, US.
Quintarelli et al., "Co-expression of sytokine and suicide genes to enhance the activity and safety of tumor-specific cytotoxic T lymphosytes," Blood, 110(8), (2007), pp. 2793-2802/.
Rettig et al., "Transduction and Selection of Human T Cells with Novel CD34/Thymidine Kinase Chimeric Suicide Genes for the Treatment of Graft-versus-Host Disease," Milecular Ther., 8(1), (2003), pp. 29-41.
Riedl et al., "The apoptosome: signalling platform of cell death," Nat. Rev. Mol. Cell Biol., 8, (2007), pp. 405-413.

(56) References Cited

OTHER PUBLICATIONS

Rossig et al., "Targeting of GD2-Positive Tumor Cells by Human T Lymphocytes Engineered to Express Chimeric T-Cell Receptor Genes," Int. J. Cancer, 94:228-236, 2001.
Rossig et al., Epstein-Barr virus-specific human T lymphocytes expressing antitumer chimeric T-cell receptors: potential for improved immunotherapy, Blood, Mar. 15, 2002; vol. 99, No. 6, 2009-2016.
Rossjohn et al., Recognition of CD1d-restricted antigens by natural killer T cells; Nat. Rev. Immunol., Dec. 2012; 12(12): 845-857.
Sadelain et al., "The promise and potential pitfalls of chimeric antigen receptors," Current Opinion in Immunology 2009, 21:215-223.
Sai et al., "Armored Glypican-3-Specific CAR T Cells for the Immunotherapy of Hepatocellular Carcinoma" Molecular Therapy, 21st Annual Meeting of the American-Society-of-Gene-and-Cell-Therapy (ASGCT); 16-19. May, vol. 26, No. 5SI, May 1, 2018 (May 1, 2018), p. 441; Chicago, IL, USA.
Sato et al., "Development of an IL-15-autocrine CD8 T-cell leukemia in IL-15-transgenic mice requires the cis expression of IL-15Ra," Blood, 117, (2011), pp. 4032-4040.
Savoldo et al., "CD28 costimulation improves expansion and persistence of chimeric antigen receptor-modified T cells in lymphoma patients," J. Clin. Invest., 112(5), (2011), pp. 1822-1826.
Shah, "T-Cell Development in Thymus," British Society for Immunology, London. Available on https://www.immunology.org/public-information/bitesized-immunology/immune-development/t-cell-development-thymus. Accessed Jun. 20, 2024.
Sica and Bronte, "Altered macrophage differentiation and immune dysfunction in tumor development," J. Clin. Invest., May 2007, vol. 117, No. 5, pp. 1155-1166.
Sica et al., "Macrophage polarization in tumour progression," Seminars in Cancer Biology, 18 ( Apr. 2008) pp. 349-355.
Slifka et al., NK Markers are Expressed on a High Percentage of Virus-Specific CD8+ and CD4+ T Cells; J. Immunol 2000; 164: 209-2015.
Sommermeyer et al., "Chimeric antigen receptor-modified T cells derived from defined COB and CD4 subsets confer superior antitumor reactivity in vivo," Leukemia 2015.
Song et al., "In Vivo Persistence, Tumor Localization, and Antitumor Activity of CAR-Engineered T Cells Is Enhanced by Costimulatory Signaling through CD137 (4-1 BB)," Cancer Research, vol. 71, No. 13, Jul. 1, 2011 (Jul. 1, 2011 ), pp. 4617-4627.
Song et al."Va24-invariant NKT cells mediate antitumor activity via killing of tumor-associated macrophages," J. Clin. Invest., 119(6), (2009), pp. 1524-1536.
Straathof et al., "An inducible caspase 9 safety switch for T-cell therapy," Blood, 105(11), (2005), pp. 4247-4254.
Suzukil et al., "Glypian-3 (GPC3) as a novel tumor for malignant ovarian tumors and malignant melanoma," Japan Molecular Tumor Markers Research Journal, 2010, vol. 25, p. 31-32.
Swann et al., "CD1-Restricted T Cells and Tumor Immunity," Curr. Top. Microbiol. immunol., 314, (2007), pp. 293-321.
Tachibana et al., "Increased Intratumor Va24-Positive Natural Killer T Cells: A Prognostic Factor for Primary Colorectal Carcinomas," Clin. Cancer Res., 11(20), (2005), pp. 7322-7327.
Takahashi et al., "Cutting edge: analysis of human V alpha 24+CD8+ NK T cells activated by alpha-galactosylceramide-pulsed monocyte-derived dendritic cells," The Journal of Immunology; 2002; 168:3140-3144.
Tey et al., "Inducible caspase 9 suicide gene to improve the safety of allodepleted T cells after haploidentical stem cell transplantation," Biol. Blood Marrow Transplant., 13(8), (2007), pp. 913-924.
Till et al., "Adoptive immunotherapy for indolent non-Hodgkin lymphoma and mantle cell lymphoma using genetically modified autologous CD20-specific T cells," Blood, 112(6), (2008), pp. 2261-2271.
Toretsky et al., "Glypican-3 Expression in Wilms Tumor and Hepatoblastoma," Journal of Pediatric Hematology/Onocolgy, Nov. 1, 2001, vol. 23, No. 8, pp. 496-499, New York, US.
Torikai et al., "Translational Implications for Off-the-shelf Immune Cells Expressing Chimeric Antigen Receptors," Molecular Therapy, May 16, 2016 (May 16, 2016), vol. 24, No. 7, pp. 1178-1186.
Uldrich et al., "NKT cell stimulation with glycolipid antigen in vivo: co-stimulation-dependent expansion, Bim-dependent contraction, and hypo-responsiveness to further antigenic challenge," J. Immunol., 175(5), (2005), pp. 3092-3101.
Vinay et al., "CD137-Deficient Mice Have Reduced NK/NKT Cell Numbers and Function, Are Resistant to Lipopolysaccharide-Induced Shock Syndromes, and Have Lower IL-4 Responses," J. Immunol., 173, (2004), pp. 4218-4229.
Wang et al., "A transgene-encoded cell surface polypeptide for selection, in vivo tracking, and ablation of engineered A cells," BLOOD, vol. 118, No. 5, Aug. 4, 2011 (Aug. 4, 2011), pp. 1255-1263.
Wang et al., "Phenotypic and functional attributes of lentivirus-modified CD19-specific human COB+central memory T cells manufactured at clinical scale," J. Immunother. 2012;35(9):689-701.
Wang et al., Tumor-derived soluble MICs impare CD3+CD56+ NKT-like cell cytotoxicity in cancer patients; Elsevier Immunology Letters 120; 2008; pp. 65-71.
Wilkie et al., "Retargeting of human T cells to tumor-associated MUC1: the evolution of a chimeric antigen receptor," J Immunol 2008; 180: 4901-4909.
Whitlow et al., "An improved linker for single-chain Fv with reduced aggregation and enhanced proteolytic stability," Protein Eng., 6(8):989-95, 1993.
Xu and Dotti, "Selection bias: maintaining less-differentiated T cells for adoptive immunotherapy," J. Clinical Invest., Jan. 2016, Vo. 126, No. 1, pp. 35-37.
Yoshida et al., "Ganglioside G(D2) in Small Cell Lung Cancer Cell Lines: Enhancement of Cell Proliferation and Mediation of Apoptosis," Cancer Research, May 15, 2001 (May 15, 2001), pp. 4244-4252.
Yvon et al., "Immunotherapy of Metastatic Melanoma Using Genetically Engineered GD3-Specific T cells," Clinical Cancer Research, 15(18):5852-5860, 2009.
Zaini et al., "OX40 ligand expressed by DCs costimulates NKT and CD4+ Th cell antitumor immunity in mice," J. Clin, Invest., 117(11), (2007), pp. 3330-3338.
Zhao et al.,"GS2 Oligosaccharide: Target for Cytotoxic T Lymphocytes" The Journal of Experimental Medicine, Rockefeller University Press, US, vol. 182, Jul. 1, 1995 (Jul. 1, 1995), pp. 67-74.
Zou et al., "Immunosuppressive networks in the tumour environment and their therapeutic relevance," Nat. Rev. Cancer, 5, (2005), pp. 263-274.
Office Communication issued in Canadian Patent Application No. 3,070,998, dated Aug. 12, 2024.
Protein [Internet]. Bethesda (MD): National Library of Medicine (US), National Center for Biotechnology Information; [1988]—Accession No. NP_000576.1, "Interleukin-15 isoform 1 preproprotein [*Homo sapiens*]," cited Oct. 17, 2000. Available from https://www.ncbi.nlm.nih.gov/protein/NP_000576.1.
English translation of Office Communication issued in Korean Patent Application No. 10-2020-7005375, dated Nov. 28, 2024.
Anonymous, "Antitope—Antibody humanization," retrieved from the Internet: http://www.antitope.com/antibody-humanization, copyright Abzena Group of Companies 2014. Retrieved on Mar. 9, 2016.
Extended European Search Report issued in European Patent Application No. 25169707.4, dated Jan. 29, 2026.

* cited by examiner

| Feature key | Position(s) | Description | Length (aa) |
|---|---|---|---|
| Signal peptide | 1 ~ 24 | | 24 |
| Topological domain | 25 ~ 645 | Extracellular | 621 |
| Transmembrane | 646 ~ 668 | Helical | 23 |
| [redacted] | 669 ~ 1210 | Cytoplasmic | 542 |

Extracellular domains

```
        10         20         30         40         50
MRPSGTAGAA LLALLAALCP ASRALEEKKG ---------- ----------
Domain>                    11111 1111111111 1111111111
        60         70         80         90        100
---------- ---------- ---------- ---------- ----------
1111111111 1111111111 1111111111 1111111111 1111111111
       110        120        130        140        150
---------- ---------- ---------- ---------- ----------
1111111111 1111111111 1111111111 1111111111 1111111111
       160        170        180        190        200
---------- ---------- ---------- ---------- ----------
1111111111 1111111111 1111111111 1111111112 2222222222
       210        220        230        240        250
---------- ---------- ---------- ---------- ----------
2222222222 2222222222 2222222222 2222222222 2222222222
       260        270        280        290        300
---------- ---------- ---------- ---------- -------NYV
2222222222 2222222222 2222222222 2222222222 2222222222
       310        320        330        340        350
VTDHGSCVRA CGADSYEMEE DGVRKCKKCE GPCRKVCNGI GIGEFKDSLS
2222222222 2222222222 2222222222 2222233333 3333333333
       360        370        380        390        400
INATNIKHFK NCTSISGDLH ILPVAFRGDS FTHTPPLDPQ ELDILKTVKE
3333333333 3333333333 3333333333 3333333333 3333333333
       410        420        430        440        450
ITGFLLIQAW PENRTDLHAF ENLEIIRGRT KQHGQFSLAV VSLNITSLGL
3333333333 3333333333 3333333333 3333333333 3333333333
       460        470        480        490        500
RSLKEISDGD VIISGNKNLC YANTINWKKL FGTSGQKTKI ISNRGENSCK
3333333333 3333333333 3333333333 3333333333 3333333333
```

FIG. 2C

| Feature key | Position(s) | Description | Length (aa) |
|---|---|---|---|
| Signal peptide | 1 ~ 24 | | 24 |
| Topological domain | 25 ~ 645 | Extracellular | 621 |
| Transmembrane | 646 ~ 668 | Helical | 23 |
| [redacted] | 669 ~ 1210 | Cytoplasmic | 542 |

Extracellular domains

```
       510        520        530        540        550
ATGQVCHALC SPEGCWGPEP RDCVSCRNVS RGRECVDKCN LLEGEPREFV
3333444444 4444444444 4444444444 4444444444 4444444444
       560        570        580        590        600
ENSECIQCHP ECLPQAMNIT CTGRGPDNCI QCAHYIDGPH CVKTCPAGVM
4444444444 4444444444 4444444444 4444444444 4444444444
       610        620        630        640        650
GENNTLVWKY ADAGHVCHLC HPNCTYGCTG PGLEGCPTNG PKIPSIATGM
4444444444 4444444444 4444444444 4444444444 44444
```

FIG. 2C continued

FIG. 3F
214 pSFG4-hCD19CAR-E3D12z clean
9,371 bp
9,371
500
1,000
1,500
2,000
2,500
3,000
3,500
4,000
4,500
5,000
5,500
6,000
6,500
7,000
7,500
8,000
8,500
9,000
LTR
rep origin
AmpR
hCD19igCAR
hCD19scFv
EvS
DAP12
CD3z
E2A
IL15
LTR

```
                                                 (A)--> 
                                                <---------------------FR1-IMGT-------------(G)
                                                 G  G  G  L  V  K  P  G  G  S  L  R  L  S  C
                         Y14934          1      GGGGGAGGCCTGGTCAAGCCTGGGGGGTCCCTGAGACTCTCCTG
V   96.0%  (264/275)     IGHV3-21*01     22     .............................................
                                                 G  G  G  L  V  K  P  G  G  S  L  R  L  S  C
v   96.0%  (264/275)     IGHV3-21*02     22     .............................................
v   95.6%  (263/275)     IGHV3-21*04     22     .............................................
    100.0% (275/275)     Y14934          1      .............................................
    99.6%  (274/275)     Y14942          1      .............................................
    99.3%  (273/275)     Y14935          1      .............................................
    96.0%  (264/275)     JX432690        22     .............................................
    96.0%  (264/275)     JX432693        22     .............................................
    96.0%  (264/275)     JX432692        22     .............................................
    96.0%  (264/275)     JX432702        22     .............................................
    96.0%  (264/275)     JX432730        22     .............................................
    96.0%  (264/275)     JX432735        22     .............................................
    96.0%  (264/275)     JX432740        22     .............................................

                                                ---------FR2-IMGT--------------------><----(H)
                                                 R  Q  A  P  G  K  G  L  E  W  V  S  S  I  T
                         Y14934          91     CCCCAGGCTCCAGGCAAGGGGCTGGACTGGGTCTCATCCATTAC
V   96.0%  (264/275)     IGHV3-21*01     112    ............................................G
                                                 R  Q  A  P  G  K  G  L  E  W  V  S  S  I  S
V   96.0%  (264/275)     IGHV3-21*02     112    ............................................G
V   95.6%  (263/275)     IGHV3-21*04     112    ............................................G
    100.0% (275/275)     Y14934          91     .............................................
    99.6%  (274/275)     Y14942          91     .............................................
    99.3%  (273/275)     Y14935          91     .............................................
    96.0%  (264/275)     JX432690        112    ............................................G
    96.0%  (264/275)     JX432693        112    ............................................G
    96.0%  (264/275)     JX432692        112    ............................................G
    96.0%  (264/275)     JX432702        112    ............................................G
    96.0%  (264/275)     JX432730        112    ............................................G
    96.0%  (264/275)     JX432735        112    ............................................G
    96.0%  (264/275)     JX432740        112    ............................................G
```

FIG. 5B (Cont'd)

C

D E → F

```
> humIGLV165 309 bp
TCTCCCAGCCTGTGCTGACTCAGCCGCCCTCCCTCTCTGCACCTCCGGATCAGCCAGACT
CTCCTGCACCCTGAGCAGTGGCTTCAGTGCTGATTTCTACTGGATATACTGGTACCAGCA
TAAACCAGGGAGCCTCCCCAGTATCTCCTGAGCCACTACCAAAATTCACTTCATGACCAG
GGCTCCGGGGTCCCCAGGCACTTCTCTGGATTAATGGAAGGCCGGTCCAATAAAGGGCTC
TTGCTCATATCTGATCTCCAGTCTGAGGATGAGGCTTACTATTACTGTATGATCGAGCAC
AGCAGAGCT

> humIGLV166 294 bp
AATTTTATGCTGACTCAGCCCCACTCTGTGTCGGAGTCTCCGGGGAAGACGGTAACCATC
TCCTGCACCGGCAGCAGTGGCAGCATTGCCAGCAACTATGTGCAGTGGTACCAGCAGCGC
CCGGGCAGTTCCCCCACCACTGTGATCTATGAGGATAACCAAAGACCCTCTGGGGTCCCT
GATCGGTTCTCTGGCTCCATCGACAGCTCCTCCAACTCTGCCTCCCTCACCATCTCTGGA
CTGAAGACTGAGGACGAGGCTGACTACTACTGTCAGTCTTATGATAGCAGCAAT

> humIGLV167 IGLV7-46*01 291 bp
CAGGCTGTGGTGACTCAGGAGCCCTCACTGACTGTGTCCCCAGGAGGGACAGTCACTCTC
ACCTGTGGCTCCAGCACTGGAGCTGTCACCAGTGGTCATTATCCCTACTGGTTCCAGCAG
AAGCCTGGCCAAGCCCCCAGGACACTGATTTATGATACAAGCAACAAACACTCCTGGACA
CCTGCCCGGTTCTCAGGCTCCCTCCTTGGGGGCAAAGCTGCCCTGACCCTTTCGGGTGCG
CAGCCTGAGGATGAGGCTGACTATTACTGCTTGCTCTCCTATAGTGGTGCT

> humIGLV168 282 bp
TCCTGTGAGCTGACACAGCCACCCTCAGTGTCAGTAGCTCCAGGACAGATGACTAGGATC
```

FIG. 5B
(Cont'd)

Figure 6C:
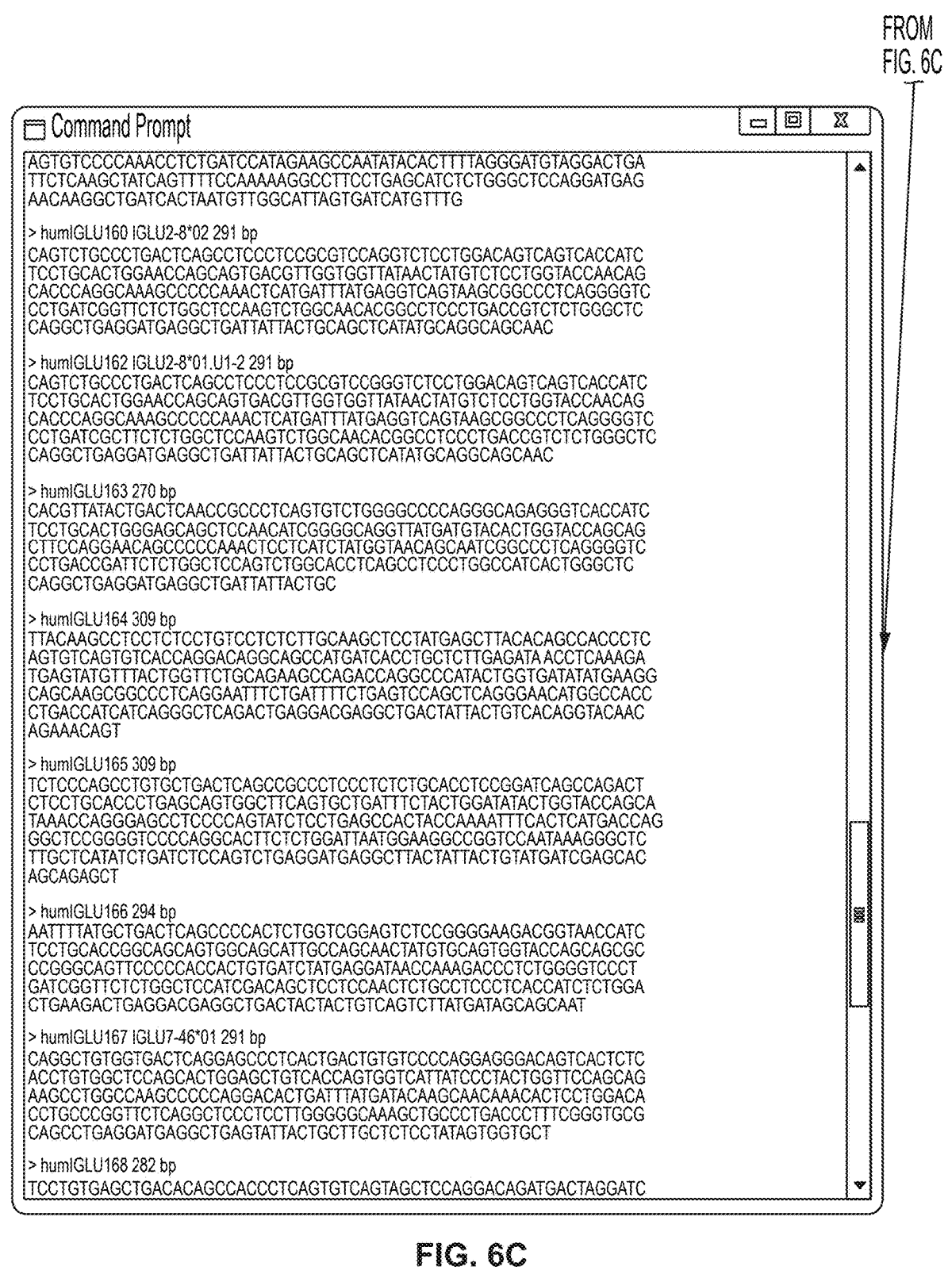

FROM FIG. 6C

Command Prompt

AGTGTCCCCAAACCTCTGATCCATAGAAGCCAATATACACTTTTAGGGATGTAGGACTGA
TTCTCAAGCTATCAGTTTTCCAAAAAGGCCTTCCTGAGCATCTCTGGGCTCCAGGATGAG
AACAAGGCTGATCACTAATGTTGGCATTAGTGATCATGTTTG

> humIGLU160 IGLU2-8*02 291 bp
CAGTCTGCCCTGACTCAGCCTCCCTCCGCGTCCAGGTCTCCTGGACAGTCAGTCACCATC
TCCTGCACTGGAACCAGCAGTGACGTTGGTGGTTATAACTATGTCTCCTGGTACCAACAG
CACCCAGGCAAAGCCCCCAAACTCATGATTTATGAGGTCAGTAAGCGGCCCTCAGGGGTC
CCTGATCGGTTCTCTGGCTCCAAGTCTGGCAACACGGCCTCCCTGACCGTCTCTGGGCTC
CAGGCTGAGGATGAGGCTGATTATTACTGCAGCTCATATGCAGGCAGCAAC > humIGLU162 IGLU2-8*01.U1-2 291 bp
CAGTCTGCCCTGACTCAGCCTCCCTCCGCGTCCGGGTCTCCTGGACAGTCAGTCACCATC
TCCTGCACTGGAACCAGCAGTGACGTTGGTGGTTATAACTATGTCTCCTGGTACCAACAG
CACCCAGGCAAAGCCCCCAAACTCATGATTTATGAGGTCAGTAAGCGGCCCTCAGGGGTC
CCTGATCGCTTCTCTGGCTCCAAGTCTGGCAACACGGCCTCCCTGACCGTCTCTGGGCTC
CAGGCTGAGGATGAGGCTGATTATTACTGCAGCTCATATGCAGGCAGCAAC > humIGLU163 270 bp
CACGTTATACTGACTCAACCGCCCTCAGTGTCTGGGGCCCCAGGGCAGAGGGTCACCATC
TCCTGCACTGGGAGCAGCTCCAACATCGGGGCAGGTTATGATGTACACTGGTACCAGCAG
CTTCCAGGAACAGCCCCCAAACTCCTCATCTATGGTAACAGCAATCGGCCCTCAGGGGTC
CCTGACCGATTCTCTGGCTCCAGTCTGGCACCTCAGCCTCCCTGGCCATCACTGGGCTC
CAGGCTGAGGATGAGGCTGATTATTACTGC > humIGLU164 309 bp
TTACAAGCCTCCTCTCCTGTCCTCTCTTGCAAGCTCCTATGAGCTTACACAGCCACCCTC
AGTGTCAGTGTCACCAGGACAGGCAGCCATGATCACCTGCTCTTGAGATA ACCTCAAAGA
TGAGTATGTTTACTGGTTCTGCAGAAGCCAGACCAGGCCCATACTGGTGATATATGAAGG
CAGCAAGCGGCCCTCAGGAATTTCTGATTTTCTGAGTCCAGCTCAGGGAACATGGCCACC
CTGACCATCATCAGGGCTCAGACTGAGGACGAGGCTGACTATTACTGTCACAGGTACAAC
AGAAACAGT > humIGLU165 309 bp
TCTCCCAGCCTGTGCTGACTCAGCCGCCCTCCCTCTCTGCACCTCCGGATCAGCCAGACT
CTCCTGCACCCTGAGCAGTGGCTTCAGTGCTGATTTCTACTGGATATACTGGTACCAGCA
TAAACCAGGGAGCCTCCCCAGTATCTCCTGAGCCACTACCAAAATTTCACTCATGACCAG
GGCTCCGGGGTCCCCAGGCACTTCTCTGGATTAATGGAAGGCCGGTCCAATAAAGGGCTC
TTGCTCATATCTGATCTCCAGTCTGAGGATGAGGCTTACTATTACTGTATGATCGAGCAC
AGCAGAGCT > humIGLU166 294 bp
AATTTTATGCTGACTCAGCCCCACTCTGGTCGGAGTCTCCGGGGAAGACGGTAACCATC
TCCTGCACCGGCAGCAGTGGCAGCATTGCCAGCAACTATGTGCAGTGGTACCAGCAGCGC
CCGGGCAGTTCCCCCACCACTGTGATCTATGAGGATAACCAAAGACCCTCTGGGGTCCCT
GATCGGTTCTCTGGCTCCATCGACAGCTCCTCCAACTCTGCCTCCCTCACCATCTCTGGA
CTGAAGACTGAGGACGAGGCTGACTACTACTGTCAGTCTTATGATAGCAGCAAT > humIGLU167 IGLU7-46*01 291 bp
CAGGCTGTGGTGACTCAGGAGCCCTCACTGACTGTGTCCCCAGGAGGGACAGTCACTCTC
ACCTGTGGCTCCAGCACTGGAGCTGTCACCAGTGGTCATTATCCCTACTGGTTCCAGCAG
AAGCCTGGCCAAGCCCCCAGGACACTGATTTATGATACAAGCAACAAACACTCCTGGACA
CCTGCCCGGTTCTCAGGCTCCCTCCTTGGGGGCAAAGCTGCCCTGACCCTTTCGGGTGCG
CAGCCTGAGGATGAGGCTGAGTATTACTGCTTGCTCTCCTATAGTGGTGCT > humIGLU168 282 bp
TCCTGTGAGCTGACACAGCCACCCTCAGTGTCAGTAGCTCCAGGACAGATGACTAGGATC

FIG. 6C hCD19 scFv $V_L$

DIQMTQSPSS LSASVGDRVT ITCRASQDIS KYLNWYQQKP GKVPKLLIYH
TSRLHSGVPD RFSGSGSGTD FTLTISSLQP EDVATYYCQQ GNTLPYTFGQ
GTKVEIKR $V_H$

EVQLVESGGG LVQPGGSLRL SCAASGVSLP DYGVSWVRQA PGKGLEWIGV
IWGSETTYYN SALKSKFIIS RDNAKNSLYL QMNSLRAEDT AVYYCARHYY
YGGSYAMDYW GQGTLVTVSS

--- mCD19 scFv $V_L$

DIQMTQTTSS LSASLGDRVT ISCRASQDIS KYLNWYQQKP DGTVKLLIYH
TSRLHSGVPS RFSGSGSGTD YSLTISNLEQ EDIATYFCQQ GNTLPYTFGG
GTKLELKR $V_H$

EVQLQQSGPG LVAPSQSLSV TCTVSGVSLP DYGVSWIRQP PRKGLEWLGV
IWGSETTYYN SALKSRLTII KDNSKSQVFL KMNSLQTDDT AIYYCAKHYY
YGGSYAMDYW GQGTTVTVSS

FIG. 7A

| | hCD19 scFv | mCD19 scFv |
|---|---|---|
| $V_L$ | • DIQMTQSPSS LSASVGDRVT ITC<br>• Ig kappa chain V region (MAR) - human (fragment) [PH0879] | • DIQMTQTTSS LSASLGDRVT ISC<br>• immunoglobulin light chain, [Mus musculus] [AAC52468] |
| $V_H$ | • EVQLVESGGG LVQPGGSLRL SCAAS<br>• immunoglobulin heavy chain variable region, partial [Homo sapiens][ACD43442] | • EVQLQQSGPG LVAPSQSLSV TCTVS<br>• immunoglubulin heavy chain variable region, partial [Mus musculus] [AAS45200] |

FIG. 7B

| scFv amino acid | scFv nucleotide |
|---|---|
| • $V_L$ identity – 80%<br>• $V_L$ homology – 91%<br>• $V_L$ alignment score – 480 | • $V_L$ identity – 70%<br>• $V_L$ homology – 70%<br>• $V_L$ alignment score – 773 |
| • $V_H$ identity – 75%<br>• $V_H$ homology – 88%<br>• $V_H$ alignment score – 502 | • $V_H$ identity – 68%<br>• $V_H$ homology – 68%<br>• $V_H$ alignment score – 741 |

FIG. 7C

Templates | Sequence Similarity | Alignment of Selected Templates | More

| Name | Title | Coverage | Identity | Method | Oligo State | Ligands |
|---|---|---|---|---|---|---|
| ☑ 2fgw.1.A | H52 FAB (LIGHT CHAIN) | | 91.67 | X-ray, 3.0Å | hetero-oligomer | None |
| ☐ 4edw.1.A | tanezumab Fab light chain | | 88.89 | X-ray, 2.5Å | hetero-oligomer | None |
| ☐ 2fgw.1.A | H52 FAB (LIGHT CHAIN) | | 91.59 | X-ray, 3.0Å | hetero-oligomer | None |
| ☐ 1fgv.1.A | H52 FV (LIGHT CHAIN) | | 89.81 | X-ray, 1.9Å | hetero-oligomer | None |
| ☐ 1bj1.1.A | FAB FRAGMENT | | 88.89 | X-ray, 2.4Å | hetero-oligomer | None |
| ☐ 1cz8.1.C | LIGHT CHAIN OF NEUTRALIZING ANTIBODY | | 87.96 | X-ray, 2.4Å | hetero-oligomer | None |

FIG. 8B

Templates | Sequence Similarity | Alignment of Selected Templates | More

| Name | Title | Coverage | Identity | Method | Oligo State | Ligands |
|---|---|---|---|---|---|---|
| 1cz8.1.E | LIGHT CHAIN OF NEUTRALIZING ANTIBODY | | 87.96 | X-ray, 2.4Å | hetero-oligomer | None |
| 3ncj.1.A | Fab15 Mut8 light chain | | 89.81 | X-ray, 1.6Å | hetero-oligomer | 4 x ZN |
| 4edw.1.A | tanezumab Fab light chain | | 88.79 | X-ray, 2.5Å | hetero-oligomer | None |
| 1bj1.1.A | FAB FRAGMENT | | 88.79 | X-ray, 2.4Å | hetero-oligomer | None |
| 3na9.1.A | Fab15 light chain | | 88.89 | X-ray, 1.7Å | hetero-oligomer | 7 x ZN |

FIG. 8B
(Cont'd)

Found Templates

| ID | Name | Seq ID | Seq Sim | Cov | Resolu | Method | GMQE | Found By |
|---|---|---|---|---|---|---|---|---|
| 16ab2a54676539ba5354b5ae4631978d23d69f0f | 2fgw.1.A | 91.667 | 0.582 | 1.000 | 3.000 | X-ray | 0.982 | BLAST |
| 919b2cfdf6b66ff490e541d188d3364a35035627 | 4edw.1.A | 88.889 | 0.575 | 1.000 | 2.480 | X-ray | 0.977 | BLAST |
| a3ebccc75776de851fdee4abc3415195d94fb9a6 | 2fgw.1.A | 91.589 | 0.582 | 0.991 | 3.000 | X-ray | 0.959 | HHblits |
| d1fac46a2f9bc24ddbd5264a18f3f086df89d329 | 1fgv.1.A | 89.815 | 0.573 | 1.000 | 1.900 | X-ray | 0.916 | HHblits |
| f537a248f491064f4d38449441e7a0a25b3f53e6 | 1bj1.1.A | 88.889 | 0.572 | 1.000 | 2.400 | X-ray | 0.977 | BLAST |
| 5185b6260c466fca1a7d8f93b28ed57ead694d44 | 1cz8.1.C | 87.963 | 0.570 | 1.000 | 2.400 | X-ray | 0.980 | BLAST |
| a5214da2aef2b06f4e6382b31e8d11ebfcd037a9 | 1cz8.1.E | 87.963 | 0.570 | 1.000 | 2.400 | X-ray | 0.980 | BLAST |
| 0f0883c8a9c05c2c3db1cac3d80d327d57955a78 | 3ncj.1.A | 89.815 | 0.569 | 1.000 | 1.600 | X-ray | 0.983 | BLAST |
| 01aa021a39308f06db24b49a645ef740f4fa9c21 | 4edw.1.A | 88.785 | 0.575 | 0.991 | 2.480 | X-ray | 0.946 | HHblits |
| 16a6f6fff3b541f1daa39194e5ff3b18d77ad45a | 1bj1.1.A | 88.785 | 0.572 | 0.991 | 2.400 | X-ray | 0.945 | HHblits |
| 66e2a7e52fa5012ef38fd0257c3fdd1772bb6264 | 3na9.1.A | 88.889 | 0.564 | 1.000 | 1.700 | X-ray | 0.980 | BLAST |
| 4eb750c9fe5c850a3e92ec8f95ecd79687ed0f39 | 3ulu.1.B | 88.889 | 0.564 | 1.000 | 3.520 | X-ray | 0.980 | BLAST |
| 12893efb7685cfa2a3929c298d073d36c92959ec | 3ulv.1.B | 88.889 | 0.564 | 1.000 | 3.522 | X-ray | 0.980 | BLAST |
| 0dc02afbccd59befd067834464c34edf96359a35 | 5veb.1.B | 87.963 | 0.563 | 1.000 | 2.340 | X-ray | 0.977 | BLAST |
| 86e7e4d61ab12f05442ec2520a2c16c2a569283a | 1cz8.1.C | 87.850 | 0.570 | 0.991 | 2.400 | X-ray | 0.940 | HHblits |
| c953ed986edb59ef472c6de925517b117e44ccb4 | 1cz8.1.E | 87.850 | 0.570 | 0.991 | 2.400 | X-ray | 0.940 | HHblits |
| a7703d4bad28b91e373050c1b9a681acd731a88f | 2kqm.1.A | 85.185 | 0.562 | 1.000 | NA | NMR | 0.885 | HHblits |
| ef9d37498230eb34b8e343f965966f1195c7a767 | 2kqm.1.B | 85.185 | 0.562 | 1.000 | NA | NMR | 0.885 | HHblits |

FIG. 8C

Found Templates

| ID | Name | Seq ID | Seq Sim | Cov | Resolu | Method | GMQE | Found By |
|---|---|---|---|---|---|---|---|---|
| c06fb1666ca2220ea35ab93c1fc958d95033cab3 | 3ncj.1.A | 89.720 | 0.569 | 0.991 | 1.600 | X-ray | 0.954 | HHblits |
| ad6c18aab86bdfe36a61ba2e4366029652321f06 | 5d1q.1.A | 84.259 | 0.560 | 1.000 | 3.220 | X-ray | 0.974 | BLAST |
| 134492e948694cb1fd1211586e652742aae21ac5 | 5it2.1.B | 87.037 | 0.560 | 1.000 | 1.700 | X-ray | 0.973 | BLAST |
| 3a667df8cf03b012f5f40604711fc4990ad8f0d1 | 5i19.1.A | 87.037 | 0.559 | 1.000 | 2.800 | X-ray | 0.972 | BLAST |
| b72cc746b30590cbe92a4d1cafe85ebdc2588d1a | 5115.1.A | 87.037 | 0.559 | 1.000 | 2.600 | X-ray | 0.972 | BLAST |
| 905c68765b1a29e6ae10da4d0e4fd6a6c610e8c9 | 4kmt.1.A | 86.111 | 0.559 | 1.000 | 2.100 | X-ray | 0.963 | BLAST |
| 54db60cc74641525f8bf9372557b269eb4862486 | 2wub.1.C | 85.185 | 0.559 | 1.000 | 2.900 | X-ray | 0.967 | BLAST |
| 399430263bb502e648291e2673e014e0f984593e | 3k2u.1.D | 85.185 | 0.559 | 1.000 | 2.350 | X-ray | 0.967 | BLAST |
| e3dc77fd87c865c0184b1f85d002bef842f032c1 | 2wuc.1.D | 85.185 | 0.559 | 1.000 | 2.700 | X-ray | 0.971 | BLAST |
| 12f2db1e2160c9dc5d754a12c238bacc9f9d8a9c | 4n1e.1.A | 86.111 | 0.558 | 1.000 | 2.230 | X-ray | 0.768 | HHblits |
| b5d1dcc7c5ee7904c2cd2869e2de56872b07135b | 4n1e.1.B | 86.111 | 0.558 | 1.000 | 2.230 | X-ray | 0.887 | HHblits |

FIG. 8C
(Cont'd)

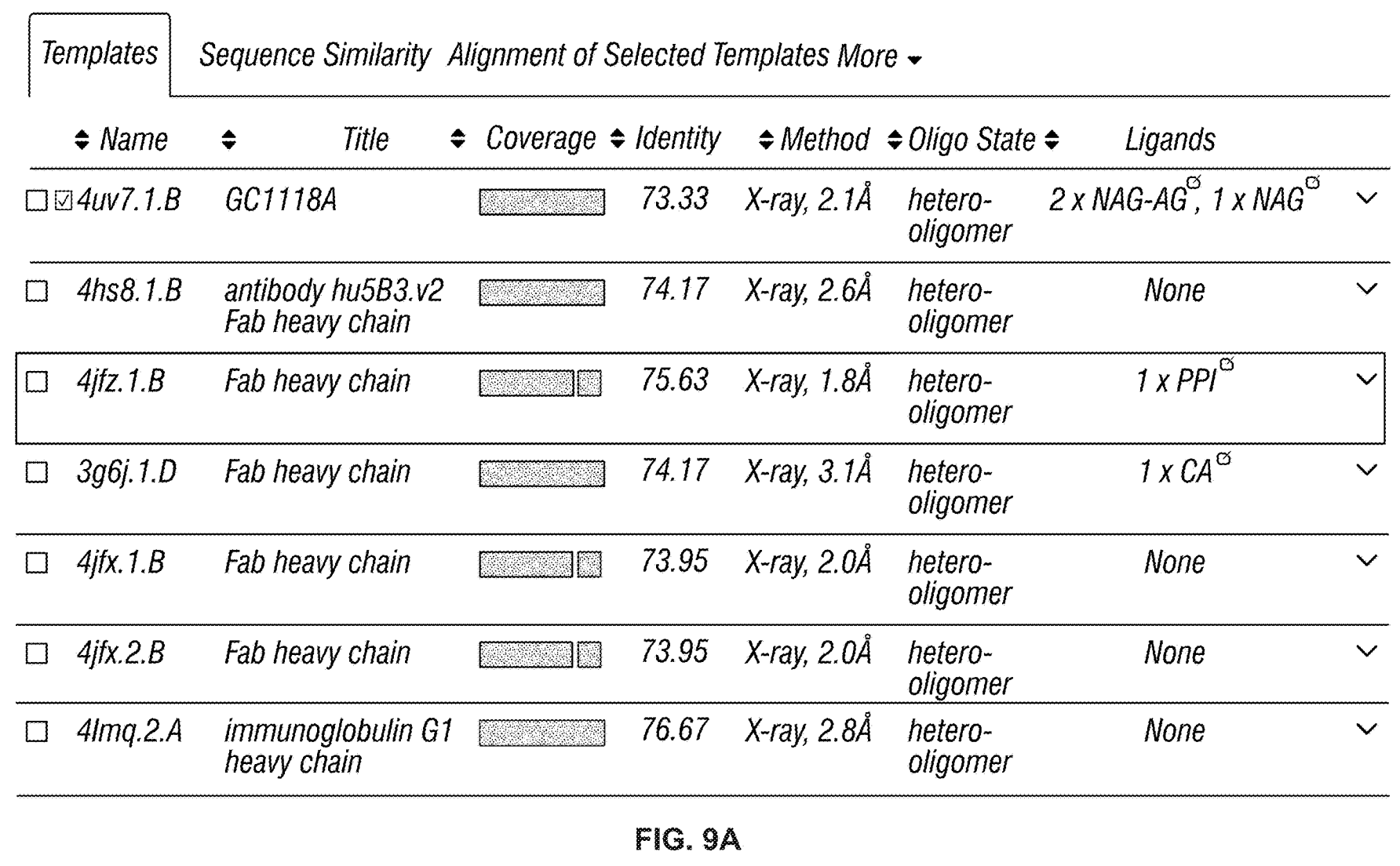

Templates | Sequence Similarity | Alignment of Selected Templates | More

| Name | Title | Coverage | Identity | Method | Oligo State | Ligands |
|---|---|---|---|---|---|---|
| 4uv7.1.B | GC1118A | | 73.33 | X-ray, 2.1Å | hetero-oligomer | 2 x NAG-AG, 1 x NAG |
| 4hs8.1.B | antibody hu5B3.v2 Fab heavy chain | | 74.17 | X-ray, 2.6Å | hetero-oligomer | None |
| 4jfz.1.B | Fab heavy chain | | 75.63 | X-ray, 1.8Å | hetero-oligomer | 1 x PPI |
| 3g6j.1.D | Fab heavy chain | | 74.17 | X-ray, 3.1Å | hetero-oligomer | 1 x CA |
| 4jfx.1.B | Fab heavy chain | | 73.95 | X-ray, 2.0Å | hetero-oligomer | None |
| 4jfx.2.B | Fab heavy chain | | 73.95 | X-ray, 2.0Å | hetero-oligomer | None |
| 4lmq.2.A | immunoglobulin G1 heavy chain | | 76.67 | X-ray, 2.8Å | hetero-oligomer | None |

FIG. 9A

Templates | Sequence Similarity | Alignment of Selected Templates | More ▾

| | Name | Title | Coverage | Identity | Method | Oligo State | Ligands |
|---|---|---|---|---|---|---|---|
| ☐ | 4lmq.1.B | immunoglobulin G1 heavy chain | | 76.67 | X-ray, 2.8Å | hetero-oligomer | None |
| ☐ | 5fuo.1.B | FAB HEAVY CHAIN | | 72.50 | X-ray, 3.6Å | hetero-oligomer | None |
| ☐ | 5fuz.1.A | 645 FAB, HEAVY CHAIN | | 72.50 | X-ray, 2.7Å | hetero-oligomer | None |
| ☐ | 1dfb.1.B | IGG1-KAPPA 3D6 FAB (HEAVY CHAIN) | | 72.50 | X-ray, 2.7Å | hetero-oligomer | None |
| ☐ | 1w72.2.C | HYB3 HEAVY CHAIN | | 77.78 | X-ray, 2.1Å | hetero-oligomer | 1 x GLU-ALA-ASP-PRO-THR-GLY-HIS-SER-TYR |
| ☐ | 1w72.1.C | HYB3 HEAVY CHAIN | | 77.78 | X-ray, 2.1Å | hetero-oligomer | 1 x GLU-ALA-ASP-PRO-THR-GLY-HIS-SER-TYR |

FIG. 9A
(Cont'd)

Found Templates

| ID | Name | Seq ID | Seq Sim | Cov | Resolu | Method | GMQE | Found By |
|---|---|---|---|---|---|---|---|---|
| 21101ec705dbd41451b58ac59ff02528b91e18a5 | 4uv7.1.B | 73.333 | 0.531 | 1.000 | 2.100 | X-ray | 0.909 | BLAST |
| 45f63856aaf6a6b3a9d9224af51a2accfcfd5071 | 4hs8.1.B | 74.167 | 0.529 | 1.000 | 2.680 | X-ray | 0.885 | BLAST |
| 03329e74435aaac544f4ced9f398115e07fb07dd | 4jfz.1.B | 75.630 | 0.532 | 0.992 | 1.750 | X-ray | 0.872 | BLAST |
| 20291db69c52a49b9c20c96a0392a6a973f761ae | 3g6j.1.D | 74.167 | 0.525 | 1.000 | 3.100 | X-ray | 0.874 | BLAST |
| 49d4e2b0048335bbae43c66a8fdebb34da268942 | 4jfx.1.B | 73.950 | 0.531 | 0.992 | 1.950 | X-ray | 0.879 | BLAST |
| 39120a1abdd0a1dd42f57e5ecd995bc82ba6d558 | 4jfx.2.B | 73.950 | 0.531 | 0.992 | 1.950 | X-ray | 0.879 | BLAST |
| 2f2ffb3012446a5178eb0b1fee9684239911cc1d | 41mq.1.B | 76.667 | 0.524 | 1.000 | 2.773 | X-ray | 0.891 | BLAST |
| a82368c848fce9786bb3af117a9aec8021b45035 | 41mq.2.A | 76.667 | 0.524 | 1.000 | 2.773 | X-ray | 0.891 | BLAST |
| a52d1879dbdbf56cfde405605006d19bd440fea6 | 5fuo.1.B | 72.500 | 0.523 | 1.000 | 3.600 | X-ray | 0.897 | BLAST |
| 51ffa985d658ff36864e1cf539ae51aace391822 | 5fuz.1.A | 72.500 | 0.523 | 1.000 | 2.680 | X-ray | 0.897 | BLAST |
| c5270bf7ad127585242f4b52059eb7bb5b509043 | 1dfb.1.B | 72.500 | 0.523 | 1.000 | 2.700 | X-ray | 0.847 | BLAST |
| 7cd2148779876e3b0b1c3bdd5c8760a87d02531b | 1w72.1.C | 77.778 | 0.542 | 0.975 | 2.150 | X-ray | 0.908 | BLAST |
| d3b90dcd3d71865671f955692083780a98ad90eb | 1w72.2.C | 77.778 | 0.542 | 0.975 | 2.150 | X-ray | 0.908 | BLAST |
| 795834131fff385ac5c440b259404b135d8694eb | 4k7p.1.B | 73.333 | 0.534 | 1.000 | 2.950 | X-ray | 0.881 | BLAST |
| 003efdc39ec26490624d65c11be86921d3cc3588 | 4qci.1.B | 75.424 | 0.534 | 0.983 | 3.353 | X-ray | 0.865 | BLAST |
| 7264514b518e4f6bd8dbc20bf912fa084848b480 | 4iof.1.C | 75.424 | 0.533 | 0.983 | 3.353 | X-ray | 0.822 | BLAST |
| d7635c25c1371e76fcad17f0cdc67241274fb164 | 4iof.1.E | 75.424 | 0.533 | 0.983 | 3.353 | X-ray | 0.822 | BLAST |

FIG. 9B

Found Templates

| ID | Name | Seq ID | Seq Sim | Cov | Resolu | Method | GMQE | Found By |
|---|---|---|---|---|---|---|---|---|
| 22691bb26c13370f94f3da002dec68503a3462aa | 4mlc.1.B | 75.424 | 0.533 | 0.983 | 3.501 | X-ray | 0.749 | BLAST |
| 2747a43a7e9de83ea8cc0bd04416d8c331610bee | 4mlc.2.B | 75.424 | 0.533 | 0.983 | 3.501 | X-ray | 0.800 | BLAST |
| 0be5beb780d160c80515d210b80f90b9a2c052da | 4q5z.1.B | 75.424 | 0.533 | 0.983 | 3.930 | X-ray | 0.822 | BLAST |
| 90b9a1b402478f8e3b4b007236e66d84370596c9 | 4jg0.1.B | 74.790 | 0.527 | 0.992 | 1.810 | X-ray | 0.874 | BLAST |
| a5c366d43831e3404129b8857853950f1aceb065 | 4jg1.1.B | 74.790 | 0.527 | 0.992 | 1.550 | X-ray | 0.861 | BLAST |
| b49139b7fabf8a6db51dc7b0f9bf6228c056c886 | 4nnp.1.B | 73.950 | 0.526 | 0.992 | 2.690 | X-ray | 0.839 | BLAST |
| 6782e472f605d22e20993c88d570d5e8656e66e3 | 5csz.1.A | 73.333 | 0.519 | 1.000 | 1.800 | X-ray | 0.807 | BLAST |
| 09293b931a2f88034b3873bdc68c3d9b715b91a6 | 3grw.1.C | 72.500 | 0.525 | 1.000 | 2.100 | X-ray | 0.883 | BLAST |
| f4c72d463469b16e04f2b47a07d3d8b316258223 | 41vh.2.A | 70.588 | 0.525 | 0.992 | 2.800 | X-ray | 0.831 | BLAST |
| 2d45fe1b130233f0d36f5254b5c073d3060232a8 | 41vh.2.C | 70.588 | 0.525 | 0.992 | 2.800 | X-ray | 0.831 | BLAST |
| fcdc5dad1e5a70b6bec51de5a4979439982ad332 | 41vh.3.A | 70.588 | 0.525 | 0.992 | 2.800 | X-ray | 0.831 | BLAST |
| 8e18bbce85cf288b0bc1c962e9546d816ceb75db | 41vh.3.C | 70.588 | 0.525 | 0.992 | 2.800 | X-ray | 0.831 | BLAST |
| a95f3b534e5f99f4314fd1655e4e2b0a20f968f2 | 3kdm.1.B | 79.310 | 0.545 | 0.967 | 1.500 | X-ray | 0.897 | BLAST |
| 552b7cbaa5ef6940b829ceb87498f5ca49ff9343 | 3kdm.2.B | 79.310 | 0.545 | 0.967 | 1.500 | X-ray | 0.897 | BLAST |

FIG. 9B (Cont'd)

*1845 hCD19VH*

| Type | Non-proprietary Name | FDA | Tradename | $V_H$ | $V_L$ |
|---|---|---|---|---|---|
| Murine | muromonabCD3 | 1992 | ORTHOCLONE OKT3® | 69.87 | 61.15 |
| Murine | ibritumomab tiuxetan | 2002 | ZEVALIN® | 66.07 | 64.58 |
| Chimeric | abciximab | 1993 | REOPRO® | 64.62 | 66.97 |
| Chimeric | rituximab | 1997 | MABTHERA®/RITUXAN® | 68.26 | 66.51 |
| Chimeric | basiliximab | 1998 | SIMULECT® | 65.26 | 66.54 |
| Chimeric | cetuximab | 2004 | ERBITUX® | 57.98 | 65.82 |
| Chimeric | siltuximab | 2014 | SYLVANT® | 74.83 | 68.67 |
| Humanized | palivizumab | 1998 | SYNAGIS® | 80.76 | |
| Humanized | trastuzumab | 1998 | HERCEPTIN® | 86.26 | 93.04 |
| Humanized | alemtuzumab | 2001 | CAMPATH® | 72.31 | 85.45 |
| Humanized | omalizumab | 2003 | XOLAIR® | 76.36 | 87.32 |
| Humanized | bevacizumab | 2004 | AVASATIN® | 73.66 | 89.18 |
| Humanized | ranibizumab | 2006 | LUCENTIS® | 72.56 | 88.54 |
| Humanized | certolizumab pegol | 2008 | CIMZIA® | 78.64 | 89.09 |
| Humanized | pertuzumab | 2012 | PURJETA® | 76.47 | 90.05 |
| Humanized | pembrolizumab | 2014 | KEYTRUDA® | 75.71 | 82.28 |

FIG. 10B

| Type | Non-proprietary Name | FDA | Tradename | $V_H$ | $V_L$ |
|---|---|---|---|---|---|
| Humanized | vedolizumab | 2014 | ENTYVIO™ | 79.88 | 84.91 |
| Humanized | elotuzumab | 2015 | EMPLICITI™ | 78.95 | 85.05 |
| Humanized | idarucizumab | 2015 | PRAXBIND® | 77.34 | 85.96 |
| Human | adalimumab | 2002 | HUMIRA® | 87.85 | 91.32 |
| Human | canakinumab | 2009 | ILARIS® | 90.51 | 30.72 |
| Human | ofatumumab | 2009 | ARZERRA® | 92.54 | 96.73 |
| Human | denosumab | 2010 | XGEVA®/PROLIA® | 90.98 | 94.41 |
| Human | ipilimumab | 2011 | YERVOY® | 90.47 | 96.62 |
| Human | nivolumab | 2014 | OPDIVO® | 90.18 | 96.64 |
| Human | ramucirumab | 2014 | CYRAMZA® | 90.78 | 82.14 |
| Human | necitumumab | 2015 | PORTRAZZA™ | 90.79 | 92.59 |
| Human | secukinumab | 2015 | COSENTYX® | 84.09 | 97.25 |

FIG. 10B
(Cont'd)

Humanization Scoring

| Antibody name | Company | Type | Reported immunogenicity* |
|---|---|---|---|
| Muromanab (OKT3) | Ortho Biotech | Murine | 25% (24) |
| Arcitumomab (CEA-scan) | Immunomedics | Murine | <1% (3/400) |
| Fanolesomab (Neutrospec) | Palatin Tech. | Murine | 0-16.6% (30~54) |
| Imciromab (Myoscint) | Centocor (Johnson & Johnson) | Murine | <1% (914) |
| Capromab (Prostascint) | Cytogen | Murine | 8%-19% (27~239) |
| Nofetumomab (Verluma) | Boehringer Ingelheim | Murine | 6% (53) |
| Ibritumomab (Zevalin) | Idec Pharma (Biogen Idec) | Murine | 1.3% (446) |
| Tositumomab (Bexxar) | GSK | Murine | 11% (230) |
| Rituximab (Rituxan) | Genentech(Roche)/Biogen/Idec | Chimeric | 11% (2578) |
| Basiliximab (Simulect) | Novartis | Chimeric | 1-2% (138~339) |
| Infliximab (Remicade) | Centocor (Johnson & Johnson) | Chimeric | 10~15% |
| Cetuximab (Erbitux) | Imclone (Eli Lilly) | Chimeric | 5% (1001) |
| Daclizumab (Zenapax) | Hoffman LaRoche | Humanized | 14~34% |
| Trastuzumab (Herceptin) | Genentech (Roche) | Humanized | <1% |
| Palivizumab (Synagis) | MedImmune (Astra Zeneca) | Humanized | 0.7%~2% (1002~639) |
| Gemtuzumab (Mylotarg) | Wyeth Pharma (Pfizer) | Humanized | 0% (277) |
| Alemtuzumab (Campath) | Ilex Pharma (Genzyme) | Humanized | 1.9-8.3% (133~211) |
| Omalizumab (Xolair) | Genentech (Roche) | Humanized | <0.1% (1723) |
| Efalizumab (Raptiva) | Genentech (Roche) | Humanized | 6.3% (1063) |
| Bevacizumab (Avastin) | Genentech (Roche) | Humanized | 0% (~500) |
| Ranibizumab (Lucentis) | Genentech (Roche) | Humanized | 1~6% |
| Eculizumab (Soliris) | Alexion Pharma | Humanized | 2% (196) |
| Natalizumab (Tysabri) | Biogen Idec | Humanized | 9% (627) |
| Cetolizumab pegol (Cimzia) | UCB | Humanized | 8% (1509) |
| Tocilizumab (Actemra) | Genentech (Roche) | Humanized | 2% (2876) |
| Canakinumab (Ilaris) | Novartis | Human | 0% (64) |
| Adalimumab (Humira) | Abbott | Human | 2.6%~26% |
| Panitumumab (Vectibix) | Amgen | Human | 4.6% (613) |
| Golimumab (Simponi) | Centocor (Johnson & Johnson) | Human | 4% (1425) |
| Ofatumumab (Arzerra) | GSK | Human | 0% (79) |
| Ustekinumab (Stelara) | Centocor (Johnson & Johnson) | Human | 3-5% (743~1198) |
| Denosumab (Prolia) | Amgen | Human | <1% (8113) |
| Abciximab (Reopro) | Centocor (Johnson & Johnson) | Chimeric Fab | 6%~44% (36) |

FIG. 10E mCD19CAR

Sequence variable region:

DIQMTQTTSSLSASLGDRVTISCRASQDISKYLNWYQQKPDGTVKLLIYHTSRLHSGVPS RFSGSGSGTDYSLTISNLEQEDIATYFCQQGNTLPYTFGGGTKLELKR

Chain: VL

Region: Framework + CDR

T20 Score: 74.07

--- hCD19CAR (RS)

Sequence variable region:

DIQMTQSPSSLSASVGDRVTITCRASQDISKYLNWYQQKPGKVPKLLIYHTSRLHSGVP DRFSGSGSGTDFTLTISSLQPEDVATYYCQQGNTLPYTFGQGTKVEIKR

Chain: VL

Region: Framework + CDR

T20 Score: 87.13

FIG. 10F mCD19CAR

Sequence variable region:

EVQLQQSGPGLVAPSQSLSVTCTVSGVSLPDYGVSWIRQPPRKGLEWLGVIWGSETTY YNSALKSRLTIIKDNSKSQVFLKMNSLQTDDTAIYYCAKHYYYGGSYAMDYWGQG TTVTVSS

Chain: VH

Region: Framework + CDR

T20 Score: 64.67

--- hCD19CAR (RS)

Sequence variable region:

EVQLVESGGGLVQPGGSLRLSCAASGVSLPDYGVSWVRQAPGKGLEWIGVIWGSETT YYNSALKSKFIISRDNAKNSLYLQMNSLRAEDTAVYYCARHYYYGGSYAMDYWGQ GTLVTVSS

Chain: VH

Region: Framework + CDR

T20 Score: 74.46

FIG. 10G

ENHANCED CHIMERIC ANTIGEN RECEPTORS AND USE THEREOF

The present application is a continuation of U.S. patent application Ser. No. 17/233,157, filed Apr. 16, 2021, which is a continuation of U.S. patent application Ser. No. 16/632,762, filed Jan. 21, 2020, which is a national phase application under 35 U.S.C. § 371 that claims priority to International Application No. PCT/US2018/043779, filed Jul. 25, 2018, which claims the priority benefit of U.S. Provisional Application Ser. No. 62/536,934, filed Jul. 25, 2017, all of which are hereby incorporated by reference in their entirety.

INCORPORATION OF SEQUENCE LISTING

The instant application contains a Sequence Listing which has been submitted in XML format and is hereby incorporated by reference in its entirety. Said XML copy, created on Jan. 1, 2025, is named "MDACP1331USC2-Sub-Seq-Listing.xml" and is 279,687 bytes in size.

BACKGROUND

1. Field

The present invention relates generally to the fields of immunology and molecular biology. More particularly, it concerns enhanced chimeric antigen receptors (CARs), such as for immune cells.

2. Description of Related Art

Despite technological advancements in the diagnosis and treatment options available to patients diagnosed with cancer, the prognosis still often remains poor and many patients cannot be cured. Immunotherapy holds the promise of offering a potent, yet targeted, treatment to patients diagnosed with various tumors with the potential to eradicate the malignant tumor cells without damaging normal tissues. In theory, the T cells of the immune system are capable of recognizing protein patterns specific for tumor cells and to mediate their destruction through a variety of effector mechanisms. The administration of immune cells expressing chimeric antigen receptors (CARs), such as adoptive T cell therapy or NK cell therapy, is an attempt to harness and amplify the tumor-eradicating capacity of a patient's own immune cells and then return these effectors to the patient in such a state that they effectively eliminate residual tumor, however without damaging healthy tissue. Commonly, CARs comprise a single chain variable fragment (scFv) of an antibody specific for a tumor associated antigen (TAA) coupled via hinge and transmembrane regions to cytoplasmic domains of T-cell signaling molecules. However, many drawbacks in the clinical use of immune cells therapy impair the full use of this approach in cancer treatments. Thus, there is an unmet need for improved CARs for use in immune cell therapy.

SUMMARY

In certain embodiments, the present disclosure provides enhanced chimeric antigen receptors and methods of their use for the treatment of diseases and disorders, including cancer and autoimmune disorders. In one embodiment, there is provided a truncated EGFRVIII, referred to as Ev3 (or tEv3), which does not comprise an endodomain or functional EGF binding domain. In particular aspects, Ev3 comprises truncated domain 1 (L1), truncated domain 2 (CR1), domain 3 (L2), and domain 4 (CR2) of EGFR (as depicted in FIG. 2B). In some aspects, the Ev3 may be located in the hinge region of a CAR and can be used for CAR detection and/or ablation of CAR-expressing cells. In some embodiments, the CAR comprises both a humanized scFv and an Ev3 hinge. In another embodiment, there are provided humanized antigen-binding domains for the CARs, such as humanized single chain variable fragments (scFvs). Further embodiments provide methods of treating immune-associated disorders by administering immune cells, such as T cells or NK cells, which express the CAR(s) of the embodiments to a subject.

In another embodiment, there is provided a chimeric antigen receptor (CAR) comprising a Ev3 in the hinge of said CAR, wherein said Ev3 hinge links an extracellular domain and at least one intracellular immune signaling domain. In some aspects, the Ev3 hinge comprises a transmembrane domain and a non-functional ectodomain of EGFRVIII. In particular aspects, the Ev3 hinge does not comprise EGFRvIII endodomain. In some aspects, the non-functional ectodomain of EGFRVIII has essentially no binding capability to epidermal growth factor (EGF).

In some aspects, the Ev3 hinge comprises an amino acid sequence with at least 80%, such as at least 81, 82, 83, 84, 85, 86, 87, 88, 89, 90, 91, 92, 93, 94, 95, 96, 97, 98, or 99% sequence identity to SEQ ID NO:2. In some aspects, the Ev3 hinge comprises an amino acid sequence of SEQ ID NO:2.

The Ev3 may comprise or have at least 80% (e.g., 81%, 82%, 83%, 84%, 85%, 86%, 87%, 88%, 89%, 90%, 91%, 92%, 93%, 94%, 95%, 96%, 97%, 98%, 99%, or 100%) sequence identity to SEQ ID NO:2 LEEKK-GNYVVTDHGSCVRACGADSYE-MEEDGVRKCKKCEGPCRK-VCNGIGIGEFKDSLSI-NATNIKHFKNCTSISGDLHILPVAFRGDSFTHTPPLD-PQELDIL KTVKEITGFLLIQAWPENRTDLHAFEN-LEIIRGRTKQHGQFSLAVVSLNITSLGLRSLK EISDGD-VIISGNKNLCYANTINWKKLFGTSGQKTKIISNRGEN-SCKATGQ-VCHALCSPEGCWGPEPRDCVSCRNVSR-GRECVDKCNLLEGEPREFVENSECIQCHPE CLPQAM-NITCTGRGPDNCIQCAHYIDGPHCVKTCPAGVM-GENNTLVWKYADAGHV CHLCHPNCTYGCTGPG-LEGCPTNGPKIPS (comprising partial Domain 1-partial Domain 2-Domain 3-Domain 4). In certain aspects, the Ev3 may have one, two, three, or more modifications.

In some aspects, the Ev3 hinge is encoded by a nucleotide sequence with at least 80%, such as at least 81, 82, 83, 84, 85, 86, 87, 88, 89, 90, 91, 92, 93, 94, 95, 96, 97, 98, or 99% sequence identity to SEQ ID NO:1. In certain aspects, the Ev3 hinge is encoded by a nucleotide sequence of SEQ ID NO:1.

In certain aspects, the extracellular domain of the CAR comprises an antigen-binding domain selected from the group consisting of F(ab')2, Fab', Fab, Fv, and scFv. In some aspects, the antigen-binding domain comprises a scFv. In specific aspects, the scFv is further defined as a humanized scFv. In some aspects, the humanized scFv is a scFv according to the embodiments.

In some aspects, the antigen binding region of the CAR binds one or more tumor associated antigens. In certain aspects, the one or more tumor associated antigens are selected from the group consisting of CD19, CD319 (CS1), ROR1, CD20, carcinoembryonic antigen, alphafetoprotein, CA-125, MUC-1, epithelial tumor antigen, melanoma-associated antigen, mutated p53, mutated ras, HER2/Neu, ERBB2, folate binding protein, HIV-1 envelope glycoprotein gp120, HIV-1 envelope glycoprotein gp41, GD2, CD5, CD123, CD23, CD30, CD56, c-Met, mesothelin, GD3, HERV-K, IL-11Ralpha, kappa chain, lambda chain, CSPG4, ERBB2, WT-1, TRAIL/DR4, VEGFR2, CD33, CLL-1 and CD99. In particular aspects, the one or more tumor-associated antigens are CD19, CD319, CD123, CD5, ROR1, mesothelin, CD33, CLL-1, and/or CD99. In some aspects, the scFv does not comprise an EGFR binding domain.

In certain aspects, the at least one signaling domain comprises CD3ξ, CD28, OX40/CD134, 4-1BB/CD137, FcεRIγ, ICOS/CD278, ILRB/CD122, IL-2RG/CD132, DAP12, CD70, CD40, or a combination thereof. In particular aspects, the at least one signaling domain comprises DAP12. In some aspects, the CAR comprises IL-15. In one specific aspects, the CAR comprises CD3ζ, CD28, DAP12, and IL-15.

In some aspects, the CAR further comprises a suicide gene. In particular aspects, the suicide gene is inducible caspase 9.

In one embodiment, there are provided isolated antigen-specific humanized single chain variable fragments (scFvs) comprising a light chain variable region ($V_L$) and a heavy chain variable region ($V_H$), wherein the scFv is:

(a) CD19-specific and wherein the $V_L$ comprises an amino acid sequence of SEQ ID NO: 7 and the $V_H$ comprises an amino acid sequence of SEQ ID NO:8;

(b) CD123-specific and wherein the $V_L$ comprises an amino acid sequence of SEQ ID NO: 13 and the $V_H$ comprises an amino acid sequence of SEQ ID NO:14;

(c) mesothelin-specific and wherein the $V_L$ comprises an amino acid sequence of SEQ ID NO: 19 and the $V_H$ comprises an amino acid sequence of SEQ ID NO:20;

(d) ROR1-specific and wherein the $V_L$ comprises an amino acid sequence of SEQ ID NO: 25 and the $V_H$ comprises an amino acid sequence of SEQ ID NO:26;

(e) CD5-specific and wherein the $V_L$ comprises an amino acid sequence of SEQ ID NO: 31 and the $V_H$ comprises an amino acid sequence of SEQ ID NO:32;

(f) CLL-1-specific and wherein the $V_L$ comprises an amino acid sequence of SEQ ID NO: 59 and the $V_H$ comprises an amino acid sequence of SEQ ID NO:60;

(g) CD99-specific and wherein the $V_L$ comprises an amino acid sequence of SEQ ID NO: 63 and the $V_H$ comprises an amino acid sequence of SEQ ID NO:64 or (h) a sequence with 90% sequence identity to framework regions of any one of (a)-(g).

In some aspects, the scFv sequences comprise 91, 92, 93, 94, 95, 96, 97, 98, or 99% sequence identity to the framework regions of SEQ ID NOs: 6, 12, 18, 24, or 30 and 100% sequence identity to the CDRs of said sequences. In certain aspects, the CDRs of said sequences may have one, two, or three modifications.

In some aspects, the scFv is CD19-specific and wherein the $V_L$ comprises an amino acid sequence of SEQ ID NO:7 and the $V_H$ comprises an amino acid sequence of SEQ ID NO: 8. In one specific aspect, the CD19-specific scFv comprises an amino acid sequence of SEQ ID NO:6. In certain aspects, the scFv is CD123-specific and wherein the $V_L$ comprises an amino acid sequence of SEQ ID NO:13 and the $V_H$ comprises an amino acid sequence of SEQ ID NO: 14. In particular aspects, the CD123-specific scFv comprises an amino acid sequence of SEQ ID NO:12. In some aspects, the scFv is mesothelin-specific and wherein the $V_L$ comprises an amino acid sequence of SEQ ID NO:19 and the $V_H$ comprises an amino acid sequence of SEQ ID NO:20. In specific aspects, the mesothelin-specific scFv comprises an amino acid sequence of SEQ ID NO:18. In some aspects, the scFv is ROR1-specific and wherein the $V_L$ comprises an amino acid sequence of SEQ ID NO:25 and the $V_H$ comprises an amino acid sequence of SEQ ID NO:26. In specific aspects, the ROR1-specific comprises an amino acid sequence of SEQ ID NO:24. In some asepcts, the scFv is CD5-specific and wherein the $V_L$ comprises an amino acid sequence of SEQ ID NO:31 and the $V_H$ comprises an amino acid sequence of SEQ ID NO:32. In certain aspects, the CD5-specific comprises an amino acid sequence of SEQ ID NO:30.

In some aspects, the scFv comprises an amino acid sequence with at least 95%, such as at least 96, 97, 98, or 99% sequence identity to framework regions an amino acid sequence of SEQ ID NO:6, 12, 18, 24, or 30.

Further provided herein are isolated polynucleotides encoding the isolated scFvs of the above embodiments. In some aspects, the polynucleotide comprises SEQ ID NO:3, 9, 15, 21, or 27. In other aspects, the polynucleotide comprises a sequence with at least 90, 91, 92, 93, 94, 95, 96, 97, 98, or 99% sequence identity to SEQ ID NO:3, 9, 15, 21, or 27.

Also provided herein are expression vectors comprising isolated nucleotides of the embodiments. In some aspects, the vector is further defined as a viral vector.

Further provided herein are isolated nucleic acids comprising a nucleotide sequence encoding the CAR according to any one of the present embodiments.

Also provided herein are host cells engineered to express a CAR comprising a humanized scFv of the present embodiments and/or a truncated EGFRvIII (Ev3) in the hinge region of said CAR. In some aspects, the CAR is according to any one of the present embodiments. In some aspects, DNA encoding the CAR is integrated into the genome of the cell.

In some aspects, the host cell is further defined as a CAR immune cell. In particular aspects, the immune cell is a T cell, peripheral blood lymphocyte, NK cell, invariant NK cell, NKT cell, or stem cell. In specific aspects, the immune cell is a T cell or a NK cell. In some aspects, the stem cell is a mesenchymal stem cell (MSC) or an induced pluripotent stem (iPS) cell. In certain aspects, the immune cell is derived from an iPS cell. In some aspects, the T cell is a $CD8^+$ T cell, $CD4^+$ T cell, or gamma-delta T cell. In certain aspects, the T cell is a cytotoxic T lymphocyte (CTL). In some aspects, the immune cell is allogeneic or autologous. In some aspects, the immune cell is isolated from peripheral blood, cord blood, or bone marrow. In certain aspects, the immune cell is isolated from cord blood. In particular aspects, the cord blood is pooled from 2 or more individual cord blood units.

Further provided herein are pharmaceutical compositions comprising a population of immune cells according to any of the present embodiments. Also provided herein are compositions comprising a population of immune cells of any one of present embodiments for use in the treatment of an immune-related disorder.

In another embodiment, there is provided a method of treating an immune-related disorder in a subject comprising administering an effective amount of CAR immune cells of any one of the present embodiments, such as comprising a humanized scFv and/or a Ev3 hinge.

In some aspects of the above embodiments, the immune-related disorder is a cancer, autoimmune disorder, graft versus host disease, allograft rejection, or inflammatory condition. In certain aspects, the immune-related disorder is an inflammatory condition and the immune cells have essentially no expression of glucocorticoid receptor. In particular aspects, the immune-related disorder is a cancer. In some aspects, the immune cells are autologous or allogeneic. In some aspects, the cancer is a solid cancer or a hematologic malignancy.

In additional aspects, the method further comprises administering at least a second therapeutic agent. In some aspects, the at least a second therapeutic agent comprises chemotherapy, immunotherapy, surgery, radiotherapy, or biotherapy. In certain aspects, the immune cells and/or the at least a second therapeutic agent are administered intravenously, intraperitoneally, intratrachcally, intratumorally, intramuscularly, endoscopically, intralesionally, percutaneously, subcutaneously, regionally, or by direct injection or perfusion.

In some aspects, the method further comprises administering an anti-EGFR antibody. In some aspects, the anti-EGFR antibody is a monoclonal antibody. In certain aspects, the anti-EGFR antibody is cetuximab or panitumumab. In some aspects, the anti-EGFR antibody selectively ablates Ev3-CAR immune cells through antibody-dependent cell-mediated cytotoxicity (ADCC). In certain aspects, the anti-EGFR antibody is fused to a detectable tag and/or a cytotoxic agent. In some aspects, the method further comprises imaging the detectable tag, thereby detecting the Ev3-CAR immune cells. In certain aspects, the anti-EGFR antibody is fused to a cytotoxic agent. In some aspects, the cytotoxic agent induces activation of the suicide gene in the Ev3-CAR immune cells. In some aspects, the cytotoxic agent results in the ablation of the Ev3-CAR immune cells.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

(FIG. 1A) The Ev3 stalk serves as an integrative structure to transduce signals from antigen binding, such as by scFv, as well as an "off" switch, such that it can be recognized by clinically accessible antibodies such as cetuximab to ablate CAR-positive immune cells. (FIG. 1B) As an enhancement over CARs, such as T cell use, DAP12 may be utilized as the signal booster in Ev3-DAP12 CARs to increase the efficacies of CAR functions in NK cells.

FIGS. 2A-2C: (FIG. 2A) Schematic depicting Ev3 as compared to EGFR which comprise the endodomain and the EGF binding domain. (FIG. 2B) Schematic depicting EGFR variants and fragmets. (FIG. 2C) Sequence of Ev3 comprising only extracellular domains.

(FIG. 3F) Construct map for CAR 2.0 using humanized scFv against CD19 which can be replaced with other scFvs.

(FIG. 4A) Ev3 antibody recognizes CAR19.Ev3.CD28.CD3ζ, CAR19.Ev3.DAP12.CD3ζ or humanized CAR19.Ev3.CD3ζ transduced NK cells. (FIG. 4B) In chromium release assays to assess the killing activity of CAR.19 transduced NK cells against CD19$^+$ Raji tumor targets, it was shown that CAR19.Ev3.CD28.DAP12 NK cells are as effective as CAR19.IgG1.CD28.CD3z transduced NK cells in killing CD19$^+$ Raji cells at multiple effector: target ratios.

(FIG. 5A) Schematic depicting platform for humanization of CARs. (FIG. 5B) Monoclonal antibody sequence analysis.

FIGS. 6A-6C: (FIGS. 6A-C) Schematic depicting isotypes, allotypes, and idiotypes of antibodies. Structural determinants of antibodies are pictured to define the elements isolated and used for the analysis and subsequent CDR/framework graftings. 5 major isotypes for human immunoglobulins are further subclassified as indicated (IgG1, 2, 3, 4, IgA1, 2).

FIGS. 7A-7C: (FIG. 7A) Amino acid sequences for hCD19 scFv and mCD19 scFv including $V_L$ and $V_H$. The CDR regions are underlined. (FIG. 7B) BLAST analysis of hCD19 scFv and mCD19 scFv to verify their respective species origins by sequence identities or homologies. (FIG. 3C) Summary of analysis comparing mCD19 scFv vs humanized CD19 scFv.

FIGS. 8A-8D: (FIG. 8A) Schematic depicting 3D structure modeling. (FIGS. 8B-D) 3D Structure modeling of human CD19 variable light chain. Using SWISS-MODEL*, a fully automated protein structure homology-modeler, 3-dimensional models of humanized $V_L$ and $V_H$ domains were generated (anti-CD19 as specific example shown). Structure files were extracted from SAbDab, a structural antibody database, as templates for homology modeling, as well as using PDB structure files which are automatically accessed within SWISS-MODEL.

FIGS. 9A-9C: 3D structure modeling of human CD19 variable heavy chain. For the specific example of hCD19$V_L$ domain, (FIG. 9A) a list was generated in SWISS-MODEL for the best matching (structurally homologous) structure with their scores (GMQE) and matching methods (BLAST or HHblits). (FIGS. 9B-C) The best scoring structure (2fgw) was then aligned with the hCD19$V_L$ domain ("target") as shown in the bottom panel.

FIGS. 10A-10G: (FIG. 10A) Schematic depicting human framework grafting showing identification and isolation of the CDR regions from mouse antibodies (left top), distillation of human framework regions (right panel), and human framework/murine CDR grafting (left bottom). The CDRs and framework regions are gleaned from sequence analysis as described above. (FIG. 10B) Baseline humanization scoring of monoclonal antibody using T20 scoring system (Gao et al., 2013) to enumerate the 'humanness' of particular Ig domains. As controls, $V_L$ and $V_H$ domains were extracted from antibodies which are currently in the market place for scoring and comparisons. The humanness scores for the indicated antibodies (right most columns) are listed for $V_L$ and $V_H$ domains. (FIG. 10C) Early therapeutic antibodies approved for the commercial marketpace are either murine or chimeric antibodies (variable mouse regions+human constant regions), while later approvals tend to be humanized or human antibodies. The humanness scores tend to cluster for antibodies of the same type (murine, chimeric, humanized, or human), with increasing humanness scores correlative to human contents. (FIG. 10D) Humanization scoring of variable heavy chains by year of FDA approval of antibody. The humanness scores tend to cluster for antibodies of the same type (murine, chimeric, humanized, or human), with increasing humanness scores correlative to human contents. Due to the larger sizes of the $V_H$ domains, the humanness scores tend to be lower (compared to $V_L$). (FIG. 10E) Humanization scoring for indicated antibodies. The frequency of anti-therapeutic antibody responses is shown as % and the size of the patient group evaluated is given in brackets. In general, the more human or humanized an antibody, the less immunogenicity is reported in clinical use. (FIG. 10F) Humanization scoring of variable light chain of hCD19-CAR (SEQ ID NO:1) and mCD19-CAR (SEQ ID NO:3). (FIG. 10G) Humanization scoring of variable heavy chain of hCD19-CAR (SEQ ID NO:2) and mCD19-CAR (SEQ ID NO:4)

(FIG. 11A) Schematic of CD19-CAR and hCD19-CAR constructs. (FIG. 11B) Transduction efficiency of CAR. (FIG. 11C) Cytotoxicity of different CAR constructs against K562 cells. (FIG. 11D) Cytotoxicity of different CAR constructs against Raji cells. (FIG. 11E) Cytotoxicity assay for cells with control CD3ζ/IgG1 CAR or humanized CD3ζ/IgG1 CAR against K562 or Raji cells at indicated effector: target ratios.

(FIG. 12A) CD319-CAR NK transduction. (FIG. 12B) Growth curve of NK cells. (FIG. 12C) CD319 expression in cell lines. (FIGS. 12D-F) CD319-CAR NK cytotoxicity assay. (FIG. 12G) Cytotoxicity assay with CD319-CAR NK cells against indicated cell types including K562, MM.1S, and OPM2. (FIGS. 12H-I) CD319-CAR NK cells have an effector phenotype.

DESCRIPTION OF ILLUSTRATIVE EMBODIMENTS

Chimeric antigen receptor (CAR) based cellular immunotherapy has shown significant efficacies in cancer treatment, in particular for treatment of leukemia and lymphoma. Nevertheless, currently available CARs can comprise various design defects. Recent clinical results using CARs to reprogram immune cells for targeted cancer immunotherapy have shown potent anti-tumor cytotoxicity. Since most CAR single chain variable fragment (scFv) modules are derivatives of murine antibodies, human anti-mouse immune-reactivity compromises the efficacy of CARs thus derived.

Thus, in some embodiments, the present disclosure provides a platform technology to engineer humanized CARs (hCARs) against antigens. The antigens may include CD19 (hCD19CAR), CD123 (hCD123CAR), mesothelin (hMesoCAR), ROR1 (hROR1CAR), CD5 (hCD5CAR), CLL-1 (hCLL-1CAR), and/or CD99 (hCD99CAR) as well as other antigens that may be targeted for treatment of a disease, such as cancer or autoimmune disorders. Accordingly, in certain embodiments, the present disclosure further provides humanized CARs and methods of their use in the treatment of cancer.

Figure 2A:
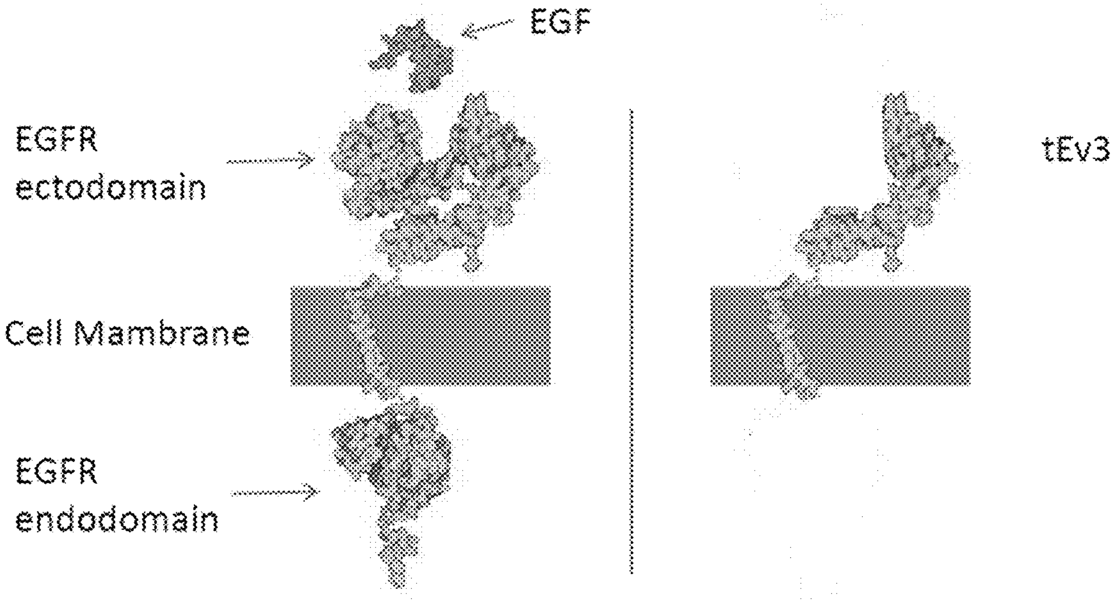

In some embodiments, the present disclosure provides a platform for the humanization of CARs, specifically the scFv of the CAR. The process follows 5 modular components as described in Example 1. These can include sequence analysis, 3D structure modeling, human framework grafting, humanization scoring, and functional analysis. Next, IgG is focused on for the humanization process, making use of extensive sequence variations in the allotypes (i.e., versions of the same isotype) to fine tune for human framework selection (FIG. 2).

In the first step, the antibody sequences for human heavy and light chains can be curated in a local database from sources such as GenBank. The variable domains may be aligned using IgBLAST (a version of BLAST) to delineate allotypes and sort the sequences according to homologies. CDR regions can then be identified and framework sequences are cataloged (FIG. 1A). 3D structure modeling may then be performed, such as using a protein structure homology-modeler (e.g., SWISS-MODEL).

In some embodiments, immune cells are engineered to express CARs with the humanized scFvs provided herein. The immune cells may be NK cells and/or T cells, such as derived from peripheral blood, umbilical cord blood, or marrow-derived infiltrating lymphocytes. The immune cells with a scFv derived from the present humanization platform can mitigate the possibility of human anti-mouse antibody (HAMA) production and associated immune-mediated rejection of genetically modified immune cell therapy products.

Thus, further embodiments provide methods of treating diseases or disorders by administering immune cells which express CARs with humanized scFvs. These methods can be used to lower immune rejection as well as longer persistence of infused cell therapy products. Exemplary subjects that may be treated include cancer patients with $CD19^+$ CLL, ALL and NHL; CD123-positive malignancies including AML, CML. MDS and BPDCN; Mesothelin-positive cancers including cancers of the cervix, endometrium, and the head and neck; ROR1-positive malignancies including CLL (e.g, without prior CAR therapy or those who relapse following CD19-CAR with CD19-negative disease), breast, ovary and pancreatic cancers; CD5-positive malignancies including ALL and NHL as well as thymic cancer.

In further embodiments, the present disclosure provides CARs comprising truncated EGFRvIII wherein the receptor does not comprise the cytoplasmic endodomain or a functional EGF binding domain, referred to herein as Ev3. EGFRvIII is an EGFR variant that is found only in tumor cells, such as glioblastoma multiforme and lung cancer, and not in normal EGFR expressing cells such as epithelial cells. EGFRvIII has a somatic mutation resulting in deletion of exons 2-7 (801 base pair in-frame deletion, 267 amino acid missing compared to wild-type). The deletion of EGFRvIII also covers most of domains 1 and 2 resulting in a truncated domain 1 and truncated domain 2. Further, EGFRvIII has a specific epitope as a result of the fusion between exon 1 and exon 8 creating an extra glycine residue (amino acids 6-273 are replaced by a glycine residue; i.e., LEEKKGNYVVTD), which forms a tumor-specific antigen, such as for glioblastoma multiforme.

Figure 2B:
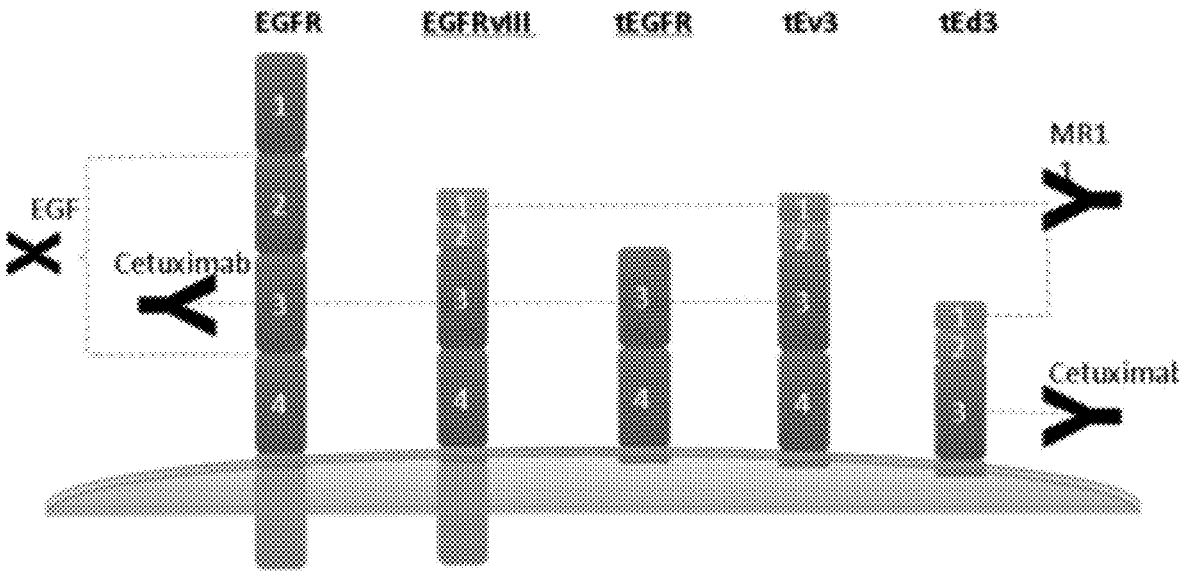
Figure 3A:
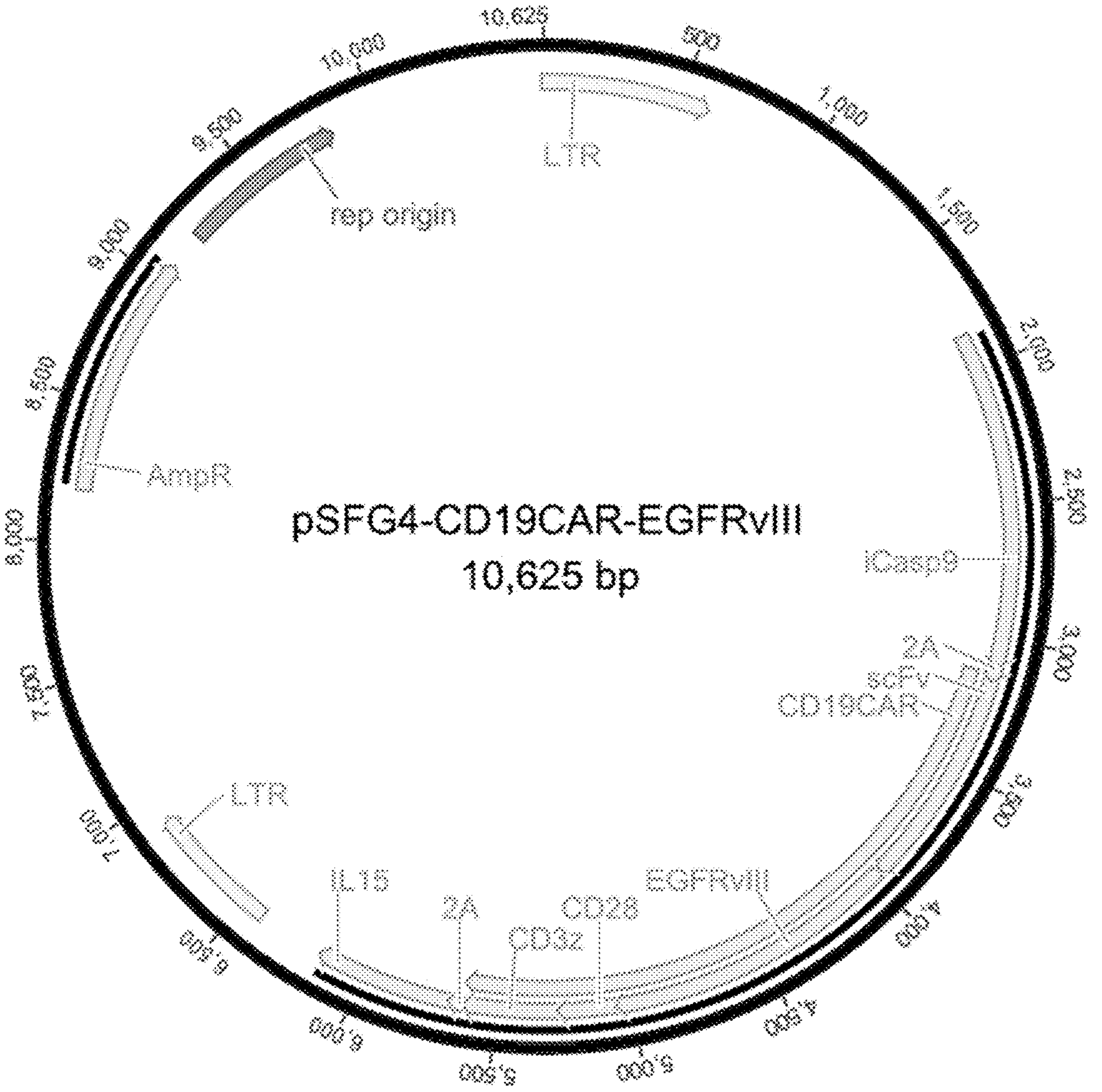
FIGS. 3A-3F: Diagrams for retroviral vectors for the antigens CD19 (FIG. 3A), hCD19 (FIG. 3B), CD123 (FIG. 3C), hCD123 (FIG. 3D), and CD99 (FIG. 3E).
Figure 3B:
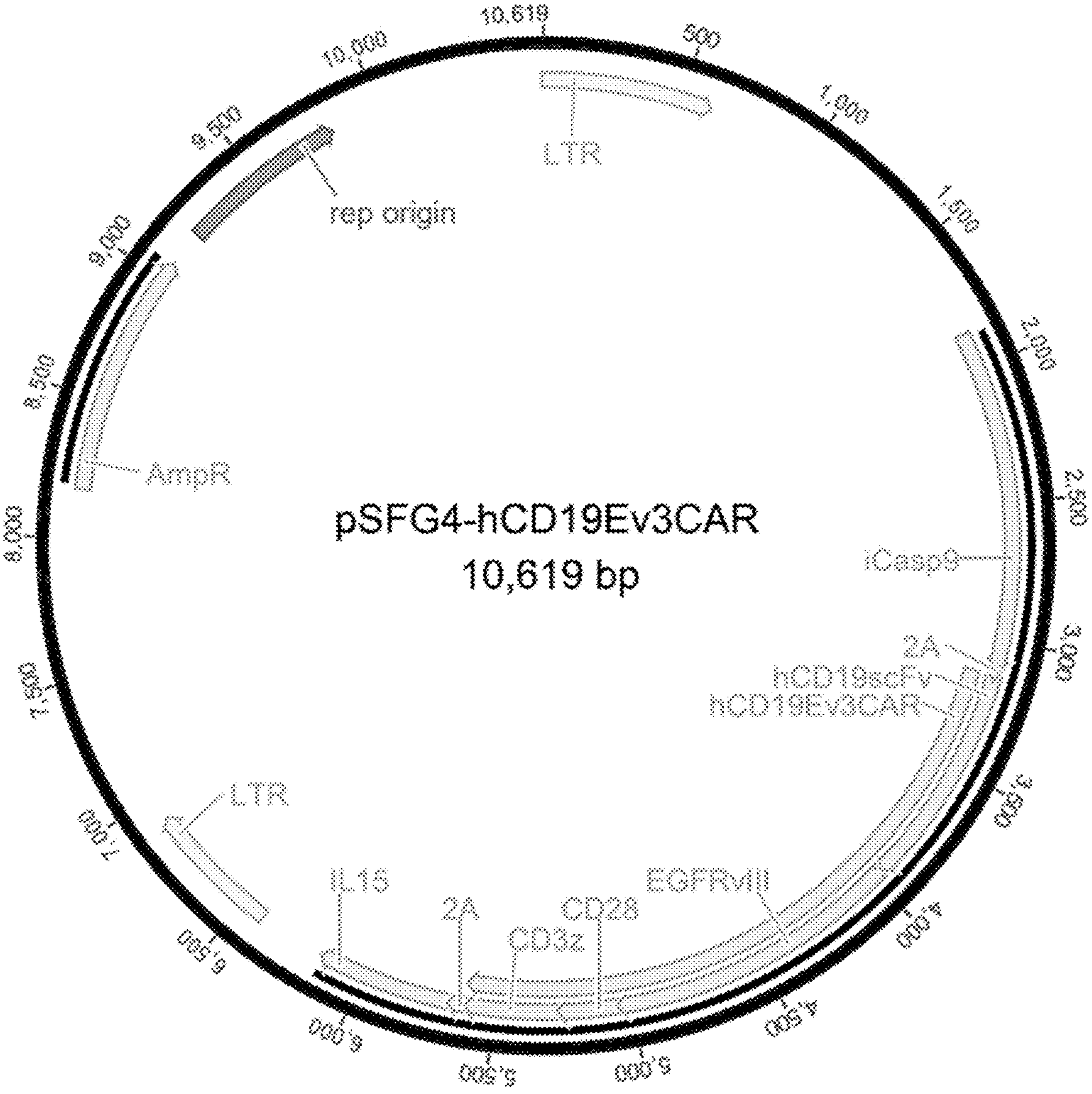
Figure 3C:
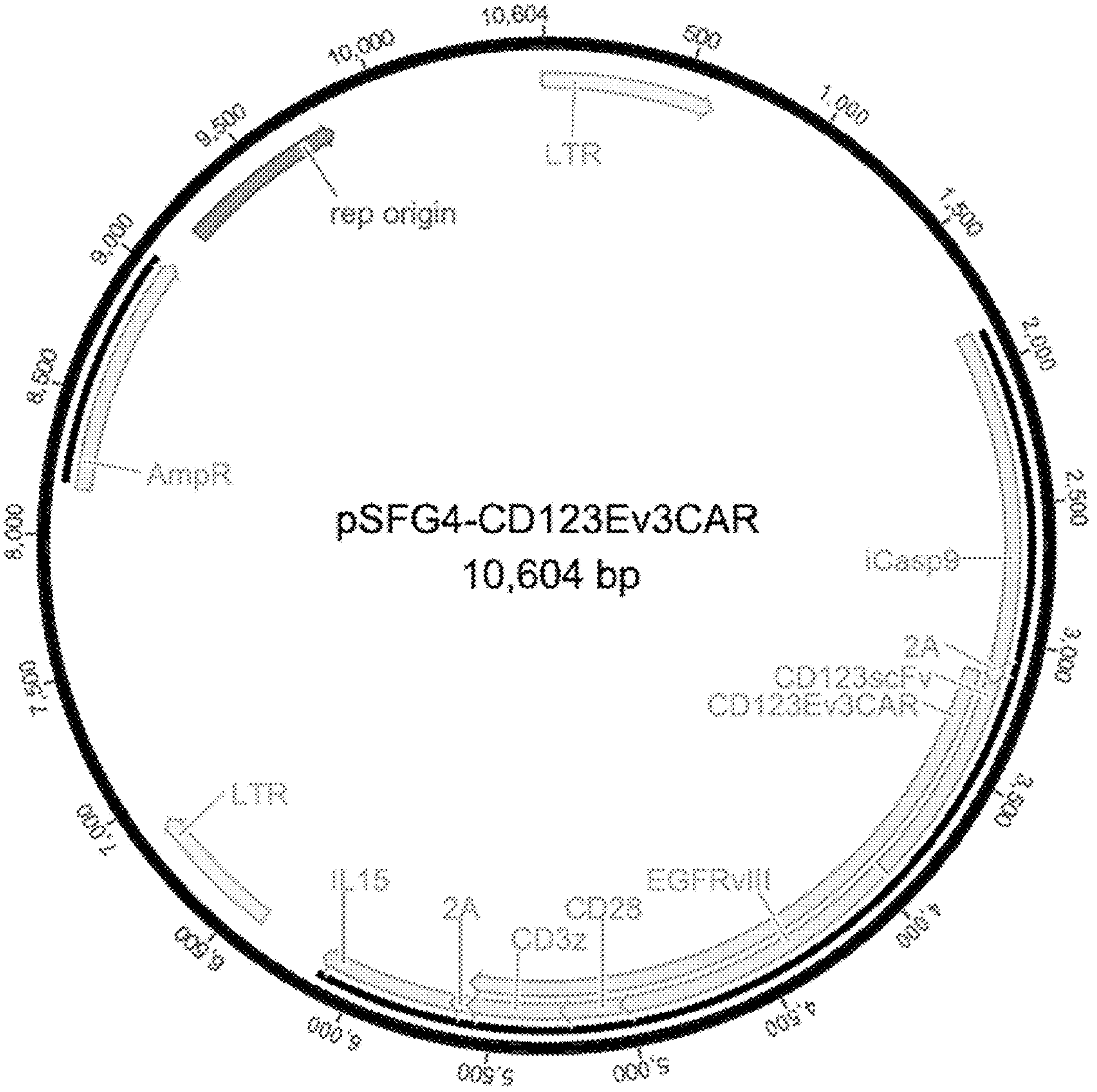
Figure 3D:
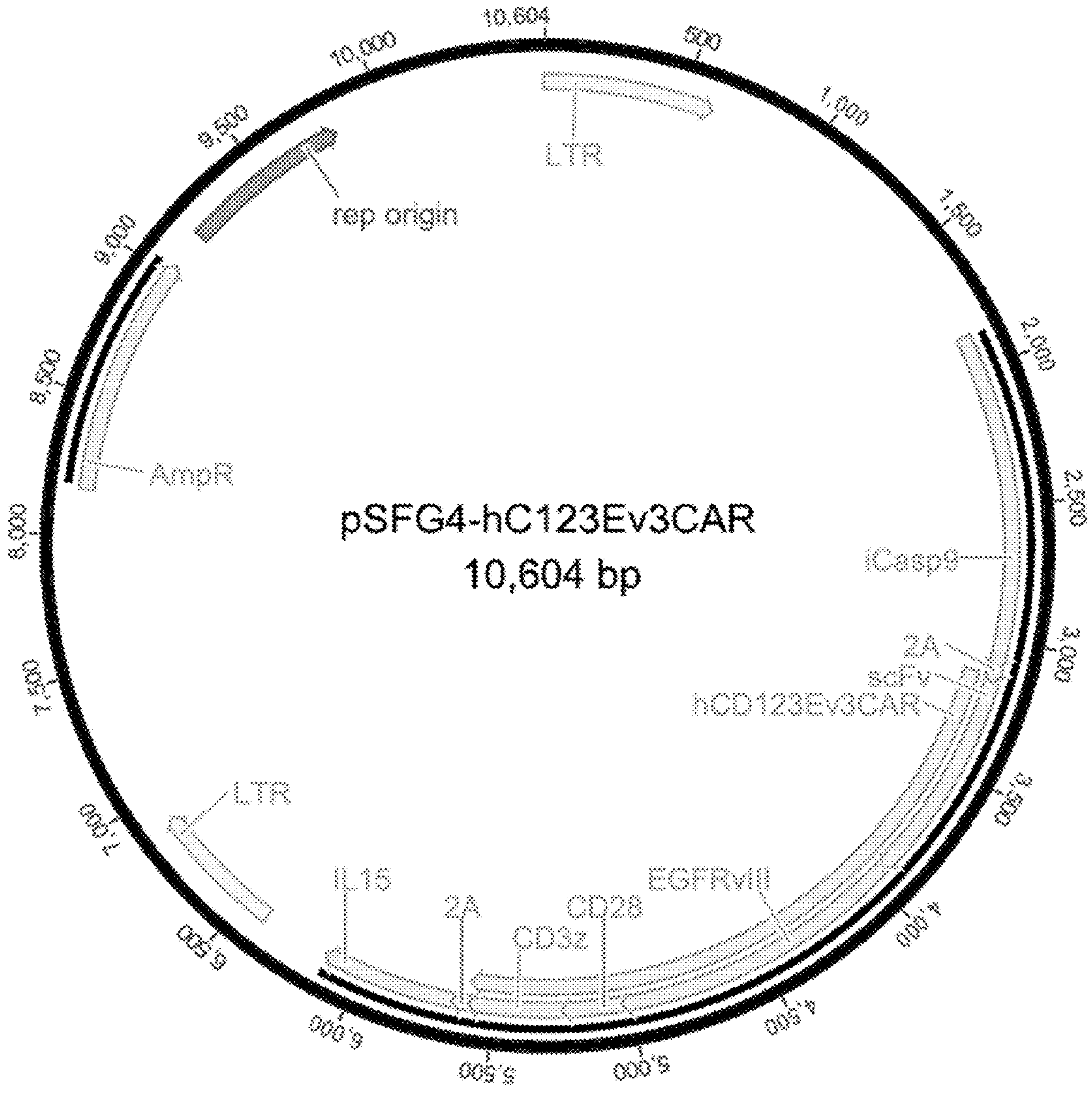
Figure 3E:
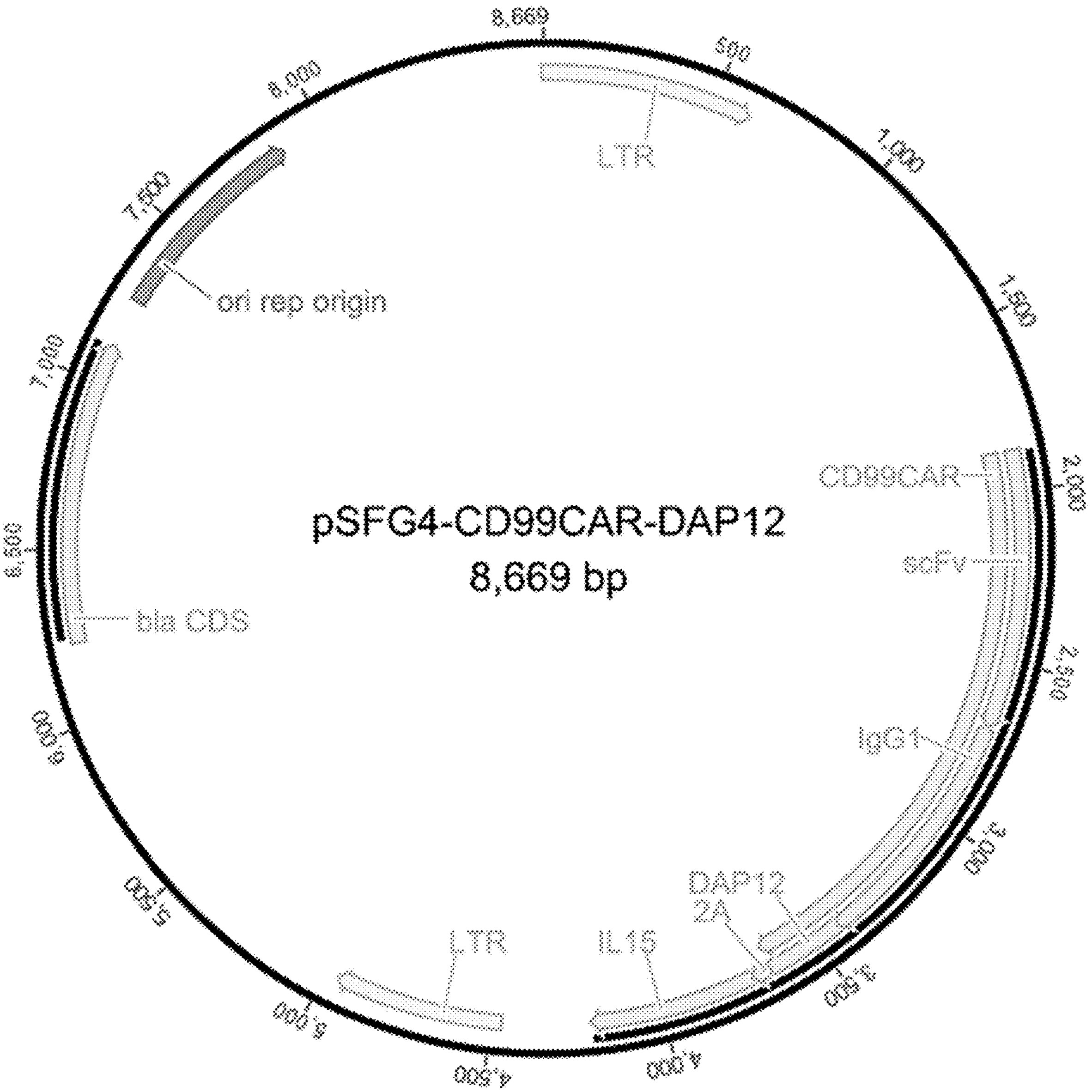
Figure 3F:

The truncated EGFRvIII provided herein, referred to as Ev3 (or tEv3), does not comprise an endodomain or functional EGF binding domain. Specifically, the Ev3 extracellular domain may be used as the CAR stalk, excluding the transmembrane and intracellular signaling domain, for a) signal transduction, b) cellular marker for assigning CAR positivity and, c) antigenic marker for cell ablation via antibody binding (e.g., with Cetuximab). In particular aspects, Ev3 comprises truncated domain 1 (L1), truncated domain 2 (CR1), domain 3 (L2), and domain 4 (CR2) of EGFR (as depicted in FIG. 2B). An exemplary sequence of Ev3 is depicted in FIG. 2C. The present Ev3 may comprise a sequence at least 90%, 95%, 96%, 97%, 98%, or 99% identical to the sequence in FIG. 2C. The cetuximab binding site (in domain 3) is preserved in both Ev3 and wild-type EGFR extracellular domains. In addition to the cetuximab (and/or panitumumab) binding site, the Ev3 epitope presents additional binding sites for other antibodies (e.g., MR1, mAb 806, and DH8.3)

The CARs provided herein can use Ev3 as an integral signal transduction hinge which can double as an antigenic safety switch to covalently link the scFv (i.e., the antigen recognition domain) with the signaling domains (i.e., CD28 and CD3ζ). The Ev3 also allows for detection of CAR immune cells in vitro and in vivo. In addition, the Ev3 hinge ensures retention of genetic loads (CARs).

A further aspect of the Ev3 hinge that is provided herein is its ability to be targeted by antibodies, such as MR1, which as specific to EGFRvIII and will not cross-react with domain III and IV of EGFR which is present in other tissues and cells, such as epithelial cells. Cetuximab and panitumumab are clinically available antibodies and FDA-approved which obviates the need to acquire regulatory approval for idiotypic antibodies for each CAR with different antigenic specificities, such as CD19, CD123, CD5, ROR1, CD33, CD99, and mesothelin. The ability to target Ev3-CARs can be used to detect CAR-positive cells and/or controlled cellular ablation. Cellular ablation may be desired in the event of adverse events, such as cytokine release syndrome, neurotoxicity, and/or on-target or off tumor activity. As Ev3 is not normally expressed in immune cells, such as T or NK cells, enforced expression of Ev3 will specifically mark genetically-modified immune cells. Finally, Ev3 does not comprise a signaling endodomain as the cytoplasmic domain is removed) or an EGF binding domain, CARs comprising Ev3 will not respond or crosstalk with EGF signaling pathways (e.g., AR, ARF4, CAV1, CAV3, CBL, CBLB, CBLC, CD44, CDC25A, CRK, CTNNB1, DCN, EGF, GRB14, Grb2, JAK2, MUC1, NCK1, NCK2, PKCα, PLCG1, PLSCR1, PTPN1, PTPN11, PTPN6, PTPRK, SH2D3A, SH3KBP1, SHC1, SOS1, Src, STAT1, STAT3, STAT3, STAT5A, UBC, WAS) either outside or inside the cell. Accordingly, in particular aspects, none of these gene products are expected to interfere with the Ev3 hinge of Ev3-CARS. In certain aspects, the Ev3 may have one, two, three, or more modifications.

In additional aspects, the function, efficacy, and cellular persistence of Ev3-CAR may be further enhanced by the incorporation of the DNAX-activation protein 12 (DAP12) signaling module, an important element in NK cells activation, in Ev3-DAP12-CARs.

Further embodiments provide methods of introducing the CARs provided herein to immune cells, such as T cell and NK cells. The CAR-T or CAR-NK cells may be administered to a subject, such as for the treatment of cancer. In particular, the cancers that may be treated by the CAR-T or CAR-NK cells include leukemia and lymphoma, such as chronic lymphocytic leukemia (CLL), acute lymphocytic leukemia (ALL), and non-hodgkin lymphoma (NHL).

I. Definitions

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.05%, preferably below 0.01%. Most preferred is a composition in which no amount of the specified component can be detected with standard analytical methods.

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more. The terms "about", "substantially" and "approximately" mean, in general, the stated value plus or minus 5%.

The term "exogenous," when used in relation to a protein, gene, nucleic acid, or polynucleotide in a cell or organism refers to a protein, gene, nucleic acid, or polynucleotide that has been introduced into the cell or organism by artificial or natural means; or in relation to a cell, the term refers to a cell that was isolated and subsequently introduced to other cells or to an organism by artificial or natural means. An exogenous nucleic acid may be from a different organism or cell, or it may be one or more additional copies of a nucleic acid that occurs naturally within the organism or cell. An exogenous cell may be from a different organism, or it may be from the same organism. By way of a non-limiting example, an exogenous nucleic acid is one that is in a chromosomal location different from where it would be in natural cells, or is otherwise flanked by a different nucleic acid sequence than that found in nature.

By "expression construct" or "expression cassette" is meant a nucleic acid molecule that is capable of directing transcription. An expression construct includes, at a minimum, one or more transcriptional control elements (such as promoters, enhancers or a structure functionally equivalent thereof) that direct gene expression in one or more desired cell types, tissues or organs. Additional elements, such as a transcription termination signal, may also be included.

A "vector" or "construct" (sometimes referred to as a gene delivery system or gene transfer "vehicle") refers to a macromolecule or complex of molecules comprising a polynucleotide to be delivered to a host cell, either in vitro or in vivo.

A "plasmid," a common type of a vector, is an extra-chromosomal DNA molecule separate from the chromosomal DNA that is capable of replicating independently of the chromosomal DNA. In certain cases, it is circular and double-stranded.

As used herein, the term "patient" or "subject" refers to a living mammalian organism, such as a human, monkey, cow, sheep, goat, dog, cat, mouse, rat, guinea pig, or transgenic species thereof. In certain embodiments, the patient or subject is a primate. Non-limiting examples of human patients are adults, juveniles, infants and fetuses.

An "immune disorder," "immune-related disorder," or "immune-mediated disorder" refers to a disorder in which the immune response plays a key role in the development or progression of the disease. Immune-mediated disorders include autoimmune disorders, allograft rejection, graft versus host disease and inflammatory and allergic conditions.

An "immune response" is a response of a cell of the immune system, such as a B cell, or a T cell, or innate immune cell to a stimulus. In one embodiment, the response is specific for a particular antigen (an "antigen-specific response").

The terms "tumor-associated antigen," "tumor antigen" and "cancer cell antigen" are used interchangeably herein. In each case, the terms refer to proteins, glycoproteins or carbohydrates that are specifically or preferentially expressed by cancer cells.

An "epitope" is the site on an antigen recognized by an antibody as determined by the specificity of the amino acid sequence. Two antibodies are said to bind to the same epitope if each competitively inhibits (blocks) binding of the other to the antigen as measured in a competitive binding assay. Alternatively, two antibodies have the same epitope if most amino acid mutations in the antigen that reduce or eliminate binding of one antibody reduce or eliminate binding of the other. Two antibodies are said to have overlapping epitopes if each partially inhibits binding of the other to the antigen, and/or if some amino acid mutations that reduce or eliminate binding of one antibody reduce or eliminate binding of the other.

"Treating" or treatment of a disease or condition refers to executing a protocol, which may include administering one or more drugs to a patient, in an effort to alleviate signs or symptoms of the disease. Desirable effects of treatment include decreasing the rate of disease progression, ameliorating or palliating the disease state, and remission or improved prognosis. Alleviation can occur prior to signs or symptoms of the disease or condition appearing, as well as after their appearance. Thus, "treating" or "treatment" may include "preventing" or "prevention" of disease or undesirable condition. In addition, "treating" or "treatment" does not require complete alleviation of signs or symptoms, does not require a cure, and specifically includes protocols that have only a marginal effect on the patient.

The term "effective," as that term is used in the specification and/or claims, means adequate to accomplish a desired, expected, or intended result. "Effective amount," "Therapeutically effective amount" or "pharmaceutically effective amount" when used in the context of treating a patient or subject with a compound means that amount of the compound which, when administered to a subject or patient for treating or preventing a disease, is an amount sufficient to effect such treatment or prevention of the disease.

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease or symptom thereof in a subject or patient that is experiencing or displaying the pathology or symptomatology of the disease.

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

As used herein, the term "framework region(s)" refers to regions of the variable region of an antibody which act as a scaffold for the CDRs. Thus, the framework regions may comprise the non-CDR sequences of the variable light chain and variable heavy chain. The CDRs of a variable region may be determined by methods known in the art, such as by using the Kabat numbering system as described in Sela-Culang et al., 2013; incorporated herein by reference in its entirety. The system described by Kabat (CITE) not only provides an unambiguous residue numbering system applicable to any variable region of an antibody, but also provides precise residue boundaries defining the three CDRs.

As generally used herein "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

"Pharmaceutically acceptable salts" means salts of compounds disclosed herein which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, and Use* (P. H. Stahl & C. G. Wermuth eds., Verlag Helvetica Chimica Acta, 2002).

A "pharmaceutically acceptable carrier," "drug carrier," or simply "carrier" is a pharmaceutically acceptable substance formulated along with the active ingredient medication that is involved in carrying, delivering and/or transporting a chemical agent. Drug carriers may be used to improve the delivery and the effectiveness of drugs, including for example, controlled-release technology to modulate drug bioavailability, decrease drug metabolism, and/or reduce drug toxicity. Some drug carriers may increase the effectiveness of drug delivery to the specific target sites. Examples of carriers include: liposomes, microspheres (e.g., made of poly(lactic-co-glycolic) acid), albumin microspheres, synthetic polymers, nanofibers, protein-DNA complexes, protein conjugates, erythrocytes, virosomes, and dendrimers.

The term "chimeric antigen receptors (CARs)," as used herein, may refer to artificial T cell receptors, chimeric T cell receptors, or chimeric immunoreceptors, for example, and encompass engineered receptors that graft an artificial specificity onto a particular immune effector cell. CARs may be employed to impart the specificity of a monoclonal antibody onto a T cell, thereby allowing a large number of specific T cells to be generated, for example, for use in adoptive cell therapy. In specific embodiments, CARs direct specificity of the cell to a tumor associated antigen, for example. In some embodiments, CARs comprise an intracellular activation domain, a transmembrane domain, and an extracellular domain comprising a tumor associated antigen binding region. In particular aspects, CARs comprise fusions of single-chain variable fragments (scFv) derived from monoclonal antibodies, fused to CD3-zeta a transmembrane domain and endodomain. The specificity of other CAR designs may be derived from ligands of receptors (e.g., peptides) or from pattern-recognition receptors, such as Dectins. In certain cases, the spacing of the antigen-recognition domain can be modified to reduce activation-induced cell death. In certain cases, CARs comprise domains for additional co-stimulatory signaling, such as CD3ζ, FcR, CD27, CD28, CD137, DAP10, and/or OX40. In some cases, molecules can be co-expressed with the CAR, including co-stimulatory molecules, reporter genes for imaging (e.g., for positron emission tomography), gene products that conditionally ablate the T cells upon addition of a pro-drug, homing receptors, chemokines, chemokine receptors, cytokines, and cytokine receptors.

The term "antigen presenting cells (APCs)" refers to a class of cells capable of presenting one or more antigens in the form of peptide-MHC complex recognizable by specific effector cells of the immune system, and thereby inducing an effective cellular immune response against the antigen or antigens being presented. APCs can be intact whole cells such as macrophages, B-cells, endothelial cells, activated T-cells, and dendritic cells; or other molecules, naturally occurring or synthetic, such as purified MHC Class I molecules complexed to β2-microglobulin. While many types of cells may be capable of presenting antigens on their cell surface for T-cell recognition, only dendritic cells have the capacity to present antigens in an efficient amount to activate naive T-cells for cytotoxic T-lymphocyte (CTL) responses.

The term "culturing" refers to the in vitro maintenance, differentiation, and/or propagation of cells in suitable media. By "enriched" is meant a composition comprising cells present in a greater percentage of total cells than is found in the tissues where they are present in an organism.

An "anti-cancer" agent is capable of negatively affecting a cancer cell/tumor in a subject, for example, by promoting killing of cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer.

The term "suicide gene" as used herein is defined as a gene which may be used to selectively target cells for killing.

A polynucleotide or polynucleotide region (or a polypeptide or polypeptide region) has a certain percentage (for example, 80%, 85%, 90%, or 95%) of "sequence identity" or "homology" to another sequence means that, when aligned, that percentage of bases (or amino acids) are the same in comparing the two sequences. This alignment and the percent homology or sequence identity can be determined using software programs known in the art, for example those described in CURRENT PROTOCOLS IN MOLECULAR BIOLOGY (F. M. Ausubel et al., eds., 1987) Supplement 30, section 7.7.18, Table 7.7.1. Preferably, default parameters are used for alignment. A preferred alignment program is BLAST, using default parameters. In particular, preferred programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR.

The term "truncated" as used herein refers to a fragment of a protein or domain of a protein which is shorter than the full length protein or domain of a protein. The truncation may be by removal of 1 or more amino acids, such as 5, 10, 15, 20, 25, 30 or more amino acids of the full length sequence.

II. Immune Cells

Certain embodiments of the present disclosure concern immune cells which express a CAR, such as with Ev3 as the hinge of the CAR and/or a humanized scFv as the antigen binding domain of the cAR. The immune cells may be T cells (e.g., regulatory T cells, $CD4^+$ T cells, $CD8^+$ T cells, or gamma-delta T cells), NK cells, invariant NK cells, NKT cells, stem cells (e.g., mesenchymal stem cells (MSCs) or induced pluripotent stem (iPSC) cells). In some embodiments, the cells are monocytes or granulocytes, e.g., myeloid cells, macrophages, neutrophils, dendritic cells, mast cells, cosinophils, and/or basophils. Also provided herein are methods of producing and engineering the immune cells as well as methods of using and administering the cells for adoptive cell therapy, in which case the cells may be autologous or allogeneic. Thus, the immune cells may be used as immunotherapy, such as to target cancer cells.

The immune cells may be isolated from subjects, particularly human subjects. The immune cells can be obtained from a subject of interest, such as a subject suspected of having a particular disease or condition, a subject suspected of having a predisposition to a particular disease or condition, or a subject who is undergoing therapy for a particular disease or condition. Immune cells can be collected from any location in which they reside in the subject including, but not limited to, blood, cord blood, spleen, thymus, lymph nodes, and bone marrow. The isolated immune cells may be used directly, or they can be stored for a period of time, such as by freezing.

The immune cells may be enriched/purified from any tissue where they reside including, but not limited to, blood (including blood collected by blood banks or cord blood banks), spleen, bone marrow, tissues removed and/or exposed during surgical procedures, and tissues obtained via biopsy procedures. Tissues/organs from which the immune cells are enriched, isolated, and/or purified may be isolated from both living and non-living subjects, wherein the non-living subjects are organ donors. In particular embodiments, the immune cells are isolated from blood, such as peripheral blood or cord blood. In some aspects, immune cells isolated from cord blood have enhanced immunomodulation capacity, such as measured by CD4- or CD8-positive T cell suppression. In specific aspects, the immune cells are isolated from pooled blood, particularly pooled cord blood, for enhanced immunomodulation capacity. The pooled blood may be from 2 or more sources, such as 3, 4, 5, 6, 7, 8, 9, 10 or more sources (e.g., donor subjects).

The population of immune cells can be obtained from a subject in need of therapy or suffering from a disease associated with reduced immune cell activity. Thus, the cells will be autologous to the subject in need of therapy. Alternatively, the population of immune cells can be obtained from a donor, preferably a histocompatibility matched donor. The immune cell population can be harvested from the peripheral blood, cord blood, bone marrow, spleen, or any other organ/tissue in which immune cells reside in said subject or donor. The immune cells can be isolated from a pool of subjects and/or donors, such as from pooled cord blood.

When the population of immune cells is obtained from a donor distinct from the subject, the donor is preferably allogeneic, provided the cells obtained are subject-compatible in that they can be introduced into the subject. Allogeneic donor cells are may or may not be human-leukocyte-antigen (HLA)-compatible.

A. T Cells

In some embodiments, the immune cells are T cells. Several basic approaches for the derivation, activation and expansion of functional anti-tumor effector cells have been described in the last two decades. These include: autologous cells, such as tumor-infiltrating lymphocytes (TILs); T cells activated ex-vivo using autologous DCs, lymphocytes, artificial antigen-presenting cells (APCs) or beads coated with T cell ligands and activating antibodies, or cells isolated by virtue of capturing target cell membrane; allogeneic cells naturally expressing anti-host tumor T cell receptor (TCR); and non-tumor-specific autologous or allogeneic cells genetically reprogrammed or "redirected" to express tumor-reactive TCR or chimeric TCR molecules displaying antibody-like tumor recognition capacity known as "T-bodies". These approaches have given rise to numerous protocols for T cell preparation and immunization which can be used in the methods described herein.

In some embodiments, the T cells are derived from the blood, bone marrow, lymph, umbilical cord, or lymphoid organs. In some aspects, the cells are human cells. The cells typically are primary cells, such as those isolated directly from a subject and/or isolated from a subject and frozen. In some embodiments, the cells include one or more subsets of T cells or other cell types, such as whole T cell populations, $CD4^+$ cells, $CD8^+$ cells, and subpopulations thereof, such as those defined by function, activation state, maturity, potential for differentiation, expansion, recirculation, localization, and/or persistence capacities, antigen-specificity, type of antigen receptor, presence in a particular organ or compartment, marker or cytokine secretion profile, and/or degree of differentiation. With reference to the subject to be treated, the cells may be allogeneic and/or autologous. In some aspects, such as for off-the-shelf technologies, the cells are pluripotent and/or multipotent, such as stem cells, such as induced pluripotent stem cells (iPSCs). In some embodiments, the methods include isolating cells from the subject, preparing, processing, culturing, and/or engineering them, as described herein, and re-introducing them into the same patient, before or after cryopreservation.

Among the sub-types and subpopulations of T cells (e.g., $CD4^+$ and/or $CD8^+$ T cells) are naive T ($T_N$) cells, effector T cells ($T_{EFF}$), memory T cells and sub-types thereof, such as stem cell memory T ($TSC_M$), central memory T ($TC_M$), effector memory T ($T_{EM}$), or terminally differentiated effector memory T cells, tumor-infiltrating lymphocytes (TIL), immature T cells, mature T cells, helper T cells, cytotoxic T cells, mucosa-associated invariant T (MAIT) cells, naturally occurring and adaptive regulatory T (Treg) cells, helper T cells, such as TH1 cells, TH2 cells, TH3 cells, TH17 cells, TH9 cells, TH22 cells, follicular helper T cells, alpha/beta T cells, and delta/gamma T cells.

In some embodiments, one or more of the T cell populations is enriched for or depleted of cells that are positive for a specific marker, such as surface markers, or that are negative for a specific marker. In some cases, such markers are those that are absent or expressed at relatively low levels on certain populations of T cells (e.g., non-memory cells) but are present or expressed at relatively higher levels on certain other populations of T cells (e.g., memory cells).

In some embodiments, T cells are separated from a PBMC sample by negative selection of markers expressed on non-T cells, such as B cells, monocytes, or other white blood cells, such as CD14. In some aspects, a $CD4^+$ or $CD8^+$ selection step is used to separate $CD4^+$ helper and $CD8^+$ cytotoxic T cells. Such $CD4^+$ and $CD8^+$ populations can be further sorted into sub-populations by positive or negative selection for markers expressed or expressed to a relatively higher degree on one or more naive, memory, and/or effector T cell subpopulations.

In some embodiments, $CD8^+$ T cells are further enriched for or depleted of naive, central memory, effector memory, and/or central memory stem cells, such as by positive or negative selection based on surface antigens associated with the respective subpopulation. In some embodiments, enrichment for central memory T ($TC_M$) cells is carried out to increase efficacy, such as to improve long-term survival, expansion, and/or engraftment following administration, which in some aspects is particularly robust in such subpopulations.

In some embodiments, the T cells are autologous T cells. In this method, tumor samples are obtained from patients and a single cell suspension is obtained. The single cell suspension can be obtained in any suitable manner, e.g., mechanically (disaggregating the tumor using, e.g., a gentleMACS™ Dissociator, Miltenyi Biotec, Auburn, Calif.) or enzymatically (e.g., collagenase or DNase). Single-cell suspensions of tumor enzymatic digests are cultured in interleukin-2 (IL-2).

The cultured T cells can be pooled and rapidly expanded. Rapid expansion provides an increase in the number of antigen-specific T-cells of at least about 50-fold (e.g., 50-, 60-, 70-, 80-, 90-, or 100-fold, or greater) over a period of about 10 to about 14 days. More preferably, rapid expansion provides an increase of at least about 200-fold (e.g., 200-, 300-, 400-, 500-, 600-, 700-, 800-, 900-, or greater) over a period of about 10 to about 14 days.

Expansion can be accomplished by any of a number of methods as are known in the art. For example, T cells can be rapidly expanded using non-specific T-cell receptor stimulation in the presence of feeder lymphocytes and either interleukin-2 (IL-2) or interleukin-15 (IL-15), with IL-2 being preferred. The non-specific T-cell receptor stimulus can include around 30 ng/ml of OKT3, a mouse monoclonal anti-CD3 antibody (available from Ortho-McNeil®, Raritan, N.J.). Alternatively, T cells can be rapidly expanded by stimulation of peripheral blood mononuclear cells (PBMC) in vitro with one or more antigens (including antigenic portions thereof, such as epitope(s), or a cell) of the cancer, which can be optionally expressed from a vector, such as an human leukocyte antigen A2 (HLA-A2) binding peptide, in the presence of a T-cell growth factor, such as 300 IU/ml IL-2 or IL-15, with IL-2 being preferred. The in vitro-induced T-cells are rapidly expanded by re-stimulation with the same antigen(s) of the cancer pulsed onto HLA-A2-expressing antigen-presenting cells. Alternatively, the T-cells can be re-stimulated with irradiated, autologous lymphocytes or with irradiated HLA-$A2^+$ allogeneic lymphocytes and IL-2, for example.

The autologous T cells can be modified to express a T cell growth factor that promotes the growth and activation of the autologous T cells. Suitable T cell growth factors include, for example, interleukin (IL)-2, IL-7, IL-15, and IL-12. Suitable methods of modification are known in the art. Sec, for instance, Sambrook et al., *Molecular Cloning: A Laboratory Manual,* 3rd ed., Cold Spring Harbor Press, Cold Spring Harbor, N.Y. 2001; and Ausubel et al., *Current Protocols in Molecular Biology*, Greene Publishing Associates and John Wiley & Sons, NY, 1994. In particular aspects, modified autologous T cells express the T cell growth factor at high levels. T cell growth factor coding sequences, such as that of IL-12, are readily available in the art, as are promoters, the operable linkage of which to a T cell growth factor coding sequence promote high-level expression.

B. NK Cells

In some embodiments, the immune cells are natural killer (NK) cells. NK cells are a subpopulation of lymphocytes that have spontaneous cytotoxicity against a variety of tumor cells, virus-infected cells, and some normal cells in the bone marrow and thymus. NK cells differentiate and mature in the bone marrow, lymph nodes, spleen, tonsils, and thymus. NK cells can be detected by specific surface markers, such as CD16, CD56, and CD8 in humans. NK cells do not express T cell antigen receptors, the pan T marker CD3, or surface immunoglobulin B cell receptors.

In certain embodiments, NK cells are derived from human peripheral blood mononuclear cells (PBMC), unstimulated leukapheresis products (PBSC), human embryonic stem cells (hESCs), induced pluripotent stem cells (iPSCs), bone marrow, or umbilical cord blood by methods well known in the art. Particularly, umbilical CB is used to derive NK cells. In certain aspects, the NK cells are isolated and expanded by the previously described method of ex vivo expansion of NK cells (Spanholtz et al., 2011; Shah et al., 2013). In this method, CB mononuclear cells are isolated by ficoll density gradient centrifugation and cultured in a bioreactor with IL-2 and artificial antigen presenting cells (aAPCs). After 7 days, the cell culture is depleted of any cells expressing CD3 and re-cultured for an additional 7 days. The cells are again CD3-depleted and characterized to determine the percentage of $CD56^+/CD3^-$ cells or NK cells. In other methods, umbilical CB is used to derive NK cells by the isolation of $CD34^+$ cells and differentiation into $CD56^+/CD3^-$ cells by culturing in medium contain SCF, IL-7, IL-15, and IL-2.

C. Stem Cells

In some embodiments, the immune cells of the present disclosure may be stem cells, such as induced pluripotent stem cells (PSCs), mesenchymal stem cells (MSCs), or hematopoietic stem cells (HSCs).

The pluripotent stem cells used herein may be induced pluripotent stem (IPS) cells, commonly abbreviated iPS cells or iPSCs. With the exception of germ cells, any cell can be used as a starting point for iPSCs. For example, cell types could be keratinocytes, fibroblasts, hematopoietic cells, mesenchymal cells, liver cells, or stomach cells. There is no limitation on the degree of cell differentiation or the age of an animal from which cells are collected; even undifferentiated progenitor cells (including somatic stem cells) and finally differentiated mature cells can be used as sources of somatic cells in the methods disclosed herein.

Somatic cells can be reprogrammed to produce iPS cells using methods known to one of skill in the art. Generally, nuclear reprogramming factors are used to produce pluripotent stem cells from a somatic cell. In some embodiments, at least three, or at least four, of Klf4, c-Myc, Oct3/4, Sox2, Nanog, and Lin28 are utilized. In other embodiments, Oct3/4, Sox2, c-Myc and Klf4 are utilized or Oct3/4, Sox2, Nanog, and Lin28.

Once derived, iPSCs can be cultured in a medium sufficient to maintain pluripotency. In certain embodiments, undefined conditions may be used; for example, pluripotent cells may be cultured on fibroblast feeder cells or a medium that has been exposed to fibroblast feeder cells in order to maintain the stem cells in an undifferentiated state. In some embodiments, the cell is cultured in the co-presence of mouse embryonic fibroblasts treated with radiation or an antibiotic to terminate the cell division, as feeder cells. Alternately, pluripotent cells may be cultured and maintained in an essentially undifferentiated state using a defined, feeder-independent culture system, such as a TESR™ medium or E8™/Essential 8™ medium.

III. Enhanced Chimeric Antigen Receptors

A. Truncated EGFRVIII (Ev3)

In certain embodiments, the present disclosure provides enhanced CARs which comprise Ev3 as the hinge or stalk region of the CAR by covalently linking the antigen binding region to the intracellular signaling domain(s). The antigen binding region may comprise a single-chain variable fragment (scFv) derived from an anti-antigen binding domain derived from an antibody, such as a mouse anti-human antibody. The scFv can target any potential antigen. The scFv may be humanized, such as in the framework region of the scFv. In particular aspects, the accessibility to the detection or ablation antibodies (e.g., via ADCC) is maintained.

The Ev3 may comprise or have at least 80% (e.g., 81%, 82%, 83%, 84%, 85%, 86%, 87%, 88%, 89%, 90%, 91%, 92%, 93%, 94%, 95%, 96%, 97%, 98%, 99%, or 100%) sequence identity to SEQ ID NO:2 LEEKKGNYVVTDHGSCVRACGADSYEMEEDGVRKCKKCEGPCRK-VCNGIGIGEFKDSLSINATNIKHFKNCTSISGDLHILPVAFRGDSFTHTPPLDPQELDIL KTVKEITGFLLIQAWPENRTDLHAFENLEIIRGRTKQHGQFSLAVVSLNITSLGLRSLK EISDGDVIISGNKNLCYANTINWKKLFGTSGQKTKIISNRGENSCKATGQ-VCHALCSPEGCWGPEPRDCVSCRNVSRGRECVDKCNLLEGEPREFVENSECIQCHPE CLPQAMNITCTGRGPDNCIQCAHYIDGPHCVKTCPAGVMGENNTLVWKYADAGHV CHLCHPNCTYGCTGPGLEGCPTNGPKIPS (comprising partial Domain 1-partial Domain 2-Domain 3-Domain 4). In certain aspects, the Ev3 may have one, two, three, or more modifications.

In one embodiment, there is provided a CD19Ev3-CAR comprising from N-terminal to C-terminal a scFv derived from a mouse anti-human CD19 monoclonal antibody, a Ev3 hinge including the transmembrane domain, a CD28 endodomain, and a CD35 endodomain. In another embodiment, the CD19Ev3-CAR comprises a humanized CD19 (hCD19) referred to as hCD19Ev3-CAR. The CAR may further comprise DAP12 endodomain, such as between the Ev3 transmembrane domain and the CD3ζ endodomain, such a CD19Ev3DAP12-CAR or hCD19Ev3DAP12-CAR.

In one embodiment, there is provided a CD123Ev3-CAR comprising from N-terminal to C-terminal a scFv derived from a mouse anti-human CD123 monoclonal antibody, a Ev3 hinge including the transmembrane domain, a CD28 endodomain, and a CD35 endodomain. In another embodiment, the CD123Ev3-CAR comprises a humanized CD123

(hCD123) referred to as hCD123Ev3-CAR. The CAR may further comprise DAP12 endodomain, such as between the Ev3 transmembrane domain and the CD32 endodomain, such a CD123Ev3DAP12-CAR or hCD123Ev3DAP12-CAR.

In one embodiment, there is provided a MesoEv3-CAR comprising from N-terminal to C-terminal a scFv derived from a mouse anti-human mesothelin monoclonal antibody, a Ev3 hinge including the transmembrane domain, a CD28 endodomain, and a CD3ζ endodomain. In another embodiment, the MesoEv3-CAR comprises a humanized Meso (hMeso) referred to as hMesoEv3-CAR. The CAR may further comprise DAP12 endodomain, such as between the Ev3 transmembrane domain and the CD3ζ endodomain, such a MesoEv3DAP12-CAR or hMesoEv3DAP12-CAR.

In one embodiment, there is provided a ROR1-Ev3-CAR comprising from N-terminal to C-terminal a scFv derived from a mouse anti-human ROR1 monoclonal antibody, a Ev3 hinge including the transmembrane domain, a CD28 endodomain, and a CD35 endodomain. In another embodiment, the ROR1-Ev3-CAR comprises a humanized ROR1 (hROR1) referred to as hROR1Ev3-CAR. The CAR may further comprise DAP12 endodomain, such as between the Ev3 transmembrane domain and the CD3ζ endodomain, such a ROR1-Ev3DAP12-CAR or hROR1-Ev3DAP12-CAR.

In one embodiment, there is provided a CD5Ev3-CAR comprising from N-terminal to C-terminal a scFv derived from a mouse anti-human CD5 monoclonal antibody, a Ev3 hinge including the transmembrane domain, a CD28 endodomain, and a CD3ζ endodomain. In another embodiment, the CD5Ev3-CAR comprises a humanized CD5 (hCD5) referred to as hCD5Ev3-CAR. The CAR may further comprise DAP12 endodomain, such as between the Ev3 transmembrane domain and the CD3ζ endodomain, such a CD5Ev3DAP12-CAR or hCD5Ev3DAP12-CAR.

In one embodiment, there is provided a CD99Ev3-CAR comprising from N-terminal to C-terminal a scFv derived from a mouse anti-human CD99 monoclonal antibody, a Ev3 hinge including the transmembrane domain, a CD28 endodomain, and a CD3ζ endodomain. In another embodiment, the CD5Ev3-CAR comprises a humanized CD99 (hCD99) referred to as hCD99Ev3-CAR. The CAR may further comprise DAP12 endodomain, such as between the Ev3 transmembrane domain and the CD3ζ endodomain, such a CD99Ev3DAP12-CAR or hCD99Ev3DAP12-CAR.

EGFRvIII is the result of a mutation of exons 2-7 of the EGFR gene which renders the mutant receptor incapable of binding any known ligand as the receptor does not have a complete ligand binding domain. The truncated EGFRVIII, Ev3, of the present disclosure further comprises a deletion of the intracellular domain or endodomain of EGFR vIII. Thus, Ev3 does not comprise a functional EGF binding domain or the intracellular signaling domain of EGFRvIII.

The Ev3 hinge may comprise a nucleotide sequence of SEQ ID NO:1 and/or an amino acid sequence of SEQ ID NO:2. In particular embodiments, the Ev3 hinge has at least 80, 85, 90, 91, 92, 93, 94, 95, 96, 97, 98, 99, or 100% sequence identity with SEQ ID NO: 1 or SEQ ID NO:2. The Ev3 hinge region may comprise a fragment of SEQ ID NO:2 or may comprise additional amino acids on the N-terminal or C-terminal end of the receptor fragment. An exemplary schematic of Ev3 is depicted in FIG. 2.

The inclusion of the truncated EGFRVIII in the hinge region of a CAR allows for retention of genetic cargo load. The Ev3 can also be used a safety switch and/or for detection of the CAR in vitro or in vivo. The integral Ev4 hinge can be recognized by antibodies, such as clinically accessible monoclonal antibodies (e.g., cetuximab), for detection or cellular ablation. In addition, the Ev3 does not comprise a ligand binding domain; thus, there is no endogenous function or crosstalk with other pathways. The Ev3 is also plays a role in the CAR signal transduction and is tumor specific which can minimize side-effects of CAR therapies.

B. Antigens

The CARs provided herein may have any antigenic specificity useful in the treatment of a disease or disorder. The CARs provided herein may comprise more than one antigen, such as two antigens. Exemplary antigens include, but are not limited to, CD19, CD123, mesothelin, CD5, CD47, CLL-1, CD33, CD99, CLL-1, U5snRNP200, CD200, CS1, BAFF-R, ROR-1, CD99, Mesothelin, or BCMA.

The humanization platform provided herein may be used for the development of a humanized CAR for any given antigen. Exemplary antigens with humanized CARs include, but are not limited to, CD19, CD123, mesothelin, CD5, CD47, CLL-1, CD33, CD99, U5snRNP200, CD200, CS1, BAFF-R, ROR-1, or BCMA.

In one embodiment, the encoded light chain variable region comprises one, two, three or all four framework regions of the human PH0879 germline sequence. The encoded heavy chain variable region of hCD19 may comprise one, two, three or all four framework regions of the human ACD43442 germline sequence.

In one embodiment, the encoded antigen binding domain is a scFv comprising a light chain and a heavy chain of an amino acid sequence of SEQ ID NO:6, 12, 18, 24, 30, 58 or 61. In one embodiment, the antigen binding domain (e.g., an scFv) comprises: a light chain variable region comprising an amino acid sequence having at least one, two or three modifications (e.g., substitutions) but not more than 10, 20 or 30 modifications (e.g., substitutions) of an amino acid sequence of a light chain variable region provided herein, or a sequence with 90-99% identity with an amino acid sequence of SEQ ID NOs: 7, 13, 19, 25, 31, 59 or 63; and/or a heavy chain variable region comprising an amino acid sequence having at least one, two or three modifications (e.g., substitutions) but not more than 10, 20 or 30 modifications (e.g., substitutions) of an amino acid sequence of a heavy chain variable region of SEQ ID NOs: 8, 14, 20, 26, 32, 60 or 64; or a sequence with 90-99% identity to an amino acid sequence of SEQ ID NOs: 6, 12, 18, 24, 30, 58 or 61.

In some embodiments, a humanized scFv for CD19 is provided herein. The humanized CD19 (hCD19) scFv may have a variable light chain sequence of SEQ ID NO:7 (DIQMTQSPSSLSASVGDRVTITCRASQDISKY-LNWYQQKPGKVPKLLIYHTSRLHS GVPDRFSGSGSGTDFTLTISSLQPED-VATYYCQQGNTLPYTFGQGTKVEIKR) and a variable heavy chain of SEQ ID NO:8 (EVQLVESGG-GLVQPGGSLRLSCAASGVSLPDYGVSWVRQAPGK-GLEWIGVIWGSE TTYYNSALKSKFIISRDNAKNS-LYLQMNSLRAEDTAVYYCARHYYYGGSYAMDY WGQGTLVTVSS). In other aspects, the hCD19 scFv may comprise a $V_L$ with at least 80%, 85%, 90%, 91%, 921%, 93%, 94%, 95%, 96%, 97%, 98%, or 99% sequence identity to SEQ ID NO: 7 and/or a $V_H$ with at least 80%, 85%, 90%, 91%, 921%, 93%, 94%, 95%, 96%, 97%, 98%, or 99% sequence identity to SEQ ID NO:8. The hCD19 scFv may comprise an amino acid sequence with at least 80%, 85%, 90%, 91%, 921%, 93%, 94%, 95%, 96%, 97%, 98%, 99%, or 100% sequence identity to SEQ ID NO:6. The hCD19 scFv may be encoded by a polynucleotide with at least 80%, 85%, 90%, 91%, 921%, 93%, 94%, 95%, 96%, 97%, 98%, 99%, or 100% sequence identity to SEQ ID NO:3. The $V_L$ of the hCD19 scFv may be encoded by a polynucleotide with at least 80%, 85%, 90%, 91%, 921%, 93%, 94%, 95%, 96%, 97%, 98%, 99%, or 100% sequence identity to SEQ ID NO:4. The $V_H$ of the hCD19 scFv may be encoded by a polynucleotide with at least 80%, 85%, 90%, 91%, 921%, 93%, 94%, 95%, 96%, 97%, 98%, 99%, or 100% sequence identity to SEQ ID NO:5.

In some embodiments, a humanized scFv for CD123 is provided herein. The humanized CD123 (hCD123) scFv may have a variable light chain sequence of SEQ ID NO: 13 and a variable heavy chain of SEQ ID NO:14. In other aspects, the hCD123 scFv may comprise a $V_L$ with at least 80%, 85%, 90%, 91%, 92%, 93%, 94%, 95%, 96%, 97%, 98%, or 99% sequence identity to SEQ ID NO: 13 and/or a $V_H$ with at least 80%, 85%, 90%, 91%, 92%, 93%, 94%, 95%, 96%, 97%, 98%, or 99% sequence identity to SEQ ID NO: 14. The hCD123 scFv may comprise an amino acid sequence with at least 80%, 85%, 90%, 91%, 92%, 93%, 94%, 95%, 96%, 97%, 98%, 99%, or 100% sequence identity to SEQ ID NO: 12. The hCD123 scFv may be encoded by a polynucleotide with at least 80%, 85%, 90%, 91%, 92%, 93%, 94%, 95%, 96%, 97%, 98%, 99%, or 100% sequence identity to SEQ ID NO:9. The $V_L$ of the hCD123 scFv may be encoded by a polynucleotide with at least 80%, 85%, 90%, 91%, 92%, 93%, 94%, 95%, 96%, 97%, 98%, 99%, or 100% sequence identity to SEQ ID NO: 10. The $V_H$ of the hCD123 scFv may be encoded by a polynucleotide with at least 80%, 85%, 90%, 91%, 92%, 93%, 94%, 95%, 96%, 97%, 98%, 99%, or 100% sequence identity to SEQ ID NO:11.

In some embodiments, a humanized scFv for mesothelin is provided herein. The humanized mesothelin (hMeso) scFv may have a variable light chain sequence of SEQ ID NO: 19 and a variable heavy chain of SEQ ID NO:20. In other aspects, the hMeso scFv may comprise a $V_L$ with at least 80%, 85%, 90%, 91%, 921%, 93%, 94%, 95%, 96%, 97%, 98%, or 99% sequence identity to SEQ ID NO: 19 and/or a $V_H$ with at least 80%, 85%, 90%, 91%, 921%, 93%, 94%, 95%, 96%, 97%, 98%, or 99% sequence identity to SEQ ID NO:20. The hMeso scFv may comprise an amino acid sequence with at least 80%, 85%, 90%, 91%, 92%, 93%, 94%, 95%, 96%, 97%, 98%, 99%, or 100% sequence identity to SEQ ID NO:18. The hMeso scFv may be encoded by a polynucleotide with at least 80%, 85%, 90%, 91%, 92%, 93%, 94%, 95%, 96%, 97%, 98%, 99%, or 100% sequence identity to SEQ ID NO:15. The $V_L$ of the hMeso scFv may be encoded by a polynucleotide with at least 80%, 85%, 90%, 91%, 92%, 93%, 94%, 95%, 96%, 97%, 98%, 99%, or 100% sequence identity to SEQ ID NO:16. The $V_H$ of the hMeso scFv may be encoded by a polynucleotide with at least 80%, 85%, 90%, 91%, 92%, 93%, 94%, 95%, 96%, 97%, 98%, 99%, or 100% sequence identity to SEQ ID NO: 17.

In some embodiments, a humanized scFv for ROR1 is provided herein. The humanized ROR1 (hROR1) scFv may have a variable light chain sequence of SEQ ID NO: 25 and a variable heavy chain of SEQ ID NO:26. In other aspects, the hROR1 scFv may comprise a $V_L$ with at least 80%, 85%, 90%, 91%, 921%, 93%, 94%, 95%, 96%, 97%, 98%, or 99% sequence identity to SEQ ID NO:25 and/or a $V_H$ with at least 80%, 85%, 90%, 91%, 92%, 93%, 94%, 95%, 96%, 97%, 98%, or 99% sequence identity to SEQ ID NO:26. The hROR1 scFv may comprise an amino acid sequence with at least 80%, 85%, 90%, 91%, 92%, 93%, 94%, 95%, 96%, 97%, 98%, 99%, or 100% sequence identity to SEQ ID NO:24. The hROR1 scFv may be encoded by a polynucleotide with at least 80%, 85%, 90%, 91%, 92%, 93%, 94%, 95%, 96%, 97%, 98%, 99%, or 100% sequence identity to SEQ ID NO:21. The $V_L$ of the hROR1 scFv may be encoded by a polynucleotide with at least 80%, 85%, 90%, 91%, 92%, 93%, 94%, 95%, 96%, 97%, 98%, 99%, or 100% sequence identity to SEQ ID NO:22. The $V_H$ of the hROR1 scFv may be encoded by a polynucleotide with at least 80%, 85%, 90%, 91%, 92%, 93%, 94%, 95%, 96%, 97%, 98%, 99%, or 100% sequence identity to SEQ ID NO:23.

In some embodiments, a humanized scFv for CD5 is provided herein. The humanized CD5 (hCD5) scFv may have a variable light chain sequence of SEQ ID NO:31 and a variable heavy chain of SEQ ID NO:32. In other aspects, the hCD5 scFv may comprise a $V_L$ with at least 80%, 85%, 90%, 91%, 921%, 93%, 94%, 95%, 96%, 97%, 98%, or 99% sequence identity to SEQ ID NO:31 and/or a $V_H$ with at least 80%, 85%, 90%, 91%, 92%, 93%, 94%, 95%, 96%, 97%, 98%, or 99% sequence identity to SEQ ID NO:32. The hCD5 scFv may comprise an amino acid sequence with at least 80%, 85%, 90%, 91%, 92%, 93%, 94%, 95%, 96%, 97%, 98%, 99%, or 100% sequence identity to SEQ ID NO:30. The hCD5 scFv may be encoded by a polynucleotide with at least 80%, 85%, 90%, 91%, 92%, 93%, 94%, 95%, 96%, 97%, 98%, 99%, or 100% sequence identity to SEQ ID NO:27. The $V_L$ of the hCD5 scFv may be encoded by a polynucleotide with at least 80%, 85%, 90%, 91%, 92%, 93%, 94%, 95%, 96%, 97%, 98%, 99%, or 100% sequence identity to SEQ ID NO:28. The $V_H$ of the hCD5 scFv may be encoded by a polynucleotide with at least 80%, 85%, 90%, 91%, 92%, 93%, 94%, 95%, 96%, 97%, 98%, 99%, or 100% sequence identity to SEQ ID NO:29.

In some embodiments, a humanized scFv for CD99 is provided herein. The humanized CD99 (hCD99) scFv may have a variable light chain sequence of SEQ ID NO: 63 and a variable heavy chain of SEQ ID NO:64. In other aspects, the hCD99 scFv may comprise a $V_L$ with at least 80%, 85%, 90%, 91%, 921%, 93%, 94%, 95%, 96%, 97%, 98%, or 99% sequence identity to SEQ ID NO:63 and/or a $V_H$ with at least 80%, 85%, 90%, 91%, 92%, 93%, 94%, 95%, 96%, 97%, 98%, or 99% sequence identity to SEQ ID NO:64. The hCD99 scFv may comprise an amino acid sequence with at least 80%, 85%, 90%, 91%, 92%, 93%, 94%, 95%, 96%, 97%, 98%, 99%, or 100% sequence identity to SEQ ID NO:61. The hCD99 scFv may be encoded by a polynucleotide with at least 80%, 85%, 90%, 91%, 92%, 93%, 94%, 95%, 96%, 97%, 98%, 99%, or 100% sequence identity to SEQ ID NO:61.

In some embodiments, a humanized scFv for CD99 is provided herein. The humanized CD99 (hCD99) scFv may have a variable light chain sequence of SEQ ID NO: 59 and a variable heavy chain of SEQ ID NO:60. In other aspects, the hCD99 scFv may comprise a $V_L$ with at least 80%, 85%, 90%, 91%, 921%, 93%, 94%, 95%, 96%, 97%, 98%, or 99% sequence identity to SEQ ID NO:59 and/or a $V_H$ with at least 80%, 85%, 90%, 91%, 92%, 93%, 94%, 95%, 96%, 97%, 98%, or 99% sequence identity to SEQ ID NO:60. The hCD99 scFv may comprise an amino acid sequence with at least 80%, 85%, 90%, 91%, 92%, 93%, 94%, 95%, 96%, 97%, 98%, 99%, or 100% sequence identity to SEQ ID NO:58. The hCD99 scFv may be encoded by a polynucleotide with at least 80%, 85%, 90%, 91%, 92%, 93%, 94%, 95%, 96%, 97%, 98%, 99%, or 100% sequence identity to SEQ ID NO:57.

Among the antigens targeted by the genetically engineered antigen receptors are those expressed in the context of a disease, condition, or cell type to be targeted via the adoptive cell therapy. Among the diseases and conditions are proliferative, neoplastic, and malignant diseases and disorders, including cancers and tumors, including hematologic cancers, cancers of the immune system, such as lymphomas, leukemias, and/or myelomas, such as B, T, and myeloid leukemias, lymphomas, and multiple myelomas. In some embodiments, the antigen is selectively expressed or overexpressed on cells of the disease or condition, e.g., the tumor or pathogenic cells, as compared to normal or non-targeted cells or tissues, antigens associated with autoimmune or alloimmune disorders, or pathogen-specific antigens. In other embodiments, the antigen is expressed on normal cells and/or is expressed on the engineered cells.

Any suitable antigen may find use in the present method. Exemplary antigens include, but are not limited to, antigenic molecules from infectious agents, auto-/self-antigens, tumor-/cancer-associated antigens, and tumor neoantigens. In particular aspects, the antigens include NY-ESO, EGFRvIII, Muc-1, Her2, CA-125, WT-1, Mage-A3, Mage-A4, Mage-A10, TRAIL/DR4, and CEA.

Tumor-associated antigens may be derived from prostate, breast, colorectal, lung, pancreatic, renal, mesothelioma, ovarian, or melanoma cancers. Exemplary tumor-associated antigens or tumor cell-derived antigens include MAGE 1, 3, and MAGE 4; PRAME; BAGE; RAGE, Lage (also known as NY ESO 1); SAGE; and HAGE or GAGE. These non-limiting examples of tumor antigens are expressed in a wide range of tumor types such as melanoma, lung carcinoma, sarcoma, and bladder carcinoma. Prostate cancer tumor-associated antigens include, for example, prostate specific membrane antigen (PSMA), prostate-specific antigen (PSA), prostatic acid phosphates, NKX3.1, and six-transmembrane epithelial antigen of the prostate (STEAP).

Other tumor associated antigens include Plu-1, HASH-1, HasH-2, Cripto and Criptin. Additionally, a tumor antigen may be a self peptide hormone, such as whole length gonadotrophin hormone releasing hormone, a short 10 amino acid long peptide, useful in the treatment of many cancers.

Tumor antigens include tumor antigens derived from cancers that are characterized by tumor-associated antigen expression, such as HER-2/neu expression. Tumor-associated antigens of interest include lineage-specific tumor antigens such as the melanocyte-melanoma lineage antigens MART-1/Melan-A, gp100, gp75, mda-7, tyrosinase and tyrosinase-related protein. Illustrative tumor-associated antigens include, but are not limited to, tumor antigens derived from or comprising any one or more of, p53, Ras, c-Myc, cytoplasmic serine/threonine kinases (e.g., A-Raf, B-Raf, and C-Raf, cyclin-dependent kinases), MAGE-A1, MAGE-A2, MAGE-A3, MAGE-A4, MAGE-A6, MAGE-A10, MAGE-A12, MART-1, BAGE, DAM-6, -10, GAGE-1, -2, -8, GAGE-3, -4, -5, -6, -7B, NA88-A, MART-1, MC1R, Gp100, PSA, PSM, Tyrosinase, TRP-1, TRP-2, ART-4, CAMEL, CEA, Cyp-B, hTERT, hTRT, iCE, MUC1, MUC2, Phosphoinositide 3-kinases (PI3Ks), TRK receptors, PRAME, P15, RU1, RU2, SART-1, SART-3, Wilms' tumor antigen (WT1), AFP, -catenin/m, Caspase-8/m, CEA, CDK-4/m, ELF2M, GnT-V, G250, HSP70-2M, HST-2, KIAA0205, MUM-1, MUM-2, MUM-3, Myosin/m, RAGE, SART-2, TRP-2/INT2, 707-AP, Annexin II, CDC27/m, TPI/mbcr-abl, BCR-ABL, interferon regulatory factor 4 (IRF4), ETV6/AML, LDLR/FUT, Pml/RAR, Tumor-associated calcium signal transducer 1 (TACSTD1) TACSTD2, receptor tyrosine kinases (e.g., Epidermal Growth Factor receptor (EGFR) (in particular, EGFRvIII), platelet derived growth factor receptor (PDGFR), vascular endothelial growth factor receptor (VEGFR), cytoplasmic tyrosine kinases (e.g., src-family, syk-ZAP70 family), integrin-linked kinase (ILK), signal transducers and activators of transcription STAT3, STATS, and STATE, hypoxia inducible factors (e.g., HIF-1 and HIF-2), Nuclear Factor-Kappa B (NF-B), Notch receptors (e.g., Notch1-4), c-Met, mammalian targets of rapamycin (mTOR), WNT, extracellular signal-regulated kinases (ERKs), and their regulatory subunits, PMSA, PR-3, MDM2, Mesothelin, renal cell carcinoma-5T4, SM22-alpha, carbonic anhydrases I (CAI) and IX (CAIX) (also known as G250), STEAD, TEL/AML1, GD2, proteinase3, hTERT, sarcoma translocation breakpoints, EphA2, ML-IAP, EpCAM, ERG (TMPRSS2 ETS fusion gene), NA17, PAX3, ALK, androgen receptor, cyclin B1, polysialic acid, MYCN, RhoC, GD3, fucosyl GM1, mesothelian, PSCA, sLe, PLAC1, GM3, BORIS, Tn, GLoboH, NY-BR-1, RGsS, SART3, STn, PAX5, OY-TES1, sperm protein 17, LCK, HMWMAA, AKAP-4, SSX2, XAGE 1, B7H3, legumain, TIE2, Page4, MAD-CT-1, FAP, MAD-CT-2, fos related antigen 1, CBX2, CLDN6, SPANX, TPTE, ACTL8, ANKRD30A, CDKN2A, MAD2L1, CTAG1B, SUNC1, LRRN1 and idiotype.

Antigens may include epitopic regions or epitopic peptides derived from genes mutated in tumor cells or from genes transcribed at different levels in tumor cells compared to normal cells, such as telomerase enzyme, survivin, mesothelin, mutated ras, bcr/abl rearrangement, Her2/neu, mutated or wild-type p53, cytochrome P450 1B1, and abnormally expressed intron sequences such as N-acetylglucosaminyltransferase-V; clonal rearrangements of immunoglobulin genes generating unique idiotypes in myeloma and B-cell lymphomas; tumor antigens that include epitopic regions or epitopic peptides derived from oncoviral processes, such as human papilloma virus proteins E6 and E7; Epstein bar virus protein LMP2; nonmutated oncofetal proteins with a tumor-selective expression, such as carcinoembryonic antigen and alpha-fetoprotein.

In other embodiments, an antigen is obtained or derived from a pathogenic microorganism or from an opportunistic pathogenic microorganism (also called herein an infectious disease microorganism), such as a virus, fungus, parasite, and bacterium. In certain embodiments, antigens derived from such a microorganism include full-length proteins.

Illustrative pathogenic organisms whose antigens are contemplated for use in the method described herein include human immunodeficiency virus (HIV), herpes simplex virus (HSV), respiratory syncytial virus (RSV), cytomegalovirus (CMV), Epstein-Barr virus (EBV), Influenza A, B, and C, vesicular stomatitis virus (VSV), vesicular stomatitis virus (VSV), polyomavirus (e.g., BK virus and JC virus), adenovirus, *Staphylococcus* species including Methicillin-resistant *Staphylococcus aureus* (MRSA), and *Streptococcus* species including *Streptococcus pneumoniae*. As would be understood by the skilled person, proteins derived from these and other pathogenic microorganisms for use as antigen as described herein and nucleotide sequences encoding the proteins may be identified in publications and in public databases such as GENBANK®, Swiss-Prot®, and TrEMBL®.

Antigens derived from human immunodeficiency virus (HIV) include any of the HIV virion structural proteins (e.g., gp120, gp41, p17, p24), protease, reverse transcriptase, or HIV proteins encoded by tat, rev, nef, vif, vpr and vpu.

Antigens derived from herpes simplex virus (e.g., HSV 1 and HSV2) include, but are not limited to, proteins expressed from HSV late genes. The late group of genes predominantly encodes proteins that form the virion particle. Such proteins include the five proteins from (UL) which form the viral capsid: UL6, UL18, UL35, UL38 and the major capsid protein UL19, UL45, and UL27, each of which may be used as an antigen as described herein. Other illustrative HSV proteins contemplated for use as antigens herein include the ICP27 (H1, H2), glycoprotein B (gB) and glycoprotein D (gD) proteins. The HSV genome comprises at least 74 genes, each encoding a protein that could potentially be used as an antigen.

Antigens derived from cytomegalovirus (CMV) include CMV structural proteins, viral antigens expressed during the immediate early and early phases of virus replication, glycoproteins I and III, capsid protein, coat protein, lower matrix protein pp65 (ppUL83), p52 (ppUL44), IE1 and 1E2 (UL123 and UL122), protein products from the cluster of genes from UL128-UL150 (Rykman, et al., 2006), envelope glycoprotein B (gB), gH, gN, and pp150. As would be understood by the skilled person, CMV proteins for use as antigens described herein may be identified in public databases such as GenBank®, Swiss-Prot®, and TrEMBL®.

Antigens derived from Epstein-Ban virus (EBV) that are contemplated for use in certain embodiments include EBV lytic proteins gp350 and gp110, EBV proteins produced during latent cycle infection including Epstein-Ban nuclear antigen (EBNA)-1, EBNA-2, EBNA-3A, EBNA-3B, EBNA-3C, EBNA-leader protein (EBNA-LP) and latent membrane proteins (LMP)-1, LMP-2A and LMP-2B.

Antigens derived from respiratory syncytial virus (RSV) that are contemplated for use herein include any of the eleven proteins encoded by the RSV genome, or antigenic fragments thereof: NS 1, NS2, N (nucleocapsid protein), M (Matrix protein) SH, G and F (viral coat proteins), M2 (second matrix protein), M2-1 (elongation factor), M2-2 (transcription regulation), RNA polymerase, and phosphoprotein P.

Antigens derived from Vesicular stomatitis virus (VSV) that are contemplated for use include any one of the five major proteins encoded by the VSV genome, and antigenic fragments thereof: large protein (L), glycoprotein (G), nucleoprotein (N), phosphoprotein (P), and matrix protein (M).

Antigens derived from an influenza virus that are contemplated for use in certain embodiments include hemagglutinin (HA), neuraminidase (NA), nucleoprotein (NP), matrix proteins M1 and M2, NS1, NS2 (NEP), PA, PB1, PB1-F2, and PB2.

Exemplary viral antigens also include, but are not limited to, adenovirus polypeptides, alphavirus polypeptides, calicivirus polypeptides (e.g., a calicivirus capsid antigen), coronavirus polypeptides, distemper virus polypeptides, Ebola virus polypeptides, enterovirus polypeptides, flavivirus polypeptides, hepatitis virus (AE) polypeptides (a hepatitis B core or surface antigen, a hepatitis C virus E1 or E2 glycoproteins, core, or non-structural proteins), herpesvirus polypeptides (including a herpes simplex virus or varicella zoster virus glycoprotein), infectious peritonitis virus polypeptides, leukemia virus polypeptides, Marburg virus polypeptides, orthomyxovirus polypeptides, papilloma virus polypeptides, parainfluenza virus polypeptides (e.g., the hemagglutinin and neuraminidase polypeptides), paramyxovirus polypeptides, parvovirus polypeptides, pestivirus polypeptides, picorna virus polypeptides (e.g., a poliovirus capsid polypeptide), pox virus polypeptides (e.g., a vaccinia virus polypeptide), rabies virus polypeptides (e.g., a rabies virus glycoprotein G), reovirus polypeptides, retrovirus polypeptides, and rotavirus polypeptides.

In certain embodiments, the antigen may be bacterial antigens. In certain embodiments, a bacterial antigen of interest may be a secreted polypeptide. In other certain embodiments, bacterial antigens include antigens that have a portion or portions of the polypeptide exposed on the outer cell surface of the bacteria.

Antigens derived from *Staphylococcus* species including Methicillin-resistant *Staphylococcus aureus* (MRSA) that are contemplated for use include virulence regulators, such as the Agr system, Sar and Sac, the Arl system, Sar homologues (Rot, MgrA, SarS, SarR, SarT, SarU, SarV, SarX, SarZ and TcaR), the Srr system and TRAP. Other *Staphylococcus* proteins that may serve as antigens include Clp proteins, HtrA, MsrR, aconitase, CcpA, SvrA, Msa, CfvA and CfvB (see, e.g., *Staphylococcus*: Molecular Genetics, 2008 Caister Academic Press, Ed. Jodi Lindsay). The genomes for two species of *Staphylococcus aureus* (N315 and Mu50) have been sequenced and are publicly available, for example at PATRIC (PATRIC: The VBI PathoSystems Resource Integration Center, Snyder et al., 2007). As would be understood by the skilled person, *Staphylococcus* proteins for use as antigens may also be identified in other public databases such as GenBank®, Swiss-Prot®, and TrEMBL®.

Antigens derived from *Streptococcus pneumoniae* that are contemplated for use in certain embodiments described herein include pneumolysin, PspA, choline-binding protein A (CbpA), NanA, NanB, SpnHL, PavA, LytA, Pht, and pilin proteins (RrgA; RrgB; RrgC). Antigenic proteins of *Streptococcus pneumoniae* are also known in the art and may be used as an antigen in some embodiments. The complete genome sequence of a virulent strain of *Streptococcus pneumoniae* has been sequenced and, as would be understood by the skilled person, *S. pneumoniae* proteins for use herein may also be identified in other public databases such as GenBank®, Swiss-Prot®, and TrEMBL®. Proteins of particular interest for antigens according to the present disclosure include virulence factors and proteins predicted to be exposed at the surface of the pneumococci.

Examples of bacterial antigens that may be used as antigens include, but are not limited to, *Actinomyces* polypeptides, *Bacillus* polypeptides, *Bacteroides* polypeptides, *Bordetella* polypeptides, *Bartonella* polypeptides, *Borrelia* polypeptides (e.g., *B. burgdorferi* OspA), *Brucella* polypeptides, *Campylobacter* polypeptides, *Capnocytophaga* polypeptides, *Chlamydia* polypeptides, *Corynebacterium* polypeptides, *Coxiella* polypeptides, *Dermatophilus* polypeptides, *Enterococcus* polypeptides, *Ehrlichia* polypeptides, *Escherichia* polypeptides, *Francisella* polypeptides, *Fusobacterium* polypeptides, *Haemobartonella* polypeptides, *Haemophilus* polypeptides (e.g., *H. influenzae* type b outer membrane protein), *Helicobacter* polypeptides, *Klebsiella* polypeptides, L-form bacteria polypeptides, *Leptospira* polypeptides, *Listeria* polypeptides, Mycobacteria polypeptides, *Mycoplasma* polypeptides, *Neisseria* polypeptides, *Neorickettsia* polypeptides, *Nocardia* polypeptides, *Pasteurella* polypeptides, *Peptococcus* polypeptides, *Peptostreptococcus* polypeptides, Pneumococcus polypeptides (i.e., *S. pneumoniae* polypeptides) (see description herein), *Proteus* polypeptides, *Pseudomonas* polypeptides, *Rickettsia* polypeptides, *Rochalimaea* polypeptides, *Salmonella* polypeptides, *Shigella* polypeptides, *Staphylococcus* polypeptides, group A *streptococcus* polypeptides (e.g., *S. pyogenes* M proteins), group B *streptococcus* (*S. agalactiae*) polypeptides, *Treponema* polypeptides, and *Yersinia* polypeptides (e.g., *Y pestis* F1 and V antigens).

Examples of fungal antigens include, but are not limited to, *Absidia* polypeptides, *Acremonium* polypeptides, *Alternaria* polypeptides, *Aspergillus* polypeptides, *Basidiobolus* polypeptides, *Bipolaris* polypeptides, *Blastomyces* polypeptides, *Candida* polypeptides, *Coccidioides* polypeptides, *Conidiobolus* polypeptides, *Cryptococcus* polypeptides, Curvalaria polypeptides, *Epidermophyton* polypeptides, *Exophiala* polypeptides, *Geotrichum* polypeptides, *Histoplasma* polypeptides, *Madurella* polypeptides, *Malassezia* polypeptides, *Microsporum* polypeptides, *Moniliella* polypeptides, *Mortierella* polypeptides, *Mucor* polypeptides, *Paecilomyces* polypeptides, *Penicillium* polypeptides, *Phialemonium* polypeptides, *Phialophora* polypeptides, *Prototheca* polypeptides, *Pseudallescheria* polypeptides, *Pseudomicrodochium* polypeptides, *Pythium* polypeptides, *Rhinosporidium* polypeptides, *Rhizopus* polypeptides, *Scolecobasidium* polypeptides, *Sporothrix* polypeptides, *Stemphylium* polypeptides, *Trichophyton* polypeptides, *Trichosporon* polypeptides, and *Xylohypha* polypeptides.

Examples of protozoan parasite antigens include, but are not limited to, *Babesia* polypeptides, *Balantidium* polypeptides, *Besnoitia* polypeptides, *Cryptosporidium* polypeptides, *Eimeria* polypeptides, *Encephalitozoon* polypeptides, *Entamoeba* polypeptides, *Giardia* polypeptides, Hammondia polypeptides, *Hepatozoon* polypeptides, *Isospora* polypeptides, *Leishmania* polypeptides, Microsporidia polypeptides, *Neospora* polypeptides, *Nosema* polypeptides, Pentatrichomonas polypeptides, *Plasmodium* polypeptides. Examples of helminth parasite antigens include, but are not limited to, Acanthocheilonema polypeptides, Aelurostrongylus polypeptides, *Ancylostoma* polypeptides, *Angiostrongylus* polypeptides, *Ascaris* polypeptides, *Brugia* polypeptides, *Bunostomum* polypeptides, *Capillaria* polypeptides, *Chabertia* polypeptides, *Cooperia* polypeptides, Crenosoma polypeptides, Dictyocaulus polypeptides, *Dioctophyme* polypeptides, Dipetalonema polypeptides, *Diphyllobothrium* polypeptides, Diplydium polypeptides, *Dirofilaria* polypeptides, *Dracunculus* polypeptides, *Enterobius* polypeptides, Filaroides polypeptides, *Haemonchus* polypeptides, Lagochilascaris polypeptides, *Loa* polypeptides, *Mansonella* polypeptides, Muellerius polypeptides, *Nanophyetus* polypeptides, *Necator* polypeptides, Nematodirus polypeptides, *Oesophagostomum* polypeptides, *Onchocerca* polypeptides, *Opisthorchis* polypeptides, *Ostertagia* polypeptides, Parafilaria polypeptides, *Paragonimus* polypeptides, *Parascaris* polypeptides, Physaloptera polypeptides, Protostrongylus polypeptides, *Setaria* polypeptides, Spirocerca polypeptides *Spirometra* polypeptides, Stephanofilaria polypeptides, *Strongyloides* polypeptides, *Strongylus* polypeptides, *Thelazia* polypeptides, Toxascaris polypeptides, *Toxocara* polypeptides, *Trichinella* polypeptides, *Trichostrongylus* polypeptides, *Trichuris* polypeptides, *Uncinaria* polypeptides, and *Wuchereria* polypeptides. (e.g., *P. falciparum* circumsporozoite (PfCSP)), sporozoite surface protein 2 (PfSSP2), carboxyl terminus of liver state antigen 1 (PfLSA1 c-term), and exported protein 1 (PfExp-1), *Pneumocystis* polypeptides, *Sarcocystis* polypeptides, *Schistosoma* polypeptides, *Theileria* polypeptides, *Toxoplasma* polypeptides, and *Trypanosoma* polypeptides.

Examples of ectoparasite antigens include, but are not limited to, polypeptides (including antigens as well as allergens) from fleas; ticks, including hard ticks and soft ticks; flies, such as midges, mosquitoes, sand flies, black flies, horse flies, horn flies, deer flies, tsetse flies, stable flies, myiasis-causing flies and biting gnats; ants; spiders, lice; mites; and true bugs, such as bed bugs and kissing bugs.

C. Chimeric Antigen Receptors

In some embodiments, the CAR contains an extracellular antigen-recognition domain that specifically binds to an antigen. In some embodiments, the antigen is a protein expressed on the surface of cells. In some embodiments, the CAR is a TCR-like CAR and the antigen is a processed peptide antigen, such as a peptide antigen of an intracellular protein, which, like a TCR, is recognized on the cell surface in the context of a major histocompatibility complex (MHC) molecule.

In some embodiments, the chimeric antigen receptor comprises: a) an intracellular signaling domain, b) a hinge and transmembrane domain, such as a Ev3 hinge, and c) an extracellular domain comprising an antigen binding region.

In some embodiments, the engineered antigen receptors include chimeric antigen receptors (CARs), including activating or stimulatory CARs, costimulatory CARs (see WO2014/055668), and/or inhibitory CARs (iCARs, see Fedorov et al., 2013). The CARs generally include an extracellular antigen (or ligand) binding domain linked to one or more intracellular signaling components, in some aspects via linkers and/or transmembrane domain(s). Such molecules typically mimic or approximate a signal through a natural antigen receptor, a signal through such a receptor in combination with a costimulatory receptor, and/or a signal through a costimulatory receptor alone.

Certain embodiments of the present disclosure concern the use of nucleic acids, including nucleic acids encoding an antigen-specific CAR polypeptide, including a CAR that has been humanized to reduce immunogenicity (hCAR), comprising an intracellular signaling domain, a transmembrane domain, and an extracellular domain comprising one or more signaling motifs. In certain embodiments, the CAR may recognize an epitope comprising the shared space between one or more antigens. In certain embodiments, the binding region can comprise complementary determining regions of a monoclonal antibody, variable regions of a monoclonal antibody, and/or antigen binding fragments thereof. In another embodiment, that specificity is derived from a peptide (e.g., cytokine) that binds to a receptor.

It is contemplated that the human CAR nucleic acids may be human genes used to enhance cellular immunotherapy for human patients. In a specific embodiment, the invention includes a full-length CAR cDNA or coding region. The antigen binding regions or domain can comprise a fragment of the $V_H$ and $V_L$ chains of a single-chain variable fragment (scFv) derived from a particular human monoclonal antibody, such as those described in U.S. Pat. No. 7,109,304, incorporated herein by reference. The fragment can also be any number of different antigen binding domains of a human antigen-specific antibody. In a more specific embodiment, the fragment is an antigen-specific scFv encoded by a sequence that is optimized for human codon usage for expression in human cells.

The arrangement could be multimeric, such as a diabody or multimers. The multimers are most likely formed by cross pairing of the variable portion of the light and heavy chains into a diabody. The hinge portion of the construct can have multiple alternatives from being totally deleted, to having the first cysteine maintained, to a proline rather than a serine substitution, to being truncated up to the first cysteine. The Fc portion can be deleted. Any protein that is stable and/or dimerizes can serve this purpose. One could use just one of the Fc domains, e.g., either the CH2 or CH3 domain from human immunoglobulin. One could also use the hinge, CH2 and CH3 region of a human immunoglobulin that has been modified to improve dimerization. One could also use just the hinge portion of an immunoglobulin. One could also use portions of CD8alpha.

In some embodiments, the CAR nucleic acid comprises a sequence encoding other costimulatory receptors, such as a transmembrane domain and a modified CD28 intracellular signaling domain. Other costimulatory receptors include, but are not limited to one or more of CD28, CD27, OX-40 (CD134), DAP10, DAP12, and 4-1BB (CD137). In addition to a primary signal initiated by CD3ζ, an additional signal provided by a human costimulatory receptor inserted in a human CAR is important for full activation of NK cells and could help improve in vivo persistence and the therapeutic success of the adoptive immunotherapy. The CAR may express one or more cytokines, such as IL-15. The inclusion of one or more cytokines may promote in vivo persistence. In some aspects, the CAR comprises the antigen binding domain, such as humanized scFv, CD3ζ, DAP12, and IL-15, optionally in combination with the Ev3 hinge.

In some embodiments, CAR is constructed with a specificity for a particular antigen (or marker or ligand), such as an antigen expressed in a particular cell type to be targeted by adoptive therapy, e.g., a cancer marker, and/or an antigen intended to induce a dampening response, such as an antigen expressed on a normal or non-diseased cell type. Thus, the CAR typically includes in its extracellular portion one or more antigen binding molecules, such as one or more antigen-binding fragment, domain, or portion, or one or more antibody variable domains, and/or antibody molecules. In some embodiments, the CAR includes an antigen-binding portion or portions of an antibody molecule, such as a single-chain antibody fragment (scFv) derived from the variable heavy ($V_H$) and variable light ($V_L$) chains of a monoclonal antibody (mAb).

In certain embodiments of the chimeric antigen receptor, the antigen-specific portion of the receptor (which may be referred to as an extracellular domain comprising an antigen binding region) comprises a tumor associated antigen or a pathogen-specific antigen binding domain. Antigens include carbohydrate antigens recognized by pattern-recognition receptors, such as Dectin-1. A tumor associated antigen may be of any kind so long as it is expressed on the cell surface of tumor cells. Exemplary embodiments of tumor associated antigens include CD19, CD319 (CS1), CD20, carcinoembryonic antigen, alphafetoprotein, CA-125, MUC-1, CD56, EGFR, c-Met, AKT, Her2, Her3, epithelial tumor antigen, melanoma-associated antigen, mutated p53, mutated ras, and so forth. In certain embodiments, the CAR may be co-expressed with a cytokine to improve persistence when there is a low amount of tumor-associated antigen. For example, CAR may be co-expressed with IL-15.

The sequence of the open reading frame encoding the chimeric receptor can be obtained from a genomic DNA source, a cDNA source, or can be synthesized (e.g., via PCR), or combinations thereof. Depending upon the size of the genomic DNA and the number of introns, it may be desirable to use cDNA or a combination thereof as it is found that introns stabilize the mRNA. Also, it may be further advantageous to use endogenous or exogenous non-coding regions to stabilize the mRNA.

It is contemplated that the chimeric construct can be introduced into immune cells as naked DNA or in a suitable vector. Methods of stably transfecting cells by electroporation using naked DNA are known in the art. Naked DNA generally refers to the DNA encoding a chimeric receptor contained in a plasmid expression vector in proper orientation for expression.

Alternatively, a viral vector (e.g., a retroviral vector, adenoviral vector, adeno-associated viral vector, or lentiviral vector) can be used to introduce the chimeric construct into immune cells. Suitable vectors for use in accordance with the method of the present disclosure are non-replicating in the immune cells. A large number of vectors are known that are based on viruses, where the copy number of the virus maintained in the cell is low enough to maintain the viability of the cell, such as, for example, vectors based on HIV, SV40, EBV, HSV, or BPV.

In some aspects, the antigen-specific binding, or recognition component is linked to one or more transmembrane and intracellular signaling domains. In some embodiments, the CAR includes a transmembrane domain fused to the extracellular domain of the CAR. In one embodiment, the transmembrane domain that naturally is associated with one of the domains in the CAR is used. In some instances, the transmembrane domain is selected or modified by amino acid substitution to avoid binding of such domains to the transmembrane domains of the same or different surface membrane proteins to minimize interactions with other members of the receptor complex.

The transmembrane domain in some embodiments is derived either from a natural or from a synthetic source. Where the source is natural, the domain in some aspects is derived from any membrane-bound or transmembrane protein. Transmembrane regions include those derived from (i.e. comprise at least the transmembrane region(s) of) the alpha, beta or zeta chain of the T-cell receptor, CD28, CD3 zeta, CD3 epsilon, CD3 gamma, CD3 delta, CD45, CD4, CD5, CD8, CD9, CD 16, CD22, CD33, CD37, CD64, CD80, CD86, CD 134, CD137, CD154, ICOS/CD278, GITR/CD357, NKG2D, and DAP molecules. Alternatively the transmembrane domain in some embodiments is synthetic. In some aspects, the synthetic transmembrane domain comprises predominantly hydrophobic residues such as leucine and valine. In some aspects, a triplet of phenylalanine, tryptophan and valine will be found at each end of a synthetic transmembrane domain.

In certain embodiments, the platform technologies disclosed herein to genetically modify immune cells, such as NK cells, comprise (i) non-viral gene transfer using an electroporation device (e.g., a nucleofector), (ii) CARs that signal through endodomains (e.g., CD28/CD3-ζ, CD137/CD3-ζ, or other combinations), (iii) CARs with variable lengths of extracellular domains connecting the antigen-recognition domain to the cell surface, and, in some cases, (iv) artificial antigen presenting cells (aAPC) derived from K562 to be able to robustly and numerically expand $CAR^+$ immune cells (Singh et al., 2008; Singh et al., 2011).

In some embodiments, the CAR may be retrovirally tranduced in the cells. The retroviral vector may be the pSFG4 vector. The retroviral transfer vector pSFG4 comprises a backbone based on pUC19 plasmid (large fragment [2.63 kb] in between HindIII and EcoRI restriction enzyme sites) carrying viral components from Moloney Murine Leukemia Virus (MoMLV) including 5' LTR, psi packaging sequence, and 3' LTR. LTRs are long terminal repeats found on either side of a retroviral provirus, and in the case of transfer vector, brackets the genetic cargo of interest (in our case mainly CARs and associated genetic components). The psi packaging sequence, which is a target site for packaging by nucleocapsid, is also incorporated in cis, sandwiched between the 5' LTR and the CAR coding sequence. Thus, the basic structure of the pSFG4 transfer vector can be outlined as such: pUC19 sequence-5' LTR-psi packaging sequence-genetic cargo of interest-3' LTR-pUC19 sequence.

D. Antigen-Presenting Cells

Antigen-presenting cells, which include macrophages, B lymphocytes, and dendritic cells, are distinguished by their expression of a particular MHC molecule. APCs internalize antigen and re-express a part of that antigen, together with the MHC molecule on their outer cell membrane. The major histocompatibility complex (MHC) is a large genetic complex with multiple loci. The MHC loci encode two major classes of MHC membrane molecules, referred to as class I and class II MHCs. T helper lymphocytes generally recognize antigen associated with MHC class II molecules, and T cytotoxic lymphocytes recognize antigen associated with MHC class I molecules. In humans the MHC is referred to as the HLA complex and in mice the H-2 complex.

aAPC systems may comprise at least one exogenous assisting molecule. Any suitable number and combination of assisting molecules may be employed. The assisting molecule may be selected from assisting molecules such as co-stimulatory molecules and adhesion molecules. Exemplary co-stimulatory molecules include CD86, CD64 (FcγRI), 41BB ligand, and IL-21. Adhesion molecules may include carbohydrate-binding glycoproteins such as selectins, transmembrane binding glycoproteins such as integrins, calcium-dependent proteins such as cadherins, and single-pass transmembrane immunoglobulin (Ig) superfamily proteins, such as intercellular adhesion molecules (ICAMs), which promote, for example, cell-to-cell or cell-to-matrix contact. Exemplary adhesion molecules include LFA-3 and ICAMs, such as ICAM-1. Techniques, methods, and reagents useful for selection, cloning, preparation, and expression of exemplary assisting molecules, including co-stimulatory molecules and adhesion molecules.

IV. Methods of Use

In some embodiments, the present disclosure provides methods for immunotherapy comprising administering an effective amount of the immune cells expressing CARs (e.g., CARs with Ev3 hinge and/or humanized scFv) of the present disclosure. In one embodiments, a medical disease or disorder is treated by transfer of an immune cell population that elicits an immune response. In certain embodiments of the present disclosure, cancer or infection is treated by transfer of an immune cell population that elicits an immune response. Provided herein are methods for treating or delaying progression of cancer in an individual comprising administering to the individual an effective amount an antigen-specific cell therapy. The present methods may be applied for the treatment of immune disorders, solid cancers, hematologic cancers, and viral infections.

In particular embodiments, methods are provided for treating cancer patients by administering immune cells, such as NK cells and/or T cells, expressing CARs provided herein with an antigen-binding domain specific for the antigen expressed by said cancer. For example, a subject with chronic lymphocytic leukemia (CLL), B cell acute lymphoblastic leukemia (ALL), or non-Hodgkin lymphoma (NHL) may be treated with CD19-Ev3-CAR immune cells to ablate CD19-positive cells such as cancer stem cells. In other aspects, the subject may have acute myeloid leukemia (AML), chronic myeloid leukemia (CML), myelodysplastic syndromes (MDS), or plasmacytoid dendritic cell leukemia (PDCL) and be treated with CD123-Ev3-CAR immune cells. In additional aspects, the subject may have T-cell leukemia and lymphoma and be treated with CD5-Ev3-CAR immune cells. Subjects with CLL, breast cancer, pancreatic cancer or lung cancer may be treated with ROR1-Ev3-CAR immune cells. Patients with cervical, endometrial or ovarian cancer may be treated with Meso-Ev3-CAR immune cells.

Subjects with multiple myeloma (MM) or other CD319-expressig cancers may be treated with CD319-CAR immune cells. In some aspects, patient with amyloidosis are treated by ablating CD319-positive cells, such as cancer stem cells. In some aspects, patients with monoclonal gammopathy of unknown significance (MGUS) or smoldering myeloma are treated with CD319-CAR immune cells. Subjects with CD319-positive cells in autoimmune disorders, such as rheumatoid arthritis, SLE, or autoimmune hemolytic anemia may be treated by immune cells of the present embodiments. In particular aspects, a CD319-expressing cancer is treated by administering immune cells expressing Ev3-CAR with CD319 scFv, CD3ζ, DAP12, and IL-15.

In some embodiments, cells comprising the Ev3 CARs provided herein may be ablated and/or detected by anti-EGFR antibodies. Exemplary anti-EGFR antibodies include, but are not limited to, cetuximab (Erbitux) and panitumumab (Vectibix) as well as biosimilars. Both of these antibodies have been approved by the FDA for treatment of colorectal cancer. In some embodiments, the detection of cells expressing Ev3-CARs comprises the administration of an anti-EGFR antibody with a detectable tag. In other aspects, the ablation of cells expressing Ev3-CARs comprises the administration of an anti-EGFR antibody which induces ADCC. In some aspects, the anti-EGFR antibody may be fused to a pro-drug or cytotoxic agent, such as a toxin.

Tumors for which the present treatment methods are useful include any malignant cell type, such as those found in a solid tumor or a hematological tumor. Exemplary solid tumors can include, but are not limited to, a tumor of an organ selected from the group consisting of pancreas, colon, cecum, stomach, brain, head, neck, ovary, kidney, larynx, sarcoma, lung, bladder, melanoma, prostate, and breast. Exemplary hematological tumors include tumors of the bone marrow, T or B cell malignancies, leukemias, lymphomas, blastomas, myelomas, and the like. Further examples of cancers that may be treated using the methods provided herein include, but are not limited to, lung cancer (including small-cell lung cancer, non-small cell lung cancer, adenocarcinoma of the lung, and squamous carcinoma of the lung), cancer of the peritoneum, gastric or stomach cancer (including gastrointestinal cancer and gastrointestinal stromal cancer), pancreatic cancer, cervical cancer, ovarian cancer, liver cancer, bladder cancer, breast cancer, colon cancer, colorectal cancer, endometrial or uterine carcinoma, salivary gland carcinoma, kidney or renal cancer, prostate cancer, vulval cancer, thyroid cancer, various types of head and neck cancer, and melanoma.

The cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis *coli*; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extramammary paraganglioma, malignant; pheochromocytoma; glomangiosarcoma; malignant melanoma; amelanotic melanoma; superficial spreading melanoma; lentigo malignant melanoma; acral lentiginous melanomas; nodular melanomas; malignant melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; hodgkin's disease; hodgkin's; paragranuloma; malignant lymphoma, small lymphocytic; malignant lymphoma, large cell, diffuse; malignant lymphoma, follicular; mycosis fungoides; other specified non-hodgkin's lymphomas; B-cell lymphoma; low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; Waldenstrom's macroglobulinemia; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; hairy cell leukemia; chronic lymphocytic leukemia (CLL); acute lymphoblastic leukemia (ALL); acute myeloid leukemia (AML); and chronic myeloblastic leukemia.

Particular embodiments concern methods of treatment of leukemia. Leukemia is a cancer of the blood or bone marrow and is characterized by an abnormal proliferation (production by multiplication) of blood cells, usually white blood cells (leukocytes). It is part of the broad group of diseases called hematological neoplasms. Leukemia is a broad term covering a spectrum of diseases. Leukemia is clinically and pathologically split into its acute and chronic forms.

In certain embodiments of the present disclosure, immune cells are delivered to an individual in need thereof, such as an individual that has cancer or an infection. The cells then enhance the individual's immune system to attack the respective cancer or pathogenic cells. In some cases, the individual is provided with one or more doses of the immune cells. In cases where the individual is provided with two or more doses of the immune cells, the duration between the administrations should be sufficient to allow time for propagation in the individual, and in specific embodiments the duration between doses is 1, 2, 3, 4, 5, 6, 7, or more days.

Certain embodiments of the present disclosure provide methods for treating or preventing an immune-mediated disorder. In one embodiment, the subject has an autoimmune disease. Non-limiting examples of autoimmune diseases include: alopecia areata, ankylosing spondylitis, antiphospholipid syndrome, autoimmune Addison's disease, autoimmune diseases of the adrenal gland, autoimmune hemolytic anemia, autoimmune hepatitis, autoimmune oophoritis and orchitis, autoimmune thrombocytopenia, Behcet's disease, bullous pemphigoid, cardiomyopathy, celiac spate-dermatitis, chronic fatigue immune dysfunction syndrome (CFIDS), chronic inflammatory demyelinating polyneuropathy, Churg-Strauss syndrome, cicatrical pemphigoid, CREST syndrome, cold agglutinin disease, Crohn's disease, discoid lupus, essential mixed cryoglobulinemia, fibromyalgia-fibromyositis, glomerulonephritis, Graves' disease, Guillain-Barre, Hashimoto's thyroiditis, idiopathic pulmonary fibrosis, idiopathic thrombocytopenia purpura (ITP), IgA neuropathy, juvenile arthritis, lichen planus, lupus erthematosus, Meniere's disease, mixed connective tissue disease, multiple sclerosis, type 1 or immune-mediated diabetes mellitus, myasthenia gravis, nephrotic syndrome (such as minimal change disease, focal glomerulosclerosis, or mebranous nephropathy), pemphigus vulgaris, pernicious anemia, polyarteritis nodosa, polychondritis, polyglandular syndromes, polymyalgia rheumatica, polymyositis and dermatomyositis, primary agammaglobulinemia, primary biliary cirrhosis, psoriasis, psoriatic arthritis, Raynaud's phenomenon, Reiter's syndrome, Rheumatoid arthritis, sarcoidosis, scleroderma, Sjogren's syndrome, stiff-man syndrome, systemic lupus erythematosus, lupus erythematosus, ulcerative colitis, uveitis, vasculitides (such as polyarteritis nodosa, takayasu arteritis, temporal arteritis/giant cell arteritis, or dermatitis herpetiformis vasculitis), vitiligo, and Wegener's granulomatosis. Thus, some examples of an autoimmune disease that can be treated using the methods disclosed herein include, but are not limited to, multiple sclerosis, rheumatoid arthritis, systemic lupus erythematosis, type I diabetes mellitus, Crohn's disease; ulcerative colitis, myasthenia gravis, glomerulonephritis, ankylosing spondylitis, vasculitis, or psoriasis. The subject can also have an allergic disorder such as Asthma.

In yet another embodiment, the subject is the recipient of a transplanted organ or stem cells and immune cells are used to prevent and/or treat rejection. In particular embodiments, the subject has or is at risk of developing graft versus host disease. GVHD is a possible complication of any transplant that uses or contains stem cells from either a related or an unrelated donor. There are two kinds of GVHD, acute and chronic. Acute GVHD appears within the first three months following transplantation. Signs of acute GVHD include a reddish skin rash on the hands and feet that may spread and become more severe, with peeling or blistering skin. Acute GVHD can also affect the stomach and intestines, in which case cramping, nausea, and diarrhea are present. Yellowing of the skin and eyes (jaundice) indicates that acute GVHD has affected the liver. Chronic GVHD is ranked based on its severity: stage/grade 1 is mild; stage/grade 4 is severe. Chronic GVHD develops three months or later following transplantation. The symptoms of chronic GVHD are similar to those of acute GVHD, but in addition, chronic GVHD may also affect the mucous glands in the eyes, salivary glands in the mouth, and glands that lubricate the stomach lining and intestines. Any of the populations of immune cells disclosed herein can be utilized. Examples of a transplanted organ include a solid organ transplant, such as kidney, liver, skin, pancreas, lung and/or heart, or a cellular transplant such as islets, hepatocytes, myoblasts, bone marrow, or hematopoietic or other stem cells. The transplant can be a composite transplant, such as tissues of the face. Immune cells can be administered prior to transplantation, concurrently with transplantation, or following transplantation. In some embodiments, the immune cells are administered prior to the transplant, such as at least 1 hour, at least 12 hours, at least 1 day, at least 2 days, at least 3 days, at least 4 days, at least 5 days, at least 6 days, at least 1 week, at least 2 weeks, at least 3 weeks, at least 4 weeks, or at least 1 month prior to the transplant. In one specific, non-limiting example, administration of the therapeutically effective amount of immune cells occurs 3-5 days prior to transplantation.

In some embodiments, the subject can be administered nonmyeloablative lymphodepleting chemotherapy prior to the immune cell therapy. The nonmyeloablative lymphodepleting chemotherapy can be any suitable such therapy, which can be administered by any suitable route. The nonmyeloablative lymphodepleting chemotherapy can comprise, for example, the administration of cyclophosphamide and fludarabine, particularly if the cancer is melanoma, which can be metastatic. An exemplary route of administering cyclophosphamide and fludarabine is intravenously. Likewise, any suitable dose of cyclophosphamide and fludarabine can be administered. In particular aspects, around 60 mg/kg of cyclophosphamide is administered for two days after which around 25 mg/$m^2$ fludarabine is administered for five days.

In certain embodiments, a growth factor that promotes the growth and activation of the immune cells is administered to the subject either concomitantly with the immune cells or subsequently to the immune cells. The immune cell growth factor can be any suitable growth factor that promotes the growth and activation of the immune cells. Examples of suitable immune cell growth factors include interleukin (IL)-2, IL-7, IL-15, and IL-12, which can be used alone or in various combinations, such as IL-2 and IL-7, IL-2 and IL-15, IL-7 and IL-15, IL-2, IL-7 and IL-15, IL-12 and IL-7, IL-12 and IL-15, or IL-12 and IL2.

Therapeutically effective amounts of immune cells can be administered by a number of routes, including parenteral administration, for example, intravenous, intraperitoneal, intramuscular, intrasternal, or intraarticular injection, or infusion.

The therapeutically effective amount of immune cells for use in adoptive cell therapy is that amount that achieves a desired effect in a subject being treated. For instance, this can be the amount of immune cells necessary to inhibit advancement, or to cause regression of an autoimmune or alloimmune disease, or which is capable of relieving symptoms caused by an autoimmune disease, such as pain and inflammation. It can be the amount necessary to relieve symptoms associated with inflammation, such as pain, edema and elevated temperature. It can also be the amount necessary to diminish or prevent rejection of a transplanted organ.

The immune cell population can be administered in treatment regimens consistent with the disease, for example a single or a few doses over one to several days to ameliorate a disease state or periodic doses over an extended time to inhibit disease progression and prevent disease recurrence. The precise dose to be employed in the formulation will also depend on the route of administration, and the seriousness of the disease or disorder, and should be decided according to the judgment of the practitioner and each patient's circumstances. The therapeutically effective amount of immune cells will be dependent on the subject being treated, the severity and type of the affliction, and the manner of administration. In some embodiments, doses that could be used in the treatment of human subjects range from at least $3.8\times10^4$, at least $3.8\times10^5$, at least $3.8\times10^6$, at least $3.8\times10^7$, at least $3.8\times10^8$, at least $3.8\times10^9$, or at least $3.8\times10^{10}$ immune cells/$m^2$. In a certain embodiment, the dose used in the treatment of human subjects ranges from about $3.8\times10^9$ to about $3.8\times10^{10}$ immune cells/$m^2$. In additional embodiments, a therapeutically effective amount of immune cells can vary from about $5\times10^6$ cells per kg body weight to about $7.5\times10^8$ cells per kg body weight, such as about $2\times10^7$ cells to about $5\times10^8$ cells per kg body weight, or about $5\times10^7$ cells to about $2\times10^8$ cells per kg body weight. The exact amount of immune cells is readily determined by one of skill in the art based on the age, weight, sex, and physiological condition of the subject. Effective doses can be extrapolated from dose-response curves derived from in vitro or animal model test systems.

The immune cells may be administered in combination with one or more other therapeutic agents for the treatment of the immune-mediated disorder. Combination therapies can include, but are not limited to, one or more antimicrobial agents (for example, antibiotics, anti-viral agents and anti-fungal agents), anti-tumor agents (for example, fluorouracil, methotrexate, paclitaxel, fludarabine, etoposide, doxorubicin, or vincristine), immune-depleting agents (for example, fludarabine, etoposide, doxorubicin, or vincristine), immunosuppressive agents (for example, azathioprine, or glucocorticoids, such as dexamethasone or prednisone), anti-inflammatory agents (for example, glucocorticoids such as hydrocortisone, dexamethasone or prednisone, or non-steroidal anti-inflammatory agents such as acetylsalicylic acid, ibuprofen or naproxen sodium), cytokines (for example, interleukin-10 or transforming growth factor-beta), hormones (for example, estrogen), or a vaccine. In addition, immunosuppressive or tolerogenic agents including but not limited to calcineurin inhibitors (e.g., cyclosporin and tacrolimus); mTOR inhibitors (e.g., Rapamycin); mycophenolate mofetil, antibodies (e.g., recognizing CD3, CD4, CD40, CD154, CD45, IVIG, or B cells); chemotherapeutic agents (e.g., Methotrexate, Treosulfan, Busulfan); irradiation; or chemokines, interleukins or their inhibitors (e.g., BAFF, IL-2, anti-IL-2R, IL-4, JAK kinase inhibitors) can be administered. Such additional pharmaceutical agents can be administered before, during, or after administration of the immune cells, depending on the desired effect. This administration of the cells and the agent can be by the same route or by different routes, and either at the same site or at a different site.

B. Pharmaceutical Compositions

Also provided herein are pharmaceutical compositions and formulations comprising immune cells (e.g., T cells or NK cells) and a pharmaceutically acceptable carrier.

Pharmaceutical compositions and formulations as described herein can be prepared by mixing the active ingredients (such as an antibody or a polypeptide) having the desired degree of purity with one or more optional pharmaceutically acceptable carriers (Remington's Pharmaceutical Sciences 22$^{nd}$ edition, 2012), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn– protein complexes); and/or non-ionic surfactants such as polyethylene glycol (PEG).

C. Combination Therapies

In certain embodiments, the compositions and methods of the present embodiments involve an immune cell population in combination with at least one additional therapy. The additional therapy may be radiation therapy, surgery (e.g., lumpectomy and a mastectomy), chemotherapy, gene therapy, DNA therapy, viral therapy, RNA therapy, immunotherapy, bone marrow transplantation, nanotherapy, monoclonal antibody therapy, or a combination of the foregoing. The additional therapy may be in the form of adjuvant or neoadjuvant therapy.

In some embodiments, the additional therapy is the administration of small molecule enzymatic inhibitor or anti-metastatic agent. In some embodiments, the additional therapy is the administration of side-effect limiting agents (e.g., agents intended to lessen the occurrence and/or severity of side effects of treatment, such as anti-nausea agents, etc.). In some embodiments, the additional therapy is radiation therapy. In some embodiments, the additional therapy is surgery. In some embodiments, the additional therapy is a combination of radiation therapy and surgery. In some embodiments, the additional therapy is gamma irradiation. In some embodiments, the additional therapy is therapy targeting PBK/AKT/mTOR pathway, HSP90 inhibitor, tubulin inhibitor, apoptosis inhibitor, and/or chemopreventative agent. The additional therapy may be one or more of the chemotherapeutic agents known in the art.

An immune cell therapy may be administered before, during, after, or in various combinations relative to an additional cancer therapy, such as immune checkpoint therapy. The administrations may be in intervals ranging from concurrently to minutes to days to weeks. In embodiments where the immune cell therapy is provided to a patient separately from an additional therapeutic agent, one would generally ensure that a significant period of time did not expire between the time of each delivery, such that the two compounds would still be able to exert an advantageously combined effect on the patient. In such instances, it is contemplated that one may provide a patient with the antibody therapy and the anti-cancer therapy within about 12 to 24 or 72 h of each other and, more particularly, within about 6-12 h of each other. In some situations it may be desirable to extend the time period for treatment significantly where several days (2, 3, 4, 5, 6, or 7) to several weeks (1, 2, 3, 4, 5, 6, 7, or 8) lapse between respective administrations.

Various combinations may be employed. For the example below a CAR immune cell therapy is "A" and an anti-cancer therapy is "B":

| | | | | | | | | |
|---|---|---|---|---|---|---|---|---|
| A/B/A | B/A/B | B/B/A | A/A/B | A/B/B | B/A/A | A/B/B/B | B/A/B/B | |
| B/B/B/A | B/B/A/B | A/A/B/B | A/B/A/B | A/B/B/A | B/B/A/A | | | |
| B/A/B/A | B/A/A/B | A/A/A/B | B/A/A/A | A/B/A/A | A/A/B/A | | | |

Administration of any compound or therapy of the present embodiments to a patient will follow general protocols for the administration of such compounds, taking into account the toxicity, if any, of the agents. Therefore, in some embodiments there is a step of monitoring toxicity that is attributable to combination therapy.

1. Chemotherapy

A wide variety of chemotherapeutic agents may be used in accordance with the present embodiments. The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis.

Examples of chemotherapeutic agents include alkylating agents, such as thiotepa and cyclosphosphamide; alkyl sulfonates, such as busulfan, improsulfan, and piposulfan; aziridines, such as benzodopa, carboquone, meturedopa, and uredopa; ethylenimines and methylamelamines, including altretamine, triethylenemelamine, trietylenephosphoramide, triethiylenethiophosphoramide, and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards, such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, and uracil mustard; nitrosureas, such as carmustine, chlorozotocin, fotemustine, lomustine, nimustine, and ranimnustine; antibiotics, such as the enediyne antibiotics (e.g., calicheamicin, especially calicheamicin gammalI and calicheamicin omegaI1); dynemicin, including dynemicin A; bisphosphonates, such as clodronate; an esperamicin; as well as neocarzinostatin chromophore and related chromoprotein enediyne antiobiotic chromophores, aclacinomysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins, such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, and zorubicin; anti-metabolites, such as methotrexate and 5-fluorouracil (5-FU); folic acid analogues, such as denopterin, pteropterin, and trimetrexate; purine analogs, such as fludarabine, 6-mercaptopurine, thiamiprine, and thioguanine; pyrimidine analogs, such as ancitabine, azacitidine, 6-azauridine, carmofur, cytarabine, dideoxyuridine, doxifluridine, enocitabine, and floxuridine; androgens, such as calusterone, dromostanolone propionate, epitiostanol, mepitiostane, and testolactone; anti-adrenals, such as mitotane and trilostane; folic acid replenisher, such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids, such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSKpolysaccharide complex; razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; taxoids, e.g., paclitaxel and docetaxel gemcitabine; 6-thioguanine; mercaptopurine; platinum coordination complexes, such as cisplatin, oxaliplatin, and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluorometlhylornithine (DMFO); retinoids, such as retinoic acid; capecitabine; carboplatin, procarbazine, plicomycin, gemcitabien, navelbine, farnesyl-protein tansferase inhibitors, transplatinum, and pharmaceutically acceptable salts, acids, or derivatives of any of the above.

2. Radiotherapy

Other factors that cause DNA damage and have been used extensively include what are commonly known as γ-rays, X-rays, and/or the directed delivery of radioisotopes to tumor cells. Other forms of DNA damaging factors are also contemplated, such as microwaves, proton beam irradiation, and UV-irradiation. It is most likely that all of these factors affect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

3. Immunotherapy

The skilled artisan will understand that additional immunotherapies may be used in combination or in conjunction with methods of the embodiments. In the context of cancer treatment, immunotherapeutics, generally, rely on the use of immune effector cells and molecules to target and destroy cancer cells. Rituximab (RITUXAN®) is such an example. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve as a targeting agent. Alternatively, the effector may be a lymphocyte carrying a surface molecule that interacts, either directly or indirectly, with a tumor cell target. Various effector cells include cytotoxic T cells and NK cells Antibody-drug conjugates (ADCs) comprise monoclonal antibodies (MAbs) that are covalently linked to cell-killing drugs and may be used in combination therapies. This approach combines the high specificity of MAbs against their antigen targets with highly potent cytotoxic drugs, resulting in "armed" MAbs that deliver the payload (drug) to tumor cells with enriched levels of the antigen. Targeted delivery of the drug also minimizes its exposure in normal tissues, resulting in decreased toxicity and improved therapeutic index. Exemplary ADC drugs inlcude ADCETRIS® (brentuximab vedotin) and KADCYLA® (trastuzumab emtansine or T-DM1).

In one aspect of immunotherapy, the tumor cell must bear some marker that is amenable to targeting, i.e., is not present on the majority of other cells. Many tumor markers exist and any of these may be suitable for targeting in the context of the present embodiments. Common tumor markers include CD20, carcinoembryonic antigen, tyrosinase (p97), gp68, TAG-72, HMFG, Sialyl Lewis Antigen, MucA, MucB, PLAP, laminin receptor, erb B, and p155. An alternative aspect of immunotherapy is to combine anticancer effects with immune stimulatory effects. Immune stimulating molecules also exist including: cytokines, such as IL-2, IL-4, IL-12, GM-CSF, gamma-IFN, chemokines, such as MIP-1, MCP-1, IL-8, and growth factors, such as FLT3 ligand.

Examples of immunotherapies include immune adjuvants, e.g., *Mycobacterium bovis, Plasmodium falciparum*, dinitrochlorobenzene, and aromatic compounds); cytokine therapy, e.g., interferons α, β, and γ, IL-1, GM-CSF, and TNF; gene therapy, e.g., TNF, IL-1, IL-2, and p53; and monoclonal antibodies, e.g., anti-CD20, anti-ganglioside GM2, and anti-p185. It is contemplated that one or more anti-cancer therapies may be employed with the antibody therapies described herein.

In some embodiments, the immunotherapy may be an immune checkpoint inhibitor. Immune checkpoints either turn up a signal (e.g., co-stimulatory molecules) or turn down a signal. Inhibitory immune checkpoints that may be targeted by immune checkpoint blockade include adenosine A2A receptor (A2AR), B7-H3 (also known as CD276), B and T lymphocyte attenuator (BTLA), cytotoxic T-lymphocyte-associated protein 4 (CTLA-4, also known as CD152), indoleamine 2,3-dioxygenase (IDO), killer-cell immunoglobulin (KIR), lymphocyte activation gene-3 (LAG3), programmed death 1 (PD-1), T-cell immunoglobulin domain and mucin domain 3 (TIM-3) and V-domain Ig suppressor of T cell activation (VISTA). In particular, the immune checkpoint inhibitors target the PD-1 axis and/or CTLA-4.

The immune checkpoint inhibitors may be drugs such as small molecules, recombinant forms of ligand or receptors, or, in particular, are antibodies, such as human antibodies. Known inhibitors of the immune checkpoint proteins or analogs thereof may be used, in particular chimerized, humanized or human forms of antibodies may be used. As the skilled person will know, alternative and/or equivalent names may be in use for certain antibodies mentioned in the present disclosure. Such alternative and/or equivalent names are interchangeable in the context of the present disclosure. For example it is known that lambrolizumab is also known under the alternative and equivalent names MK-3475 and pembrolizumab.

In some embodiments, the PD-1 binding antagonist is a molecule that inhibits the binding of PD-1 to its ligand binding partners. In a specific aspect, the PD-1 ligand binding partners are PDL1 and/or PDL2. In another embodiment, a PDL1 binding antagonist is a molecule that inhibits the binding of PDL1 to its binding partners. In a specific aspect, PDL1 binding partners are PD-1 and/or B7-1. In another embodiment, the PDL2 binding antagonist is a molecule that inhibits the binding of PDL2 to its binding partners. In a specific aspect, a PDL2 binding partner is PD-1. The antagonist may be an antibody, an antigen binding fragment thereof, an immunoadhesin, a fusion protein, or oligopeptide.

In some embodiments, the PD-1 binding antagonist is an anti-PD-1 antibody (e.g., a human antibody, a humanized antibody, or a chimeric antibody). In some embodiments, the anti-PD-1 antibody is selected from the group consisting of nivolumab, pembrolizumab, and CT-011. In some embodiments, the PD-1 binding antagonist is an immunoadhesin (e.g., an immunoadhesin comprising an extracellular or PD-1 binding portion of PDL1 or PDL2 fused to a constant region (e.g., an Fc region of an immunoglobulin sequence). In some embodiments, the PD-1 binding antagonist is AMP-224. Nivolumab, also known as MDX-1106-04, MDX-1106, ONO-4538, BMS-936558, and OPDIVO®, is an anti-PD-1 antibody that may be used. Pembrolizumab, also known as MK-3475, Merck 3475, lambrolizumab, KEYTRUDA®, and SCH-900475, is an exemplary anti-PD-1 antibody. CT-011, also known as hBAT or hBAT-1, is also an anti-PD-1 antibody. AMP-224, also known as B7-DCIg, is a PDL2-Fc fusion soluble receptor.

Another immune checkpoint that can be targeted in the methods provided herein is the cytotoxic T-lymphocyte-associated protein 4 (CTLA-4), also known as CD152. The complete cDNA sequence of human CTLA-4 has the Genbank accession number L15006. CTLA-4 is found on the surface of T cells and acts as an "off" switch when bound to CD80 or CD86 on the surface of antigen-presenting cells. CTLA4 is a member of the immunoglobulin superfamily that is expressed on the surface of Helper T cells and transmits an inhibitory signal to T cells. CTLA4 is similar to the T-cell co-stimulatory protein, CD28, and both molecules bind to CD80 and CD86, also called B7-1 and B7-2 respectively, on antigen-presenting cells. CTLA4 transmits an inhibitory signal to T cells, whereas CD28 transmits a stimulatory signal. Intracellular CTLA4 is also found in regulatory T cells and may be important to their function. T cell activation through the T cell receptor and CD28 leads to increased expression of CTLA-4, an inhibitory receptor for B7 molecules.

In some embodiments, the immune checkpoint inhibitor is an anti-CTLA-4 antibody (e.g., a human antibody, a humanized antibody, or a chimeric antibody), an antigen binding fragment thereof, an immunoadhesin, a fusion protein, or oligopeptide.

Anti-human-CTLA-4 antibodies (or VH and/or VL domains derived therefrom) suitable for use in the present methods can be generated using methods well known in the art. Alternatively, art recognized anti-CTLA-4 antibodies can be used. An exemplary anti-CTLA-4 antibody is ipilimumab (also known as 10D1, MDX-010, MDX-101, and Yervoy®) or antigen binding fragments and variants thereof. In other embodiments, the antibody comprises the heavy and light chain CDRs or VRs of ipilimumab. Accordingly, in one embodiment, the antibody comprises the CDR1, CDR2, and CDR3 domains of the VH region of ipilimumab, and the CDR1, CDR2 and CDR3 domains of the VL region of ipilimumab. In another embodiment, the antibody competes for binding with and/or binds to the same epitope on CTLA-4 as the above-mentioned antibodies. In another embodiment, the antibody has at least about 90% variable region amino acid sequence identity with the above-mentioned antibodies (e.g., at least about 90%, 95%, or 99% variable region identity with ipilimumab).

4. Surgery

Approximately 60% of persons with cancer will undergo surgery of some type, which includes preventative, diagnostic or staging, curative, and palliative surgery. Curative surgery includes resection in which all or part of cancerous tissue is physically removed, excised, and/or destroyed and may be used in conjunction with other therapies, such as the treatment of the present embodiments, chemotherapy, radiotherapy, hormonal therapy, gene therapy, immunotherapy, and/or alternative therapies. Tumor resection refers to physical removal of at least part of a tumor. In addition to tumor resection, treatment by surgery includes laser surgery, cryosurgery, electrosurgery, and microscopically-controlled surgery (Mohs' surgery).

Upon excision of part or all of cancerous cells, tissue, or tumor, a cavity may be formed in the body. Treatment may be accomplished by perfusion, direct injection, or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

5. Other Agents

It is contemplated that other agents may be used in combination with certain aspects of the present embodiments to improve the therapeutic efficacy of treatment. These additional agents include agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Increases in intercellular signaling by elevating the number of GAP junctions would increase the anti-hyperproliferative effects on the neighboring hyperproliferative cell population. In other embodiments, cytostatic or differentiation agents can be used in combination with certain aspects of the present embodiments to improve the anti-hyperproliferative efficacy of the treatments. Inhibitors of cell adhesion are contemplated to improve the efficacy of the present embodiments. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with certain aspects of the present embodiments to improve the treatment efficacy.

V. Articles of Manufacture or Kits

An article of manufacture or a kit is provided comprising immune cells is also provided herein. The article of manufacture or kit can further comprise a package insert comprising instructions for using the immune cells to treat or delay progression of cancer in an individual or to enhance immune function of an individual having cancer. Any of the antigen-specific immune cells described herein may be included in the article of manufacture or kits. Suitable containers include, for example, bottles, vials, bags and syringes. The container may be formed from a variety of materials such as glass, plastic (such as polyvinyl chloride or polyolefin), or metal alloy (such as stainless steel or hastelloy). In some embodiments, the container holds the formulation and the label on, or associated with, the container may indicate directions for use. The article of manufacture or kit may further include other materials desirable from a commercial and user standpoint, including other buffers, diluents, filters, needles, syringes, and package inserts with instructions for use. In some embodiments, the article of manufacture further includes one or more of another agent (e.g., a chemotherapeutic agent, and anti-neoplastic agent). Suitable containers for the one or more agent include, for example, bottles, vials, bags and syringes.

VI. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Development of Truncated EGFRvIII (Ev3) CAR

Figure 1A:
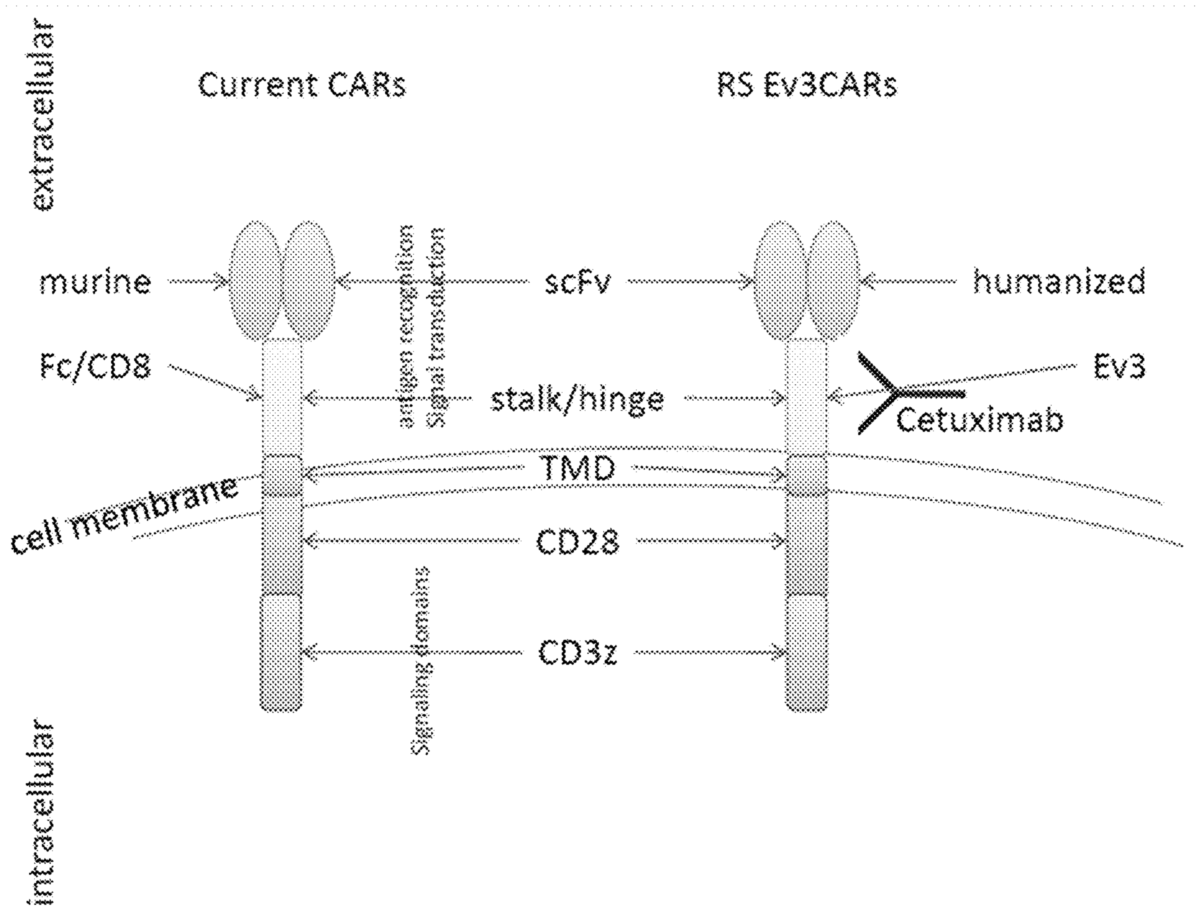
FIGS. 1A-1B: Comparisons between current CARs and Ev3-CAR designs.
Figure 1B:
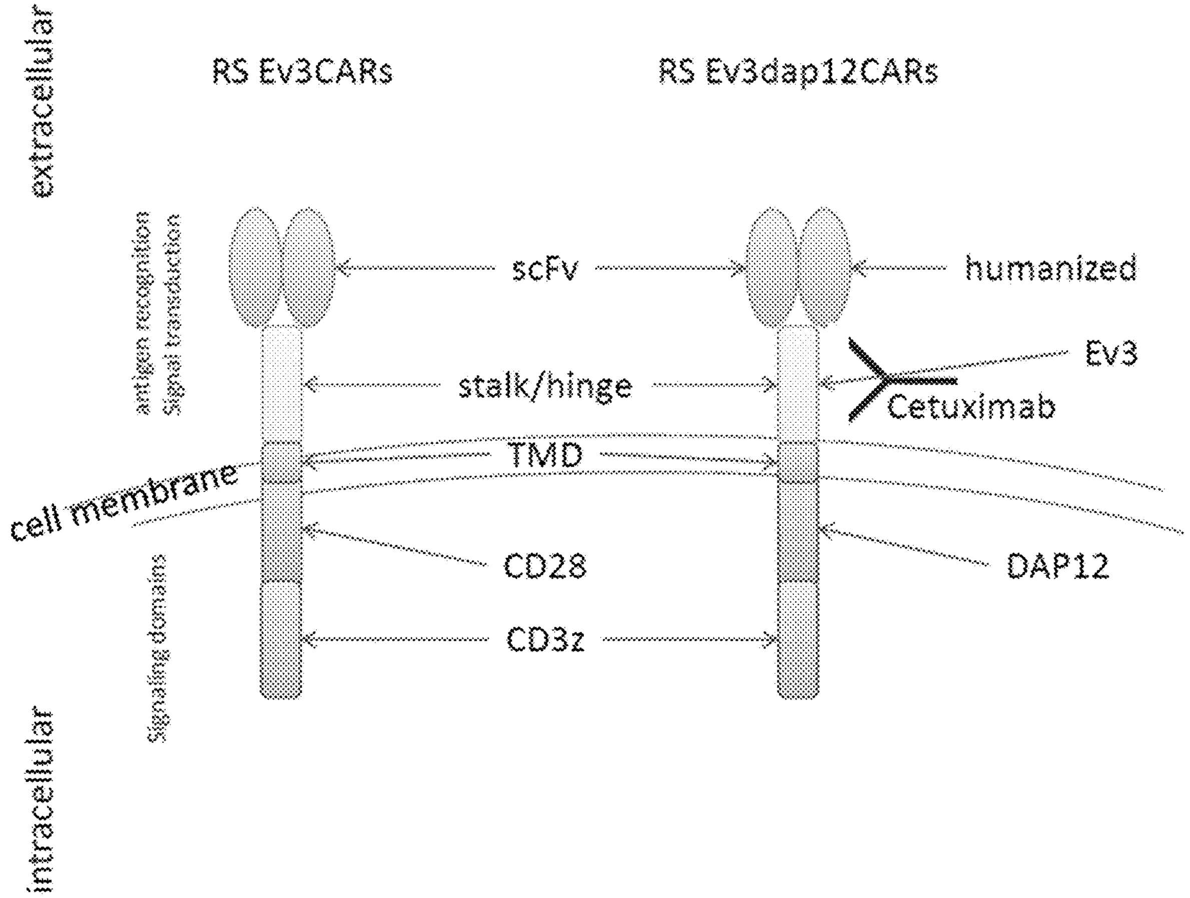

An Ev3-CAR was designed in which the Ev3 stalk serves as an integrative structure to transduce signals from antigen binding, such as by scFv, as well as an "off" switch, meaning it can be recognized by clinically accessible antibodies such as cetuximab to ablate CAR-positive immune cells (FIG. 1A). The Ev3-CAR may further comprise DAP12 signaling domain and is designated Ev3-DAP12-CAR. A schematic depicting Ev3 as compared to EGFR which comprise the endodomain and the EGF binding domain is shown in FIG. 2.

Retroviral vectors encoding the Ev3-CAR or Ev3-DAP12-CAR with various antigen binding domains were generated as depicted in FIGS. 3A-3D. The antigen-binding domain was both the scFv derived from the mouse anti-human antibody as well as a humanized scFv. The vectors comprise CD28 and CD3ζ signaling domains and, optionally, DAP12. The vectors also comprise a suicide gene, inducible caspase 9.

Figure 4A:
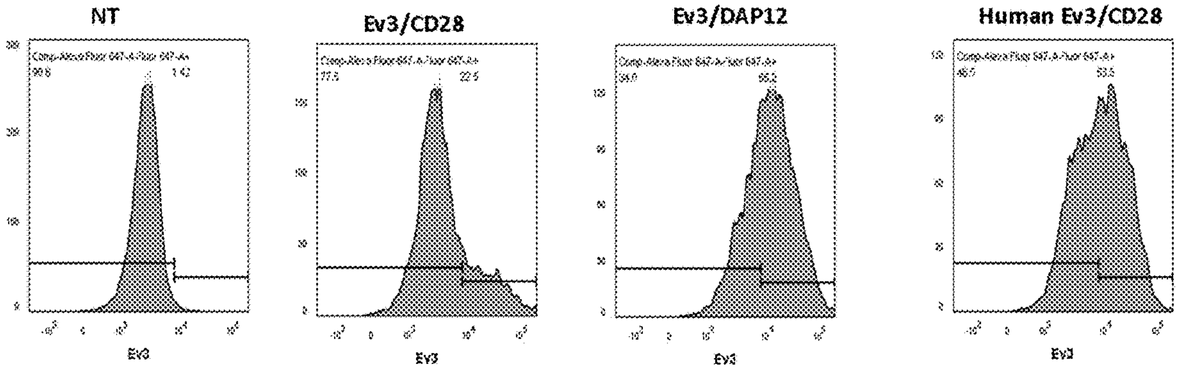
FIGS. 4A-4B.
Figure 4B:
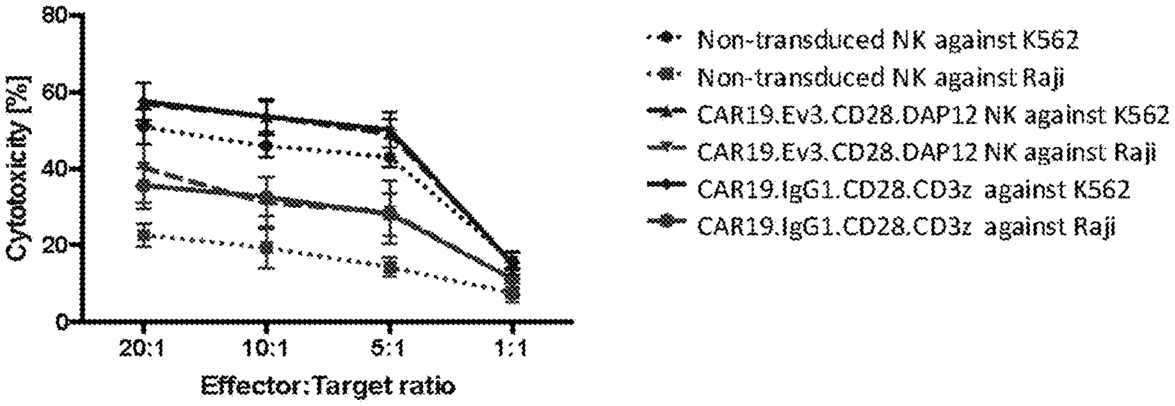

The CD19-specific CARs including CAR19.Ev3.CD28.CD34, CAR19.Ev3.DAP12.CD3ζ or humanized CAR19.Ev3.CD3ζ were transduced into NK cells (FIG. 4A). The CAR-NK cells were tested for their efficacy at killing $CD19^+$ Raji or K562 cells (FIG. 4B). The CAR19-Ev3-CD28-DAP12-CAR NK cells were observed to have the highest cytoxicity. Thus, the use of Ev3 in the hinge region of the CAR in combination with DAP12 endodomain produces CARs that are highly cytotoxic against target cells.

Example 2—Development of Humanized CARs

A platform was developed to generate humanized scFvs for use in producing humanized CARs. Due to structural constraints, some residues contribute more to antigen binding, thus 3-D modeling was used to identify potentially critical interactions to generate the humanized CARs. The stepwise process detailed below may be repeated iteratively to improve on previous cycles.

Figure 5A:
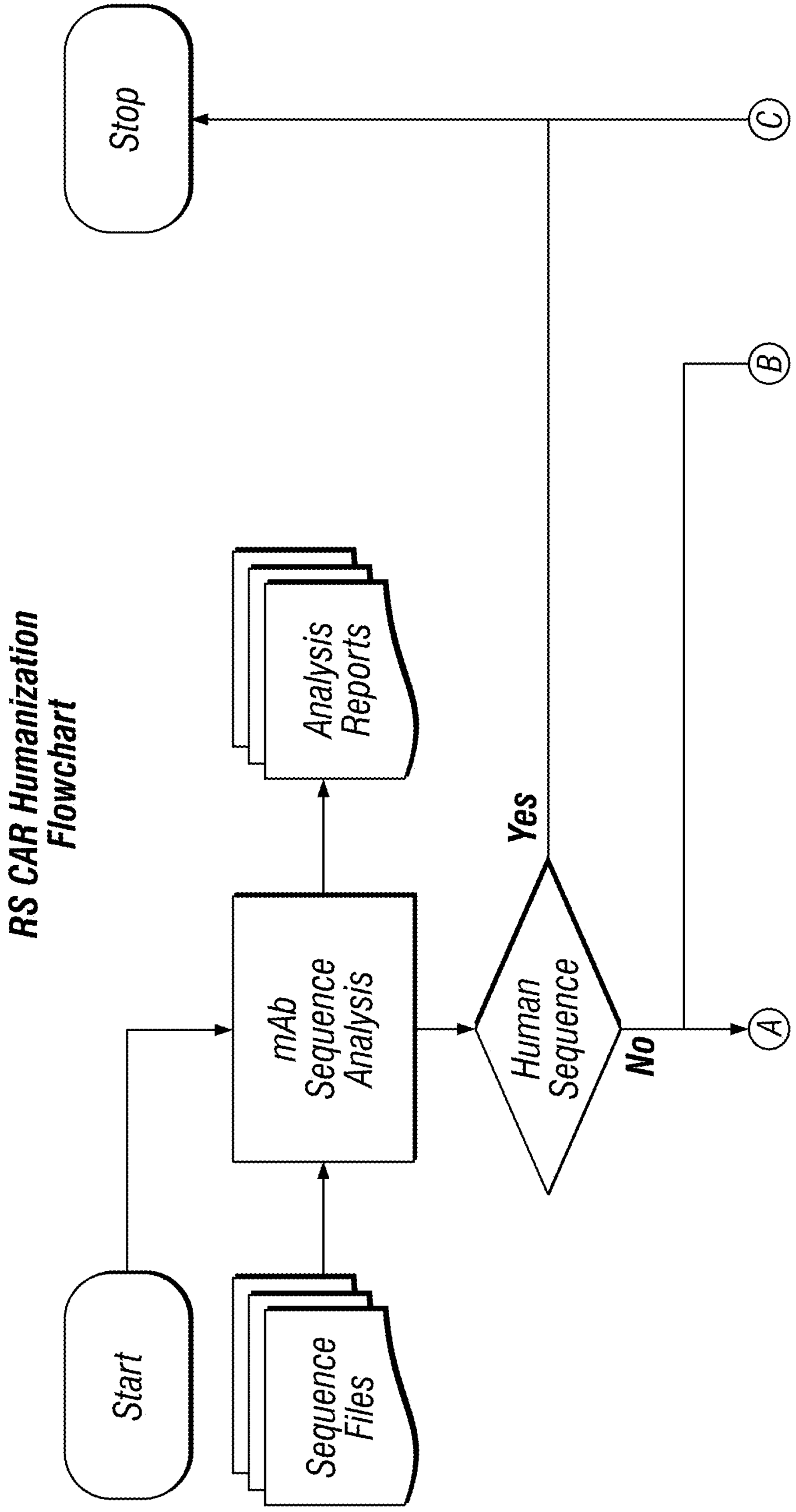
FIGS. 5A-5B.
Figure 5A:
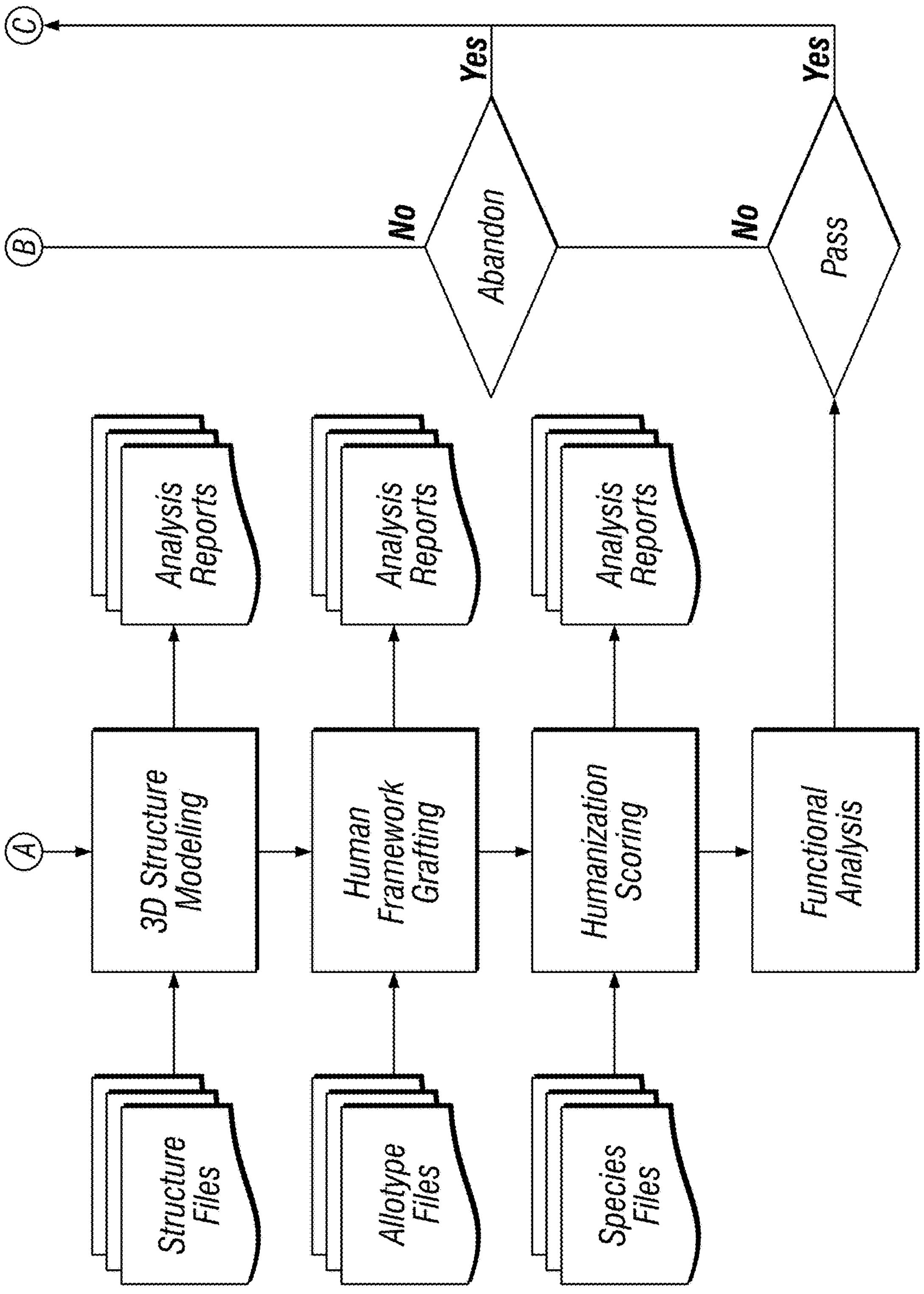

The CAR humanization workflow provided herein comprises 5 basic process modules as detailed below and depicted in FIG. 5A.

Figure 5B:
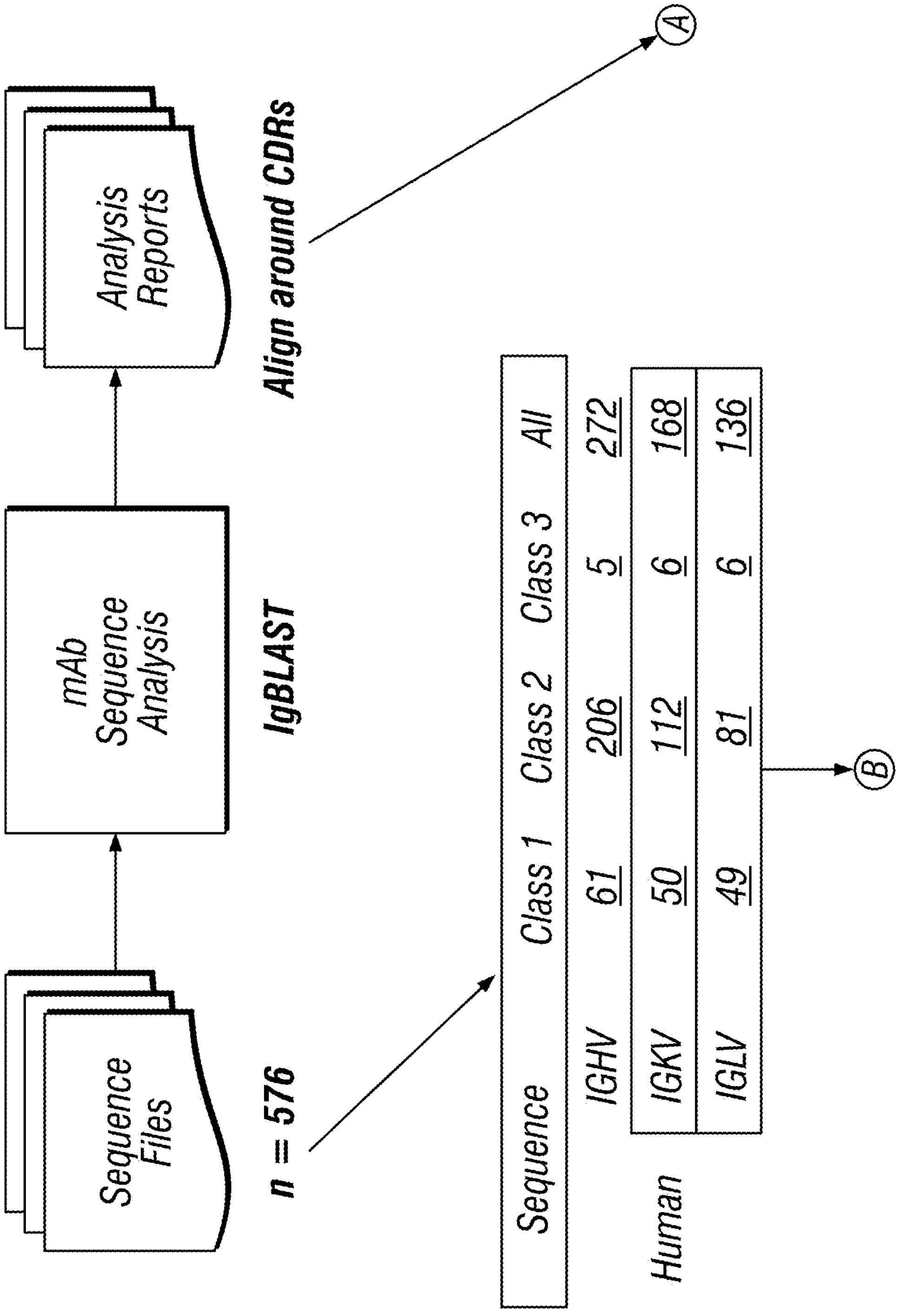
Figure 5B:
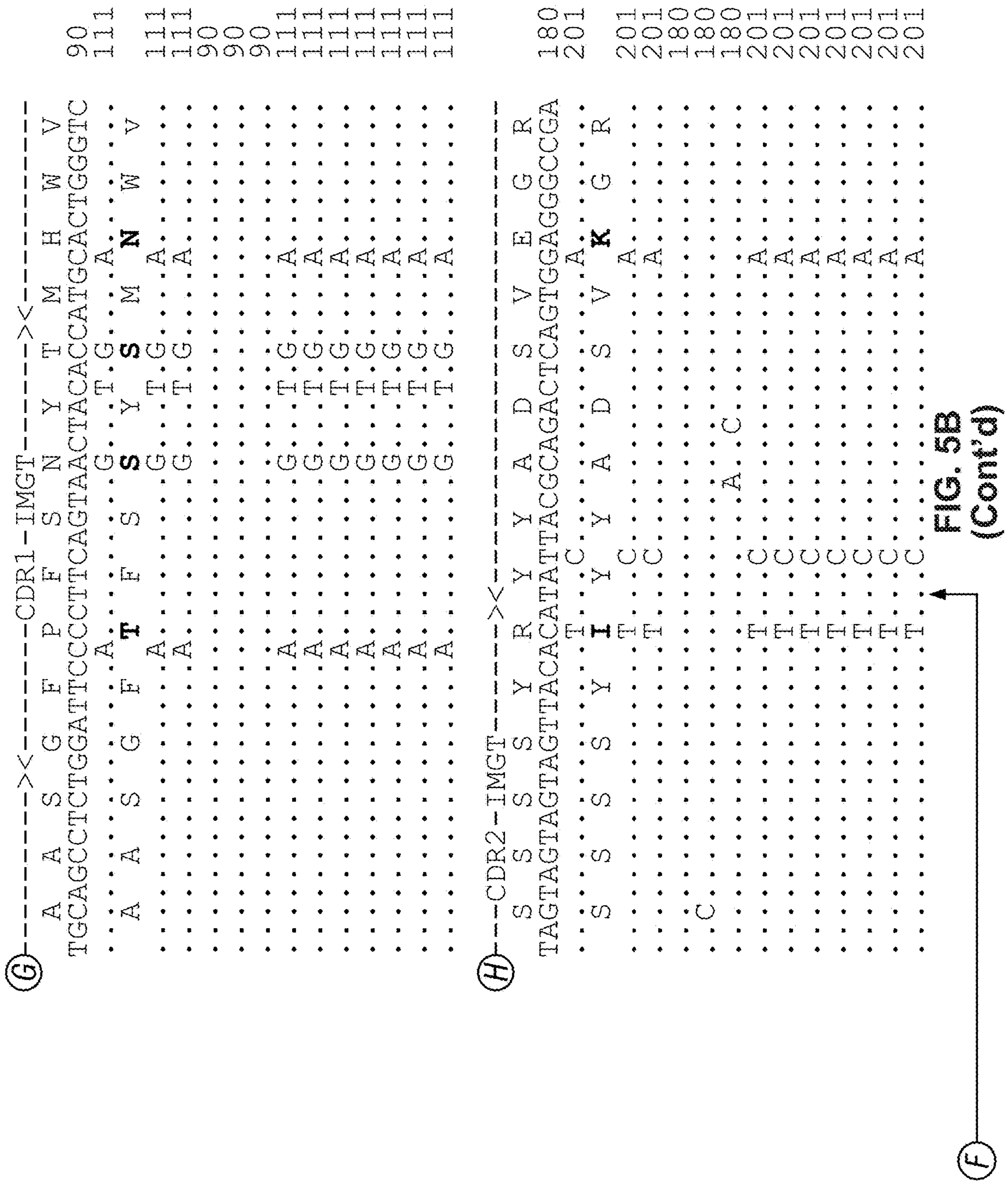
Figure 5B:
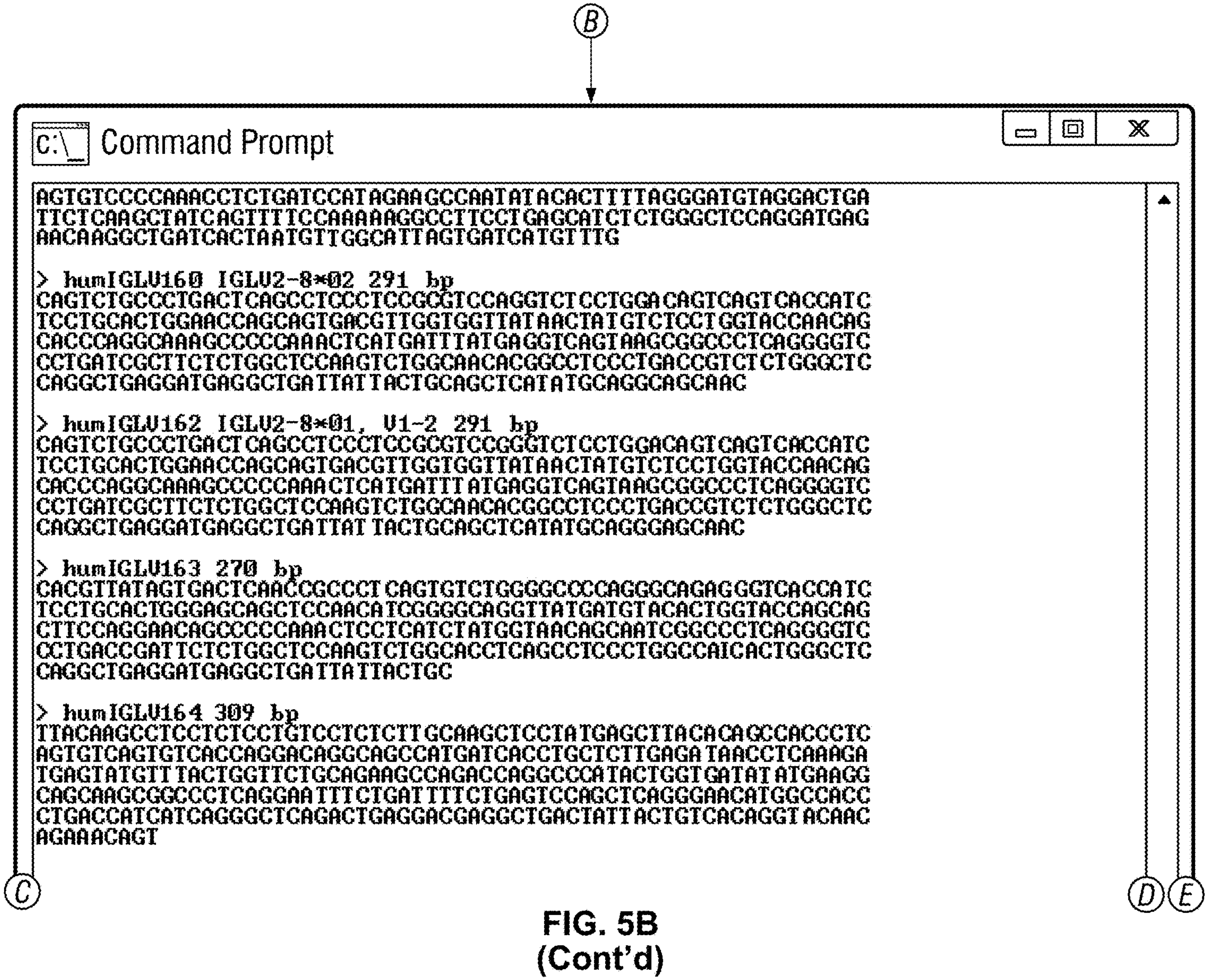

Module I comprises monoclonal antibody (mAb) sequence analysis. The BLAST program was harnessed in search of immunoglobulin (IG) sequences for the best match against the starting queries, such as the murine mAb sequences (FIG. 5B). BLAST can analyze nucleotide and amino acid sequences, either in series (one-by-one) or in parallel (in batches), as well as search against germline gene databases including curated sequence databases simultaneously thus maximizing the chance of getting the best matching variable (V gene. For reference sequences, databases of germline variable (V), diversity (D) and joining (J) genes were used to delineate IG V domain framework regions (FR1-4s) and complementarity determining regions (CDRs). For each antibody, the variable domains were analyzed for the light and heavy chains, each are encoded by multiple genes, including the gene V, D and J genes. The focus of this study was mainly on the V genes to compare variations in the context of defined regions, finding the boundaries for each FR and CDR regions and comparing with other IG sequences in a database.

Figure 6A:
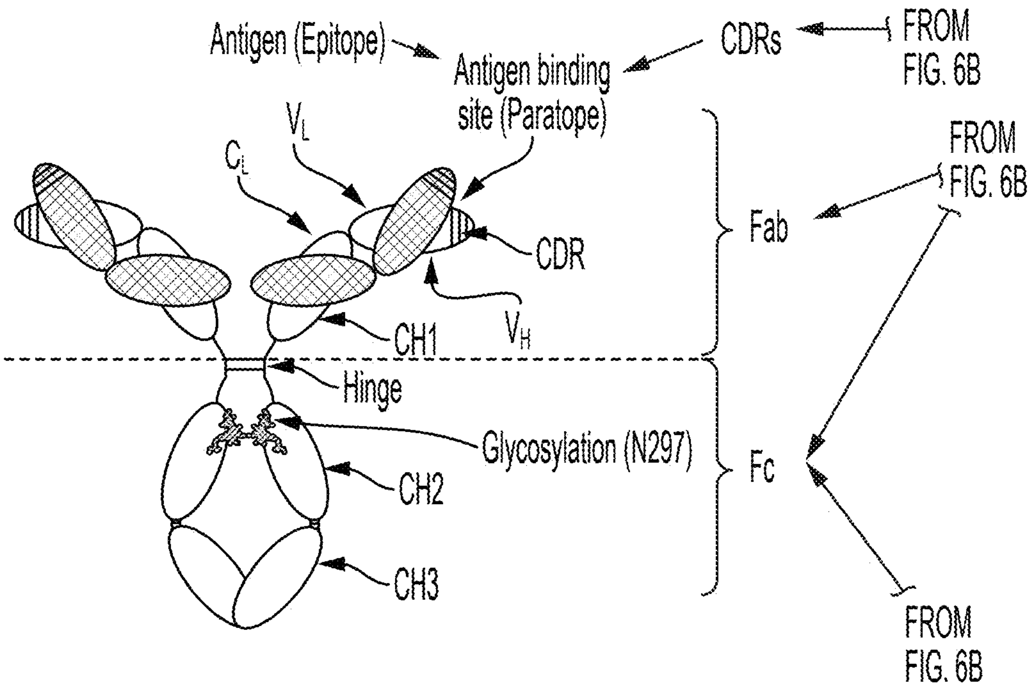
Figure 6B:
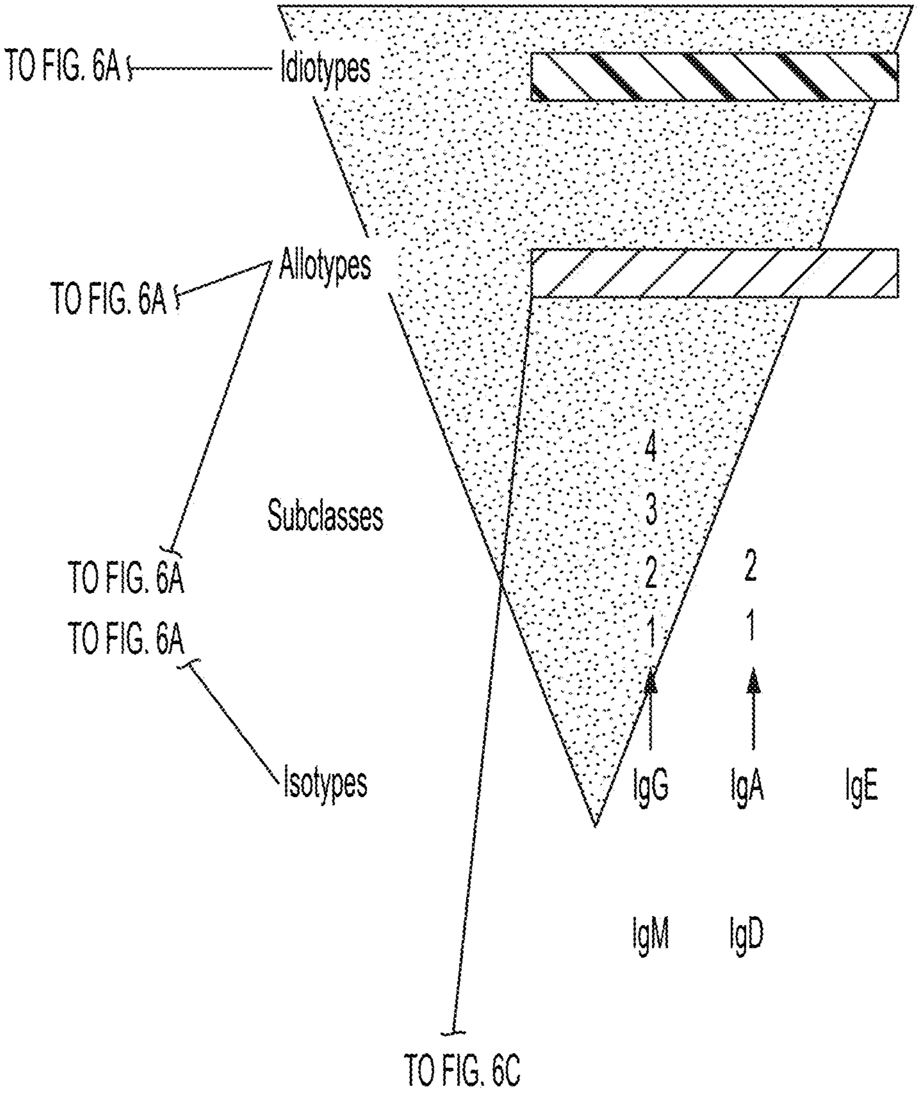

Due to individual variations within the genomic sequences (i.e., estimated at 1 single nucleotide polymorphism per 1,000 bp DNA sequence), the germline IG sequences comprise many thousands of allotypes (i.e., alleles or versions of a gene) (FIG. 6). Databases of human allotypes were generated and exploited for CAR humanization.

As an example, a humanized domain was derived using a particular human allotype by CDR-grafting to transform an anti-human CD19-binding domain VL and VH sequences from a mouse antibody (clone FMC63) (FIG. 7A). The CDR regions are underlined in FIG. 7A.

The sources of the framework sequences were confirmed by BLAST (Altshul et al., 1997) analyses shown in FIG. 7B. Additionally, the sequence homologies and identities were readily quantified and are summarized in FIG. 7C. As a comparison, the sequences that were created de novo were compared to previously available sequences and substantial and readily distinguishable differences were detected at the amino acid and nucleotide levels.

Module II comprised 3D structure modeling. To identify critical residues for antigen binding, 3D structures were built to evaluate the constructs. SWISS-MODEL is a protein structure homology-modeler that was used to make 3-dimensional models of humanized mAbs. Structure files were extracted from SAbDab, a structural antibody database, as templates for homology modeling. As an example of characterizing the 3D conformation of CDR regions of VL and VH domains, homology modeling was employed using SWISS-MODEL (Arnold et al., 2006; Benkert et al., 2011) algorithms with the following primary amino acid sequences:

hCD19 $V_L$ (SEQ ID NO: 9):

```
DIQMTQSPSSLSASVGDRVTITCRASQDISKYLNWYQQKP

GKVPKLLIYHTSRLHSGVPDRFSGSGSGTDFTLTISSLQP

EDVATYYCQQGNTLPYTFGQGTKVEIKR
```

-continued hCD19 $V_H$ (SEQ ID NO: 8):
EVQLVESGGGLVQPGGSLRLSCAASGVSLPDYGVSWVRQA

PGKGLEWIGVIWGSETTYYNSALKSKFIISRDNAKNSLYL

QMNSLRAEDTAVYYCARHYYYGGSYAMDYWGQGTLVTVSS

The SWISS-MODEL template library (SMTL version 2017 Jun. 28, PDB release 2017 Jun. 23) was searched with BLAST (Altschul et al., 1997) and HHblits (Remmert et al., 2012) for evolutionary related structures matching the target sequences hCD19 $V_L$ and hCD19 $V_H$.

Figure 8A:
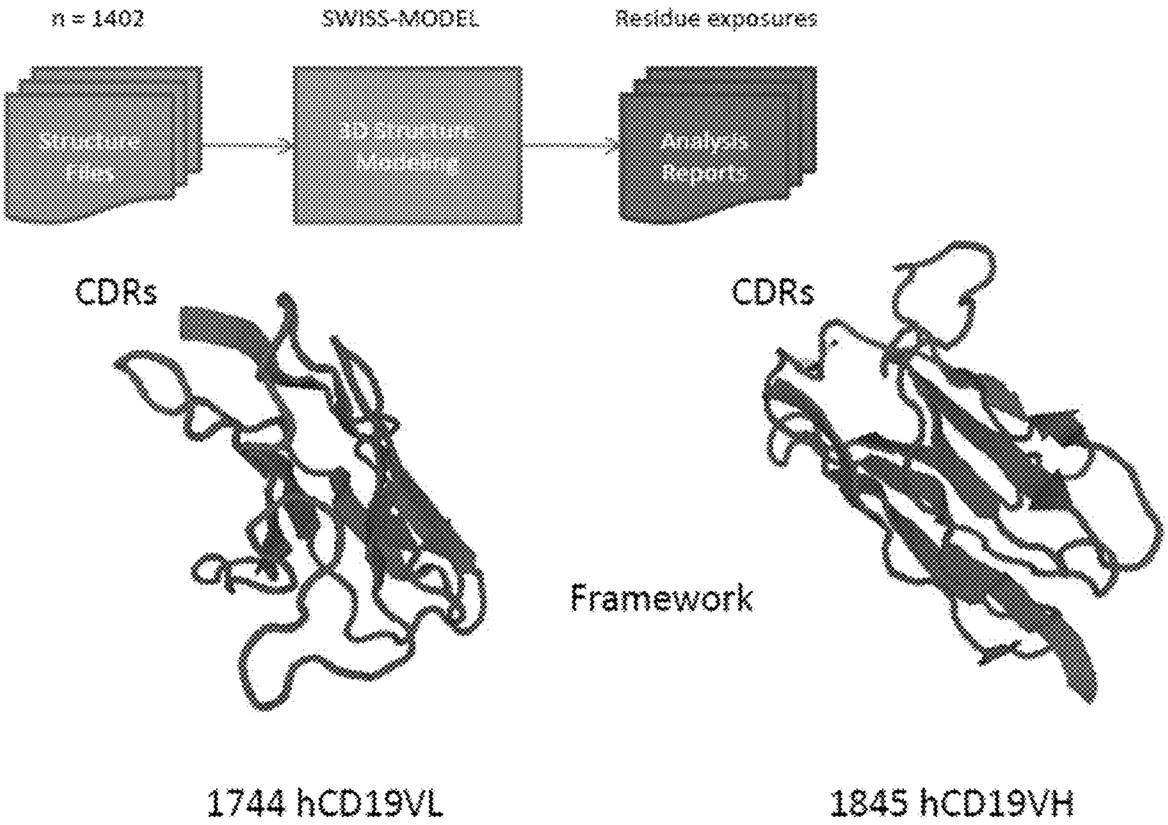
Figure 8C:
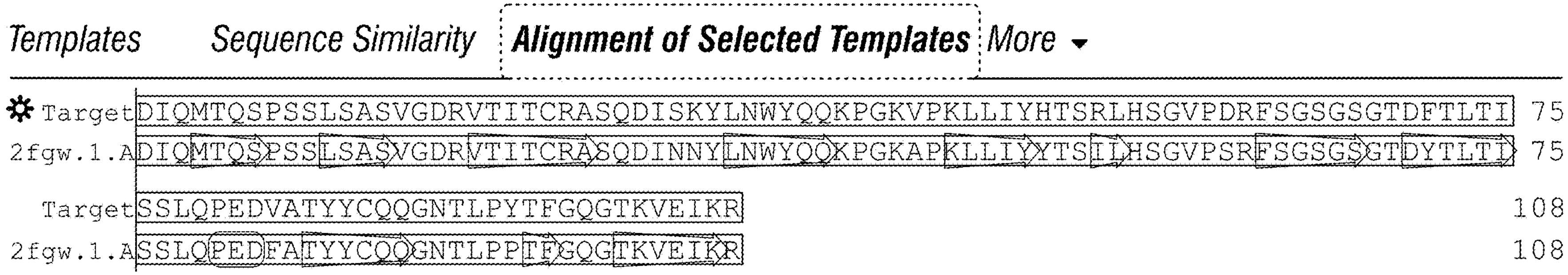
Figure 8D:
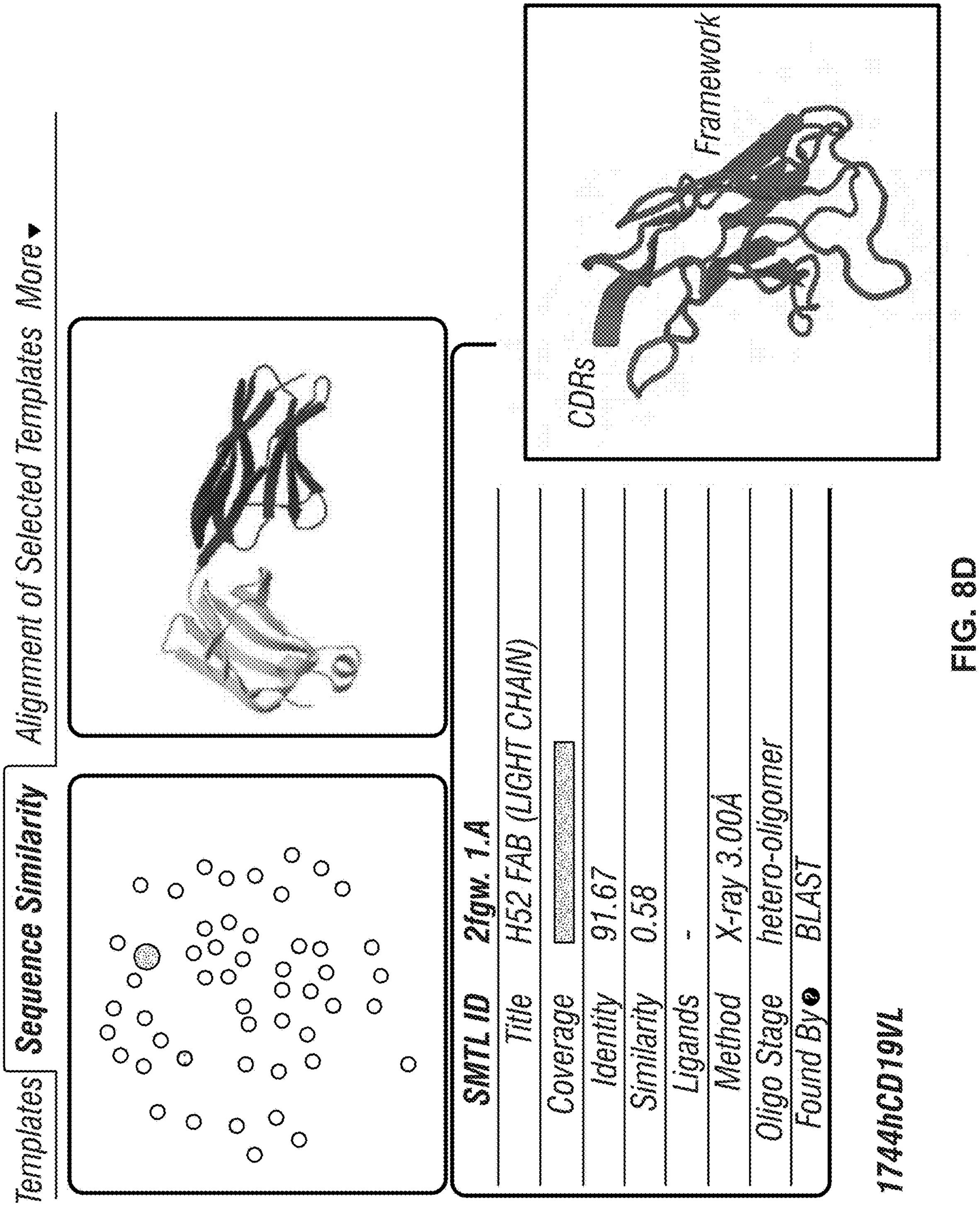
Figure 9B:
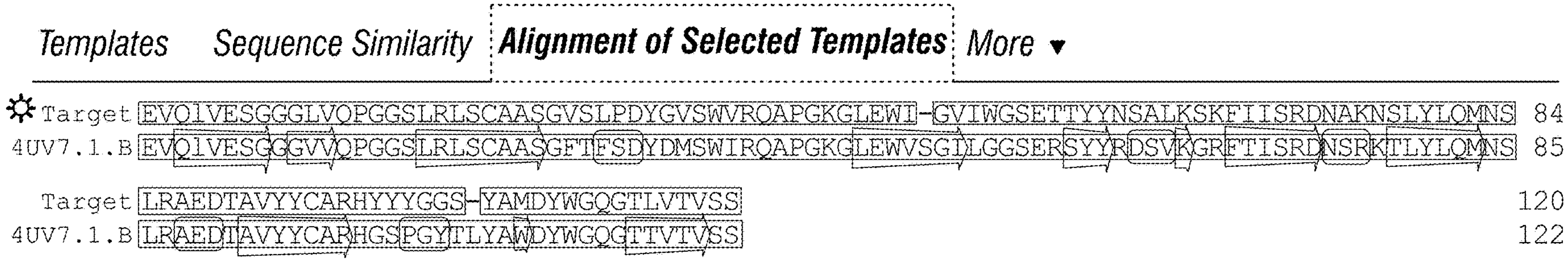
Figure 9C:
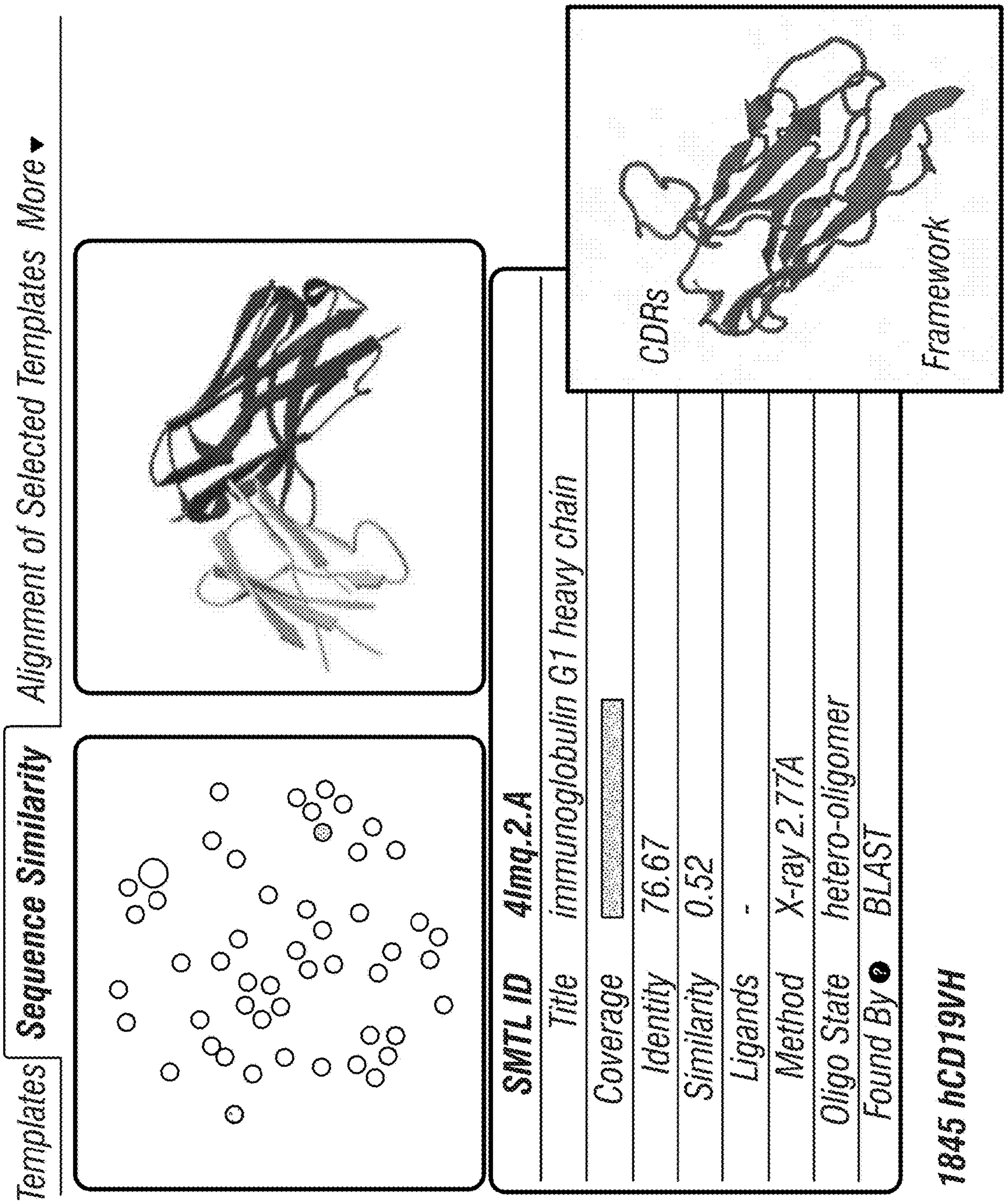

Overall, 13,535 templates were found for hCD19 $V_L$, with 2fgw.1.A showing the best fit (FIG. 8A) and used for further analysis. The target sequence (hCD19 $V_L$) was searched with BLAST against the primary amino acid sequence contained in the SMTL. A total of 761 templates were found. An initial HHblits profile had been built using the procedure outlined by Remmert et al., followed by 1 iteration of HHblits against NR20. The profile thus obtained was then searched against all profiles of the SMTL. A total of 12,946 templates were found.

In all, 14,631 templates were found for hCD19 $V_H$, with 4uv7.1.B showing the best fit (FIG. 8A) and used for further analysis. The target sequence (hCD19 $V_L$) was searched with BLAST against the primary amino acid sequence contained in the SMTL. A total of 755 templates were found. An initial HHblits profile had been built using the procedure outlined by Remmert et al., followed by 1 iteration of HHblits against NR20. The profile thus obtained was then searched against all profiles of the SMTL. A total of 13,964 templates were found.

Template Selection: For each identified template, the template's quality had been predicted from features of the target-template alignment. The templates with the highest quality were then been selected for model building.

Model Building: Models were built based on the target-template alignment using ProMod3. Coordinates which were conserved between the target and the template were copied from the template to the model. Insertions and deletions were remodeled using a fragment library. Side chains were then rebuilt. Finally, the geometry of the resulting model was regularized by using a force field. In case loop modeling with ProMod3 failed, an alternative model was built with PROMOD-II (Geux et al., 1997).

Model Quality Estimation: The global and per-residue model quality had been assessed using the QMEAN scoring function (Benkert et al., 2011). For improved performance, weights of the individual QMEAN terms had been trained specifically for SWISS-MODEL.

The 3-dimensional models of hCD19 $V_L$ and hCD19 $V_H$ showed that the CDR residues exposed the water-phase and were able to form paratopic surfaces consistently with their antigen binding properties.

Module III comprised human framework grafting. As part of the synthetic CAR building process, a robust and reliable CDR grafting technique was included in the platform technology. The antigen binding sequences (CDRs) were identified and spliced using custom analysis algorithms (a combination of traditional Kabat/IMGT and novel methods) from antibody variable domains into selective human framework sequences (carefully curated custom databases based homology and position of key residues) to create a panel of full length humanized scFvs for robust expression.

Fully humanized scFvs are an essential step in the process of incorporating the antigen-binding domains of mAbs into CARs for clinical application while reducing the possibility of human anti-mouse reactivity ensuring persistence and viability of CAR-modified therapeutic cells. The present CAR humanization platform's efficacy was shown by the de novo creation of a panel of at least 5 high quality, full-length, humanized CARs for expression characterization, functional verification, and pre-clinical testing.

Module IV comprises humanization scoring. Scoring metrics were used to quantify and objectively evaluate the synthetic constructs as part of the CAR humanization process. The T20[1] scoring algorithm was applied to a series of commercially available and FDA-approved monoclonal antibodies (mAbs) as listed in FIG. 10B to test its utility. As expected, the $V_L$ and $V_H$ (FIG. 10C) sequences score higher with increasing degrees of humanization. Interestingly, $V_L$ sequences trend higher in T20 scores as compared to paired $V_H$ sequences.

As a correlative analysis, information regarding FDA approved antibody therapeutics was assessed and the level of reported immunogenicity observed in patients from prescribing information in the public domain. As summarized in FIG. 10E, higher levels of humanization tend to be correlated with decreased instances of reported immunotoxicity in patients.

Figure 10A:
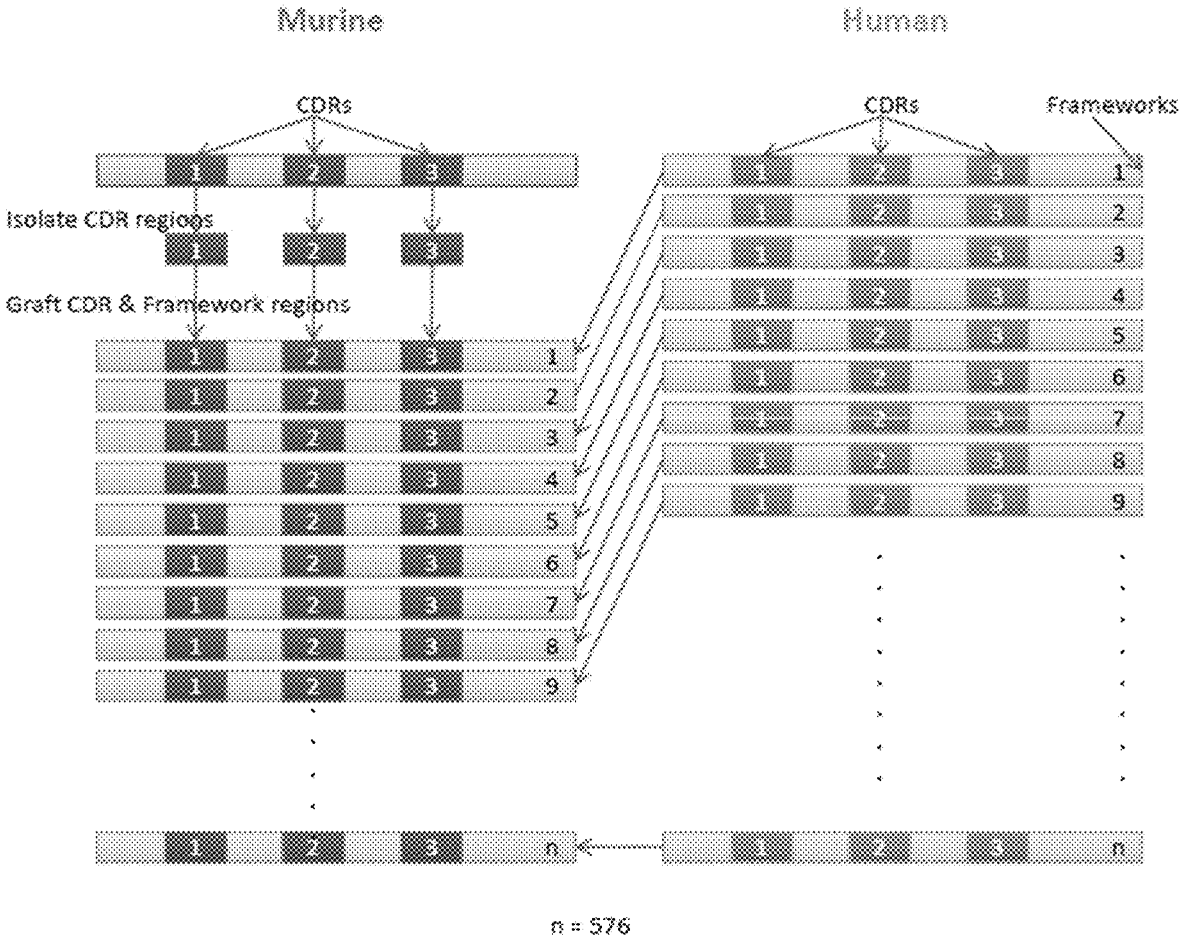
Figure 10C:
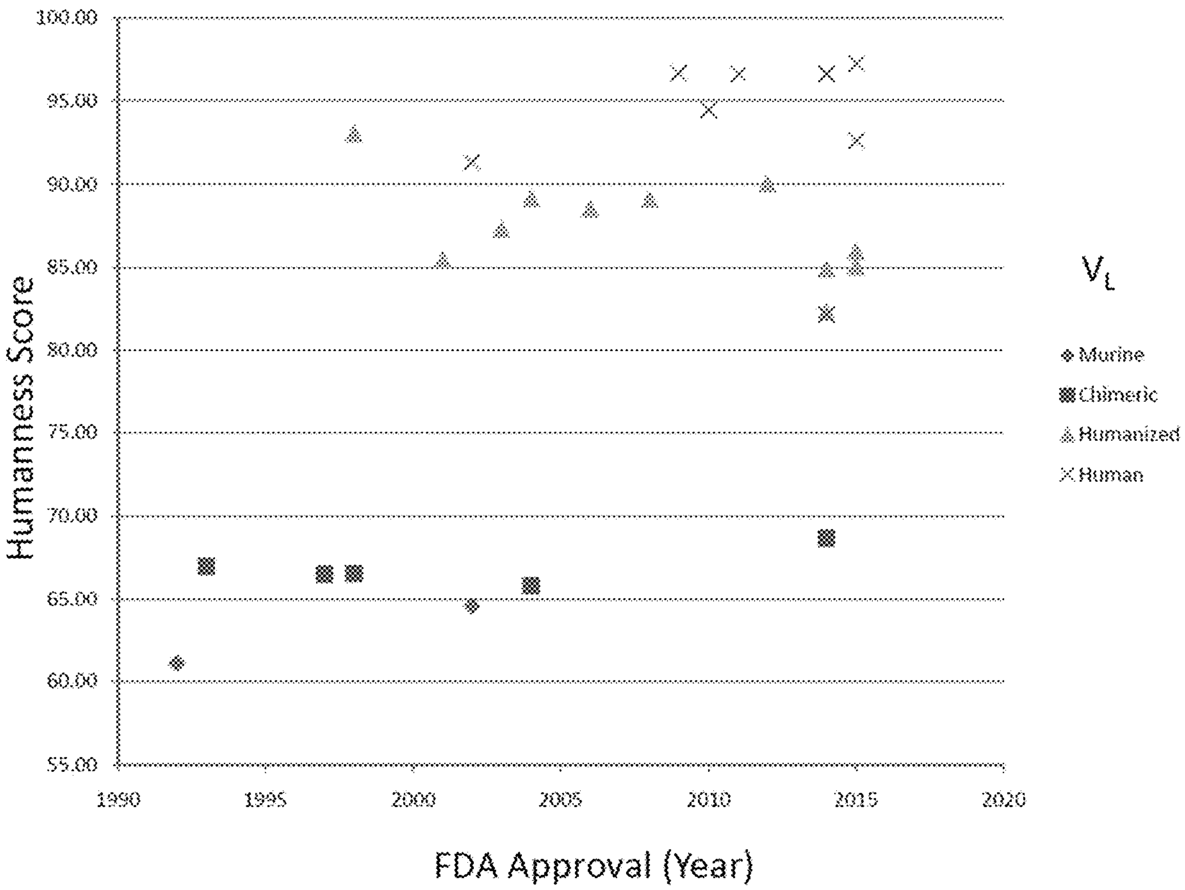
Figure 10D:
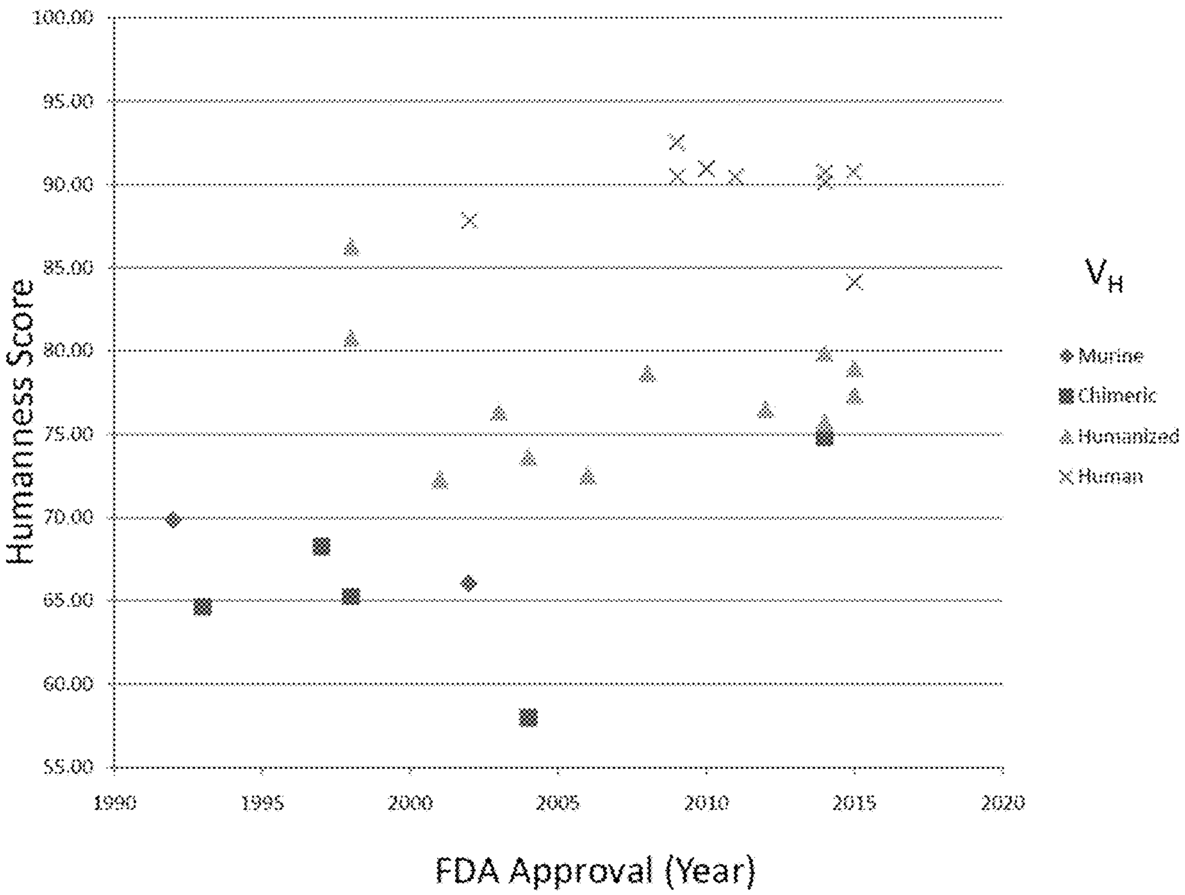
Figure 11A:
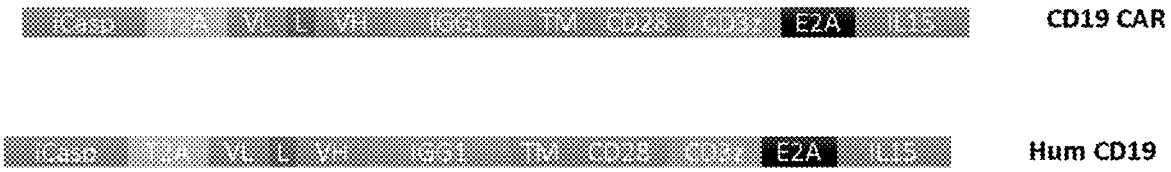
FIGS. 11A-11E.
Figure 11B:
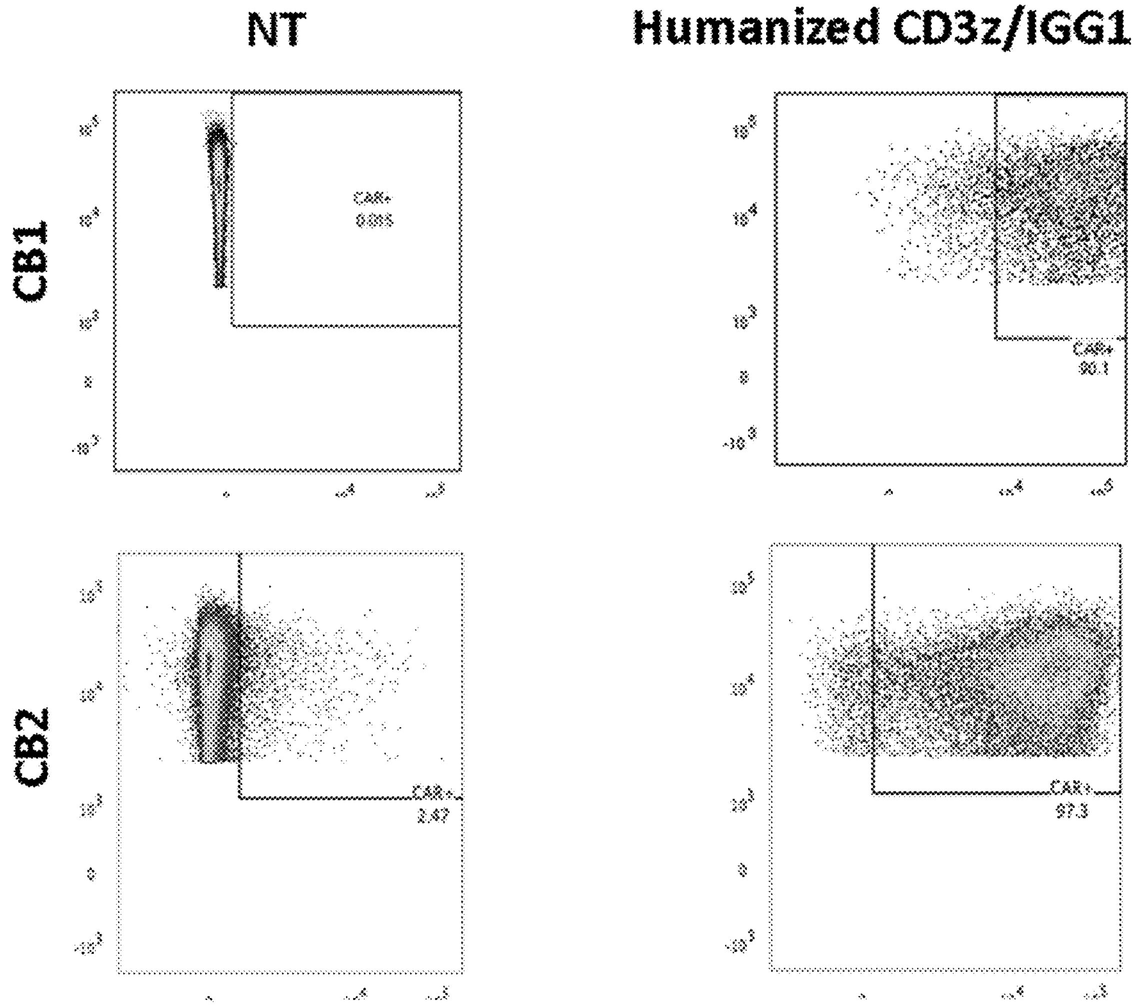
Figure 11C:
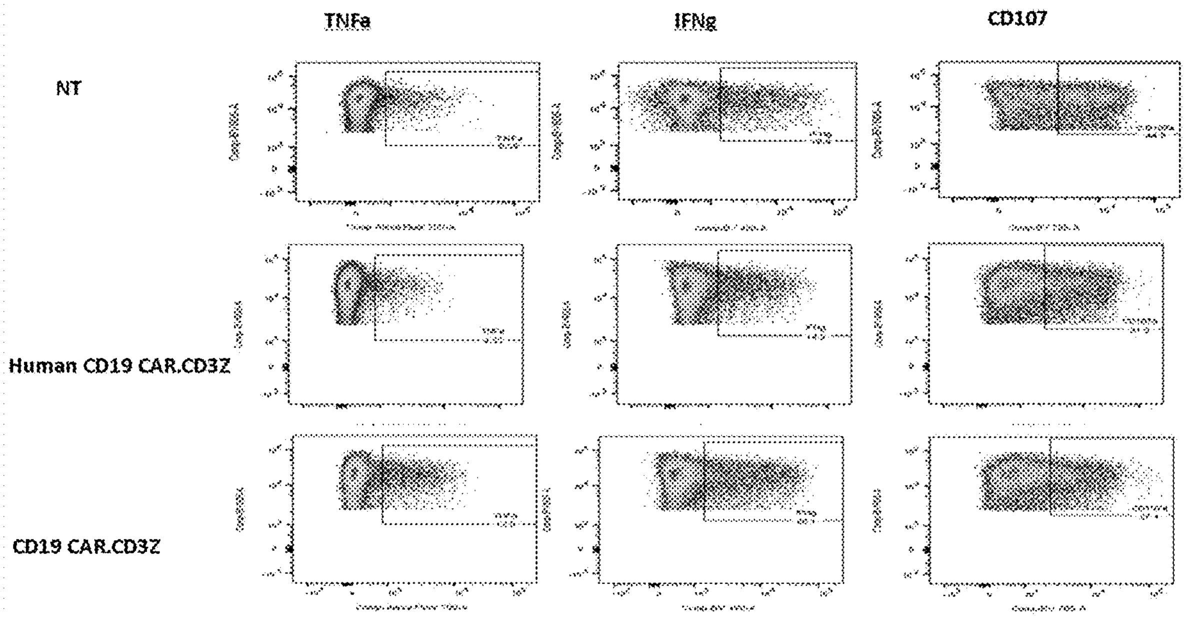
Figure 11D:
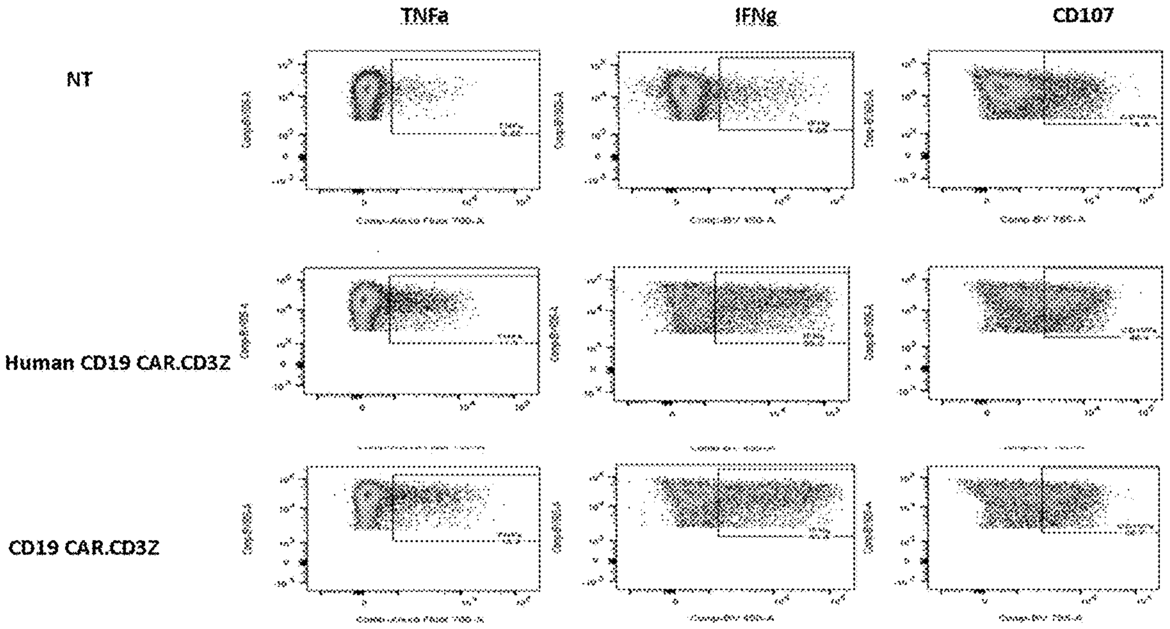
Figure 11E:
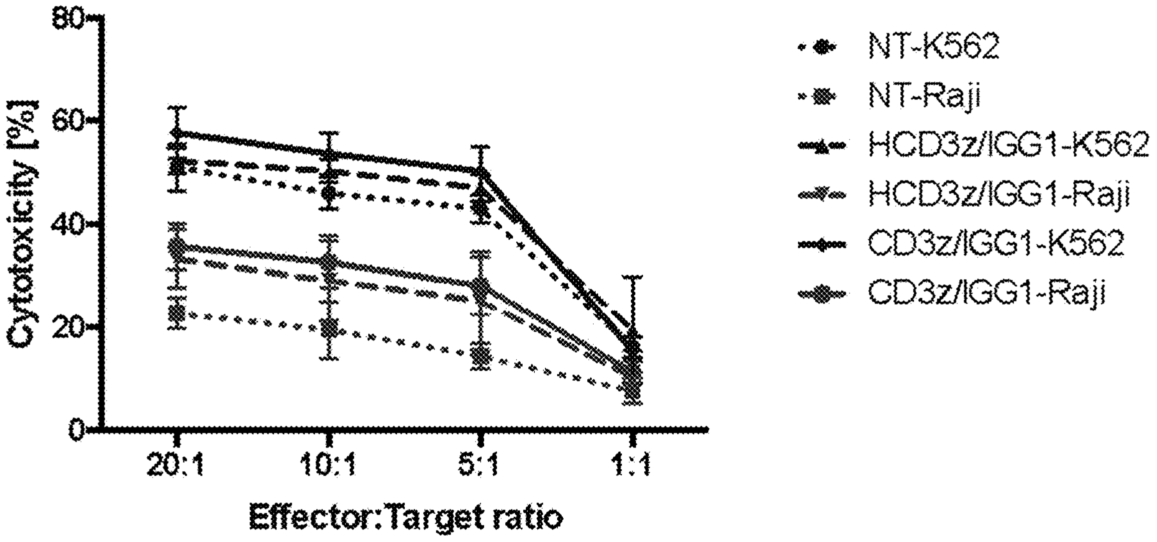
Figure 12A:
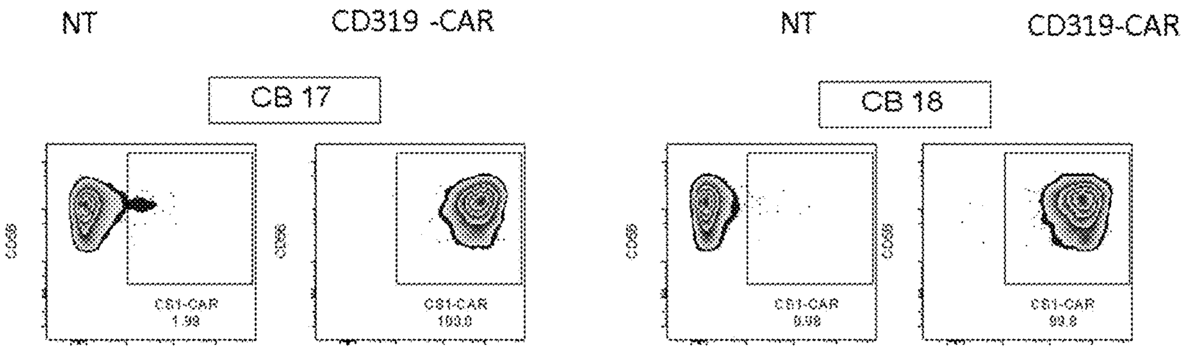
FIGS. 12A-12I.
Figure 12B:
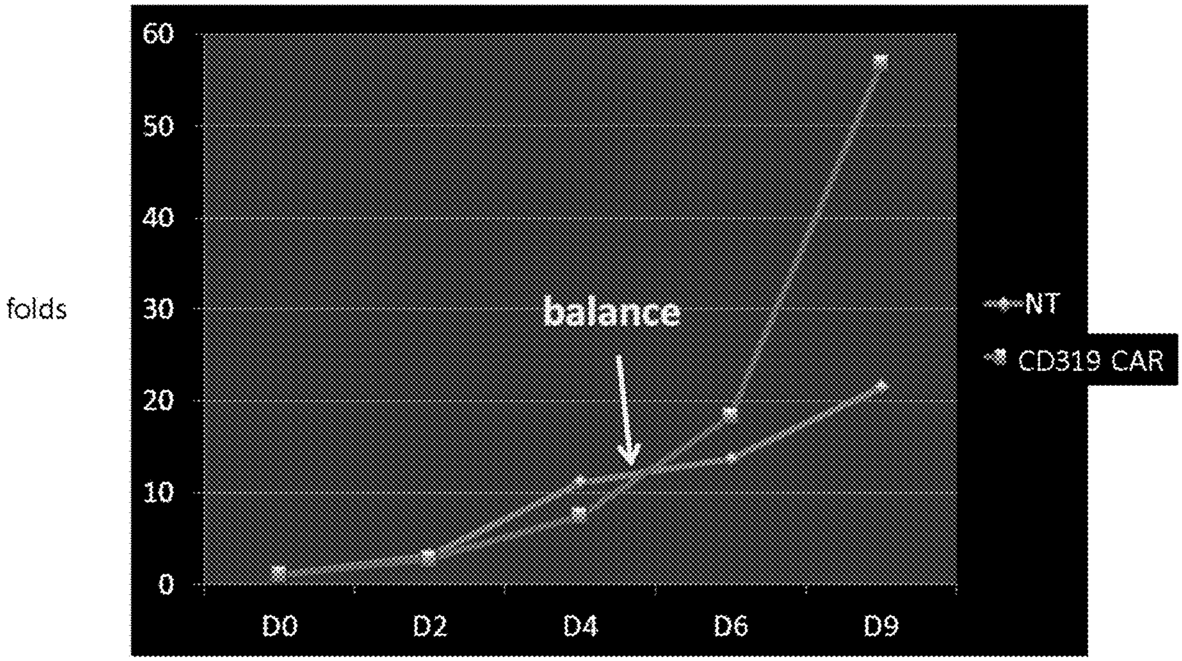
Figure 12C:
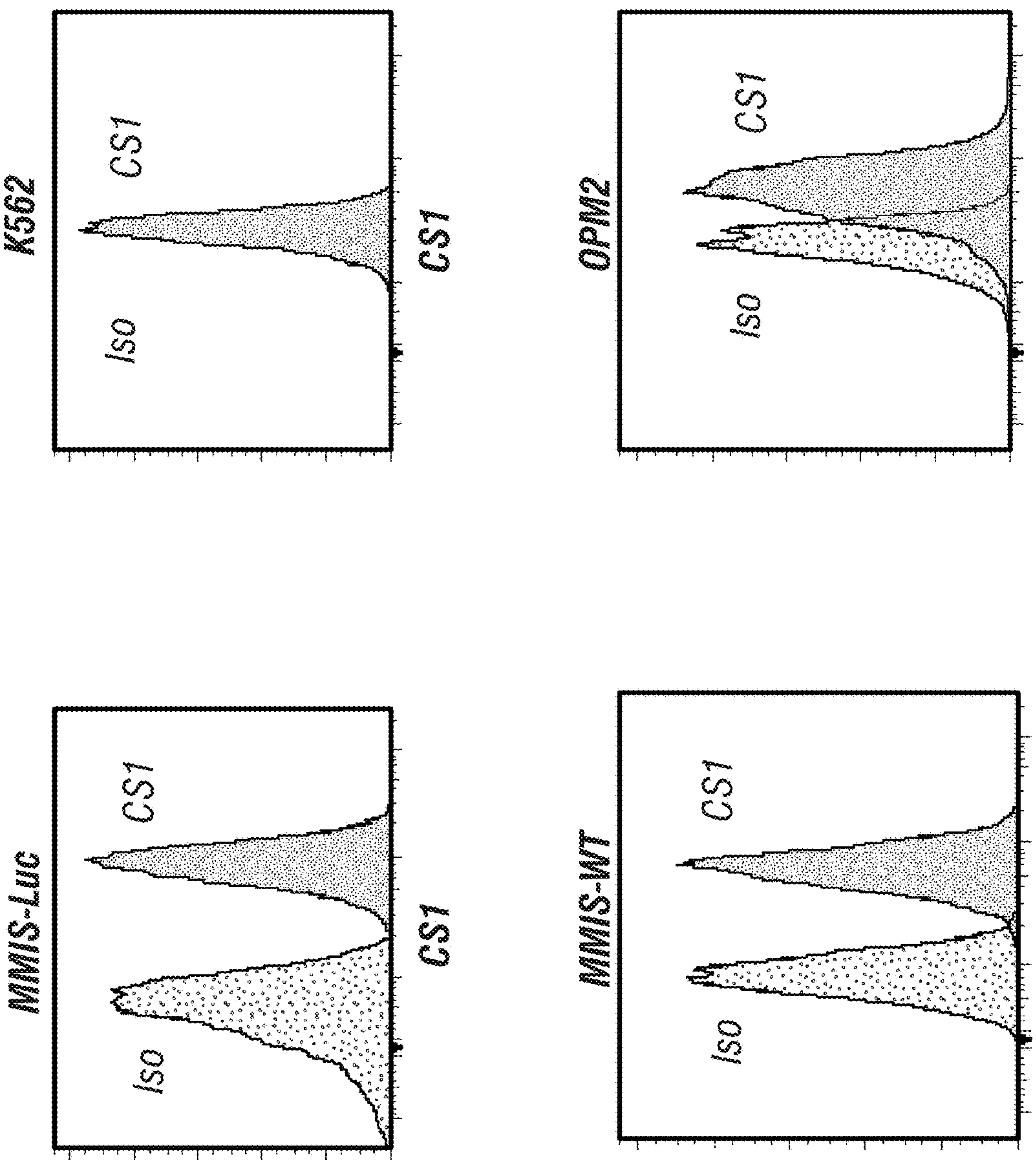
Figure 12D:
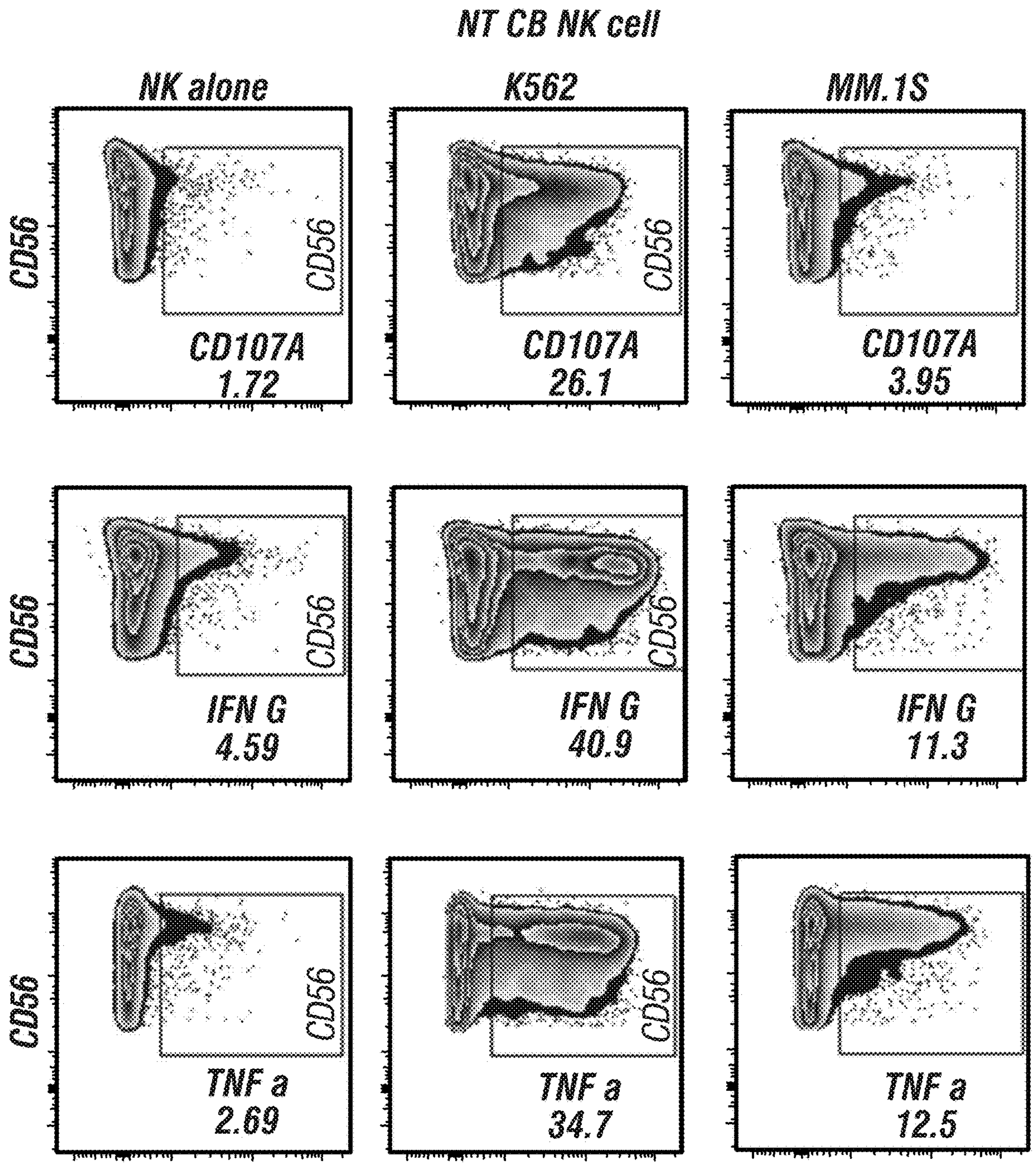
Figure 12D:
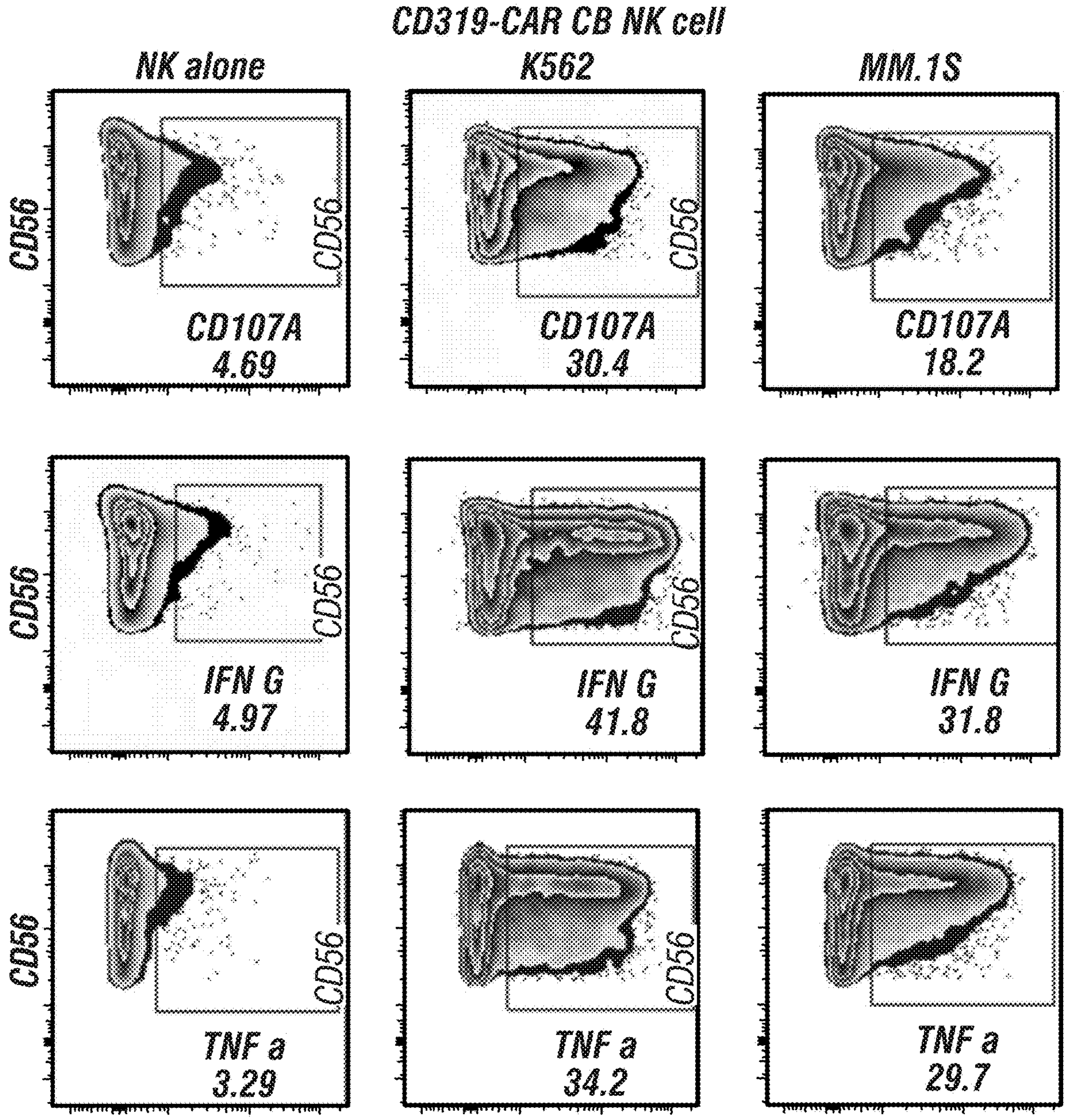
Figure 12E:
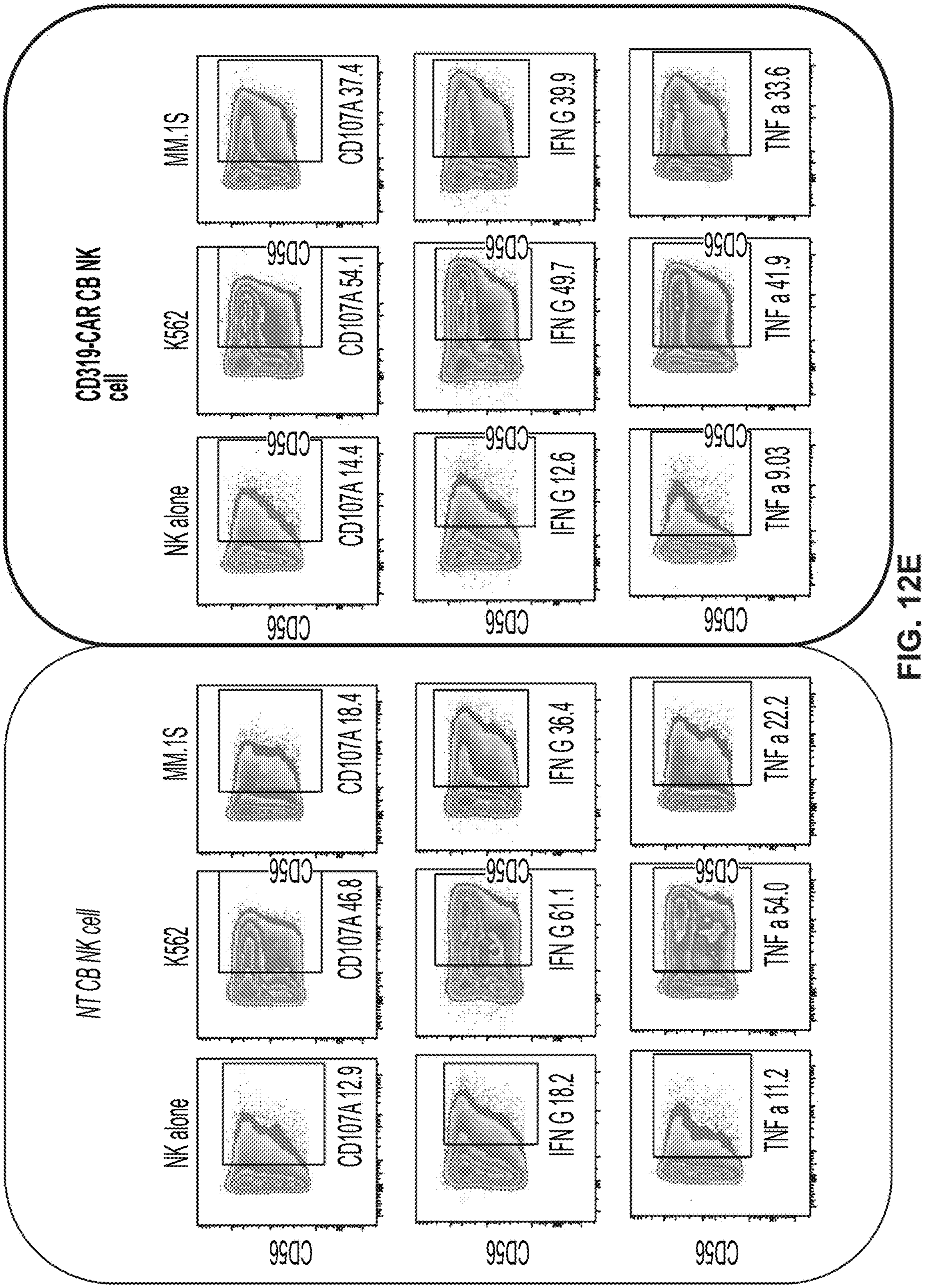
Figure 12F:
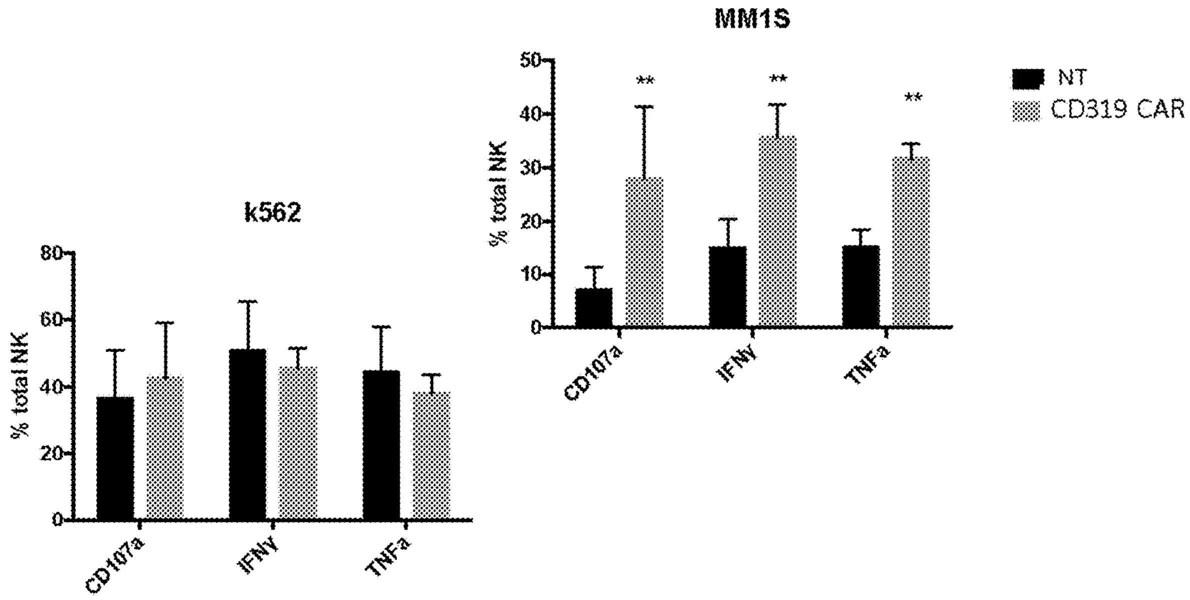
Figure 12G:
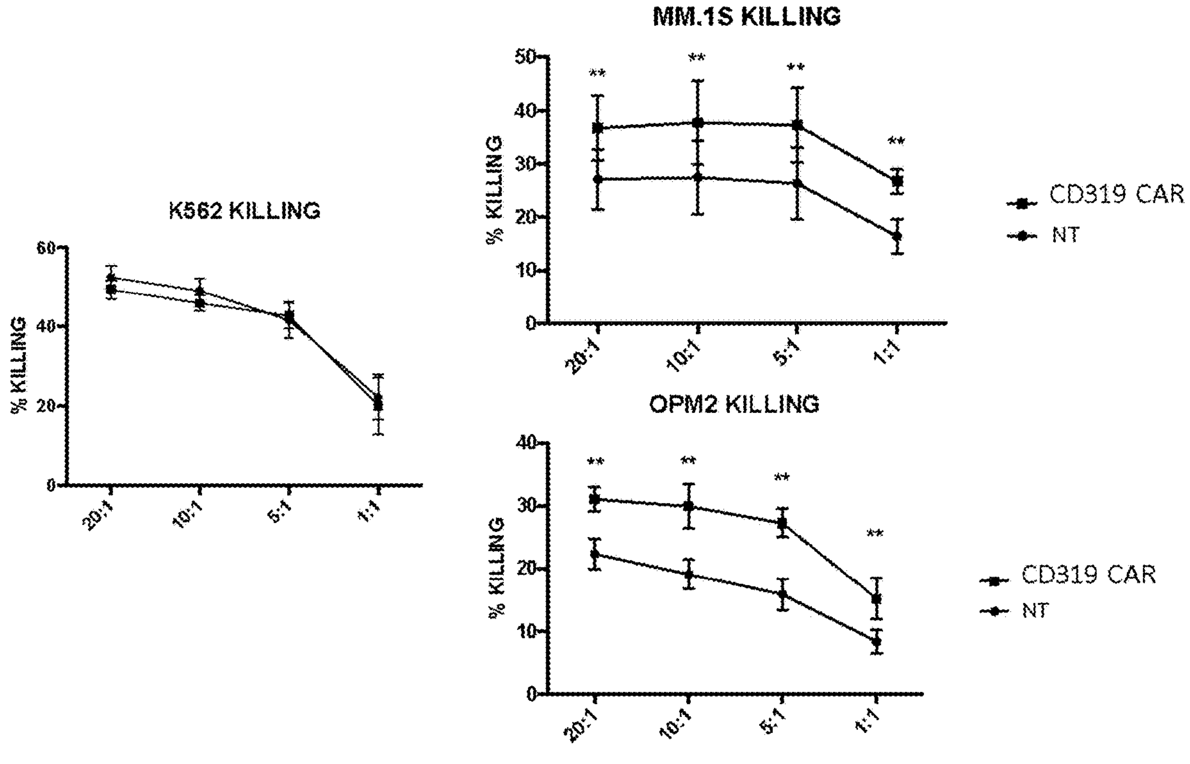
Figure 12H:
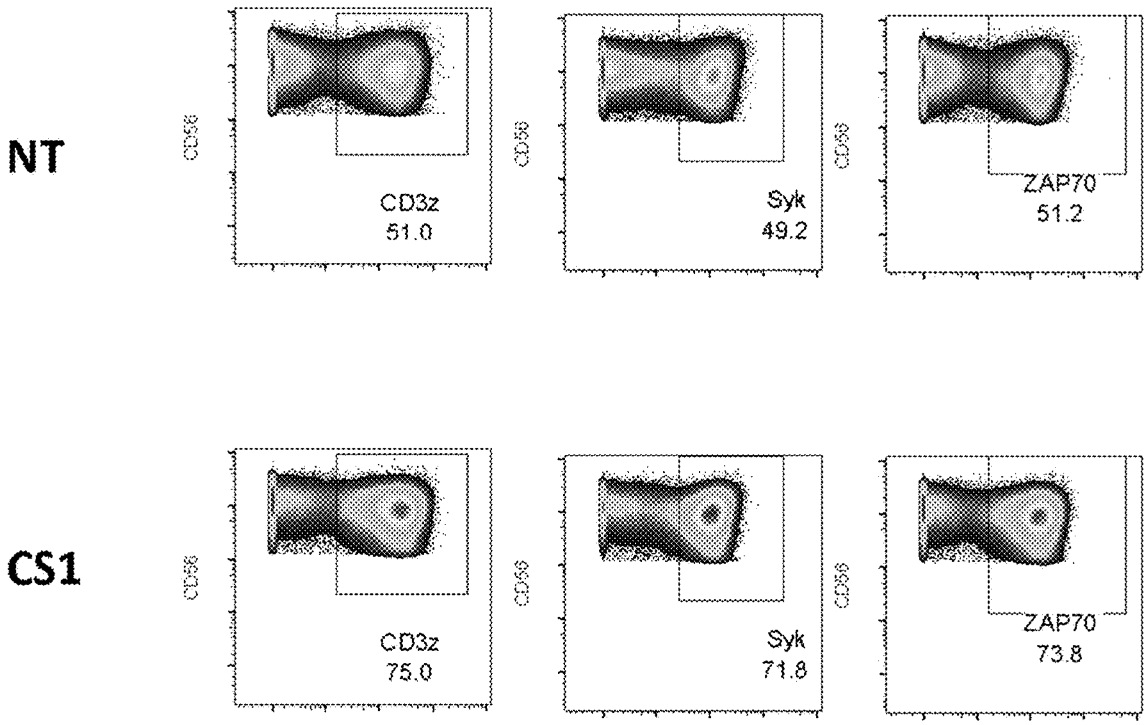
Figure 12I:
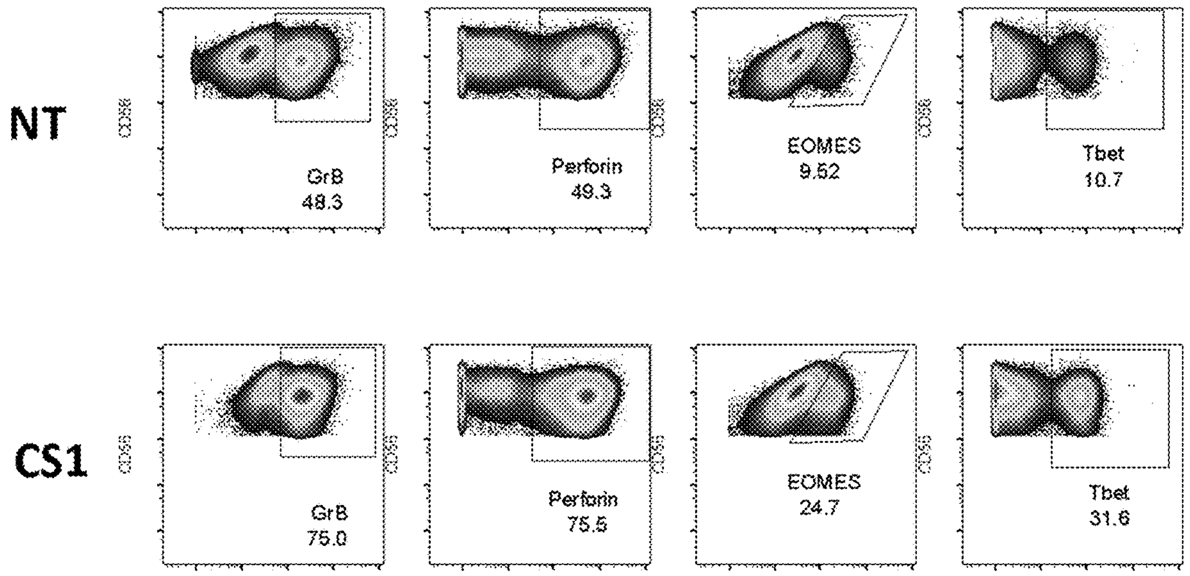

As an example of humanization scoring, T20 scores for the $V_L$ and $V_H$ sequences were evaluated before and after the humanization process for mCD19CAR vs hCD19CAR (FIGS. 10F-G). Indeed, higher T20 scores were observed for both processed fragments (humanized $V_L$ and $V_H$). Since the workflow can be iterative, the CAR humanization process can be used to produce CARs with lower immunogenicity, better persistence, and robust function.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Altschul, S. F., et al., *Nucleic Acids Res,* 25, 3389-3402, 1997.
Arnold, K., et al., *Bioinformatics,* 22, 195-201, 2006.
Benkert, P., et al., *Bioinformatics,* 27, 343-350, 2011.
Fedorov et al., *Sci. Transl. Medicine,* 5 (215), 2013.
Gao S H, et al., *BMC Biotechnology.* 13:55, 2013.
Guex, N. et al., *Electrophoresis,* 18, 2714-2723, 1997.
Marco Biasini et al., *Nucleic Acids Research,* 42 (W1): W252-W258, 2014.
Remmert, M., et al., *Nat Methods,* 9, 173-175, 2012.
Sela-Culang et al., *Frontiers in Immunology,* 4:302, 2013.
Shah et al., *PLOS One,* 8: e776781, 2013.
Singh et al., *Cancer Research,* 68:2961-2971, 2008.
Singh et al., *Cancer Research,* 71:3516-3527, 2011.
U.S. Pat. No. 7,109,304

SEQUENCE LISTING

```
Sequence total quantity: 69
SEQ ID NO: 1           moltype = DNA  length = 1062
FEATURE                Location/Qualifiers
source                 1..1062
                       mol_type = genomic DNA
                       organism = Homo sapiens
SEQUENCE: 1
ctggaagaga agaaaggcaa ttacgtcgtg accgaccacg gcagctgtgt gcgggcttgt  60
ggcgccgata gctacgagat ggaagaggac ggcgtgcgga agtgcaagaa gtgcgagggc  120
ccctgcagaa aagtgtgcaa cggcatcggc atcggagagt tcaaggatag cctgagcatc  180
aacgccacca acatcaagca cttcaagaac tgcaccagca tcagcggcga cctgcacatc  240
ctgcccgtgg cctttagagg cgacagcttc acccacaccc ccccactgga tccccaggaa  300
ctggacatcc tgaaaaccgt gaaagagatc acaggctttc tgctgattca ggcctggccc  360
gagaaccgga cagacctgca cgccttcgag aacctggaaa tcatcagagg ccggaccaag  420
cagcacggcc agttttctct ggccgtggtg tccctgaaca tcaccagcct gggcctgcgg  480
agcctgaaag aaatcagcga cggcgacgtg atcatctccg gcaacaagaa cctgtgctac  540
gccaacacca tcaattggaa gaagctgttc ggcacctccg gccagaaaac aaagatcatc  600
tctaaccggg gcgagaacag ctgcaaagcc accggacaag tgtgccacgc cctgtgtagc  660
cctgagggct gttggggacc cgagcccaga gattgcgtgt cctgccggaa tgtgtccaga  720
ggccgcgagt gcgtggacaa gtgcaacctg ctggaaggcg agccccgcga gtttgtggaa  780
aacagcgagt gcatccagtg ccaccccgag tgtctgcccc aggccatgaa cattacctgc  840
accggcagag gccccgacaa ctgtatccag tgcgcccact acatcgacgg cccccactgc  900
gtgaaaacct gtccagctgg cgtgatggga gagaacaaca ccctcgtgtg gaagtacgcc  960
gacgccggcc atgtgtgcca cctgtgtcac cccaattgca cctacggctg taccggccct  1020
ggcctggaag gctgtcctac caacggcccc aagatccctt ct                     1062

SEQ ID NO: 2           moltype = AA  length = 354
FEATURE                Location/Qualifiers
source                 1..354
                       mol_type = protein
                       organism = Homo sapiens
SEQUENCE: 2
LEEKKGNYVV TDHGSCVRAC GADSYEMEED GVRKCKKCEG PCRKVCNGIG IGEFKDSLSI  60
NATNIKHFKN CTSISGDLHI LPVAFRGDSF THTPPLDPQE LDILKTVKEI TGFLLIQAWP  120
ENRTDLHAFE NLEIIRGRTK QHGQFSLAVV SLNITSLGLR SLKEISDGDV IISGNKNLCY  180
ANTINWKKLF GTSGQKTKII SNRGENSCKA TGQVCHALCS PEGCWGPEPR DCVSCRNVSR  240
GRECVDKCNL LEGEPREFVE NSECIQCHPE CLPQAMNITC TGRGPDNCIQ CAHYIDGPHC  300
VKTCPAGVMG ENNTLVWKYA DAGHVCHLCH PNCTYGCTGP GLEGCPTNGP KIPS        354

SEQ ID NO: 3           moltype = DNA  length = 801
FEATURE                Location/Qualifiers
misc_feature           1..801
                       note = hCD19-scFv
source                 1..801
                       mol_type = other DNA
                       organism = synthetic construct
SEQUENCE: 3
atggagttcg gtttgagctg gctctttctt gttgctatcc tcaagggggt gcagtgttca  60
agggatatcc agatgactca gagccctagc tcccttagcg cgtccgtcgg cgaccgggtt  120
acaattactt gtcgcgcatc acaagacata agtaaatact tgaactggta tcaacaaaag  180
ccaggaaagg ttccaaaact cctcatctat cacacgagta gactccattc cggggtccct  240
gatcggttct caggctctgg ttctggaact gacttcactc tcacgatctc tagtctgcaa  300
cctgaggatg tcgctaccta ttattgccaa cagggaaaca ccctccctta cacatttggc  360
caaggtacca aagttgagat caagaggggc tccacatctg gagcgggaa accgggaagt  420
ggagaaggct caaccaaagg tgaggtgcaa cttgtagaga gtggtggagg cctggttcag  480
ccgggagggt ccctcagact tagttgcgcg gcttctggcg tttcactgcc ggactacggg  540
gtcagttggg ttaggcaggc gcctgggaaa ggacttgagt ggatcggcgt gatatggggt  600
agtgaaacaa cctactacaa tagtgctctt aaatcaaaat tcattatcag ccgagacaat  660
gctaagaact ccctctatct ccaaatgaat agtcttagag cagaagacac agccgtttat  720
tactgtgccc gccattatta ctatgggggc agctacgcaa tggattattg gggccaaggg  780
accctggtca cggtatcaag c                                            801

SEQ ID NO: 4           moltype = DNA  length = 324
FEATURE                Location/Qualifiers
misc_feature           1..324
                       note = hCD19-scFv VL
source                 1..324
                       mol_type = other DNA
                       organism = synthetic construct
SEQUENCE: 4
gatatccaga tgactcagag ccctagctcc cttagcgcgt ccgtcggcga ccgggttaca  60
attacttgtc gcgcatcaca agacataagt aaatacttga actggtatca acaaaagcca  120
ggaaaggttc caaaactcct catctatcac acgagtagac tccattccgg ggtccctgat  180
cggttctcag gctctggttc tggaactgac ttcactctca cgatctctag tctgcaacct  240
gaggatgtcg ctacctatta ttgccaacag ggaaacaccc tcccttacac atttggccaa  300
ggtaccaaag ttgagatcaa gagg                                         324

SEQ ID NO: 5           moltype = DNA  length = 360
```

```
FEATURE                 Location/Qualifiers
misc_feature            1..360
                        note = hCD19-scFv VH
source                  1..360
                        mol_type = other DNA
                        organism = synthetic construct
SEQUENCE: 5
gaggtgcaac ttgtagagag tggtggaggc ctggttcagc cgggagggtc cctcagactt  60
agttgcgcgg cttctggcgt ttcactgccg gactacgggg tcagttgggt taggcaggcg  120
cctgggaaag gacttgagtg gatcggcgtg atatggggta gtgaaacaac ctactacaat  180
agtgctctta aatcaaaatt cattatcagc cgagacaatg ctaagaactc cctctatctc  240
caaatgaata gtcttagagc agaagacaca gccgtttatt actgtgcccg ccattattac  300
tatgggggca gctacgcaat ggattattgg ggccaaggga ccctggtcac ggtatcaagc  360

SEQ ID NO: 6            moltype = AA  length = 267
FEATURE                 Location/Qualifiers
REGION                  1..267
                        note = hCD19-scFv
source                  1..267
                        mol_type = protein
                        organism = synthetic construct
SEQUENCE: 6
MEFGLSWLFL VAILKGVQCS RDIQMTQSPS SLSASVGDRV TITCRASQDI SKYLNWYQQK  60
PGKVPKLLIY HTSRLHSGVP DRFSGSGSGT DFTLTISSLQ PEDVATYYCQ QGNTLPYTFG  120
QGTKVEIKRG STSGSGKPGS GEGSTKGEVQ LVESGGGLVQ PGGSLRLSCA ASGVSLPDYG  180
VSWVRQAPGK GLEWIGVIWG SETTYYNSAL KSKFIISRDN AKNSLYLQMN SLRAEDTAVY  240
YCARHYYYGG SYAMDYWGQG TLVTVSS                                     267

SEQ ID NO: 7            moltype = AA  length = 108
FEATURE                 Location/Qualifiers
REGION                  1..108
                        note = hCD19-scFv VL
source                  1..108
                        mol_type = protein
                        organism = synthetic construct
SEQUENCE: 7
DIQMTQSPSS LSASVGDRVT ITCRASQDIS KYLNWYQQKP GKVPKLLIYH TSRLHSGVPD  60
RFSGSGSGTD FTLTISSLQP EDVATYYCQQ GNTLPYTFGQ GTKVEIKR              108

SEQ ID NO: 8            moltype = AA  length = 120
FEATURE                 Location/Qualifiers
REGION                  1..120
                        note = hCD19-scFv VH
source                  1..120
                        mol_type = protein
                        organism = synthetic construct
SEQUENCE: 8
EVQLVESGGG LVQPGGSLRL SCAASGVSLP DYGVSWVRQA PGKGLEWIGV IWGSETTYYN  60
SALKSKFIIS RDNAKNSLYL QMNSLRAEDT AVYYCARHYY YGGSYAMDYW GQGTLVTVSS  120

SEQ ID NO: 9            moltype = DNA  length = 786
FEATURE                 Location/Qualifiers
misc_feature            1..786
                        note = hCD123-scFv
source                  1..786
                        mol_type = other DNA
                        organism = synthetic construct
SEQUENCE: 9
atggaattcg ggctttcatg gttgttcctc gttgcgatac ttaaaggcgt tcagtgcagt  60
agagacattc agatgaccca aagccctagt agcctctccg ccagtgtggg tgaccgcgtg  120
actattacgt gccgagcaag caagagtatt agcaaagatt tggcatggta ccagcagaaa  180
ccaggcaagg tccctaagtt gcttatatat agcgggtcta cactccaatc tggagtgccg  240
gatcgcttct caggttccgg atcaggaacc gatttcactc ttacaatttc ctctctgcaa  300
ccggaggacg tggcaacata ctattgccag cagcataaca aatatcccta tactttcggt  360
caaggtacaa aagtagaaat aaaacgaggt tccacctccg ggagtgggaa gcccggctcc  420
ggcgaaggat ccaccaaagg cgaggtacag ctcgttgaaa gcgggggcgg tctcgtccaa  480
ccaggagggt ctcttcgact ttcttgtgct gcaagtgggt acacgtttac ttcctattgg  540
atgaattggg ttcggcaagc ccccggtaaa gggcttgaat ggatagggag gatagacccc  600
tacgattctg agacgcatta taatcagaaa ttcaaagata agttcataat aagcagagac  660
aatgcaaaaa atagtttgta cctccagatg aatagtcttc gggcagaaga cacagcggta  720
tattactgtg ctcggggtaa ctgggatgat tactggggtc agggaactct ggttactgtg  780
tctagc                                                            786

SEQ ID NO: 10           moltype = DNA  length = 324
FEATURE                 Location/Qualifiers
misc_feature            1..324
                        note = hCD123-scFv VL
```

```
source                  1..324
                        mol_type = other DNA
                        organism = synthetic construct
SEQUENCE: 10
gacattcaga tgacccaaag ccctagtagc ctctccgcca gtgtgggtga ccgcgtgact  60
attacgtgcc gagcaagcaa gagtattagc aaagatttgg catggtacca gcagaaacca  120
ggcaaggtcc ctaagttgct tatatatagc gggtctacac tccaatctgg agtgccggat  180
cgcttctcag gttccggatc aggaaccgat ttcactctta caatttcctc tctgcaaccg  240
gaggacgtgg caacatacta ttgccagcag cataacaaat atccctatac tttcggtcaa  300
ggtacaaaag tagaaataaa acga                                         324

SEQ ID NO: 11           moltype = DNA  length = 345
FEATURE                 Location/Qualifiers
misc_feature            1..345
                        note = hCD123-scFv VH
source                  1..345
                        mol_type = other DNA
                        organism = synthetic construct
SEQUENCE: 11
gaggtacagc tcgttgaaag cgggggcggt ctcgtccaac caggagggtc tcttcgactt  60
tcttgtgctg caagtgggta cacgtttact tcctattgga tgaattgggt tcggcaagcc  120
cccggtaaag ggcttgaatg gatagggagg atagacccct acgattctga gacgcattat  180
aatcagaaat tcaaagataa gttcataata agcagagaca atgcaaaaaa tagtttgtac  240
ctccagatga atagtcttcg ggcagaagac acagcggtat attactgtgc tcggggtaac  300
tgggatgatt actggggtca gggaactctg gttactgtgt ctagc                  345

SEQ ID NO: 12           moltype = AA  length = 262
FEATURE                 Location/Qualifiers
REGION                  1..262
                        note = hCD123-scFv
source                  1..262
                        mol_type = protein
                        organism = synthetic construct
SEQUENCE: 12
MEFGLSWLFL VAILKGVQCS RDIQMTQSPS SLSASVGDRV TITCRASKSI SKDLAWYQQK  60
PGKVPKLLIY SGSTLQSGVP DRFSGSGSGT DFTLTISSLQ PEDVATYYCQ QHNKYPYTFG  120
QGTKVEIKRG STSGSGKPGS GEGSTKGEVQ LVESGGGLVQ PGGSLRLSCA ASGYTFTSYW  180
MNWVRQAPGK GLEWIGRIDP YDSETHYNQK FKDKFIISRD NAKNSLYLQM NSLRAEDTAV  240
YYCARGNWDD YWGQGTLVTV SS                                           262

SEQ ID NO: 13           moltype = AA  length = 108
FEATURE                 Location/Qualifiers
REGION                  1..108
                        note = hCD123-scFv VL
source                  1..108
                        mol_type = protein
                        organism = synthetic construct
SEQUENCE: 13
DIQMTQSPSS LSASVGDRVT ITCRASKSIS KDLAWYQQKP GKVPKLLIYS GSTLQSGVPD  60
RFSGSGSGTD FTLTISSLQP EDVATYYCQQ HNKYPYTFGQ GTKVEIKR               108

SEQ ID NO: 14           moltype = AA  length = 115
FEATURE                 Location/Qualifiers
REGION                  1..115
                        note = hCD123-scFv VH
source                  1..115
                        mol_type = protein
                        organism = synthetic construct
SEQUENCE: 14
EVQLVESGGG LVQPGGSLRL SCAASGYTFT SYWMNWVRQA PGKGLEWIGR IDPYDSETHY  60
NQKFKDKFII SRDNAKNSLY LQMNSLRAED TAVYYCARGN WDDYWGQGTL VTVSS       115

SEQ ID NO: 15           moltype = DNA  length = 777
FEATURE                 Location/Qualifiers
misc_feature            1..777
                        note = hMeso-scFv
source                  1..777
                        mol_type = other DNA
                        organism = synthetic construct
SEQUENCE: 15
atggagttcg gcctttcttg gctgtttttg gtcgcaatat tgaagggcgt tcagtgttca  60
agggacatac agatgacgca gtcacctagc tctctttcag cctctgtggg agaccgcgtt  120
acaattacgt gttctgcttc tagttcagtg tcttacatgc attggtacca gcaaaaaccc  180
ggcaaggttc caaagctcct tatatacgat acgtccaaac tggcttcagg cgtgccagac  240
aggtttagtg gatctgggag cggcactgac ttcacactta caatatccag tctgcaaccc  300
gaagatgttg cgacatacta ttgtcagcaa tggagcggct atccgctcac cggacagggg  360
acaaaagtgg agataaagcg gggctccacc agtggttccg ggaagcctgg tagtggtgag  420
ggttctacga aaggcgaagt gcagttggtg gagtctggtg gcgggcttgt tcaacccggt  480
ggttctctca ggcttagctg tgcagcctct gggtacacaa tgaattgggt aaggcaagcg  540
```

```
cctggaaagg gccttgagtg gatcggtttg ataaccccat acaacggagc ttcaagttac  600
aaccaaaagt tccgcgggaa gtttattata agcagggata acgcaaagaa cagcctctat  660
cttcaaatga actcactccg ggctgaagac acagccgtct attattgtgc ccggggggc   720
tacgacggac gagggttcga ttactggggt cagggcacac tcgtgaccgt gtcaagc     777

SEQ ID NO: 16          moltype = DNA  length = 318
FEATURE                Location/Qualifiers
misc_feature           1..318
                       note = hMeso-scFv VL
source                 1..318
                       mol_type = other DNA
                       organism = synthetic construct
SEQUENCE: 16
gacatacaga tgacgcagtc acctagctct ctttcagcct ctgtgggaga ccgcgttaca  60
attacgtgtt ctgcttctag ttcagtgtct tacatgcatt ggtaccagca aaaacccggc  120
aaggttccaa agctccttat atacgatacg tccaaactgg cttcaggcgt gccagacagg  180
tttagtggat ctgggagcgg cactgacttc acacttacaa tatccagtct gcaacccgaa  240
gatgttgcga catactattg tcagcaatgg agcggctatc cgctcaccgg acaggggaca  300
aaagtggaga taaagcgg                                                318

SEQ ID NO: 17          moltype = DNA  length = 342
FEATURE                Location/Qualifiers
misc_feature           1..342
                       note = hMeso-scFv VH
source                 1..342
                       mol_type = other DNA
                       organism = synthetic construct
SEQUENCE: 17
gaagtgcagt tggtggagtc tggtggcggg cttgttcaac ccggtggttc tctcaggctt  60
agctgtgcag cctctgggta cacaatgaat tgggtaaggc aagcgcctgg aaagggcctt  120
gagtggatcg gtttgataac cccatacaac ggagcttcaa gttacaacca aaagttccgc  180
gggaagttta ttataagcag ggataacgca aagaacagcc tctatcttca aatgaactca  240
ctccgggctg aagacacagc cgtctattat tgtgcccggg ggggctacga cggacgaggg  300
ttcgattact ggggtcaggg cacactcgtg accgtgtcaa gc                     342

SEQ ID NO: 18          moltype = AA  length = 259
FEATURE                Location/Qualifiers
REGION                 1..259
                       note = hMeso-scFv
source                 1..259
                       mol_type = protein
                       organism = synthetic construct
SEQUENCE: 18
MEFGLSWLFL VAILKGVQCS RDIQMTQSPS SLSASVGDRV TITCSASSSV SYMHWYQQKP  60
GKVPKLLIYD TSKLASGVPD RFSGSGSGTD FTLTISSLQP EDVATYYCQQ WSGYPLTGQG  120
TKVEIKRGST SGSGKPGSGE GSTKGEVQLV ESGGGLVQPG GSLRLSCAAS GYTMNWVRQA  180
PGKGLEWIGL ITPYNGASSY NQKFRGKFII SRDNAKNSLY LQMNSLRAED TAVYYCARGG  240
YDGRGFDYWG QGTLVTVSS                                               259

SEQ ID NO: 19          moltype = AA  length = 106
FEATURE                Location/Qualifiers
REGION                 1..106
                       note = hMeso-scFv VL
source                 1..106
                       mol_type = protein
                       organism = synthetic construct
SEQUENCE: 19
DIQMTQSPSS LSASVGDRVT ITCSASSSVS YMHWYQQKPG KVPKLLIYDT SKLASGVPDR  60
FSGSGSGTDF TLTISSLQPE DVATYYCQQW SGYPLTGQGT KVEIKR                 106

SEQ ID NO: 20          moltype = AA  length = 114
FEATURE                Location/Qualifiers
REGION                 1..114
                       note = hMeso-scFv VH
source                 1..114
                       mol_type = protein
                       organism = synthetic construct
SEQUENCE: 20
EVQLVESGGG LVQPGGSLRL SCAASGYTMN WVRQAPGKGL EWIGLITPYN GASSYNQKFR  60
GKFIISRDNA KNSLYLQMNS LRAEDTAVYY CARGGYDGRG FDYWGQGTLV TVSS        114

SEQ ID NO: 21          moltype = DNA  length = 798
FEATURE                Location/Qualifiers
misc_feature           1..798
                       note = hROR1-scFv
source                 1..798
                       mol_type = other DNA
                       organism = synthetic construct
```

```
SEQUENCE: 21
atggagttcg gacttagttg gcttttcctc gtcgccatac tcaaaggtgt acaatgctca  60
cgcgatatac aaatgacgca gagtccatcc tcactgtctg cctcagtagg cgacagggtc  120
acaataacct gtaaagcaag cccggatatc aactcttacc tcagttggtt ccaacagaaa  180
ccaggaaagg tgccgaagtt gttgatttac cgcgcaaacc gcctcgttga cggcgtgcca  240
gataggtttt ctggcagcgg gagcggcact gactttacgc tcactatatc aagcctgcag  300
ccggaggacg tagcaactta ctattgcctc caatacgacg aattccctta cacgttcggg  360
caaggaacta aagttgaaat aaaaagagga agcacaagtg gttctggaaa acccggttcc  420
ggtgagggca gtaccaaagg agaggtgcag ttggtagagt ctggtggggg tttggtgcaa  480
cccggagggt ctctgaggtt gtcttgcgcg gcatccggct ttactttttc ctcatatgcg  540
atgtcatggg tacgacaggc cccaggcaag ggactggagt ggatcgcatc tatttcacga  600
ggagggacga catattaccc ggattcagtg aagggcaaat tcataatttc acgcgataac  660
gccaagaact ccctctacct gcaaatgaac agtcttagag cggaagatac ggctgtgtat  720
tactgtgcgc gatatgacta cgatggatat tacgcgatgg attattgggg acaaggtaca  780
ctggtaaccg tttccagc                                              798

SEQ ID NO: 22           moltype = DNA  length = 324
FEATURE                 Location/Qualifiers
misc_feature            1..324
                        note = hROR1-scFv VL
source                  1..324
                        mol_type = other DNA
                        organism = synthetic construct
SEQUENCE: 22
gatatacaaa tgacgcagag tccatcctca ctgtctgcct cagtaggcga cagggtcaca  60
ataacctgta aagcaagccc ggatatcaac tcttacctca gttggttcca acagaaacca  120
ggaaaggtgc cgaagttgtt gatttaccgc gcaaaccgcc tcgttgacgg cgtgccagat  180
aggttttctg gcagcgggag cggcactgac tttacgctca ctatatcaag cctgcagccg  240
gaggacgtag caacttacta ttgcctccaa tacgacgaat tcccttacac gttcgggcaa  300
ggaactaaag ttgaaataaa aaga                                       324

SEQ ID NO: 23           moltype = DNA  length = 357
FEATURE                 Location/Qualifiers
misc_feature            1..357
                        note = hROR1-scFv VH
source                  1..357
                        mol_type = other DNA
                        organism = synthetic construct
SEQUENCE: 23
gaggtgcagt tggtagagtc tggtgggggt ttggtgcaac ccggagggtc tctgaggttg  60
tcttgcgcgg catccggctt tactttttcc tcatatgcga tgtcatgggt acgacaggcc  120
ccaggcaagg gactggagtg gatcgcatct atttcacgag gagggacgac atattacccg  180
gattcagtga agggcaaatt cataatttca cgcgataacg ccaagaactc cctctacctg  240
caaatgaaca gtcttagagc ggaagatacg gctgtgtatt actgtgcgcg atatgactac  300
gatggatatt acgcgatgga ttattgggga caaggtacac tggtaaccgt ttccagc    357

SEQ ID NO: 24           moltype = AA  length = 266
FEATURE                 Location/Qualifiers
REGION                  1..266
                        note = hROR1-scFv
source                  1..266
                        mol_type = protein
                        organism = synthetic construct
SEQUENCE: 24
MEFGLSWLFL VAILKGVQCS RDIQMTQSPS SLSASVGDRV TITCKASPDI NSYLSWFQQK  60
PGKVPKLLIY RANRLVDGVP DRFSGSGSGT DFTLTISSLQ PEDVATYYCL QYDEFPYTFG  120
QGTKVEIKRG STSGSGKPGS GEGSTKGEVQ LVESGGGLVQ PGGSLRLSCA ASGFTFSSYA  180
MSWVRQAPGK GLEWIASISR GGTTYYPDSV KGKFIISRDN AKNSLYLQMN SLRAEDTAVY  240
YCARYDYDGY YAMDYWGQGT LVTVSS                                     266

SEQ ID NO: 25           moltype = AA  length = 108
FEATURE                 Location/Qualifiers
REGION                  1..108
                        note = hROR1-scFv VL
source                  1..108
                        mol_type = protein
                        organism = synthetic construct
SEQUENCE: 25
DIQMTQSPSS LSASVGDRVT ITCKASPDIN SYLSWFQQKP GKVPKLLIYR ANRLVDGVPD  60
RFSGSGSGTD FTLTISSLQP EDVATYYCLQ YDEFPYTFGQ GTKVEIKR             108

SEQ ID NO: 26           moltype = AA  length = 119
FEATURE                 Location/Qualifiers
REGION                  1..119
                        note = hROR1-scFv VH
source                  1..119
                        mol_type = protein
                        organism = synthetic construct
```

```
SEQUENCE: 26
EVQLVESGGG LVQPGGSLRL SCAASGFTFS SYAMSWVRQA PGKGLEWIAS ISRGGTTYYP  60
DSVKGKFIIS RDNAKNSLYL QMNSLRAEDT AVYYCARYDY DGYYAMDYWG QGTLVTVSS   119

SEQ ID NO: 27          moltype = DNA  length = 792
FEATURE                Location/Qualifiers
misc_feature           1..792
                       note = hCD5-scFv
source                 1..792
                       mol_type = other DNA
                       organism = synthetic construct
SEQUENCE: 27
atggagttcg gtctcagttg gctgtttttg gttgctatct tgaagggcgt ccaatgcagc  60
cgggacatcc agatgaccca gtctccctct agcatgtcag cgagtcttgg tgatcgagtg  120
acgattacct gcagagcctc tcaagatata aacagctatc tttcatggtt ccaacagaag  180
ccggggaagt ccccaaaaac tctcatatac agggcgaatc gactcgtaga cggtgtgcct  240
tcaaggtttt ccgggagtgg tagtggcaca gattacacac ttacaatctc ttcattgcag  300
tatgaggatt tcgggatcta ctactgtcaa cagtacgacg aatccccatg gacgtttggg  360
ggcgggacca aacttgagat aaaagggagc acatctggaa gtggtaaacc tgggtcaggg  420
gagggttcca caaaaggaca aattcaactt gtccaaagcg gtcctggtct taagaagcct  480
ggagggtctg tcaggataag ttgtgcggca tccggctaca ccttcaccaa ctatgggatg  540
aactgggtga aacaagcgcc tgggaaaggt cttcgatgga tgggctggat taatacccac  600
actggagagc ccacttacgc tgatgatttc aaaggacgat ttaccttctc cttggatact  660
tccaagagta ccgcgtactt gcaaatcaac agtctccggg ctgaagacac ggccacatac  720
ttctgtacgc ggagagggta tgactggtat tttgatgtgt ggggtcaggg aacaaccgtg  780
actgtttcaa gc                                                      792

SEQ ID NO: 28          moltype = DNA  length = 321
FEATURE                Location/Qualifiers
misc_feature           1..321
                       note = hCD5-scFv VL
source                 1..321
                       mol_type = other DNA
                       organism = synthetic construct
SEQUENCE: 28
gacatccaga tgacccagtc tccctctagc atgtcagcga gtcttggtga tcgagtgacg  60
attacctgca gagcctctca agatataaac agctatcttt catggttcca acagaagccg  120
gggaagtccc caaaaactct catatacagg gcgaatcgac tcgtagacgg tgtgccttca  180
aggttttccg ggagtggtag tggcacagat tacacactta caatctcttc attgcagtat  240
gaggatttcg ggatctacta ctgtcaacag tacgacgaat ccccatggac gtttgggggc  300
gggaccaaac ttgagataaa a                                            321

SEQ ID NO: 29          moltype = DNA  length = 354
FEATURE                Location/Qualifiers
misc_feature           1..354
                       note = hCD5-scFv VH
source                 1..354
                       mol_type = other DNA
                       organism = synthetic construct
SEQUENCE: 29
caaattcaac ttgtccaaag cggtcctggt cttaagaagc ctggagggtc tgtcaggata  60
agttgtgcgg catccggcta caccttcacc aactatggga tgaactgggt gaaacaagcg  120
cctgggaaag gtcttcgatg gatgggctgg attaataccc acactggaga gcccacttac  180
gctgatgatt tcaaaggacg atttaccttc tccttggata cttccaagag taccgcgtac  240
ttgcaaatca acagtctccg ggctgaagac acggccacat acttctgtac gcggagaggg  300
tatgactggt attttgatgt gtggggtcag ggaacaaccg tgactgtttc aagc        354

SEQ ID NO: 30          moltype = AA  length = 264
FEATURE                Location/Qualifiers
REGION                 1..264
                       note = hCD5-scFv
source                 1..264
                       mol_type = protein
                       organism = synthetic construct
SEQUENCE: 30
MEFGLSWLFL VAILKGVQCS RDIQMTQSPS SMSASLGDRV TITCRASQDI NSYLSWFQQK  60
PGKSPKTLIY RANRLVDGVP SRFSGSGSGT DYTLTISSLQ YEDFGIYYCQ QYDESPWTFG  120
GGTKLEIKGS TSGSGKPGSG EGSTKGQIQL VQSGPGLKKP GGSVRISCAA SGYTFTNYGM  180
NWVKQAPGKG LRWMGWINTH TGEPTYADDF KGRFTFSLDT SKSTAYLQIN SLRAEDTATY  240
FCTRRGYDWY FDVWGQGTTV TVSS                                         264

SEQ ID NO: 31          moltype = AA  length = 107
FEATURE                Location/Qualifiers
REGION                 1..107
                       note = hCD5-scFv VL
source                 1..107
                       mol_type = protein
                       organism = synthetic construct
```

```
SEQUENCE: 31
DIQMTQSPSS MSASLGDRVT ITCRASQDIN SYLSWFQQKP GKSPKTLIYR ANRLVDGVPS  60
RFSGSGSGTD YTLTISSLQY EDFGIYYCQQ YDESPWTFGG GTKLEIK                107

SEQ ID NO: 32          moltype = AA  length = 118
FEATURE                Location/Qualifiers
REGION                 1..118
                       note = hCD5-scFv VH
source                 1..118
                       mol_type = protein
                       organism = synthetic construct
SEQUENCE: 32
QIQLVQSGPG LKKPGGSVRI SCAASGYTFT NYGMNWVKQA PGKGLRWMGW INTHTGEPTY  60
ADDFKGRFTF SLDTSKSTAY LQINSLRAED TATYFCTRRG YDWYFDVWGQ GTTVTVSS    118

SEQ ID NO: 33          moltype = DNA  length = 10253
FEATURE                Location/Qualifiers
misc_feature           1..10253
                       note = hCD19-CAR
source                 1..10253
                       mol_type = other DNA
                       organism = synthetic construct
SEQUENCE: 33
aatgaaagac cccacctgta ggtttggcaa gctagcttaa gtaacgccat tttgcaaggc  60
atggaaaaat acataactga gaatagaaaa gttcagatca aggtcaggaa cagatggaac  120
agctgaatat gggccaaaca ggatatctgt ggtaagcagt tcctgccccg gctcagggcc  180
aagaacagat ggaacagctg aatatgggcc aaacaggata tctgtggtaa gcagttcctg  240
ccccggctca gggccaagaa cagatggtcc ccagatgcgg tccagccctc agcagtttct  300
agagaaccat cagatgtttc cagggtgccc caaggacctg aaatgaccct gtgccttatt  360
tgaactaacc aatcagttcg cttctcgctt ctgttcgcgc gcttatgctc cccgagctca  420
ataaaagagc ccacaacccc tcactcgggg cgccagtcct ccgattgact gagtcgcccg  480
ggtacccgtg tatccaataa accctcttgc agttgcatcc gacttgtggt ctcgctgttc  540
cttgggaggg tctcctctga gtgattgact acccgtcagc gggggtcttt catttggggg  600
ctcgtccggg atcgggagac ccctgcccag ggaccaccga cccaccaccg ggaggtaagc  660
tggccagcaa cttatctgtg tctgtccgat tgtctagtgt ctatgactga ttttatgcgc  720
ctgcgtcggt actagttagc taactagctc tgtatctggc ggacccgtgg tggaactgac  780
gagttcggaa cacccggccg caaccctggg agacgtccca gggacttcgg gggccgtttt  840
tgtggcccga cctgagtcct aaaatcccga tcgtttagga ctctttggtg cacccccctt  900
agaggaggga tatgtggttc tggtaggaga cgagaaccta aaacagttcc cgcctccgtc  960
tgaatttttg ctttcggttt gggaccgaag ccgcgccgcg cgtcttgtct gctgcagcat  1020
cgttctgtgt tgtctctgtc tgactgtgtt tctgtatttg tctgaaaata tgggcccggg  1080
ctagcctgtt accactccct taagtttgac cttaggtcac tggaaagatg tcgagcggat  1140
cgctcacaac cagtcggtag atgtcaagaa gagacgttgg gttaccttct gctctgcaga  1200
atggccaacc tttaacgtcg gatggccgcg agacggcacc tttaaccgag acctcatcac  1260
ccaggttaag atcaaggtct tttcacctgg cccgcatgga cacccagacc aggtggggta  1320
catcgtgacc tgggaagcct tggcttttga cccccctccc tgggtcaagc cctttgtaca  1380
ccctaagcct ccgcctcctc ttcctccatc cgccccgtct ctcccccttg aacctcctcg  1440
ttcgaccccg cctcgatcct ccctttatcc agccctcact ccttctctag gcgcccccat  1500
atggccatat gagatcttat atggggcacc cccgcccctt gtaaacttcc ctgaccctga  1560
catgacaaga gttactaaca gcccctctct ccaagctcac ttacaggctc tctacttagt  1620
ccagcacgaa gtctggagac ctctggcggc agcctaccaa gaacaactgg accgaccggt  1680
ggtacctcac ccttaccgag tcggcgacac agtgtgggtc cgccgacacc agactaagaa  1740
cctagaacct cgctggaaag gaccttacac agtcctgctg accacccccca ccgccctcaa  1800
agtagacggc atcgcagctt ggatacacgc cgcccacgtg aaggctgccg accccggggg  1860
tggaccatcc tctagactgc catgctcgag ggagtgcagg tggaaaccat ctccccagga  1920
gacgggcgca ccttccccaa gcgcggccag acctgcgtgg tgcactacac cgggatgctt  1980
gaagatggaa agaaagttga ttcctcccgg gacagaaaca agccctttaa gtttatgcta  2040
ggcaagcagg aggtgatccg aggctgggaa gaaggggttg cccagatgag tgtgggtcag  2100
agagccaaac tgactatatc tccagattat gcctatggtg ccactgggca cccaggcatc  2160
atcccaccac atgccactct cgtcttcgat gtggagcttc taaaactgga atctggcggt  2220
ggatccggag tcgacggatt tggtgatgtc ggtgctcttg agagtttgag ggaaatgca  2280
gatttggctt acatcctgag catggagccc tgtggccact gcctcattat caacaatgtg  2340
aacttctgcc gtgagtccgg gctccgcacc cgcactggct ccaacatcga ctgtgagaag  2400
ttgcggcgtc gcttctcctc gctgcatttc atggtggagg tgaagggcga cctgactgcc  2460
aagaaaatgg tgctggcttt gctggagctg gcgcagcagg accacggtgc tctggactgc  2520
tgcgtggtgg tcattctctc tcacggctgt caggccagcc acctgcagtt cccaggggct  2580
gtctacggca cagatggatg ccctgtgtcg gtcgagaaga ttgtgaacat cttcaatggg  2640
accagctgcc ccagcctggg agggaagccc aagctctttt tcatccaggc ctgtggtggg  2700
gagcagaaag accatgggtt tgaggtggcc tccacttccc ctgaagacga gtcccctggc  2760
agtaaccccg agccagatgc caccccgttc caggaaggtt tgaggacctt cgaccagctg  2820
gacgccatat ctagtttgcc cacacccagt gacatctttg tgtcctactc tactttccca  2880
ggttttgttt cctggaggga ccccaagagt ggctcctggt acgttgagac cctggacgac  2940
atctttgagc agtgggctca ctctgaagac ctgcagtccc tcctgcttag ggtcgctaat  3000
gctgtttcgg tgaaagggat ttataaacag atgcctggtt gctttaattt cctccggaaa  3060
aaacttttct ttaaaacatc agctagcaga gccgagggca ggggaagtct tctaacatgc  3120
ggggacgtgg aggaaaatcc cgggcccatg gagttcggtt tgagctggct ctttcttgtt  3180
gctatcctca agggggtgca gtgttcaagg gatatccaga tgactcagag ccctagctcc  3240
cttagcgcgt ccgtcggcga ccgggttaca attacttgtc gcgcatcaca agacataagt  3300
aaatacttga actggtatca acaaaagcca ggaaaggttc caaaactcct catctatcac  3360
```

-continued

```
acgagtagac tccattccgg ggtccctgat cggttctcag gctctggttc tggaactgac  3420
ttcactctca cgatctctag tctgcaacct gaggatgtcg ctacctatta ttgccaacag  3480
ggaaacaccc tcccttacac atttggccaa ggtaccaaag ttgagatcaa gaggggctcc  3540
acatctggga gcgggaaacc gggaagtgga gaaggctcaa ccaaaggtga ggtgcaactt  3600
gtagagagtg gtggaggcct ggttcagccg ggagggtccc tcagacttag ttgcgcggct  3660
tctggcgttt cactgccgga ctacggggtc agttgggtta ggcaggcgcc tgggaaagga  3720
cttgagtgga tcggcgtgat atggggtagt gaaacaacct actacaatag tgctcttaaa  3780
tcaaaattca ttatcagccg agacaatgct aagaactccc tctatctcca aatgaatagt  3840
cttagagcag aagacacagc cgtttattac tgtgcccgcc attattacta tgggggcagc  3900
tacgcaatgg attattgggg ccaagggacc ctggtcacgg tatcaagcta cgtcaccgtc  3960
tcttcacagg atcccgccga gcccaaatct cctgacaaaa ctcacacatg cccaccgtgc  4020
ccagcacctg aactcctggg gggaccgtca gtcttcctct tccccccaaa acccaaggac  4080
accctcatga tctcccggac ccctgaggtc acatgcgtgg tggtggacgt gagccacgaa  4140
gaccctgagg tcaagttcaa ctggtacgtg gacggcgtgg aggtgcataa tgccaagaca  4200
aagccgcggg aggagcagta caacagcacg taccgtgtgg tcagcgtcct caccgtcctg  4260
caccaggact ggctgaatgg caaggagtac aagtgcaagg tctccaacaa agccctccca  4320
gcccccatcg agaaaaccat ctccaaagcc aaagggcagc cccgagaacc acaggtgtac  4380
accctgcccc catcccggga tgagctgacc aagaaccagg tcagcctgac ctgcctggtc  4440
aaaggcttct atcccagcga catcgccgtg gagtgggaga gcaatgggca accggagaac  4500
aactacaaga ccacgcctcc cgtgctggac tccgacggct ccttcttcct ctacagcaag  4560
ctcaccgtgg acaagagcag gtggcagcag gggaacgtct tctcatgctc cgtgatgcat  4620
gaggctctgc acaaccacta cacgcagaag agcctctccc tgtctccggg taaaaaagat  4680
cccaaatttt gggtgctggt ggtggttggt ggagtcctgg cttgctatag cttgctagta  4740
acagtggcct ttattatttt ctgggtgagg agtaagagga gcaggctcct gcacagtgac  4800
tacatgaaca tgactccccg ccgccccggg cccacccgca agcattacca gccctatgcc  4860
ccaccacgcg acttcgcagc ctatcgctcc agagtgaagt tcagcaggag cgcagacgcc  4920
cccgcgtacc agcagggcca gaaccagctc tataacgagc tcaatctagg acgaagagag  4980
gagtacgatg ttttggacaa gagacgtggc cgggaccctg agatgggggg aaagccgaga  5040
aggaagaacc ctcaggaagg cctgtacaat gaactgcaga aagataagat ggcggaggcc  5100
tacagtgaga ttgggatgaa aggcgagcgc cggaggggca aggggcacga tggcctttac  5160
cagggtctca gtacagccac caaggacacc tacgacgccc ttcacatgca ggccctgccc  5220
cctcgcggac cgcagtgtac taattatgct ctcttgaaat tggctggaga tgttgagagc  5280
aatcccgggc ccatgcggat cagcaagccc cacctgcgga gcatcagcat ccagtgctac  5340
ctgtgcctgc tgctgaacag ccacttcctg accgaggccg gcatccacgt gttcatcctg  5400
ggctgcttca gcgccggact gcccaagacc gaggccaact gggtgaacgt gatcagcgac  5460
ctgaagaaga tcgaggacct gatccagagc atgcacatcg acgccaccct gtacaccgag  5520
agcgacgtgc accccagctg caaggtgacc gccatgaagt gctttctgct ggaactgcag  5580
gtgatcagcc tggaaagcgg cgacgccagc atccacgaca ccgtggagaa cctgatcatc  5640
ctggccaaca acagcctgag cagcaacggc aacgtgaccg agagcggctg caaagagtgc  5700
gaggaactgg aagagaagaa catcaaagag tttctgcaga gcttcgtgca catcgtgcag  5760
atgttcatca acaccagctg acgcgtcatc atcgatccgg attagtccaa tttgttaaag  5820
acaggatatc agtggtccag gctctagttt tgactcaaca atatcaccag ctgaagccta  5880
tagagtacga gccatagata aaataaaaga ttttatttag tctccagaaa aaggggggaa  5940
tgaaagaccc cacctgtagg tttggcaagc tagcttaagt aacgccattt tgcaaggcat  6000
ggaaaaatac ataactgaga atagagaagt tcagatcaag gtcaggaaca gatggaacag  6060
ctgaatatgg gccaaacagg atatctgtgg taagcagttc ctgccccggc tcagggccaa  6120
gaacagatgg aacagctgaa tatgggccaa acaggatatc tgtggtaagc agttcctgcc  6180
ccggctcagg gccaagaaca gatggtcccc agatgcggtc cagccctcag cagtttctag  6240
agaaccatca gatgtttcca gggtgcccca aggacctgaa atgaccctgt gccttatttg  6300
aactaaccaa tcagttcgct tctcgcttct gttcgcgcgc ttctgctccc cgagctcaat  6360
aaaagagccc acaacccctc actcggggcg ccagtcctcc gattgactga gtcgcccggg  6420
tacccgtgta tccaataaac cctcttgcag ttgcatccga cttgtggtct cgctgttcct  6480
tgggagggtc tcctctgagt gattgactac ccgtcagcgg gggtctttca cacatgcagc  6540
atgtatcaaa attaatttgg ttttttttct taagtattta cattaaatgg ccatagtact  6600
taaagttaca ttggcttcct tgaaataaac atggagtatt cagaatgtgt cataaatatt  6660
tctaatttta agatagtatc tccattggct ttctactttt tcttttattt tttttgtcc  6720
tctgtcttcc atttgttgtt gttgttgttt gtttgtttgt ttgttggttg gttggttaat  6780
tttttttaa agatcctaca ctatagttca agctagacta ttagctactc tgtaacccag  6840
ggtgaccttg aagtcatggg tagcctgctg ttttagcctt cccacatcta agattacagg  6900
tatgagctat catttttggt atattgattg attgattgat tgatgtgtgt gtgtgtgatt  6960
gtgtttgtgt gtgtgactgt gaaaatgtgt gtatgggtgt gtgtgaatgt gtgtatgtat  7020
gtgtgtgtgt gagtgtgtgt gtgtgtgtgt gcatgtgtgt gtgtgtgact gtgtctatgt  7080
gtatgactgt gtgtgtgtgt gtgtgtgtgt gtgtgtgtgt gtgtgtgtgt gtgttgtgaa  7140
aaaatattct atggtagtga gagccaacgc tccggctcag gtgtcaggtt ggtttttgag  7200
acagagtctt tcacttagct tggaattcac tggccgtcgt tttacaacgt cgtgactggg  7260
aaaaccctgg cgttacccaa cttaatcgcc ttgcagcaca tccccctttc gccagctggc  7320
gtaatagcga agaggcccgc accgatcgcc cttcccaaca gttgcgcagc ctgaatggcg  7380
aatggcgcct gatgcggtat tttctcctta cgcatctgtg cggtatttca caccgcatat  7440
ggtgcactct cagtacaatc tgctctgatg ccgcatagtt aagccagccc cgacacccgc  7500
caacacccgc tgacgcgccc tgacgggctt gtctgctccc ggcatccgct tacagacaag  7560
ctgtgaccgt ctccgggagc tgcatgtgtc agaggttttc accgtcatca ccgaaacgcg  7620
cgagacgaaa gggcctcgtg atacgcctat ttttataggt taatgtcatg ataataatgg  7680
tttcttagac gtcaggtggc acttttcggg gaaatgtgcg cggaacccct atttgtttat  7740
ttttctaaat acattcaaat atgtatccgc tcatgagaca ataaccctga taaatgcttc  7800
aataatattg aaaaaggaag agtatgagta ttcaacattt ccgtgtcgcc cttattccct  7860
tttttgcggc attttgcctt cctgtttttg ctcacccaga aacgctggtg aaagtaaaag  7920
atgctgaaga tcagttgggt gcacgagtgg gttacatcga actggatctc aacagcggta  7980
agatccttga gagttttcgc cccgaagaac gttttccaat gatgagcact tttaaagttc  8040
tgctatgtgg cgcggtatta tcccgtattg acgccgggca agagcaactc ggtcgccgca  8100
```

```
tacactattc tcagaatgac ttggttgagt actcaccagt cacagaaaag catcttacgg  8160
atggcatgac agtaagagaa ttatgcagtg ctgccataac catgagtgat aacactgcgg  8220
ccaacttact tctgacaacg atcggaggac cgaaggagct aaccgctttt ttgcacaaca  8280
tgggggatca tgtaactcgc cttgatcgtt gggaaccgga gctgaatgaa gccataccaa  8340
acgacgagcg tgacaccacg atgcctgtag caatggcaac aacgttgcgc aaactattaa  8400
ctggcgaact acttactcta gcttcccggc aacaattaat agactggatg gaggcggata  8460
aagttgcagg accacttctg cgctcggccc ttccggctgg ctggtttatt gctgataaat  8520
ctggagccgg tgagcgtggg tctcgcggta tcattgcagc actggggcca gatggtaagc  8580
cctcccgtat cgtagttatc tacacgacgg ggagtcaggc aactatggat gaacgaaata  8640
gacagatcgc tgagataggt gcctcactga ttaagcattg gtaactgtca gaccaagttt  8700
actcatatat actttagatt gatttaaaac ttcattttta atttaaaagg atctaggtga  8760
agatcctttt tgataatctc atgaccaaaa tcccttaacg tgagttttcg ttccactgag  8820
cgtcagaccc cgtagaaaag atcaaaggat cttcttgaga tccttttttt ctgcgcgtaa  8880
tctgctgctt gcaaacaaaa aaaccaccgc taccagcggt ggtttgtttg ccggatcaag  8940
agctaccaac tctttttccg aaggtaactg gcttcagcag agcgcagata ccaaatactg  9000
ttcttctagt gtagccgtag ttaggccacc acttcaagaa ctctgtagca ccgcctacat  9060
acctcgctct gctaatcctg ttaccagtgg ctgctgccag tggcgataag tcgtgtctta  9120
ccgggttgga ctcaagacga tagttaccgg ataaggcgca gcggtcgggc tgaacggggg  9180
gttcgtgcac acagcccagc ttggagcgaa cgacctacac cgaactgaga tacctacagc  9240
gtgagctatg agaaagcgcc acgcttcccg aagggagaaa ggcggacagg tatccggtaa  9300
gcggcagggt cggaacagga gagcgcacga gggagcttcc agggggaaac gcctggtatc  9360
tttatagtcc tgtcgggttt cgccacctct gacttgagcg tcgatttttg tgatgctcgt  9420
caggggggcg gagcctatgg aaaaacgcca gcaacgcggc ctttttacgg ttcctggcct  9480
tttgctggcc ttttgctcac atgttctttc ctgcgttatc ccctgattct gtggataacc  9540
gtattaccgc ctttgagtga gctgataccg ctcgccgcag ccgaacgacc gagcgcagcg  9600
agtcagtgag cgaggaagcg gaagagcgcc caatacgcaa accgcctctc cccgcgcgtt  9660
ggccgattca ttaatgcagc tggcacgaca ggtttcccga ctggaaagcg ggcagtgagc  9720
gcaacgcaat taatgtgagt tagctcactc attaggcacc ccaggcttta cactttatgc  9780
ttccggctcg tatgttgtgt ggaattgtga gcggataaca atttcacaca ggaaacagct  9840
atgaccatga ttacgccaag ctttgctctt aggagtttcc taatacatcc caaactcaaa  9900
tatataaagc atttgacttg ttctatgccc taggggggcgg ggggaagcta agccagcttt  9960
ttttaacatt taaaatgtta attccatttt aaatgcacag atgtttttat ttcataaggg  10020
tttcaatgtg catgaatgct gcaatattcc tgttaccaaa gctagtataa ataaaaatag  10080
ataaacgtgg aaattactta gagtttctgt cattaacgtt tccttcctca gttgacaaca  10140
taaatgcgct gctgagcaag ccagtttgca tctgtcagga tcaatttccc attatgccag  10200
tcatattaat tactagtcaa ttagttgatt tttattttg acatatacat gtg         10253
```

```
SEQ ID NO: 34          moltype = DNA  length = 10238
FEATURE                Location/Qualifiers
misc_feature           1..10238
                       note = hCD123-CAR
source                 1..10238
                       mol_type = other DNA
                       organism = synthetic construct
SEQUENCE: 34
aatgaaagac cccacctgta ggtttggcaa gctagcttaa gtaacgccat tttgcaaggc  60
atggaaaaat acataactga gaatagaaaa gttcagatca aggtcaggaa cagatggaac  120
agctgaatat gggccaaaca ggatatctgt ggtaagcagt tcctgccccg gctcagggcc  180
aagaacagat ggaacagctg aatatgggcc aaacaggata tctgtggtaa gcagttcctg  240
ccccggctca gggccaagaa cagatggtcc ccagatgcgg tccagccctc agcagtttct  300
agagaaccat cagatgtttc cagggtgccc caaggacctg aaatgaccct gtgccttatt  360
tgaactaacc aatcagttcg cttctcgctt ctgttcgcgc gcttatgctc cccgagctca  420
ataaaagagc ccacaacccc tcactcgggg cgccagtcct ccgattgact gagtcgcccg  480
ggtacccgtg tatccaataa accctcttgc agttgcatcc gacttgtggt ctcgctgttc  540
cttgggaggg tctcctctga gtgattgact acccgtcagc gggggtcttt catttggggg  600
ctcgtccggg atcgggagac ccctgcccag ggaccaccga cccaccaccg ggaggtaagc  660
tggccagcaa cttatctgtg tctgtccgat tgtctagtgt ctatgactga ttttatgcgc  720
ctgcgtcggt actagttagc taactagctc tgtatctggc ggacccgtgg tggaactgac  780
gagttcggaa cacccggccg caaccctggg agacgtccca gggacttcgg gggccgtttt  840
tgtggcccga cctgagtcct aaaatcccga tcgtttagga ctctttggtg cacccccctt  900
agaggaggga tatgtggttc tggtaggaga cgagaaccta aaacagttcc cgcctccgtc  960
tgaatttttg ctttcggttt gggaccgaag ccgcgccgcg cgtcttgtct gctgcagcat  1020
cgttctgtgt tgtctctgtc tgactgtgtt tctgtatttg tctgaaaata tgggcccggg  1080
ctagcctgtt accactccct taagtttgac cttaggtcac tggaaagatg tcgagcggat  1140
cgctcacaac cagtcggtag atgtcaagaa gagacgttgg gttaccttct gctctgcaga  1200
atggccaacc tttaacgtcg gatggccgcg agacggcacc tttaaccgag acctcatcac  1260
ccaggttaag atcaaggtct tttcacctgg cccgcatgga cacccagacc aggtggggta  1320
catcgtgacc tgggaagcct tggcttttga cccccctccc tgggtcaagc cctttgtaca  1380
ccctaagcct ccgcctcctc ttcctccatc cgccccgtct ctcccccttg aacctcctcg  1440
ttcgaccccg cctcgatcct cccttttatcc agccctcact ccttctctag gcgcccccat  1500
atggccatat gagatcttat atggggcacc cccgcccctt gtaaacttcc ctgaccctga  1560
catgacaaga gttactaaca gcccctctct ccaagctcac ttacaggctc tctacttagt  1620
ccagcacgaa gtctggagac ctctggcggc agcctaccaa gaacaactgg accgaccggt  1680
ggtacctcac ccttaccgag tcggcgacac agtgtgggtc cgccgacacc agactaagaa  1740
cctagaacct cgctggaaag gaccttacac agtcctgctg accaccccca ccgccctcaa  1800
agtagacggc atcgcagctt ggatacacgc cgcccacgtg aaggctgccg accccggggg  1860
tggaccatcc tctagactgc catgctcgag ggagtgcagg tggaaaccat ctccccagga  1920
gacgggcgca ccttccccaa gcgcggccag acctgcgtgg tgcactacac cgggatgctt  1980
gaagatggaa agaaagttga ttcctcccgg gacagaaaca agccctttaa gtttatgcta  2040
```

```
ggcaagcagg aggtgatccg aggctgggaa gaaggggttg cccagatgag tgtgggtcag  2100
agagccaaac tgactatatc tccagattat gcctatggtg ccactgggca cccaggcatc  2160
atcccaccac atgccactct cgtcttcgat gtggagcttc taaaactgga atctggcggt  2220
ggatccggag tcgacggatt tggtgatgtc ggtgctcttg agagtttgag gggaaatgca  2280
gatttggctt acatcctgag catggagccc tgtggccact gcctcattat caacaatgtg  2340
aacttctgcc gtgagtccgg gctccgcacc cgcactggct ccaacatcga ctgtgagaag  2400
ttgcggcgtc gcttctcctc gctgcatttc atggtggagg tgaagggcga cctgactgcc  2460
aagaaaatgg tgctggcttt gctggagctg gcgcagcagg accacggtgc tctggactgc  2520
tgcgtggtgg tcattctctc tcacggctgt caggccagcc acctgcagtt cccaggggct  2580
gtctacggca cagatggatg ccctgtgtcg gtcgagaaga ttgtgaacat cttcaatggg  2640
accagctgcc ccagcctggg agggaagccc aagctctttt tcatccaggc ctgtggtggg  2700
gagcagaaag accatgggtt tgaggtggcc tccacttccc ctgaagacga gtcccctggc  2760
agtaaccccg agccagatgc caccccgttc caggaaggtt tgaggacctt cgaccagctg  2820
gacgccatat ctagtttgcc cacacccagt gacatctttg tgtcctactc tactttccca  2880
ggttttgttt cctggaggga ccccaagagt ggctcctggt acgttgagac cctggacgac  2940
atctttgagc agtgggctca ctctgaagac ctgcagtccc tcctgcttag ggtcgctaat  3000
gctgtttcgg tgaaagggat ttataaacag atgcctggtt gctttaattt cctccggaaa  3060
aaacttttct ttaaaacatc agctagcaga gccgagggca ggggaagtct tctaacatgc  3120
ggggacgtgg aggaaaatcc cggcccatg gaattcgggc tttcatggtt gttcctcgtt  3180
gcgatactta aaggcgttca gtgcagtaga gacattcaga tgacccaaag ccctagtagc  3240
ctctccgcca gtgtgggtga ccgcgtgact attacgtgcc gagcaagcaa gagtattagc  3300
aaagatttgg catggtacca gcagaaacca ggcaaggtcc ctaagttgct tatatatagc  3360
gggtctacac tccaatctgg agtgccggat cgcttctcag gttccggatc aggaaccgat  3420
ttcactctta caatttcctc tctgcaaccg gaggacgtgg caacatacta ttgccagcag  3480
cataacaaat atccctatac tttcggtcaa ggtacaaaag tagaaataaa acgaggttcc  3540
acctccggga gtgggaagcc cggctccggc gaaggatcca ccaaaggcga ggtacagctc  3600
gttgaaagcg ggggcggtct cgtccaacca ggagggtctc ttcgactttc ttgtgctgca  3660
agtgggtaca cgtttacttc ctattggatg aattgggttc ggcaagcccc cggtaaaggg  3720
cttgaatgga tagggaggat agacccctac gattctgaga cgcattataa tcagaaattc  3780
aaagataagt tcataataag cagagacaat gcaaaaaata gtttgtacct ccagatgaat  3840
agtcttcggg cagaagacac agcggtatat tactgtgctc ggggtaactg ggatgattac  3900
tggggtcagg gaactctggt tactgtgtct agctacgtca ccgtctcttc acaggatccc  3960
gccgagccca aatctcctga caaaactcac acatgcccac cgtgcccagc acctgaactc  4020
ctggggggac cgtcagtctt cctcttcccc ccaaaaccca aggacaccct catgatctcc  4080
cggacccctg aggtcacatg cgtggtggtg gacgtgagcc acgaagaccc tgaggtcaag  4140
ttcaactggt acgtggacgg cgtggaggtg cataatgcca agacaaagcc gcgggaggag  4200
cagtacaaca gcacgtaccg tgtggtcagc gtcctcaccg tcctgcacca ggactggctg  4260
aatggcaagg agtacaagtg caaggtctcc aacaaagccc tcccagcccc catcgagaaa  4320
accatctcca aagccaaagg gcagccccga gaaccacagg tgtacaccct gcccccatcc  4380
cgggatgagc tgaccaagaa ccaggtcagc ctgacctgcc tggtcaaagg cttctatccc  4440
agcgacatcg ccgtggagtg ggagagcaat gggcaaccgg agaacaacta caagaccacg  4500
cctcccgtgc tggactccga cggctccttc ttcctctaca gcaagctcac cgtggacaag  4560
agcaggtggc agcaggggaa cgtcttctca tgctccgtga tgcatgaggc tctgcacaac  4620
cactacacgc agaagagcct ctccctgtct ccgggtaaaa aagatcccaa attttgggtg  4680
ctggtggtgg ttggtggagt cctggcttgc tatagcttgc tagtaacagt ggcctttatt  4740
attttctggg tgaggagtaa gaggagcagg ctcctgcaca gtgactacat gaacatgact  4800
ccccgccgcc ccgggcccac ccgcaagcat taccagccct atgccccacc acgcgacttc  4860
gcagcctatc gctccagagt gaagttcagc aggagcgcag acgcccccgc gtaccagcag  4920
ggccagaacc agctctataa cgagctcaat ctaggacgaa gagaggagta cgatgttttg  4980
gacaagagac gtggccggga ccctgagatg gggggaaagc cgagaaggaa gaaccctcag  5040
gaaggcctgt acaatgaact gcagaaagat aagatggcgg aggcctacag tgagattggg  5100
atgaaaggcg agcgccggag gggcaagggg cacgatggcc tttaccaggg tctcagtaca  5160
gccaccaagg acacctacga cgcccttcac atgcaggccc tgccccctcg cggaccgcag  5220
tgtactaatt atgctctctt gaaattggct ggagatgttg agagcaatcc cgggcccatg  5280
cggatcagca agccccacct gcggagcatc agcatccagt gctacctgtg cctgctgctg  5340
aacagccact tcctgaccga ggccggcatc cacgtgttca tcctgggctg cttcagcgcc  5400
ggactgccca agaccgaggc caactgggtg aacgtgatca gcgacctgaa gaagatcgag  5460
gacctgatcc agagcatgca catcgacgcc accctgtaca ccgagagcga cgtgcacccc  5520
agctgcaagg tgaccgccat gaagtgcttt ctgctggaac tgcaggtgat cagcctggaa  5580
agcggcgacg ccagcatcca cgacaccgtg gagaacctga tcatcctggc caacaacagc  5640
ctgagcagca acggcaacgt gaccgagagc ggctgcaaag agtgcgagga actggaagag  5700
aagaacatca aagagtttct gcagagcttc gtgcacatcg tgcagatgtt catcaacacc  5760
agctgacgcg tcatcatcga tccggattag tccaatttgt taaagacagg atatcagtgg  5820
tccaggctct agttttgact caacaatatc accagctgaa gcctatagag tacgagccat  5880
agataaaata aaagatttta tttagtctcc agaaaaaggg gggaatgaaa gaccccacct  5940
gtaggtttgg caagctagct taagtaacgc cattttgcaa ggcatggaaa aatacataac  6000
tgagaataga gaagttcaga tcaaggtcag gaacagatgg aacagctgaa tatgggccaa  6060
acaggatatc tgtggtaagc agttcctgcc ccggctcagg gccaagaaca gatggaacag  6120
ctgaatatgg gccaaacagg atatctgtgg taagcagttc ctgccccggc tcagggccaa  6180
gaacagatgg tccccagatg cggtccagcc ctcagcagtt tctagagaac catcagatgt  6240
ttccagggtg ccccaaggac ctgaaatgac cctgtgcctt atttgaacta accaatcagt  6300
tcgcttctcg cttctgttcg cgcgcttctg ctccccgagc tcaataaaag agcccacaac  6360
ccctcactcg gggcgccagt cctccgattg actgagtcgc ccgggtaccc gtgtatccaa  6420
taaaccctct tgcagttgca tccgacttgt ggtctcgctg ttccttggga gggtctcctc  6480
tgagtgattg actacccgtc agcgggggtc tttcacacat gcagcatgta tcaaaattaa  6540
tttggttttt tttcttaagt atttacatta aatggccata gtacttaaag ttacattggc  6600
ttccttgaaa taaacatgga gtattcagaa tgtgtcataa atatttctaa ttttaagata  6660
gtatctccat tggctttcta ctttttcttt tatttttttt tgtcctctgt cttccatttg  6720
ttgttgttgt tgtttgtttg tttgtttgtt ggttggttgg ttaatttttt tttaaagatc  6780
```

-continued ctacactata gttcaagcta gactattagc tactctgtaa cccagggtga ccttgaagtc 6840
atgggtagcc tgctgtttta gccttcccac atctaagatt acaggtatga gctatcattt 6900
ttggtatatt gattgattga ttgattgatg tgtgtgtgtg tgattgtgtt tgtgtgtgtg 6960
actgtgaaaa tgtgtgtatg ggtgtgtgtg aatgtgtgta tgtatgtgtg tgtgtgagtg 7020
tgtgtgtgtg tgtgtgcatg tgtgtgtgtg tgactgtgtc tatgtgtatg actgtgtgtg 7080
tgtgtgtgtg tgtgtgtgtg tgtgtgtgtg tgtgtgtgtt gtgaaaaaat attctatggt 7140
agtgagagcc aacgctccgg ctcaggtgtc aggttggttt ttgagacaga gtctttcact 7200
tagcttggaa ttcactggcc gtcgttttac aacgtcgtga ctgggaaaac cctggcgtta 7260
cccaacttaa tcgccttgca gcacatcccc ctttcgccag ctggcgtaat agcgaagagg 7320
cccgcaccga tcgcccttcc caacagttgc gcagcctgaa tggcgaatgg cgcctgatgc 7380
ggtattttct ccttacgcat ctgtgcggta tttcacaccg catatggtgc actctcagta 7440
caatctgctc tgatgccgca tagttaagcc agccccgaca cccgccaaca cccgctgacg 7500
cgccctgacg ggcttgtctg ctcccggcat ccgcttacag acaagctgtg accgtctccg 7560
ggagctgcat gtgtcagagg ttttcaccgt catcaccgaa acgcgcgaga cgaaagggcc 7620
tcgtgatacg cctattttta taggttaatg tcatgataat aatggtttct tagacgtcag 7680
gtggcacttt tcggggaaat gtgcgcggaa cccctatttg tttatttttc taaatacatt 7740
caaatatgta tccgctcatg agacaataac cctgataaat gcttcaataa tattgaaaaa 7800
ggaagagtat gagtattcaa catttccgtg tcgcccttat tccctttttt gcggcatttt 7860
gccttcctgt ttttgctcac ccagaaacgc tggtgaaagt aaaagatgct gaagatcagt 7920
tgggtgcacg agtgggttac atcgaactgg atctcaacag cggtaagatc cttgagagtt 7980
ttcgccccga agaacgtttt ccaatgatga gcacttttaa agttctgcta tgtggcgcgg 8040
tattatcccg tattgacgcc gggcaagagc aactcggtcg ccgcatacac tattctcaga 8100
atgacttggt tgagtactca ccagtcacag aaaagcatct tacggatggc atgacagtaa 8160
gagaattatg cagtgctgcc ataaccatga gtgataacac tgcggccaac ttacttctga 8220
caacgatcgg aggaccgaag gagctaaccg cttttttgca caacatgggg gatcatgtaa 8280
ctcgccttga tcgttgggaa ccggagctga atgaagccat accaaacgac gagcgtgaca 8340
ccacgatgcc tgtagcaatg gcaacaacgt tgcgcaaact attaactggc gaactactta 8400
ctctagcttc ccggcaacaa ttaatagact ggatggaggc ggataaagtt gcaggaccac 8460
ttctgcgctc ggcccttccg gctggctggt ttattgctga taaatctgga gccggtgagc 8520
gtgggtctcg cggtatcatt gcagcactgg ggccagatgg taagccctcc cgtatcgtag 8580
ttatctacac gacggggagt caggcaacta tggatgaacg aaatagacag atcgctgaga 8640
taggtgcctc actgattaag cattggtaac tgtcagacca agtttactca tatatacttt 8700
agattgattt aaaacttcat ttttaattta aaaggatcta ggtgaagatc ctttttgata 8760
atctcatgac caaaatccct taacgtgagt tttcgttcca ctgagcgtca gaccccgtag 8820
aaaagatcaa aggatcttct tgagatcctt tttttctgcg cgtaatctgc tgcttgcaaa 8880
caaaaaaacc accgctacca gcggtggttt gtttgccgga tcaagagcta ccaactcttt 8940
ttccgaaggt aactggcttc agcagagcgc agataccaaa tactgttctt ctagtgtagc 9000
cgtagttagg ccaccacttc aagaactctg tagcaccgcc tacatacctc gctctgctaa 9060
tcctgttacc agtggctgct gccagtggcg ataagtcgtg tcttaccggg ttggactcaa 9120
gacgatagtt accggataag gcgcagcggt cgggctgaac ggggggttcg tgcacacagc 9180
ccagcttgga gcgaacgacc tacaccgaac tgagatacct acagcgtgag ctatgagaaa 9240
gcgccacgct tcccgaaggg agaaaggcgg acaggtatcc ggtaagcggc agggtcggaa 9300
caggagagcg cacgagggag cttccagggg gaaacgcctg gtatctttat agtcctgtcg 9360
ggtttcgcca cctctgactt gagcgtcgat ttttgtgatg ctcgtcaggg gggcggagcc 9420
tatggaaaaa cgccagcaac gcggcctttt tacggttcct ggccttttgc tggccttttg 9480
ctcacatgtt ctttcctgcg ttatcccctg attctgtgga taaccgtatt accgcctttg 9540
agtgagctga taccgctcgc cgcagccgaa cgaccgagcg cagcgagtca gtgagcgagg 9600
aagcggaaga gcgcccaata cgcaaaccgc ctctccccgc gcgttggccg attcattaat 9660
gcagctggca cgacaggttt cccgactgga aagcgggcag tgagcgcaac gcaattaatg 9720
tgagttagct cactcattag gcaccccagg ctttacactt tatgcttccg gctcgtatgt 9780
tgtgtggaat tgtgagcgga taacaatttc acacaggaaa cagctatgac catgattacg 9840
ccaagctttg ctcttaggag tttcctaata catcccaaac tcaaatatat aaagcatttg 9900
acttgttcta tgccctaggg ggcgggggga agctaagcca gcttttttta acatttaaaa 9960
tgttaattcc attttaaatg cacagatgtt tttatttcat aagggtttca atgtgcatga 10020
atgctgcaat attcctgtta ccaaagctag tataaataaa aatagataaa cgtggaaatt 10080
acttagagtt tctgtcatta acgtttcctt cctcagttga caacataaat gcgctgctga 10140
gcaagccagt ttgcatctgt caggatcaat ttcccattat gccagtcata ttaattacta 10200
gtcaattagt tgatttttat ttttgacata tacatgtg 10238

SEQ ID NO: 35 moltype = DNA length = 10229
FEATURE Location/Qualifiers
misc_feature 1..10229
note = hMeso-CAR
source 1..10229
mol_type = other DNA
organism = synthetic construct
SEQUENCE: 35
aatgaaagac cccacctgta ggtttggcaa gctagcttaa gtaacgccat tttgcaaggc 60
atggaaaaat acataactga gaatagaaaa gttcagatca aggtcaggaa cagatggaac 120
agctgaatat gggccaaaca ggatatctgt ggtaagcagt tcctgccccg gctcagggcc 180
aagaacagat ggaacagctg aatatgggcc aaacaggata tctgtggtaa gcagttcctg 240
ccccggctca gggccaagaa cagatggtcc ccagatgcgg tccagccctc agcagtttct 300
agagaaccat cagatgtttc cagggtgccc caaggacctg aaatgaccct gtgccttatt 360
tgaactaacc aatcagttcg cttctcgctt ctgttcgcgc gcttatgctc cccgagctca 420
ataaaagagc ccacaacccc tcactcgggg cgccagtcct ccgattgact gagtcgcccg 480
ggtacccgtg tatccaataa accctcttgc agttgcatcc gacttgtggt ctcgctgttc 540
cttgggaggg tctcctctga gtgattgact acccgtcagc gggggtcttt catttggggg 600
ctcgtccggg atcgggagac ccctgcccag ggaccaccga cccaccaccg ggaggtaagc 660
tggccagcaa cttatctgtg tctgtccgat tgtctagtgt ctatgactga ttttatgcgc 720

```
ctgcgtcggt actagttagc taactagctc tgtatctggc ggacccgtgg tggaactgac  780
gagttcggaa cacccggccg caaccctggg agacgtccca gggacttcgg gggccgtttt  840
tgtggcccga cctgagtcct aaaatcccga tcgtttagga ctctttggtg caccccccctt  900
agaggaggga tatgtggttc tggtaggaga cgagaaccta aaacagttcc cgcctccgtc  960
tgaatttttg ctttcggttt gggaccgaag ccgcgccgcg cgtcttgtct gctgcagcat  1020
cgttctgtgt tgtctctgtc tgactgtgtt tctgtatttg tctgaaaata tgggcccggg  1080
ctagcctgtt accactccct taagtttgac cttaggtcac tggaaagatg tcgagcggat  1140
cgctcacaac cagtcggtag atgtcaagaa gagacgttgg gttaccttct gctctgcaga  1200
atggccaacc tttaacgtcg gatggccgcg agacggcacc tttaaccgag acctcatcac  1260
ccaggttaag atcaaggtct tttcacctgg cccgcatgga cacccagacc aggtggggta  1320
catcgtgacc tgggaagcct tggcttttga cccccctccc tgggtcaagc cctttgtaca  1380
ccctaagcct ccgcctcctc ttcctccatc cgccccgtct ctcccccttg aacctcctcg  1440
ttcgaccccg cctcgatcct cccctttatcc agccctcact ccttctctag gcgcccccat  1500
atggccatat gagatcttat atggggcacc cccgcccctt gtaaacttcc ctgaccctga  1560
catgacaaga gttactaaca gcccctctct ccaagctcac ttacaggctc tctacttagt  1620
ccagcacgaa gtctggagac ctctggcggc agcctaccaa gaacaactgg accgaccggt  1680
ggtacctcac ccttaccgag tcggcgacac agtgtgggtc cgccgacacc agactaagaa  1740
cctagaacct cgctggaaag gaccttacac agtcctgctg accaccccca ccgccctcaa  1800
agtagacggc atcgcagctt ggatacacgc cgcccacgtg aaggctgccg accccggggg  1860
tggaccatcc tctagactgc catgctcgag ggagtgcagg tggaaaccat ctccccagga  1920
gacgggcgca ccttccccaa gcgcggccag acctgcgtgg tgcactacac cgggatgctt  1980
gaagatggaa agaaagttga ttcctcccgg gacagaaaca agccctttaa gtttatgcta  2040
ggcaagcagg aggtgatccg aggctgggaa gaaggggttg cccagatgag tgtgggtcag  2100
agagccaaac tgactatatc tccagattat gcctatggtg ccactgggca cccaggcatc  2160
atcccaccac atgccactct cgtcttcgat gtggagcttc taaaactgga atctggcggt  2220
ggatccggag tcgacggatt tggtgatgtc ggtgctcttg agagtttgag gggaaatgca  2280
gatttggctt acatcctgag catggagccc tgtggccact gcctcattat caacaatgtg  2340
aacttctgcc gtgagtccgg gctccgcacc cgcactggct ccaacatcga ctgtgagaag  2400
ttgcggcgtc gcttctcctc gctgcatttc atggtggagg tgaagggcga cctgactgcc  2460
aagaaaatgg tgctggcttt gctggagctg gcgcagcagg accacggtgc tctggactgc  2520
tgcgtggtgg tcattctctc tcacggctgt caggccagcc acctgcagtt cccaggggct  2580
gtctacggca cagatggatg ccctgtgtcg gtcgagaaga ttgtgaacat cttcaatggg  2640
accagctgcc ccagcctggg agggaagccc aagctctttt tcatccaggc ctgtggtggg  2700
gagcagaaag accatgggtt tgaggtggcc tccacttccc ctgaagacga gtcccctggc  2760
agtaaccccg agccagatgc caccccgttc caggaaggtt tgaggacctt cgaccagctg  2820
gacgccatat ctagtttgcc cacacccagt gacatctttg tgtcctactc tactttccca  2880
ggttttgttt cctggaggga ccccaagagt ggctcctggt acgttgagac cctggacgac  2940
atctttgagc agtgggctca ctctgaagac ctgcagtccc tcctgcttag ggtcgctaat  3000
gctgtttcgg tgaaagggat ttataaacag atgcctggtt gctttaattt cctccggaaa  3060
aaactttttct ttaaaacatc agctagcaga gccgagggca ggggaagtct tctaacatgc  3120
ggggacgtgg aggaaaatcc cgggcccatg gagttcggcc tttcttggct gtttttggtc  3180
gcaatattga agggcgttca gtgttcaagg gacatacaga tgacgcagtc acctagctct  3240
ctttcagcct ctgtgggaga ccgcgttaca attacgtgtt ctgcttctag ttcagtgtct  3300
tacatgcatt ggtaccagca aaaacccggc aaggttccaa agctccttat atacgatacg  3360
tccaaactgg cttcaggcgt gccagacagg tttagtggat ctgggagcgg cactgacttc  3420
acacttacaa tatccagtct gcaacccgaa gatgttgcga catactattg tcagcaatgg  3480
agcggctatc cgctcaccgg acaggggaca aaagtggaga taaagcgggg ctccaccagt  3540
ggttccggga agcctggtag tggtgagggt tctacgaaag gcgaagtgca gttggtggag  3600
tctggtggcg ggcttgttca acccggtggt tctctcaggc ttagctgtgc agcctctggg  3660
tacacaatga attgggtaag gcaagcgcct ggaaagggcc ttgagtggat cggtttgata  3720
accccataca acggagcttc aagttacaac caaaagttcc gcgggaagtt tattataagc  3780
agggataacg caaagaacag cctctatctt caaatgaact cactccgggc tgaagacaca  3840
gccgtctatt attgtgcccg ggggggctac gacggacgag ggttcgatta ctggggtcag  3900
ggcacactcg tgaccgtgtc aagctacgtc accgtctctt cacaggatcc cgccgagccc  3960
aaatctcctg acaaaactca cacatgccca ccgtgcccag cacctgaact cctgggggga  4020
ccgtcagtct tcctcttccc cccaaaaccc aaggacaccc tcatgatctc ccggacccct  4080
gaggtcacat gcgtggtggt ggacgtgagc cacgaagacc ctgaggtcaa gttcaactgg  4140
tacgtggacg gcgtggaggt gcataatgcc aagacaaagc cgcgggagga gcagtacaac  4200
agcacgtacc gtgtggtcag cgtcctcacc gtcctgcacc aggactggct gaatggcaag  4260
gagtacaagt gcaaggtctc caacaaagcc ctcccagccc ccatcgagaa aaccatctcc  4320
aaagccaaag ggcagccccg agaaccacag gtgtacaccc tgcccccatc ccgggatgag  4380
ctgaccaaga accaggtcag cctgacctgc ctggtcaaag gcttctatcc cagcgacatc  4440
gccgtggagt gggagagcaa tgggcaaccg gagaacaact acaagaccac gcctcccgtg  4500
ctggactccg acggctcctt cttcctctac agcaagctca ccgtggacaa gagcaggtgg  4560
cagcagggga acgtcttctc atgctccgtg atgcatgagg ctctgcacaa ccactacacg  4620
cagaagagcc tctccctgtc tccgggtaaa aaagatccca aattttgggt gctggtggtg  4680
gttggtggag tcctggcttg ctatagcttg ctagtaacag tggcctttat tatttttctgg  4740
gtgaggagta agaggagcag gctcctgcac agtgactaca tgaacatgac tccccgccgc  4800
cccgggccca cccgcaagca ttaccagccc tatgccccac cacgcgactt cgcagcctat  4860
cgctccagag tgaagttcag caggagcgca gacgcccccg cgtaccagca gggccagaac  4920
cagctctata acgagctcaa tctaggacga agagaggagt acgatgtttt ggacaagaga  4980
cgtggccggg accctgagat gggggggaaag ccgagaagga agaaccctca ggaaggcctg  5040
tacaatgaac tgcagaaaga taagatggcg gaggcctaca gtgagattgg gatgaaaggc  5100
gagcgccgga ggggcaaggg gcacgatggc ctttaccagg gtctcagtac agccaccaag  5160
gacacctacg acgcccttca catgcaggcc ctgcccccctc gcggaccgca gtgtactaat  5220
tatgctctct tgaaattggc tggagatgtt gagagcaatc ccgggcccat gcggatcagc  5280
aagccccacc tgcggagcat cagcatccag tgctacctgt gcctgctgct gaacagccac  5340
ttcctgaccg aggccggcat ccacgtgttc atcctgggct gcttcagcgc cggactgccc  5400
aagaccgagg ccaactgggt gaacgtgatc agcgacctga agaagatcga ggacctgatc  5460
```

-continued

```
cagagcatgc acatcgacgc caccctgtac accgagagcg acgtgcaccc cagctgcaag  5520
gtgaccgcca tgaagtgctt tctgctggaa ctgcaggtga tcagcctgga aagcggcgac  5580
gccagcatcc acgacaccgt ggagaacctg atcatcctgg ccaacaacag cctgagcagc  5640
aacggcaacg tgaccgagag cggctgcaaa gagtgcgagg aactggaaga gaagaacatc  5700
aaagagtttc tgcagagctt cgtgcacatc gtgcagatgt tcatcaacac cagctgacgc  5760
gtcatcatcg atccggatta gtccaatttg ttaaagacag gatatcagtg gtccaggctc  5820
tagttttgac tcaacaatat caccagctga agcctataga gtacgagcca tagataaaat  5880
aaaagatttt atttagtctc cagaaaaagg ggggaatgaa agaccccacc tgtaggtttg  5940
gcaagctagc ttaagtaacg ccattttgca aggcatggaa aaatacataa ctgagaatag  6000
agaagttcag atcaaggtca ggaacagatg gaacagctga atatgggcca aacaggatat  6060
ctgtggtaag cagttcctgc cccggctcag ggccaagaac agatggaaca gctgaatatg  6120
ggccaaacag gatatctgtg gtaagcagtt cctgccccgg ctcagggcca agaacagatg  6180
gtccccagat gcggtccagc cctcagcagt ttctagagaa ccatcagatg tttccagggt  6240
gccccaagga cctgaaatga ccctgtgcct tatttgaact aaccaatcag ttcgcttctc  6300
gcttctgttc gcgcgcttct gctccccgag ctcaataaaa gagcccacaa cccctcactc  6360
ggggcgccag tcctccgatt gactgagtcg cccgggtacc cgtgtatcca ataaaccctc  6420
ttgcagttgc atccgacttg tggtctcgct gttccttggg agggtctcct ctgagtgatt  6480
gactacccgt cagcgggggt ctttcacaca tgcagcatgt atcaaaatta atttggtttt  6540
ttttcttaag tatttacatt aaatggccat agtacttaaa gttacattgg cttccttgaa  6600
ataaacatgg agtattcaga atgtgtcata aatatttcta attttaagat agtatctcca  6660
ttggcttttct actttttctt ttattttttt ttgtcctctg tcttccattt gttgttgttg  6720
ttgtttgttt gtttgtttgt tggttggttg gttaattttt ttttaaagat cctacactat  6780
agttcaagct agactattag ctactctgta acccagggtg accttgaagt catgggtagc  6840
ctgctgtttt agccttccca catctaagat tacaggtatg agctatcatt tttggtatat  6900
tgattgattg attgattgat gtgtgtgtgt gtgattgtgt ttgtgtgtgt gactgtgaaa  6960
atgtgtgtat gggtgtgtgt gaatgtgtgt atgtatgtgt gtgtgtgagt gtgtgtgtgt  7020
gtgtgtgcat gtgtgtgtgt gtgactgtgt ctatgtgtat gactgtgtgt gtgtgtgtgt  7080
gtgtgtgtgt gtgtgtgtgt gtgtgtgtgt tgtgaaaaaa tattctatgg tagtgagagc  7140
caacgctccg gctcaggtgt caggttggtt tttgagacag agtctttcac ttagcttgga  7200
attcactggc cgtcgtttta caacgtcgtg actgggaaaa ccctggcgtt acccaactta  7260
atcgccttgc agcacatccc cctttcgcca gctggcgtaa tagcgaagag gcccgcaccg  7320
atcgcccttc ccaacagttg cgcagcctga atggcgaatg gcgcctgatg cggtattttc  7380
tccttacgca tctgtgcggt atttcacacc gcatatggtg cactctcagt acaatctgct  7440
ctgatgccgc atagttaagc cagccccgac acccgccaac acccgctgac gcgccctgac  7500
gggcttgtct gctcccggca tccgcttaca gacaagctgt gaccgtctcc gggagctgca  7560
tgtgtcagag gttttcaccg tcatcaccga aacgcgcgag acgaaagggc ctcgtgatac  7620
gcctattttt ataggttaat gtcatgataa taatggtttc ttagacgtca ggtggcactt  7680
ttcggggaaa tgtgcgcgga acccctattt gtttattttt ctaaatacat tcaaatatgt  7740
atccgctcat gagacaataa ccctgataaa tgcttcaata atattgaaaa aggaagagta  7800
tgagtattca acatttccgt gtcgccctta ttcccttttt tgcggcattt tgccttcctg  7860
tttttgctca cccagaaacg ctggtgaaag taaaagatgc tgaagatcag ttgggtgcac  7920
gagtgggtta catcgaactg gatctcaaca gcggtaagat ccttgagagt tttcgccccg  7980
aagaacgttt tccaatgatg agcactttta aagttctgct atgtggcgcg gtattatccc  8040
gtattgacgc cgggcaagag caactcggtc gccgcataca ctattctcag aatgacttgg  8100
ttgagtactc accagtcaca gaaaagcatc ttacggatgg catgacagta agagaattat  8160
gcagtgctgc cataaccatg agtgataaca ctgcggccaa cttacttctg acaacgatcg  8220
gaggaccgaa ggagctaacc gcttttttgc acaacatggg ggatcatgta actcgccttg  8280
atcgttggga accggagctg aatgaagcca taccaaacga cgagcgtgac accacgatgc  8340
ctgtagcaat ggcaacaacg ttgcgcaaac tattaactgg cgaactactt actctagctt  8400
cccggcaaca attaatagac tggatggagg cggataaagt tgcaggacca cttctgcgct  8460
cggcccttcc ggctggctgg tttattgctg ataaatctgg agccggtgag cgtgggtctc  8520
gcggtatcat tgcagcactg gggccagatg gtaagccctc ccgtatcgta gttatctaca  8580
cgacggggag tcaggcaact atggatgaac gaaatagaca gatcgctgag ataggtgcct  8640
cactgattaa gcattggtaa ctgtcagacc aagtttactc atatatactt tagattgatt  8700
taaaacttca tttttaattt aaaaggatct aggtgaagat cctttttgat aatctcatga  8760
ccaaaatccc ttaacgtgag ttttcgttcc actgagcgtc agaccccgta gaaaagatca  8820
aaggatcttc ttgagatcct ttttttctgc gcgtaatctg ctgcttgcaa acaaaaaaac  8880
caccgctacc agcggtggtt tgtttgccgg atcaagagct accaactctt tttccgaagg  8940
taactggctt cagcagagcg cagataccaa atactgttct tctagtgtag ccgtagttag  9000
gccaccactt caagaactct gtagcaccgc ctacatacct cgctctgcta atcctgttac  9060
cagtggctgc tgccagtggc gataagtcgt gtcttaccgg gttggactca agacgatagt  9120
taccggataa ggcgcagcgg tcgggctgaa cggggggttc gtgcacacag cccagcttgg  9180
agcgaacgac ctacaccgaa ctgagatacc tacagcgtga gctatgagaa agcgccacgc  9240
ttcccgaagg gagaaaggcg gacaggtatc cggtaagcgg cagggtcgga acaggagagc  9300
gcacgaggga gcttccaggg ggaaacgcct ggtatcttta tagtcctgtc gggtttcgcc  9360
acctctgact tgagcgtcga tttttgtgat gctcgtcagg ggggcggagc ctatggaaaa  9420
acgccagcaa cgcggccttt ttacggttcc tggccttttg ctggcctttt gctcacatgt  9480
tctttcctgc gttatcccct gattctgtgg ataaccgtat taccgccttt gagtgagctg  9540
ataccgctcg ccgcagccga acgaccgagc gcagcgagtc agtgagcgag gaagcggaag  9600
agcgcccaat acgcaaaccg cctctccccg cgcgttggcc gattcattaa tgcagctggc  9660
acgacaggtt tcccgactgg aaagcgggca gtgagcgcaa cgcaattaat gtgagttagc  9720
tcactcatta ggcaccccag gctttacact ttatgcttcc ggctcgtatg ttgtgtggaa  9780
ttgtgagcgg ataacaattt cacacaggaa acagctatga ccatgattac gccaagcttt  9840
gctcttagga gtttcctaat acatcccaaa ctcaaatata taaagcattt gacttgttct  9900
atgccctagg gggcgggggg aagctaagcc agcttttttt aacatttaaa atgttaattc  9960
cattttaaat gcacagatgt ttttatttca taagggtttc aatgtgcatg aatgctgcaa  10020
tattcctgtt accaaagcta gtataaataa aaatagataa acgtggaaat tacttagagt  10080
```

-continued

```
ttctgtcatt aacgtttcct tcctcagttg acaacataaa tgcgctgctg agcaagccag  10140
tttgcatctg tcaggatcaa tttcccatta tgccagtcat attaattact agtcaattag  10200
ttgattttta tttttgacat atacatgtg                                    10229

SEQ ID NO: 36           moltype = DNA  length = 10250
FEATURE                 Location/Qualifiers
misc_feature            1..10250
                        note = hROR1-CAR
source                  1..10250
                        mol_type = other DNA
                        organism = synthetic construct
SEQUENCE: 36
aatgaaagac cccacctgta ggtttggcaa gctagcttaa gtaacgccat tttgcaaggc  60
atggaaaaat acataactga gaatagaaaa gttcagatca aggtcaggaa cagatggaac  120
agctgaatat gggccaaaca ggatatctgt ggtaagcagt tcctgccccg gctcagggcc  180
aagaacagat ggaacagctg aatatgggcc aaacaggata tctgtggtaa gcagttcctg  240
ccccggctca gggccaagaa cagatggtcc ccagatgcgg tccagccctc agcagtttct  300
agagaaccat cagatgtttc cagggtgccc caaggacctg aaatgaccct gtgccttatt  360
tgaactaacc aatcagttcg cttctcgctt ctgttcgcgc gcttatgctc cccgagctca  420
ataaaagagc ccacaacccc tcactcgggg cgccagtcct ccgattgact gagtcgcccg  480
ggtacccgtg tatccaataa accctcttgc agttgcatcc gacttgtggt ctcgctgttc  540
cttgggaggg tctcctctga gtgattgact acccgtcagc gggggtcttt catttggggg  600
ctcgtccggg atcgggagac ccctgcccag ggaccaccga cccaccaccg ggaggtaagc  660
tggccagcaa cttatctgtg tctgtccgat tgtctagtgt ctatgactga ttttatgcgc  720
ctgcgtcggt actagttagc taactagctc tgtatctggc ggacccgtgg tggaactgac  780
gagttcggaa cacccggccg caaccctggg agacgtccca gggacttcgg gggccgtttt  840
tgtggcccga cctgagtcct aaaatcccga tcgtttagga ctctttggtg caccccccctt  900
agaggaggga tatgtggttc tggtaggaga cgagaaccta aaacagttcc cgcctccgtc  960
tgaatttttg ctttcggttt gggaccgaag ccgcgccgcg cgtcttgtct gctgcagcat  1020
cgttctgtgt tgtctctgtc tgactgtgtt tctgtatttg tctgaaaata tgggcccggg  1080
ctagcctgtt accactccct taagtttgac cttaggtcac tggaaagatg tcgagcggat  1140
cgctcacaac cagtcggtag atgtcaagaa gagacgttgg gttaccttct gctctgcaga  1200
atggccaacc tttaacgtcg gatggccgcg agacggcacc tttaaccgag acctcatcac  1260
ccaggttaag atcaaggtct tttcacctgg cccgcatgga cacccagacc aggtggggta  1320
catcgtgacc tgggaagcct tggcttttga cccccctccc tgggtcaagc cctttgtaca  1380
ccctaagcct ccgcctcctc ttcctccatc cgccccgtct ctccccccttg aacctcctcg  1440
ttcgaccccg cctcgatcct ccctttatcc agccctcact ccttctctag gcgcccccat  1500
atggccatat gagatcttat atggggcacc cccgcccctt gtaaacttcc ctgaccctga  1560
catgacaaga gttactaaca gcccctctct ccaagctcac ttacaggctc tctacttagt  1620
ccagcacgaa gtctggagac ctctggcggc agcctaccaa gaacaactgg accgaccggt  1680
ggtacctcac ccttaccgag tcggcgacac agtgtgggtc cgccgacacc agactaagaa  1740
cctagaacct cgctggaaag gaccttacac agtcctgctg accaccccca ccgccctcaa  1800
agtagacggc atcgcagctt ggatacacgc cgcccacgtg aaggctgccg accccggggg  1860
tggaccatcc tctagactgc catgctcgag ggagtgcagg tggaaaccat ctccccagga  1920
gacgggcgca ccttccccaa gcgcggccag acctgcgtgg tgcactacac cgggatgctt  1980
gaagatggaa agaaagttga ttcctcccgg gacagaaaca agccctttaa gtttatgcta  2040
ggcaagcagg aggtgatccg aggctgggaa gaaggggttg cccagatgag tgtgggtcag  2100
agagccaaac tgactatatc tccagattat gcctatggtg ccactgggca cccaggcatc  2160
atcccaccac atgccactct cgtcttcgat gtggagcttc taaaactgga atctggcggt  2220
ggatccggag tcgacggatt tggtgatgtc ggtgctcttg agagtttgag gggaaatgca  2280
gatttggctt acatcctgag catggagccc tgtggccact gcctcattat caacaatgtg  2340
aacttctgcc gtgagtccgg gctccgcacc cgcactggct ccaacatcga ctgtgagaag  2400
ttgcggcgtc gcttctcctc gctgcatttc atggtggagg tgaagggcga cctgactgcc  2460
aagaaaatgg tgctggcttt gctggagctg gcgcagcagg accacggtgc tctggactgc  2520
tgcgtggtgg tcattctctc tcacggctgt caggccagcc acctgcagtt cccaggggct  2580
gtctacggca cagatggatg ccctgtgtcg gtcgagaaga ttgtgaacat cttcaatggg  2640
accagctgcc ccagcctggg agggaagccc aagctctttt tcatccaggc ctgtggtggg  2700
gagcagaaag accatgggtt tgaggtggcc tccacttccc ctgaagacga gtcccctggc  2760
agtaaccccg agccagatgc caccccgttc caggaaggtt tgaggacctt cgaccagctg  2820
gacgccatat ctagtttgcc cacacccagt gacatctttg tgtcctactc tactttccca  2880
ggttttgttt cctggaggga ccccaagagt ggctcctggt acgttgagac cctggacgac  2940
atctttgagc agtgggctca ctctgaagac ctgcagtccc tcctgcttag ggtcgctaat  3000
gctgtttcgg tgaaagggat ttataaacag atgcctggtt gctttaattt cctccggaaa  3060
aaactttttct ttaaaacatc agctagcaga gccgagggca ggggaagtct tctaacatgc  3120
ggggacgtgg aggaaaatcc cgggcccatg gagttcggac ttagttggct tttcctcgtc  3180
gccatactca aggtgtaca atgctcacgc gatatacaaa tgacgcagag tccatcctca  3240
ctgtctgcct cagtaggcga cagggtcaca ataacctgta aagcaagccc ggatatcaac  3300
tcttacctca gttggttcca acagaaacca ggaaaggtgc cgaagttgtt gatttaccgc  3360
gcaaaccgcc tcgttgacgg cgtgccagat aggttttctg gcagcgggag cggcactgac  3420
tttacgctca ctatatcaag cctgcagccg gaggacgtag caacttacta ttgcctccaa  3480
tacgacgaat tcccttacac gttcgggcaa ggaactaaag ttgaaataaa aagaggaagc  3540
acaagtggtt ctggaaaacc cggttccggt gagggcagta ccaaaggaga ggtgcagttg  3600
gtagagtctg gtgggggttt ggtgcaaccc ggagggtctc tgaggttgtc ttgcgcggca  3660
tccggcttta ctttttcctc atatgcgatg tcatgggtac gacaggcccc aggcaaggga  3720
ctggagtgga tcgcatctat ttcacgagga gggacgacat attaccccgga ttcagtgaag  3780
ggcaaattca taatttcacg cgataacgcc aagaactccc tctacctgca aatgaacagt  3840
cttagagcgg aagatacggc tgtgtattac tgtgcgcgat atgactacga tggatattac  3900
gcgatggatt attggggaca aggtacactg gtaaccgttt ccagctacgt caccgtctct  3960
tcacaggatc ccgccgagcc caaatctcct gacaaaactc acacatgccc accgtgccca  4020
```

-continued

```
gcacctgaac tcctgggggg accgtcagtc ttcctcttcc ccccaaaacc caaggacacc  4080
ctcatgatct cccggacccc tgaggtcaca tgcgtggtgg tggacgtgag ccacgaagac  4140
cctgaggtca agttcaactg gtacgtggac ggcgtggagg tgcataatgc caagacaaag  4200
ccgcgggagg agcagtacaa cagcacgtac cgtgtggtca gcgtcctcac cgtcctgcac  4260
caggactggc tgaatggcaa ggagtacaag tgcaaggtct ccaacaaagc cctcccagcc  4320
cccatcgaga aaaccatctc caaagccaaa gggcagcccc gagaaccaca ggtgtacacc  4380
ctgcccccat cccgggatga gctgaccaag aaccaggtca gcctgacctg cctggtcaaa  4440
ggcttctatc ccagcgacat cgccgtggag tgggagagca atgggcaacc ggagaacaac  4500
tacaagacca cgcctcccgt gctggactcc gacggctcct tcttcctcta cagcaagctc  4560
accgtggaca agagcaggtg gcagcagggg aacgtcttct catgctccgt gatgcatgag  4620
gctctgcaca accactacac gcagaagagc ctctccctgt ctccgggtaa aaaagatccc  4680
aaattttggg tgctggtggt ggttggtgga gtcctggctt gctatagctt gctagtaaca  4740
gtggccttta ttattttctg ggtgaggagt aagaggagca ggctcctgca cagtgactac  4800
atgaacatga ctccccgccg ccccgggccc acccgcaagc attaccagcc ctatgcccca  4860
ccacgcgact tcgcagccta tcgctccaga gtgaagttca gcaggagcgc agacgccccc  4920
gcgtaccagc agggccagaa ccagctctat aacgagctca atctaggacg aagagaggag  4980
tacgatgttt tggacaagag acgtggccgg gaccctgaga tgggggggaaa gccgagaagg  5040
aagaaccctc aggaaggcct gtacaatgaa ctgcagaaag ataagatggc ggaggcctac  5100
agtgagattg ggatgaaagg cgagcgccgg aggggcaagg ggcacgatgg cctttaccag  5160
ggtctcagta cagccaccaa ggacacctac gacgcccttc acatgcaggc cctgcccccct  5220
cgcggaccgc agtgtactaa ttatgctctc ttgaaattgg ctggagatgt tgagagcaat  5280
cccgggccca tgcggatcag caagccccac ctgcggagca tcagcatcca gtgctacctg  5340
tgcctgctgc tgaacagcca cttcctgacc gaggccggca tccacgtgtt catcctgggc  5400
tgcttcagcg ccggactgcc caagaccgag gccaactggg tgaacgtgat cagcgacctg  5460
aagaagatcg aggacctgat ccagagcatg cacatcgacg ccaccctgta caccgagagc  5520
gacgtgcacc ccagctgcaa ggtgaccgcc atgaagtgct ttctgctgga actgcaggtg  5580
atcagcctgg aaagcggcga cgccagcatc cacgacaccg tggagaacct gatcatcctg  5640
gccaacaaca gcctgagcag caacggcaac gtgaccgaga gcggctgcaa agagtgcgag  5700
gaactggaag agaagaacat caaagagttt ctgcagagct tcgtgcacat cgtgcagatg  5760
ttcatcaaca ccagctgacg cgtcatcatc gatccggatt agtccaattt gttaaagaca  5820
ggatatcagt ggtccaggct ctagttttga ctcaacaata tcaccagctg aagcctatag  5880
agtacgagcc atagataaaa taaaagattt tatttagtct ccagaaaaag gggggaatga  5940
aagaccccac ctgtaggttt ggcaagctag cttaagtaac gccattttgc aaggcatgga  6000
aaaatacata actgagaata gagaagttca gatcaaggtc aggaacagat ggaacagctg  6060
aatatgggcc aaacaggata tctgtggtaa gcagttcctg ccccggctca gggccaagaa  6120
cagatggaac agctgaatat gggccaaaca ggatatctgt ggtaagcagt tcctgccccg  6180
gctcagggcc aagaacagat ggtccccaga tgcggtccag ccctcagcag tttctagaga  6240
accatcagat gtttccaggg tgccccaagg acctgaaatg accctgtgcc ttatttgaac  6300
taaccaatca gttcgcttct cgcttctgtt cgcgcgcttc tgctccccga gctcaataaa  6360
agagcccaca acccctcact cggggcgcca gtcctccgat tgactgagtc gcccgggtac  6420
ccgtgtatcc aataaaccct cttgcagttg catccgactt gtggtctcgc tgttccttgg  6480
gagggtctcc tctgagtgat tgactacccg tcagcggggg tctttcacac atgcagcatg  6540
tatcaaaatt aatttggttt tttttcttaa gtatttacat taaatggcca tagtacttaa  6600
agttacattg gcttccttga aataaacatg gagtattcag aatgtgtcat aaatatttct  6660
aattttaaga tagtatctcc attggctttc tacttttttct tttatttttt tttgtcctct  6720
gtcttccatt tgttgttgtt gttgtttgtt tgtttgtttg ttggttggtt ggttaatttt  6780
tttttaaaga tcctacacta tagttcaagc tagactatta gctactctgt aacccagggt  6840
gaccttgaag tcatgggtag cctgctgttt tagccttccc acatctaaga ttacaggtat  6900
gagctatcat ttttggtata ttgattgatt gattgattga tgtgtgtgtg tgtgattgtg  6960
tttgtgtgtg tgactgtgaa aatgtgtgta tgggtgtgtg tgaatgtgtg tatgtatgtg  7020
tgtgtgtgag tgtgtgtgtg tgtgtgtgca tgtgtgtgtg tgtgactgtg tctatgtgta  7080
tgactgtgtg tgtgtgtgtg tgtgtgtgtg tgtgtgtgtg tgtgtgtgtg ttgtgaaaaa  7140
atattctatg gtagtgagag ccaacgctcc ggctcaggtg tcaggttggt ttttgagaca  7200
gagtctttca cttagcttgg aattcactgg ccgtcgtttt acaacgtcgt gactgggaaa  7260
accctggcgt tacccaactt aatcgccttg cagcacatcc ccctttcgcc agctggcgta  7320
atagcgaaga ggcccgcacc gatcgccctt cccaacagtt gcgcagcctg aatggcgaat  7380
ggcgcctgat gcggtatttt ctccttacgc atctgtgcgg tatttcacac cgcatatggt  7440
gcactctcag tacaatctgc tctgatgccg catagttaag ccagccccga cacccgccaa  7500
cacccgctga cgcgccctga cgggcttgtc tgctcccggc atccgcttac agacaagctg  7560
tgaccgtctc cgggagctgc atgtgtcaga ggttttcacc gtcatcaccg aaacgcgcga  7620
gacgaaaggg cctcgtgata cgcctatttt tataggttaa tgtcatgata ataatggttt  7680
cttagacgtc aggtggcact tttcggggaa atgtgcgcgg aacccctatt tgtttatttt  7740
tctaaataca ttcaaatatg tatccgctca tgagacaata accctgataa atgcttcaat  7800
aatattgaaa aaggaagagt atgagtattc aacatttccg tgtcgccctt attccctttt  7860
ttgcggcatt ttgccttcct gtttttgctc acccagaaac gctggtgaaa gtaaaagatg  7920
ctgaagatca gttgggtgca cgagtgggtt acatcgaact ggatctcaac agcggtaaga  7980
tccttgagag ttttcgcccc gaagaacgtt ttccaatgat gagcactttt aaagttctgc  8040
tatgtggcgc ggtattatcc cgtattgacg ccgggcaaga gcaactcggt cgccgcatac  8100
actattctca gaatgacttg gttgagtact caccagtcac agaaaagcat cttacggatg  8160
gcatgacagt aagagaatta tgcagtgctg ccataaccat gagtgataac actgcggcca  8220
acttacttct gacaacgatc ggaggaccga aggagctaac cgcttttttg cacaacatgg  8280
gggatcatgt aactcgcctt gatcgttggg aaccggagct gaatgaagcc ataccaaacg  8340
acgagcgtga caccacgatg cctgtagcaa tggcaacaac gttgcgcaaa ctattaactg  8400
gcgaactact tactctagct tcccggcaac aattaataga ctggatggag gcggataaag  8460
ttgcaggacc acttctgcgc tcggcccttc cggctggctg gtttattgct gataaatctg  8520
gagccggtga gcgtgggtct cgcggtatca ttgcagcact ggggccagat ggtaagccct  8580
cccgtatcgt agttatctac acgacgggga gtcaggcaac tatggatgaa cgaaatagac  8640
agatcgctga gataggtgcc tcactgatta agcattggta actgtcagac caagtttact  8700
catatatact ttagattgat ttaaaacttc atttttaatt taaaaggatc taggtgaaga  8760
```

-continued

```
tcctttttga taatctcatg accaaaatcc cttaacgtga gttttcgttc cactgagcgt  8820
cagaccccgt agaaaagatc aaaggatctt cttgagatcc tttttttctg cgcgtaatct  8880
gctgcttgca aacaaaaaaa ccaccgctac cagcggtggt ttgtttgccg gatcaagagc  8940
taccaactct ttttccgaag gtaactggct tcagcagagc gcagatacca aatactgttc  9000
ttctagtgta gccgtagtta ggccaccact tcaagaactc tgtagcaccg cctacatacc  9060
tcgctctgct aatcctgtta ccagtggctg ctgccagtgg cgataagtcg tgtcttaccg  9120
ggttggactc aagacgatag ttaccggata aggcgcagcg gtcgggctga acggggggtt  9180
cgtgcacaca gcccagcttg gagcgaacga cctacaccga actgagatac ctacagcgtg  9240
agctatgaga aagcgccacg cttcccgaag ggagaaaggc ggacaggtat ccggtaagcg  9300
gcagggtcgg aacaggagag cgcacgaggg agcttccagg gggaaacgcc tggtatcttt  9360
atagtcctgt cgggtttcgc cacctctgac ttgagcgtcg atttttgtga tgctcgtcag  9420
gggggcggag cctatggaaa aacgccagca acgcggcctt tttacggttc ctggcctttt  9480
gctggccttt tgctcacatg ttctttcctg cgttatcccc tgattctgtg gataaccgta  9540
ttaccgcctt tgagtgagct gataccgctc gccgcagccg aacgaccgag cgcagcgagt  9600
cagtgagcga ggaagcggaa gagcgcccaa tacgcaaacc gcctctcccc gcgcgttggc  9660
cgattcatta atgcagctgg cacgacaggt ttcccgactg gaaagcgggc agtgagcgca  9720
acgcaattaa tgtgagttag ctcactcatt aggcacccca ggctttacac tttatgcttc  9780
cggctcgtat gttgtgtgga attgtgagcg gataacaatt tcacacagga aacagctatg  9840
accatgatta cgccaagctt tgctcttagg agtttcctaa tacatcccaa actcaaatat  9900
ataaagcatt tgacttgttc tatgccctag gggcggggg gaagctaagc cagcttttt  9960
taacatttaa aatgttaatt ccattttaaa tgcacagatg tttttatttc ataagggttt  10020
caatgtgcat gaatgctgca atattcctgt taccaaagct agtataaata aaaatagata  10080
aacgtggaaa ttacttagag tttctgtcat taacgtttcc ttcctcagtt gacaacataa  10140
atgcgctgct gagcaagcca gtttgcatct gtcaggatca atttcccatt atgccagtca  10200
tattaattac tagtcaatta gttgattttt atttttgaca tatacatgtg             10250

SEQ ID NO: 37           moltype = DNA  length = 10244
FEATURE                 Location/Qualifiers
misc_feature            1..10244
                        note = hCD5-CAR
source                  1..10244
                        mol_type = other DNA
                        organism = synthetic construct
SEQUENCE: 37
aatgaaagac cccacctgta ggtttggcaa gctagcttaa gtaacgccat tttgcaaggc  60
atggaaaaat acataactga gaatagaaaa gttcagatca aggtcaggaa cagatggaac  120
agctgaatat gggccaaaca ggatatctgt ggtaagcagt tcctgccccg gctcagggcc  180
aagaacagat ggaacagctg aatatgggcc aaacaggata tctgtggtaa gcagttcctg  240
ccccggctca gggccaagaa cagatggtcc ccagatgcgg tccagccctc agcagtttct  300
agagaaccat cagatgtttc cagggtgccc caaggacctg aaatgaccct gtgccttatt  360
tgaactaacc aatcagttcg cttctcgctt ctgttcgcgc gcttatgctc cccgagctca  420
ataaaagagc ccacaacccc tcactcgggg cgccagtcct ccgattgact gagtcgcccg  480
ggtacccgtg tatccaataa accctcttgc agttgcatcc gacttgtggt ctcgctgttc  540
cttgggaggg tctcctctga gtgattgact acccgtcagc gggggtcttt catttggggg  600
ctcgtccggg atcgggagac ccctgcccag ggaccaccga cccaccaccg ggaggtaagc  660
tggccagcaa cttatctgtg tctgtccgat tgtctagtgt ctatgactga ttttatgcgc  720
ctgcgtcggt actagttagc taactagctc tgtatctggc ggacccgtgg tggaactgac  780
gagttcggaa cacccggccg caaccctggg agacgtccca gggacttcgg gggccgtttt  840
tgtggcccga cctgagtcct aaaatcccga tcgtttagga ctctttggtg cacccccctt  900
agaggaggga tatgtggttc tggtaggaga cgagaaccta aaacagttcc cgcctccgtc  960
tgaatttttg ctttcggttt gggaccgaag ccgcgccgcg cgtcttgtct gctgcagcat  1020
cgttctgtgt tgtctctgtc tgactgtgtt tctgtatttg tctgaaaata tgggcccggg  1080
ctagcctgtt accactccct taagtttgac cttaggtcac tggaaagatg tcgagcggat  1140
cgctcacaac cagtcggtag atgtcaagaa gagacgttgg gttaccttct gctctgcaga  1200
atggccaacc tttaacgtcg gatggccgcg agacggcacc tttaaccgag acctcatcac  1260
ccaggttaag atcaaggtct tttcacctgg cccgcatgga cacccagacc aggtggggta  1320
catcgtgacc tgggaagcct tggcttttga cccccctccc tgggtcaagc cctttgtaca  1380
ccctaagcct ccgcctcctc ttcctccatc cgccccgtct ctcccccttg aacctcctcg  1440
ttcgaccccg cctcgatcct ccctttatcc agccctcact ccttctctag gcgcccccat  1500
atggccatat gagatcttat atggggcacc cccgcccctt gtaaacttcc ctgaccctga  1560
catgacaaga gttactaaca gcccctctct ccaagctcac ttacaggctc tctacttagt  1620
ccagcacgaa gtctggagac ctctggcggc agcctaccaa gaacaactgg accgaccggt  1680
ggtacctcac ccttaccgag tcggcgacac agtgtgggtc cgccgacacc agactaagaa  1740
cctagaacct cgctggaaag gaccttacac agtcctgctg accaccccca ccgccctcaa  1800
agtagacggc atcgcagctt ggatacacgc cgcccacgtg aaggctgccg accccggggg  1860
tggaccatcc tctagactgc catgctcgag ggagtgcagg tggaaaccat ctccccagga  1920
gacgggcgca ccttccccaa gcgcggccag acctgcgtgg tgcactacac cgggatgctt  1980
gaagatggaa agaaagttga ttcctcccgg gacagaaaca agccctttaa gtttatgcta  2040
ggcaagcagg aggtgatccg aggctgggaa gaaggggttg cccagatgag tgtgggtcag  2100
agagccaaac tgactatatc tccagattat gcctatggtg ccactgggca cccaggcatc  2160
atcccaccac atgccactct cgtcttcgat gtggagcttc taaaactgga atctggcggt  2220
ggatccggag tcgacggatt tggtgatgtc ggtgctcttg agagtttgag ggaaatgca  2280
gatttggctt acatcctgag catggagccc tgtggccact gcctcattat caacaatgtg  2340
aacttctgcc gtgagtccgg gctccgcacc cgcactggct ccaacatcga ctgtgagaag  2400
ttgcggcgtc gcttctcctc gctgcatttc atggtggagg tgaagggcga cctgactgcc  2460
aagaaaatgg tgctggcttt gctggagctg gcgcagcagg accacggtgc tctggactgc  2520
tgcgtggtgg tcattctctc tcacggctgt caggccagcc acctgcagtt cccaggggct  2580
gtctacggca cagatggatg ccctgtgtcg gtcgagaaga ttgtgaacat cttcaatggg  2640
accagctgcc ccagcctggg agggaagccc aagctctttt tcatccaggc ctgtggtggg  2700
```

```
gagcagaaag accatgggtt tgaggtggcc tccacttccc ctgaagacga gtcccctggc  2760
agtaaccccg agccagatgc caccccgttc caggaaggtt tgaggacctt cgaccagctg  2820
gacgccatat ctagtttgcc cacacccagt gacatctttg tgtcctactc tactttccca  2880
ggttttgttt cctggaggga ccccaagagt ggctcctggt acgttgagac cctggacgac  2940
atctttgagc agtgggctca ctctgaagac ctgcagtccc tcctgcttag ggtcgctaat  3000
gctgtttcgg tgaaagggat ttataaacag atgcctggtt gctttaattt cctccggaaa  3060
aaacttttct ttaaaacatc agctagcaga gccgagggca ggggaagtct tctaacatgc  3120
ggggacgtgg aggaaaatcc cgggcccatg gagttcggtc tcagttggct gtttttggtt  3180
gctatcttga agggcgtcca atgcagccgg gacatccaga tgacccagtc tccctctagc  3240
atgtcagcga gtcttggtga tcgagtgacg attacctgca gagcctctca agatataaac  3300
agctatcttt catggttcca acagaagccg gggaagtccc caaaaactct catatacagg  3360
gcgaatcgac tcgtagacgg tgtgccttca aggttttccg ggagtggtag tggcacagat  3420
tacacactta caatctcttc attgcagtat gaggatttcg ggatctacta ctgtcaacag  3480
tacgacgaat ccccatggac gtttgggggc gggaccaaac ttgagataaa agggagcaca  3540
tctggaagtg gtaaacctgg gtcaggggag ggttccacaa aggacaaat tcaacttgtc  3600
caaagcggtc ctggtcttaa gaagcctgga gggtctgtca ggataagttg tgcggcatcc  3660
ggctacacct tcaccaacta tgggatgaac tgggtgaaac aagcgcctgg gaaaggtctt  3720
cgatggatgg gctggattaa tacccacact ggagagccca cttacgctga tgatttcaaa  3780
ggacgattta ccttctcctt ggatacttcc aagagtaccg cgtacttgca aatcaacagt  3840
ctccgggctg aagacacggc cacatacttc tgtacgcgga gagggtatga ctggtatttt  3900
gatgtgtggg gtcagggaac aaccgtgact gtttcaagct acgtcaccgt ctcttcacag  3960
gatcccgccg agcccaaatc tcctgacaaa actcacacat gcccaccgtg cccagcacct  4020
gaactcctgg ggggaccgtc agtcttcctc ttccccccaa aacccaagga caccctcatg  4080
atctcccgga cccctgaggt cacatgcgtg gtggtggacg tgagccacga agaccctgag  4140
gtcaagttca actggtacgt ggacggcgtg gaggtgcata atgccaagac aaagccgcgg  4200
gaggagcagt acaacagcac gtaccgtgtg gtcagcgtcc tcaccgtcct gcaccaggac  4260
tggctgaatg gcaaggagta caagtgcaag gtctccaaca aagccctccc agcccccatc  4320
gagaaaacca tctccaaagc caaagggcag ccccgagaac cacaggtgta caccctgccc  4380
ccatcccggg atgagctgac caagaaccag gtcagcctga cctgcctggt caaaggcttc  4440
tatcccagcg acatcgccgt ggagtgggag agcaatgggc aaccggagaa caactacaag  4500
accacgcctc ccgtgctgga ctccgacggc tccttcttcc tctacagcaa gctcaccgtg  4560
gacaagagca ggtggcagca ggggaacgtc ttctcatgct ccgtgatgca tgaggctctg  4620
cacaaccact acacgcagaa gagcctctcc ctgtctccgg gtaaaaaaga tcccaaattt  4680
tgggtgctgg tggtggttgg tggagtcctg gcttgctata gcttgctagt aacagtggcc  4740
tttattattt tctgggtgag gagtaagagg agcaggctcc tgcacagtga ctacatgaac  4800
atgactcccc gccgccccgg gcccacccgc aagcattacc agccctatgc cccaccacgc  4860
gacttcgcag cctatcgctc cagagtgaag ttcagcagga gcgcagacgc cccccgcgtac  4920
cagcagggcc agaaccagct ctataacgag ctcaatctag gacgaagaga ggagtacgat  4980
gttttggaca agagacgtgg ccgggaccct gagatggggg gaaagccgag aaggaagaac  5040
cctcaggaag gcctgtacaa tgaactgcag aaagataaga tggcggaggc ctacagtgag  5100
attgggatga aaggcgagcg ccggaggggc aaggggcacg atggccttta ccagggtctc  5160
agtacagcca ccaaggacac ctacgacgcc cttcacatgc aggccctgcc ccctcgcgga  5220
ccgcagtgta ctaattatgc tctcttgaaa ttggctggag atgttgagag caatcccggg  5280
cccatgcgga tcagcaagcc ccacctgcgg agcatcagca tccagtgcta cctgtgcctg  5340
ctgctgaaca gccacttcct gaccgaggcc ggcatccacg tgttcatcct gggctgcttc  5400
agcgccggac tgcccaagac cgaggccaac tgggtgaacg tgatcagcga cctgaagaag  5460
atcgaggacc tgatccagag catgcacatc gacgccaccc tgtacaccga gagcgacgtg  5520
caccccagct gcaaggtgac cgccatgaag tgctttctgc tggaactgca ggtgatcagc  5580
ctggaaagcg gcgacgccag catccacgac accgtggaga acctgatcat cctggccaac  5640
aacagcctga gcagcaacgg caacgtgacc gagagcggct gcaaagagtg cgaggaactg  5700
gaagagaaga acatcaaaga gtttctgcag agcttcgtgc acatcgtgca gatgttcatc  5760
aacaccagct gacgcgtcat catcgatccg gattagtcca atttgttaaa gacaggatat  5820
cagtggtcca ggctctagtt ttgactcaac aatatcacca gctgaagcct atagagtacg  5880
agccatagat aaaataaaag attttattta gtctccagaa aaaggggggga atgaaagacc  5940
ccacctgtag gtttggcaag ctagcttaag taacgccatt ttgcaaggca tggaaaaata  6000
cataactgag aatagagaag ttcagatcaa ggtcaggaac agatggaaca gctgaatatg  6060
ggccaaacag gatatctgtg gtaagcagtt cctgccccgg ctcagggcca agaacagatg  6120
gaacagctga atatgggcca aacaggatat ctgtggtaag cagttcctgc cccggctcag  6180
ggccaagaac agatggtccc cagatgcggt ccagccctca gcagtttcta gagaaccatc  6240
agatgtttcc agggtgcccc aaggacctga aatgaccctg tgccttattt gaactaacca  6300
atcagttcgc ttctcgcttc tgttcgcgcg cttctgctcc ccgagctcaa taaaagagcc  6360
cacaacccct cactcggggc gccagtcctc cgattgactg agtcgcccgg gtacccgtgt  6420
atccaataaa ccctcttgca gttgcatccg acttgtggtc tcgctgttcc ttgggagggt  6480
ctcctctgag tgattgacta cccgtcagcg ggggtctttc acacatgcag catgtatcaa  6540
aattaatttg gttttttttc ttaagtattt acattaaatg gccatagtac ttaaagttac  6600
attggcttcc ttgaaataaa catggagtat tcagaatgtg tcataaatat ttctaatttt  6660
aagatagtat ctccattggc tttctacttt ttcttttatt tttttttgtc ctctgtcttc  6720
catttgttgt tgttgttgtt tgtttgtttg tttgttggtt ggttggttaa tttttttta  6780
aagatcctac actatagttc aagctagact attagctact ctgtaaccca gggtgacctt  6840
gaagtcatgg gtagcctgct gttttagcct tcccacatct aagattacag gtatgagcta  6900
tcatttttgg tatattgatt gattgattga ttgatgtgtg tgtgtgtgat tgtgtttgtg  6960
tgtgtgactg tgaaaatgtg tgtatgggtg tgtgtgaatg tgtgtatgta tgtgtgtgtg  7020
tgagtgtgtg tgtgtgtgtg tgcatgtgtg tgtgtgtgac tgtgtctatg tgtatgactg  7080
tgtgtgtgtg tgtgtgtgtg tgtgtgtgtg tgtgtgtgtg tgtgttgtga aaaaatattc  7140
tatggtagtg agagccaacg ctccggctca ggtgtcaggt tggtttttga gacagagtct  7200
ttcacttagc ttggaattca ctggccgtcg ttttacaacg tcgtgactgg gaaaaccctg  7260
gcgttaccca acttaatcgc cttgcagcac atccccctttt cgccagctgg cgtaatagcg  7320
aagaggcccg caccgatcgc ccttcccaac agttgcgcag cctgaatggc gaatggcgcc  7380
tgatgcggta ttttctcctt acgcatctgt gcggtatttc acaccgcata tggtgcactc  7440
```

```
tcagtacaat ctgctctgat gccgcatagt taagccagcc ccgacacccg ccaacacccg  7500
ctgacgcgcc ctgacgggct tgtctgctcc cggcatccgc ttacagacaa gctgtgaccg  7560
tctccgggag ctgcatgtgt cagaggtttt caccgtcatc accgaaacgc gcgagacgaa  7620
agggcctcgt gatacgccta tttttatagg ttaatgtcat gataataatg gtttcttaga  7680
cgtcaggtgg cacttttcgg ggaaatgtgc gcggaacccc tatttgttta tttttctaaa  7740
tacattcaaa tatgtatccg ctcatgagac aataaccctg ataaatgctt caataatatt  7800
gaaaaaggaa gagtatgagt attcaacatt tccgtgtcgc ccttattccc ttttttgcgg  7860
cattttgcct tcctgttttt gctcacccag aaacgctggt gaaagtaaaa gatgctgaag  7920
atcagttggg tgcacgagtg ggttacatcg aactggatct caacagcggt aagatccttg  7980
agagttttcg ccccgaagaa cgttttccaa tgatgagcac ttttaaagtt ctgctatgtg  8040
gcgcggtatt atcccgtatt gacgccgggc aagagcaact cggtcgccgc atacactatt  8100
ctcagaatga cttggttgag tactcaccag tcacagaaaa gcatcttacg gatggcatga  8160
cagtaagaga attatgcagt gctgccataa ccatgagtga taacactgcg gccaacttac  8220
ttctgacaac gatcggagga ccgaaggagc taaccgcttt tttgcacaac atgggggatc  8280
atgtaactcg ccttgatcgt tgggaaccgg agctgaatga agccatacca aacgacgagc  8340
gtgacaccac gatgcctgta gcaatggcaa caacgttgcg caaactatta actggcgaac  8400
tacttactct agcttcccgg caacaattaa tagactggat ggaggcggat aaagttgcag  8460
gaccacttct gcgctcggcc cttccggctg gctggtttat tgctgataaa tctggagccg  8520
gtgagcgtgg gtctcgcggt atcattgcag cactggggcc agatggtaag ccctcccgta  8580
tcgtagttat ctacacgacg gggagtcagg caactatgga tgaacgaaat agacagatcg  8640
ctgagatagg tgcctcactg attaagcatt ggtaactgtc agaccaagtt tactcatata  8700
tactttagat tgatttaaaa cttcattttt aatttaaaag gatctaggtg aagatccttt  8760
ttgataatct catgaccaaa atcccttaac gtgagttttc gttccactga gcgtcagacc  8820
ccgtagaaaa gatcaaagga tcttcttgag atcctttttt tctgcgcgta atctgctgct  8880
tgcaaacaaa aaaaccaccg ctaccagcgg tggtttgttt gccggatcaa gagctaccaa  8940
ctctttttcc gaaggtaact ggcttcagca gagcgcagat accaaatact gttcttctag  9000
tgtagccgta gttaggccac cacttcaaga actctgtagc accgcctaca tacctcgctc  9060
tgctaatcct gttaccagtg gctgctgcca gtggcgataa gtcgtgtctt accgggttgg  9120
actcaagacg atagttaccg gataaggcgc agcggtcggg ctgaacgggg ggttcgtgca  9180
cacagcccag cttggagcga acgacctaca ccgaactgag atacctacag cgtgagctat  9240
gagaaagcgc cacgcttccc gaagggagaa aggcggacag gtatccggta agcggcaggg  9300
tcggaacagg agagcgcacg agggagcttc caggggggaaa cgcctggtat ctttatagtc  9360
ctgtcgggtt tcgccacctc tgacttgagc gtcgattttt gtgatgctcg tcaggggggc  9420
ggagcctatg gaaaaacgcc agcaacgcgg cctttttacg gttcctggcc ttttgctggc  9480
cttttgctca catgttcttt cctgcgttat cccctgattc tgtggataac cgtattaccg  9540
cctttgagtg agctgatacc gctcgccgca gccgaacgac cgagcgcagc gagtcagtga  9600
gcgaggaagc ggaagagcgc ccaatacgca aaccgcctct ccccgcgcgt tggccgattc  9660
attaatgcag ctggcacgac aggtttcccg actggaaagc gggcagtgag cgcaacgcaa  9720
ttaatgtgag ttagctcact cattaggcac cccaggcttt acactttatg cttccggctc  9780
gtatgttgtg tggaattgtg agcggataac aatttcacac aggaaacagc tatgaccatg  9840
attacgccaa gctttgctct taggagtttc ctaatacatc ccaaactcaa atatataaag  9900
catttgactt gttctatgcc ctagggggcg gggggaagct aagccagctt tttttaacat  9960
ttaaaatgtt aattccattt taaatgcaca gatgttttta tttcataagg gtttcaatgt  10020
gcatgaatgc tgcaatattc ctgttaccaa agctagtata aataaaaata gataaacgtg  10080
gaaattactt agagtttctg tcattaacgt ttccttcctc agttgacaac ataaatgcgc  10140
tgctgagcaa gccagtttgc atctgtcagg atcaatttcc cattatgcca gtcatattaa  10200
ttactagtca attagttgat ttttattttt gacatataca tgtg                    10244
```

```
SEQ ID NO: 38          moltype = DNA  length = 10625
FEATURE                Location/Qualifiers
misc_feature           1..10625
                       note = pSFG4-CD19CAR-Ev3
source                 1..10625
                       mol_type = other DNA
                       organism = synthetic construct
SEQUENCE: 38
aatgaaagac cccacctgta ggtttggcaa gctagcttaa gtaacgccat tttgcaaggc  60
atggaaaaat acataactga gaatagaaaa gttcagatca aggtcaggaa cagatggaac  120
agctgaatat gggccaaaca ggatatctgt ggtaagcagt tcctgccccg gctcagggcc  180
aagaacagat ggaacagctg aatatgggcc aaacaggata tctgtggtaa gcagttcctg  240
ccccggctca gggccaagaa cagatggtcc ccagatgcgg tccagccctc agcagtttct  300
agagaaccat cagatgtttc cagggtgccc caaggacctg aaatgaccct gtgccttatt  360
tgaactaacc aatcagttcg cttctcgctt ctgttcgcgc gcttatgctc cccgagctca  420
ataaaagagc ccacaacccc tcactcgggg cgccagtcct ccgattgact gagtcgcccg  480
ggtacccgtg tatccaataa accctcttgc agttgcatcc gacttgtggt ctcgctgttc  540
cttgggaggg tctcctctga gtgattgact acccgtcagc gggggtcttt catttggggg  600
ctcgtccggg atcgggagac ccctgcccag ggaccaccga cccaccaccg ggaggtaagc  660
tggccagcaa cttatctgtg tctgtccgat tgtctagtgt ctatgactga ttttatgcgc  720
ctgcgtcggt actagttagc taactagctc tgtatctggc ggacccgtgg tggaactgac  780
gagttcggaa cacccggccg caaccctggg agacgtccca gggacttcgg gggccgtttt  840
tgtggcccga cctgagtcct aaaatcccga tcgtttagga ctctttggtg cacccccctt  900
agaggaggga tatgtggttc tggtaggaga cgagaaccta aaacagttcc cgcctccgtc  960
tgaatttttg ctttcggttt gggaccgaag ccgcgccgcg cgtcttgtct gctgcagcat  1020
cgttctgtgt tgtctctgtc tgactgtgtt tctgtatttg tctgaaaata tgggcccggg  1080
ctagcctgtt accactccct taagtttgac cttaggtcac tggaaagatg tcgagcggat  1140
cgctcacaac cagtcggtag atgtcaagaa gagacgttgg gttaccttct gctctgcaga  1200
atggccaacc tttaacgtcg gatggccgcg agacggcacc tttaaccgag acctcatcac  1260
ccaggttaag atcaaggtct tttcacctgg cccgcatgga cacccagacc aggtggggta  1320
catcgtgacc tgggaagcct tggcttttga cccccctccc tgggtcaagc cctttgtaca  1380
```

-continued

```
ccctaagcct ccgcctcctc ttcctccatc cgccccgtct ctccccccttg aacctcctcg  1440
ttcgaccccg cctcgatcct ccctttatcc agccctcact ccttctctag gcgcccccat  1500
atggccatat gagatcttat atggggcacc cccgcccctt gtaaacttcc ctgaccctga  1560
catgacaaga gttactaaca gcccctctct ccaagctcac ttacaggctc tctacttagt  1620
ccagcacgaa gtctggagac ctctggcggc agcctaccaa gaacaactgg accgaccggt  1680
ggtacctcac ccttaccgag tcggcgacac agtgtgggtc cgccgacacc agactaagaa  1740
cctagaacct cgctggaaag gaccttacac agtcctgctg accacccccca ccgccctcaa  1800
agtagacggc atcgcagctt ggatacacgc cgcccacgtg aaggctgccg accccggggg  1860
tggaccatcc tctagactgc catgctcgag ggagtgcagg tggaaaccat ctccccagga  1920
gacgggcgca ccttccccaa gcgcggccag acctgcgtgg tgcactacac cgggatgctt  1980
gaagatggaa agaaagttga ttcctcccgg gacagaaaca agccctttaa gtttatgcta  2040
ggcaagcagg aggtgatccg aggctgggaa gaaggggttg cccagatgag tgtgggtcag  2100
agagccaaac tgactatatc tccagattat gcctatggtg ccactgggca cccaggcatc  2160
atcccaccac atgccactct cgtcttcgat gtggagcttc taaaactgga atctggcggt  2220
ggatccggag tcgacggatt tggtgatgtc ggtgctcttg agagtttgag gggaaatgca  2280
gatttggctt acatcctgag catggagccc tgtggccact gcctcattat caacaatgtg  2340
aacttctgcc gtgagtccgg gctccgcacc cgcactggct ccaacatcga ctgtgagaag  2400
ttgcggcgtc gcttctcctc gctgcatttc atggtggagg tgaagggcga cctgactgcc  2460
aagaaaatgg tgctggcttt gctggagctg gcgcagcagg accacggtgc tctggactgc  2520
tgcgtggtgg tcattctctc tcacggctgt caggccagcc acctgcagtt cccaggggct  2580
gtctacggca cagatggatg ccctgtgtcg gtcgagaaga ttgtgaacat cttcaatggg  2640
accagctgcc ccagcctggg agggaagccc aagctctttt tcatccaggc ctgtggtggg  2700
gagcagaaag accatgggtt tgaggtggcc tccacttccc ctgaagacga gtcccctggc  2760
agtaaccccg agccagatgc caccccgttc caggaaggtt tgaggacctt cgaccagctg  2820
gacgccatat ctagtttgcc cacacccagt gacatctttg tgtcctactc tactttccca  2880
ggttttgttt cctggaggga ccccaagagt ggctcctggt acgttgagac cctggacgac  2940
atctttgagc agtgggctca ctctgaagac ctgcagtccc tcctgcttag ggtcgctaat  3000
gctgtttcgg tgaaagggat ttataaacag atgcctggtt gctttaattt cctccggaaa  3060
aaacttttct ttaaaacatc agctagcaga gccgagggca ggggaagtct tctaacatgc  3120
ggggacgtgg aggaaaatcc cgggcccatg gagtttgggc tgagctggct tttcttgtg  3180
gctattttaa aaggtgtcca gtgctctaga gacatccaga tgacacagac tacatcctcc  3240
ctgtctgcct ctctgggaga cagagtcacc atcagttgca gggcaagtca ggacattagt  3300
aaatatttaa attggtatca gcagaaacca gatggaactg ttaaactcct gatctaccat  3360
acatcaagat tacactcagg agtcccatca aggttcagtg gcagtgggtc tggaacagat  3420
tattctctca ccattagcaa cctggagcaa gaagatattg ccacttactt ttgccaacag  3480
ggtaatacgc ttccgtacac gttcggaggg gggaccaagc tggagctgaa acgtggtggt  3540
ggtggttctg gtggtggtgg ttctggcggc ggcggctccg gtggtggtgg atccgaggtg  3600
cagctgcagc agtctggacc tggcctggtg gcgccctcac agagcctgtc cgtcacatgc  3660
actgtctcag ggtctcatt acccgactat ggtgtaagct ggattcgcca gcctccacga  3720
aagggtctgg agtggctggg agtaatatgg ggtagtgaaa ccacatacta taattcagct  3780
ctcaaatcca gactgaccat catcaaggac aactccaaga gccaagtttt cttaaaaatg  3840
aacagtctgc aaactgatga cacagccatt tactactgtg ccaaacatta ttactacggt  3900
ggtagctatg ctatggacta ctggggccaa gggaccacgg tcaccgtctc ctcgtacgtc  3960
accgtctctt cacaggatcc cgccctggaa gagaagaaag gcaattacgt cgtgaccgac  4020
cacggcagct gtgtgcgggc ttgtggcgcc gatagctacg agatggaaga ggacggcgtg  4080
cggaagtgca agaagtgcga gggcccctgc agaaaagtgt gcaacggcat cggcatcgga  4140
gagttcaagg atagcctgag catcaacgcc accaacatca agcacttcaa gaactgcacc  4200
agcatcagcg gcgacctgca catcctgccc gtggccttta gaggcgacag cttcacccac  4260
acccccccac tggatcccca ggaactggac atcctgaaaa ccgtgaaaga gatcacaggc  4320
tttctgctga ttcaggcctg gcccgagaac cggacagacc tgcacgcctt cgagaacctg  4380
gaaatcatca gaggccggac caagcagcac ggccagtttt ctctggccgt ggtgtccctg  4440
aacatcacca gcctgggcct gcggagcctg aaagaaatca gcgacggcga cgtgatcatc  4500
tccggcaaca agaacctgtg ctacgccaac accatcaatt ggaagaagct gttcggcacc  4560
tccggccaga aaacaaagat catctctaac cggggcgaga acagctgcaa agccaccgga  4620
caagtgtgcc acgccctgtg tagccctgag ggctgttggg gacccgagcc cagagattgc  4680
gtgtcctgcc ggaatgtgtc cagaggccgc gagtgcgtgg acaagtgcaa cctgctggaa  4740
ggcgagcccc gcgagtttgt ggaaaacagc gagtgcatcc agtgccaccc cgagtgtctg  4800
ccccaggcca tgaacattac ctgcaccggc agaggccccg acaactgtat ccagtgcgcc  4860
cactacatcg acggccccca ctgcgtgaaa acctgtccag ctggcgtgat gggagagaac  4920
aacaccctcg tgtggaagta cgccgacgcc ggccatgtgt gccacctgtg tcaccccaat  4980
tgcacctacg gctgtaccgg ccctggcctg gaaggctgtc ctaccaacgg ccccaagatc  5040
ccttctaaag atcccaaatt ttgggtgctg gtggtggttg gtggagtcct ggcttgctat  5100
agcttgctag taacagtggc ctttattatt ttctgggtga ggagtaagag gagcaggctc  5160
ctgcacagtg actacatgaa catgactccc cgccgccccg ggcccacccg caagcattac  5220
cagccctatg ccccaccacg cgacttcgca gcctatcgct ccagagtgaa gttcagcagg  5280
agcgcagacg cccccgcgta ccagcagggc cagaaccagc tctataacga gctcaatcta  5340
ggacgaagag aggagtacga tgttttggac aagagacgtg gccgggaccc tgagatgggg  5400
ggaaagccga gaaggaagaa ccctcaggaa ggcctgtaca atgaactgca gaaagataag  5460
atggcggagg cctacagtga gattgggatg aaaggcgagc gccggagggg caaggggcac  5520
gatggccttt accagggtct cagtacagcc accaaggaca cctacgacgc ccttcacatg  5580
caggccctgc cccctcgcgg accgcagtgt actaattatg ctctcttgaa attggctgga  5640
gatgttgaga gcaatcccgg gcccatgcgg atcagcaagc cccacctgcg gagcatcagc  5700
atccagtgct acctgtgcct gctgctgaac agccacttcc tgaccgaggc cggcatccac  5760
gtgttcatcc tgggctgctt cagcgccgga ctgcccaaga ccgaggccaa ctgggtgaac  5820
gtgatcagcg acctgaagaa gatcgaggac ctgatccaga gcatgcacat cgacgccacc  5880
ctgtacaccg agagcgacgt gcaccccagc tgcaaggtga ccgccatgaa gtgctttctg  5940
ctggaactgc aggtgatcag cctggaaagc ggcgacgcca gcatccacga caccgtggag  6000
aacctgatca tcctggccaa caacagcctg agcagcaacg gcaacgtgac cgagagcggc  6060
tgcaaagagt gcgaggaact ggaagagaag aacatcaaag agtttctgca gagcttcgtg  6120
```

```
cacatcgtgc agatgttcat caacaccagc tgacgcgtca tcatcgatcc ggattagtcc  6180
aatttgttaa agacaggata tcagtggtcc aggctctagt tttgactcaa caatatcacc  6240
agctgaagcc tatagagtac gagccataga taaaataaaa gattttattt agtctccaga  6300
aaaagggggg aatgaaagac cccacctgta ggtttggcaa gctagcttaa gtaacgccat  6360
tttgcaaggc atggaaaaat acataactga gaatagagaa gttcagatca aggtcaggaa  6420
cagatggaac agctgaatat gggccaaaca ggatatctgt ggtaagcagt tcctgccccg  6480
gctcagggcc aagaacagat ggaacagctg aatatgggcc aaacaggata tctgtggtaa  6540
gcagttcctg ccccggctca gggccaagaa cagatggtcc ccagatgcgg tccagccctc  6600
agcagtttct agagaaccat cagatgtttc cagggtgccc caaggacctg aaatgaccct  6660
gtgccttatt tgaactaacc aatcagttcg cttctcgctt ctgttcgcgc gcttctgctc  6720
cccgagctca ataaaagagc ccacaacccc tcactcgggg cgccagtcct ccgattgact  6780
gagtcgcccg ggtacccgtg tatccaataa accctcttgc agttgcatcc gacttgtggt  6840
ctcgctgttc cttgggaggg tctcctctga gtgattgact acccgtcagc gggggtcttt  6900
cacacatgca gcatgtatca aaattaattt ggttttttt cttaagtatt tacattaaat  6960
ggccatagta cttaaagtta cattggcttc cttgaaataa acatggagta ttcagaatgt  7020
gtcataaata tttctaattt taagatagta tctccattgg ctttctactt tttcttttat  7080
tttttttgt cctctgtctt ccatttgttg ttgttgttgt ttgtttgttt gtttgttggt  7140
tggttggtta attttttttt aaagatccta cactatagtt caagctagac tattagctac  7200
tctgtaaccc agggtgacct tgaagtcatg ggtagcctgc tgttttagcc ttcccacatc  7260
taagattaca ggtatgagct atcatttttg gtatattgat tgattgattg attgatgtgt  7320
gtgtgtgtga ttgtgtttgt gtgtgtgact gtgaaaatgt gtgtatgggt gtgtgtgaat  7380
gtgtgtatgt atgtgtgtgt gtgagtgtgt gtgtgtgtgt gtgcatgtgt gtgtgtgtga  7440
ctgtgtctat gtgtatgact gtgtgtgtgt gtgtgtgtgt gtgtgtgtgt gtgtgtgtgt  7500
gtgtgttgtg aaaaaatatt ctatggtagt gagagccaac gctccggctc aggtgtcagg  7560
ttggtttttg agacagagtc tttcacttag cttggaattc actggccgtc gttttacaac  7620
gtcgtgactg ggaaaaccct ggcgttaccc aacttaatcg ccttgcagca catccccctt  7680
tcgccagctg gcgtaatagc gaagaggccc gcaccgatcg cccttcccaa cagttgcgca  7740
gcctgaatgg cgaatggcgc ctgatgcggt attttctcct tacgcatctg tgcggtattt  7800
cacaccgcat atggtgcact ctcagtacaa tctgctctga tgccgcatag ttaagccagc  7860
cccgacaccc gccaacaccc gctgacgcgc cctgacgggc ttgtctgctc ccggcatccg  7920
cttacagaca agctgtgacc gtctccggga gctgcatgtg tcagaggttt tcaccgtcat  7980
caccgaaacg cgcgagacga aagggcctcg tgatacgcct atttttatag gttaatgtca  8040
tgataataat ggtttcttag acgtcaggtg gcacttttcg gggaaatgtg cgcggaaccc  8100
ctatttgttt atttttctaa atacattcaa atatgtatcc gctcatgaga caataaccct  8160
gataaatgct tcaataatat tgaaaaagga agagtatgag tattcaacat ttccgtgtcg  8220
cccttattcc cttttttgcg gcattttgcc ttcctgtttt tgctcaccca gaaacgctgg  8280
tgaaagtaaa agatgctgaa gatcagttgg gtgcacgagt gggttacatc gaactggatc  8340
tcaacagcgg taagatcctt gagagttttc gccccgaaga acgttttcca atgatgagca  8400
cttttaaagt tctgctatgt ggcgcggtat tatcccgtat tgacgccggg caagagcaac  8460
tcggtcgccg catacactat tctcagaatg acttggttga gtactcacca gtcacagaaa  8520
agcatcttac ggatggcatg acagtaagag aattatgcag tgctgccata accatgagtg  8580
ataacactgc ggccaactta cttctgacaa cgatcggagg accgaaggag ctaaccgctt  8640
ttttgcacaa catgggggat catgtaactc gccttgatcg ttgggaaccg gagctgaatg  8700
aagccatacc aaacgacgag cgtgacacca cgatgcctgt agcaatggca acaacgttgc  8760
gcaaactatt aactggcgaa ctacttactc tagcttcccg gcaacaatta atagactgga  8820
tggaggcgga taaagttgca ggaccacttc tgcgctcggc ccttccggct ggctggttta  8880
ttgctgataa atctggagcc ggtgagcgtg ggtctcgcgg tatcattgca gcactggggc  8940
cagatggtaa gccctcccgt atcgtagtta tctacacgac ggggagtcag gcaactatgg  9000
atgaacgaaa tagacagatc gctgagatag gtgcctcact gattaagcat tggtaactgt  9060
cagaccaagt ttactcatat atactttaga ttgatttaaa acttcatttt taatttaaaa  9120
ggatctaggt gaagatcctt tttgataatc tcatgaccaa aatcccttaa cgtgagtttt  9180
cgttccactg agcgtcagac cccgtagaaa agatcaaagg atcttcttga gatccttttt  9240
ttctgcgcgt aatctgctgc ttgcaaacaa aaaaaccacc gctaccagcg gtggtttgtt  9300
tgccggatca agagctacca actctttttc cgaaggtaac tggcttcagc agagcgcaga  9360
taccaaatac tgttcttcta gtgtagccgt agttaggcca ccacttcaag aactctgtag  9420
caccgcctac atacctcgct ctgctaatcc tgttaccagt ggctgctgcc agtggcgata  9480
agtcgtgtct taccgggttg gactcaagac gatagttacc ggataaggcg cagcggtcgg  9540
gctgaacggg gggttcgtgc acacagccca gcttggagcg aacgacctac accgaactga  9600
gatacctaca gcgtgagcta tgagaaagcg ccacgcttcc cgaagggaga aaggcggaca  9660
ggtatccggt aagcggcagg gtcggaacag gagagcgcac gagggagctt ccagggggaa  9720
acgcctggta tctttatagt cctgtcgggt ttcgccacct ctgacttgag cgtcgatttt  9780
tgtgatgctc gtcagggggg cggagcctat ggaaaaacgc cagcaacgcg gcctttttac  9840
ggttcctggc cttttgctgg ccttttgctc acatgttctt tcctgcgtta tcccctgatt  9900
ctgtggataa ccgtattacc gcctttgagt gagctgatac cgctcgccgc agccgaacga  9960
ccgagcgcag cgagtcagtg agcgaggaag cggaagagcg cccaatacgc aaaccgcctc  10020
tccccgcgcg ttggccgatt cattaatgca gctggcacga caggtttccc gactggaaag  10080
cgggcagtga gcgcaacgca attaatgtga gttagctcac tcattaggca ccccaggctt  10140
tacactttat gcttccggct cgtatgttgt gtggaattgt gagcggataa caatttcaca  10200
caggaaacag ctatgaccat gattacgcca agctttgctc ttaggagttt cctaatacat  10260
cccaaactca aatatataaa gcatttgact tgttctatgc cctagggggc ggggggaagc  10320
taagccagct ttttttaaca tttaaaatgt taattccatt ttaaatgcac agatgttttt  10380
atttcataag ggtttcaatg tgcatgaatg ctgcaatatt cctgttacca aagctagtat  10440
aaataaaaat agataaacgt ggaaattact tagagtttct gtcattaacg tttccttcct  10500
cagttgacaa cataaatgcg ctgctgagca agccagtttg catctgtcag gatcaatttc  10560
ccattatgcc agtcatatta attactagtc aattagttga tttttatttt tgacatatac  10620
atgtg                                                              10625
```

SEQ ID NO: 39 moltype = DNA length = 10619
FEATURE Location/Qualifiers

```
misc_feature          1..10619
                      note = pSFG4-hCD19-Ev3-CAR
source                1..10619
                      mol_type = other DNA
                      organism = synthetic construct
SEQUENCE: 39
aatgaaagac cccacctgta ggtttggcaa gctagcttaa gtaacgccat tttgcaaggc  60
atggaaaaat acataactga gaatagaaaa gttcagatca aggtcaggaa cagatggaac  120
agctgaatat gggccaaaca ggatatctgt ggtaagcagt tcctgccccg gctcagggcc  180
aagaacagat ggaacagctg aatatgggcc aaacaggata tctgtggtaa gcagttcctg  240
ccccggctca gggccaagaa cagatggtcc ccagatgcgg tccagccctc agcagtttct  300
agagaaccat cagatgtttc cagggtgccc caaggacctg aaatgaccct gtgccttatt  360
tgaactaacc aatcagttcg cttctcgctt ctgttcgcgc gcttatgctc cccgagctca  420
ataaaagagc ccacaacccc tcactcgggg cgccagtcct ccgattgact gagtcgcccg  480
ggtacccgtg tatccaataa accctcttgc agttgcatcc gacttgtggt ctcgctgttc  540
cttgggaggg tctcctctga gtgattgact acccgtcagc gggggtcttt catttggggg  600
ctcgtccggg atcgggagac ccctgcccag ggaccaccga cccaccaccg ggaggtaagc  660
tggccagcaa cttatctgtg tctgtccgat tgtctagtgt ctatgactga ttttatgcgc  720
ctgcgtcggt actagttagc taactagctc tgtatctggc ggacccgtgg tggaactgac  780
gagttcggaa cacccggccg caaccctggg agacgtccca gggacttcgg gggccgtttt  840
tgtggcccga cctgagtcct aaaatcccga tcgtttagga ctctttggtg cacccccctt  900
agaggaggga tatgtggttc tggtaggaga cgagaaccta aaacagttcc cgcctccgtc  960
tgaatttttg ctttcggttt gggaccgaag ccgcgccgcg cgtcttgtct gctgcagcat  1020
cgttctgtgt tgtctctgtc tgactgtgtt tctgtatttg tctgaaaata tgggcccggg  1080
ctagcctgtt accactccct taagtttgac cttaggtcac tggaaagatg tcgagcggat  1140
cgctcacaac cagtcggtag atgtcaagaa gagacgttgg gttaccttct gctctgcaga  1200
atggccaacc tttaacgtcg gatggccgcg agacggcacc tttaaccgag acctcatcac  1260
ccaggttaag atcaaggtct tttcacctgg cccgcatgga cacccagacc aggtggggta  1320
catcgtgacc tgggaagcct tggcttttga cccccctccc tgggtcaagc cctttgtaca  1380
ccctaagcct ccgcctcctc ttcctccatc cgccccgtct ctcccccttg aacctcctcg  1440
ttcgaccccg cctcgatcct ccctttatcc agccctcact ccttctctag gcgcccccat  1500
atggccatat gagatcttat atggggcacc cccgcccctt gtaaacttcc ctgaccctga  1560
catgacaaga gttactaaca gcccctctct ccaagctcac ttacaggctc tctacttagt  1620
ccagcacgaa gtctggagac ctctggcggc agcctaccaa gaacaactgg accgaccggt  1680
ggtacctcac ccttaccgag tcggcgacac agtgtgggtc cgccgacacc agactaagaa  1740
cctagaacct cgctggaaag gaccttacac agtcctgctg accaccccca ccgccctcaa  1800
agtagacggc atcgcagctt ggatacacgc cgcccacgtg aaggctgccg accccggggg  1860
tggaccatcc tctagactgc catgctcgag ggagtgcagg tggaaaccat ctccccagga  1920
gacgggcgca ccttccccaa gcgcggccag acctgcgtgg tgcactacac cgggatgctt  1980
gaagatggaa agaaagttga ttcctcccgg gacagaaaca agccctttaa gtttatgcta  2040
ggcaagcagg aggtgatccg aggctgggaa gaaggggttg cccagatgag tgtgggtcag  2100
agagccaaac tgactatatc tccagattat gcctatggtg ccactgggca cccaggcatc  2160
atcccaccac atgccactct cgtcttcgat gtggagcttc taaaactgga atctggcggt  2220
ggatccggag tcgacggatt tggtgatgtc ggtgctcttg agagtttgag ggaaatgca  2280
gatttggctt acatcctgag catggagccc tgtggccact gcctcattat caacaatgtg  2340
aacttctgcc gtgagtccgg gctccgcacc cgcactggct ccaacatcga ctgtgagaag  2400
ttgcggcgtc gcttctcctc gctgcatttc atggtggagg tgaagggcga cctgactgcc  2460
aagaaaatgg tgctggcttt gctggagctg gcgcagcagg accacggtgc tctggactgc  2520
tgcgtggtgg tcattctctc tcacggctgt caggccagcc acctgcagtt cccaggggct  2580
gtctacggca cagatggatg ccctgtgtcg gtcgagaaga ttgtgaacat cttcaatggg  2640
accagctgcc ccagcctggg agggaagccc aagctctttt tcatccaggc ctgtggtggg  2700
gagcagaaag accatgggtt tgaggtggcc tccacttccc ctgaagacga gtcccctggc  2760
agtaaccccg agccagatgc caccccgttc caggaaggtt tgaggacctt cgaccagctg  2820
gacgccatat ctagtttgcc cacacccagt gacatctttg tgtcctactc tactttccca  2880
ggttttgttt cctggaggga ccccaagagt ggctcctggt acgttgagac cctggacgac  2940
atctttgagc agtgggctca ctctgaagac ctgcagtccc tcctgcttag ggtcgctaat  3000
gctgtttcgg tgaaagggat ttataaacag atgcctggtt gctttaattt cctccggaaa  3060
aaacttttct ttaaaacatc agctagcaga gccgagggca ggggaagtct tctaacatgc  3120
ggggacgtgg aggaaaatcc cgggcccatg gagttcggtt tgagctggct ctttcttgtt  3180
gctatcctca agggggtgca gtgttcaagg gatatccaga tgactcagag ccctagctcc  3240
cttagcgcgt ccgtcggcga ccgggttaca attacttgtc gcgcatcaca agacataagt  3300
aaatacttga actggtatca acaaaagcca ggaaaggttc caaaactcct catctatcac  3360
acgagtagac tccattccgg ggtccctgat cggttctcag gctctggttc tggaactgac  3420
ttcactctca cgatctctag tctgcaacct gaggatgtcg ctacctatta ttgccaacag  3480
ggaaacaccc tcccttacac atttggccaa ggtaccaaag ttgagatcaa gaggggctcc  3540
acatctggga gcgggaaacc gggaagtgga gaaggctcaa ccaaaggtga ggtgcaactt  3600
gtagagagtg gtggaggcct ggttcagccg ggagggtccc tcagacttag ttgcgcggct  3660
tctggcgttt cactgccgga ctacggggtc agttgggtta ggcaggcgcc tgggaaagga  3720
cttgagtgga tcggcgtgat atggggtagt gaaacaacct actacaatag tgctcttaaa  3780
tcaaaattca ttatcagccg agacaatgct aagaactccc tctatctcca aatgaatagt  3840
cttagagcag aagacacagc cgtttattac tgtgcccgcc attattacta tgggggcagc  3900
tacgcaatgg attattgggg ccaagggacc ctggtcacgg tatcaagcta cgtcaccgtc  3960
tcttcacagg atcccgccct ggaagagaag aaaggcaatt acgtcgtgac cgaccacggc  4020
agctgtgtgc gggcttgtgg cgccgatagc tacgagatgg aagaggacgg cgtgcggaag  4080
tgcaagaagt gcgagggccc ctgcagaaaa gtgtgcaacg gcatcggcat cggagagttc  4140
aaggatagcc tgagcatcaa cgccaccaac atcaagcact tcaagaactg caccagcatc  4200
agcggcgacc tgcacatcct gcccgtggcc tttagaggcg acagcttcac ccacaccccc  4260
ccactggatc cccaggaact ggacatcctg aaaaccgtga aagagatcac aggctttctg  4320
ctgattcagg cctggcccga gaaccggaca gacctgcacg ccttcgagaa cctggaaatc  4380
```

atcagaggcc ggaccaagca gcacggccag ttttctctgg ccgtggtgtc cctgaacatc 4440
accagcctgg gcctgcggag cctgaaagaa atcagcgacg gcgacgtgat catctccggc 4500
aacaagaacc tgtgctacgc caacaccatc aattggaaga agctgttcgg cacctccggc 4560
cagaaaacaa agatcatctc taaccggggc gagaacagct gcaaagccac cggacaagtg 4620
tgccacgccc tgtgtagccc tgagggctgt tggggacccg agcccagaga ttgcgtgtcc 4680
tgccggaatg tgtccagagg ccgcgagtgc gtggacaagt gcaacctgct ggaaggcgag 4740
ccccgcgagt ttgtggaaaa cagcgagtgc atccagtgcc accccgagtg tctgccccag 4800
gccatgaaca ttacctgcac cggcagaggc cccgacaact gtatccagtg cgcccactac 4860
atcgacggcc cccactgcgt gaaaacctgt ccagctggcg tgatgggaga gaacaacacc 4920
ctcgtgtgga agtacgccga cgccggccat gtgtgccacc tgtgtcaccc caattgcacc 4980
tacggctgta ccggccctgg cctggaaggc tgtcctacca acggccccaa gatcccttct 5040
aaagatccca aattttgggt gctggtggtg gttggtggag tcctggcttg ctatagcttg 5100
ctagtaacag tggcctttat tattttctgg gtgaggagta agaggagcag gctcctgcac 5160
agtgactaca tgaacatgac tccccgccgc cccgggccca cccgcaagca ttaccagccc 5220
tatgccccac cacgcgactt cgcagcctat cgctccagag tgaagttcag caggagcgca 5280
gacgcccccg cgtaccagca gggccagaac cagctctata acgagctcaa tctaggacga 5340
agagaggagt acgatgtttt ggacaagaga cgtggccggg accctgagat gggggggaaag 5400
ccgagaagga agaaccctca ggaaggcctg tacaatgaac tgcagaaaga taagatggcg 5460
gaggcctaca gtgagattgg gatgaaaggc gagcgccgga ggggcaaggg gcacgatggc 5520
ctttaccagg gtctcagtac agccaccaag gacacctacg acgcccttca catgcaggcc 5580
ctgccccctc gcggaccgca gtgtactaat tatgctctct tgaaattggc tggagatgtt 5640
gagagcaatc ccgggcccat gcggatcagc aagccccacc tgcggagcat cagcatccag 5700
tgctacctgt gcctgctgct gaacagccac ttcctgaccg aggccggcat ccacgtgttc 5760
atcctgggct gcttcagcgc cggactgccc aagaccgagg ccaactgggt gaacgtgatc 5820
agcgacctga agaagatcga ggacctgatc cagagcatgc acatcgacgc caccctgtac 5880
accgagagcg acgtgcaccc cagctgcaag gtgaccgcca tgaagtgctt tctgctggaa 5940
ctgcaggtga tcagcctgga aagcggcgac gccagcatcc acgacaccgt ggagaacctg 6000
atcatcctgg ccaacaacag cctgagcagc aacggcaacg tgaccgagag cggctgcaaa 6060
gagtgcgagg aactggaaga gaagaacatc aaagagtttc tgcagagctt cgtgcacatc 6120
gtgcagatgt tcatcaacac cagctgacgc gtcatcatcg atccggatta gtccaatttg 6180
ttaaagacag gatatcagtg gtccaggctc tagttttgac tcaacaatat caccagctga 6240
agcctataga gtacgagcca tagataaaat aaaagatttt atttagtctc cagaaaaagg 6300
ggggaatgaa agaccccacc tgtaggtttg gcaagctagc ttaagtaacg ccattttgca 6360
aggcatggaa aaatacataa ctgagaatag agaagttcag atcaaggtca ggaacagatg 6420
gaacagctga atatgggcca aacaggatat ctgtggtaag cagttcctgc cccggctcag 6480
ggccaagaac agatggaaca gctgaatatg ggccaaacag gatatctgtg gtaagcagtt 6540
cctgccccgg ctcagggcca agaacagatg gtccccagat gcggtccagc cctcagcagt 6600
ttctagagaa ccatcagatg tttccagggt gccccaagga cctgaaatga ccctgtgcct 6660
tatttgaact aaccaatcag ttcgcttctc gcttctgttc gcgcgcttct gctccccgag 6720
ctcaataaaa gagcccacaa cccctcactc ggggcgccag tcctccgatt gactgagtcg 6780
cccgggtacc cgtgtatcca ataaaccctc ttgcagttgc atccgacttg tggtctcgct 6840
gttccttggg agggtctcct ctgagtgatt gactacccgt cagcgggggt ctttcacaca 6900
tgcagcatgt atcaaaatta atttggtttt ttttcttaag tatttacatt aaatggccat 6960
agtacttaaa gttacattgg cttccttgaa ataaacatgg agtattcaga atgtgtcata 7020
aatatttcta attttaagat agtatctcca ttggctttct acttttttct ttattttttt 7080
ttgtcctctg tcttccattt gttgttgttg ttgtttgttt gtttgtttgt tggttggttg 7140
gttaattttt ttttaaagat cctacactat agttcaagct agactattag ctactctgta 7200
acccagggtg accttgaagt catgggtagc ctgctgtttt agccttccca catctaagat 7260
tacaggtatg agctatcatt tttggtatat tgattgattg attgattgat gtgtgtgtgt 7320
gtgattgtgt ttgtgtgtgt gactgtgaaa atgtgtgtat gggtgtgtgt gaatgtgtgt 7380
atgtatgtgt gtgtgtgagt gtgtgtgtgt gtgtgtgcat gtgtgtgtgt gtgactgtgt 7440
ctatgtgtat gactgtgtgt gtgtgtgtgt gtgtgtgtgt gtgtgtgtgt gtgtgtgtgt 7500
tgtgaaaaaa tattctatgg tagtgagagc caacgctccg gctcaggtgt caggttggtt 7560
tttgagacag agtctttcac ttagcttgga attcactggc cgtcgtttta caacgtcgtg 7620
actgggaaaa ccctggcgtt acccaactta atcgccttgc agcacatccc cctttcgcca 7680
gctggcgtaa tagcgaagag gcccgcaccg atcgcccttc ccaacagttg cgcagcctga 7740
atggcgaatg gcgcctgatg cggtattttc tccttacgca tctgtgcggt atttcacacc 7800
gcatatggtg cactctcagt acaatctgct ctgatgccgc atagttaagc cagccccgac 7860
acccgccaac acccgctgac gcgccctgac gggcttgtct gctcccggca tccgcttaca 7920
gacaagctgt gaccgtctcc gggagctgca tgtgtcagag gttttcaccg tcatcaccga 7980
aacgcgcgag acgaaagggc ctcgtgatac gcctattttt ataggttaat gtcatgataa 8040
taatggtttc ttagacgtca ggtggcactt ttcggggaaa tgtgcgcgga acccctattt 8100
gtttattttt ctaaatacat tcaaatatgt atccgctcat gagacaataa ccctgataaa 8160
tgcttcaata atattgaaaa aggaagagta tgagtattca acatttccgt gtcgccctta 8220
ttcccttttt tgcggcattt tgccttcctg tttttgctca cccagaaacg ctggtgaaag 8280
taaaagatgc tgaagatcag ttgggtgcac gagtgggtta catcgaactg gatctcaaca 8340
gcggtaagat ccttgagagt tttcgccccg aagaacgttt tccaatgatg agcactttta 8400
aagttctgct atgtggcgcg gtattatccc gtattgacgc cgggcaagag caactcggtc 8460
gccgcataca ctattctcag aatgacttgg ttgagtactc accagtcaca gaaaagcatc 8520
ttacggatgg catgacagta agagaattat gcagtgctgc cataaccatg agtgataaca 8580
ctgcggccaa cttacttctg acaacgatcg gaggaccgaa ggagctaacc gcttttttgc 8640
acaacatggg ggatcatgta actcgccttg atcgttggga accggagctg aatgaagcca 8700
taccaaacga cgagcgtgac accacgatgc ctgtagcaat ggcaacaacg ttgcgcaaac 8760
tattaactgg cgaactactt actctagctt cccggcaaca attaatagac tggatggagg 8820
cggataaagt tgcaggacca cttctgcgct cggcccttcc ggctggctgg tttattgctg 8880
ataaatctgg agccggtgag cgtgggtctc gcggtatcat tgcagcactg gggccagatg 8940
gtaagccctc ccgtatcgta gttatctaca cgacggggag tcaggcaact atggatgaac 9000
gaaatagaca gatcgctgag ataggtgcct cactgattaa gcattggtaa ctgtcagacc 9060
aagtttactc atatatactt tagattgatt taaaacttca tttttaattt aaaaggatct 9120

```
aggtgaagat cctttttgat aatctcatga ccaaaatccc ttaacgtgag ttttcgttcc  9180
actgagcgtc agaccccgta gaaaagatca aaggatcttc ttgagatcct ttttttctgc  9240
gcgtaatctg ctgcttgcaa acaaaaaaac caccgctacc agcggtggtt tgtttgccgg  9300
atcaagagct accaactctt tttccgaagg taactggctt cagcagagcg cagataccaa  9360
atactgttct tctagtgtag ccgtagttag gccaccactt caagaactct gtagcaccgc  9420
ctacatacct cgctctgcta atcctgttac cagtggctgc tgccagtggc gataagtcgt  9480
gtcttaccgg gttggactca agacgatagt taccggataa ggcgcagcgg tcgggctgaa  9540
cggggggttc gtgcacacag cccagcttgg agcgaacgac ctacaccgaa ctgagatacc  9600
tacagcgtga gctatgagaa agcgccacgc ttcccgaagg gagaaaggcg gacaggtatc  9660
cggtaagcgg cagggtcgga acaggagagc gcacgaggga gcttccaggg ggaaacgcct  9720
ggtatcttta tagtcctgtc gggtttcgcc acctctgact tgagcgtcga tttttgtgat  9780
gctcgtcagg ggggcggagc ctatggaaaa acgccagcaa cgcggccttt ttacggttcc  9840
tggccttttg ctggcctttt gctcacatgt tctttcctgc gttatcccct gattctgtgg  9900
ataaccgtat taccgccttt gagtgagctg ataccgctcg ccgcagccga acgaccgagc  9960
gcagcgagtc agtgagcgag gaagcggaag agcgcccaat acgcaaaccg cctctccccg  10020
cgcgttggcc gattcattaa tgcagctggc acgacaggtt tcccgactgg aaagcgggca  10080
gtgagcgcaa cgcaattaat gtgagttagc tcactcatta ggcaccccag gctttacact  10140
ttatgcttcc ggctcgtatg ttgtgtggaa ttgtgagcgg ataacaattt cacacaggaa  10200
acagctatga ccatgattac gccaagcttt gctcttagga gtttcctaat acatcccaaa  10260
ctcaaatata taaagcattt gacttgttct atgccctagg gggcgggggg aagctaagcc  10320
agcttttttt aacatttaaa atgttaattc cattttaaat gcacagatgt tttatttca   10380
taagggtttc aatgtgcatg aatgctgcaa tattcctgtt accaaagcta gtataaataa  10440
aaatagataa acgtggaaat tacttagagt ttctgtcatt aacgtttcct tcctcagttg  10500
acaacataaa tgcgctgctg agcaagccag tttgcatctg tcaggatcaa tttcccatta  10560
tgccagtcat attaattact agtcaattag ttgattttta tttttgacat atacatgtg   10619

SEQ ID NO: 40          moltype = DNA  length = 10604
FEATURE                Location/Qualifiers
misc_feature           1..10604
                       note = pSFG4-CD123-Ev3-CAR
source                 1..10604
                       mol_type = other DNA
                       organism = synthetic construct
SEQUENCE: 40
aatgaaagac cccacctgta ggtttggcaa gctagcttaa gtaacgccat tttgcaaggc  60
atggaaaaat acataactga gaatagaaaa gttcagatca aggtcaggaa cagatggaac  120
agctgaatat gggccaaaca ggatatctgt ggtaagcagt tcctgccccg gctcagggcc  180
aagaacagat ggaacagctg aatatgggcc aaacaggata tctgtggtaa gcagttcctg  240
ccccggctca gggccaagaa cagatggtcc ccagatgcgg tccagccctc agcagtttct  300
agagaaccat cagatgtttc cagggtgccc caaggacctg aaatgaccct gtgccttatt  360
tgaactaacc aatcagttcg cttctcgctt ctgttcgcgc gcttatgctc cccgagctca  420
ataaaagagc ccacaacccc tcactcgggg cgccagtcct ccgattgact gagtcgcccg  480
ggtacccgtg tatccaataa accctcttgc agttgcatcc gacttgtggt ctcgctgttc  540
cttgggaggg tctcctctga gtgattgact acccgtcagc gggggtcttt catttggggg  600
ctcgtccggg atcgggagac ccctgcccag ggaccaccga cccaccaccg ggaggtaagc  660
tggccagcaa cttatctgtg tctgtccgat tgtctagtgt ctatgactga ttttatgcgc  720
ctgcgtcggt actagttagc taactagctc tgtatctggc ggacccgtgg tggaactgac  780
gagttcggaa cacccggccg caaccctggg agacgtccca gggacttcgg gggccgtttt  840
tgtggcccga cctgagtcct aaaatcccga tcgtttagga ctctttggtg cacccccctt  900
agaggaggga tatgtggttc tggtaggaga cgagaaccta aaacagttcc cgcctccgtc  960
tgaatttttg ctttcggttt gggaccgaag ccgcgccgcg cgtcttgtct gctgcagcat  1020
cgttctgtgt tgtctctgtc tgactgtgtt tctgtatttg tctgaaaata tgggcccggg  1080
ctagcctgtt accactccct taagtttgac cttaggtcac tggaaagatg tcgagcggat  1140
cgctcacaac cagtcggtag atgtcaagaa gagacgttgg gttaccttct gctctgcaga  1200
atggccaacc tttaacgtcg gatggccgcg agacggcacc tttaaccgag acctcatcac  1260
ccaggttaag atcaaggtct tttcacctgg cccgcatgga cacccagacc aggtggggta  1320
catcgtgacc tgggaagcct tggcttttga cccccctccc tgggtcaagc cctttgtaca  1380
ccctaagcct ccgcctcctc ttcctccatc cgccccgtct ctcccccttg aacctcctcg  1440
ttcgaccccg cctcgatcct ccctttatcc agccctcact ccttctctag gcgcccccat  1500
atggccatat gagatcttat atggggcacc cccgcccctt gtaaacttcc ctgaccctga  1560
catgacaaga gttactaaca gcccctctct ccaagctcac ttacaggctc tctacttagt  1620
ccagcacgaa gtctggagac ctctggcggc agcctaccaa gaacaactgg accgaccggt  1680
ggtacctcac ccttaccgag tcggcgacac agtgtgggtc cgccgacacc agactaagaa  1740
cctagaacct cgctggaaag gaccttacac agtcctgctg accaccccca ccgccctcaa  1800
agtagacggc atcgcagctt ggatacacgc cgcccacgtg aaggctgccg accccggggg  1860
tggaccatcc tctagactgc catgctcgag ggagtgcagg tggaaaccat ctccccagga  1920
gacgggcgca ccttccccaa gcgcggccag acctgcgtgg tgcactacac cgggatgctt  1980
gaagatggaa agaaagttga ttcctcccgg gacagaaaca agccctttaa gtttatgcta  2040
ggcaagcagg aggtgatccg aggctgggaa gaaggggttg cccagatgag tgtgggtcag  2100
agagccaaac tgactatatc tccagattat gcctatggtg ccactgggca cccaggcatc  2160
atcccaccac atgccactct cgtcttcgat gtggagcttc taaaactgga atctggcggt  2220
ggatccggag tcgacggatt tggtgatgtc ggtgctcttg agagtttgag ggaaatgca   2280
gatttggctt acatcctgag catggagccc tgtggccact gcctcattat caacaatgtg  2340
aacttctgcc gtgagtccgg gctccgcacc cgcactggct ccaacatcga ctgtgagaag  2400
ttgcggcgtc gcttctcctc gctgcatttc atggtggagg tgaagggcga cctgactgcc  2460
aagaaaatgg tgctggcttt gctggagctg gcgcagcagg accacggtgc tctggactgc  2520
tgcgtggtgg tcattctctc tcacggctgt caggccagcc acctgcagtt cccaggggct  2580
gtctacggca cagatggatg ccctgtgtcg gtcgagaaga ttgtgaacat cttcaatggg  2640
accagctgcc ccagcctggg agggaagccc aagctctttt tcatccaggc ctgtggtggg  2700
```

-continued

```
gagcagaaag accatgggtt tgaggtggcc tccacttccc ctgaagacga gtcccctggc  2760
agtaaccccg agccagatgc caccccgttc caggaaggtt tgaggacctt cgaccagctg  2820
gacgccatat ctagtttgcc cacacccagt gacatctttg tgtcctactc tactttccca  2880
ggttttgttt cctggaggga ccccaagagt ggctcctggt acgttgagac cctggacgac  2940
atctttgagc agtgggctca ctctgaagac ctgcagtccc tcctgcttag ggtcgctaat  3000
gctgtttcgg tgaaagggat ttataaacag atgcctggtt gctttaattt cctccggaaa  3060
aaacttttct ttaaaacatc agctagcaga gccgagggca ggggaagtct tctaacatgc  3120
ggggacgtgg aggaaaatcc cgggcccatg gagtttggac tgtcatggct tttctggtt  3180
gctatattga aaggtgtcca atgcagtaga gacgtacaaa taactcaatc ccctagttac  3240
ttggctgcgt caccaggaga gaccataaca attaactgta gagcgagcaa atctattagc  3300
aaggaccttg catggtacca ggaaaagccc ggaaaaacga ataaacttct tatatactct  3360
ggctcaactt tgcaaagtgg aattccgtca agatttagtg gtagcgggtc tggaaccgac  3420
ttcacattga ctataagttc cttggagccg gaggattttg cgatgtatta ttgccagcaa  3480
cataataaat atccctatac tttcggggga ggaactaaat tggagataaa gggttcaact  3540
tctgggtctg gtaaacctgg cagcggcgaa ggtagcacaa aagggcaagt ccaactccag  3600
cagcccggcg cggaactcgt gcgacctggc gcttcagtta agctgagctg caaggcctca  3660
ggatacacct tcacaagcta ctggatgaat tgggtgaagc agaggcctga tcaaggactc  3720
gaatggatag gtagaattga tccctacgac tccgagacgc attataacca gaaatttaag  3780
gataaggcga ttcttaccgt ggacaaaagt tcttcaacgg catatatgca actgagcagt  3840
ttgacatcag aagacagtgc tgtttattac tgcgcgagag gtaactggga tgactactgg  3900
ggccagggca ctaccttggt taccgtgtca agctacgtca ccgtctcttc acaggatccc  3960
gccctggaag agaagaaagg caattacgtc gtgaccgacc acggcagctg tgtgcgggct  4020
tgtggcgccg atagctacga gatggaagag gacggcgtgc ggaagtgcaa gaagtgcgag  4080
ggcccctgca gaaaagtgtg caacggcatc ggcatcggag agttcaagga tagcctgagc  4140
atcaacgcca ccaacatcaa gcacttcaag aactgcacca gcatcagcgg cgacctgcac  4200
atcctgcccg tggcctttag aggcgacagc ttcacccaca cccccccact ggatccccag  4260
gaactggaca tcctgaaaac cgtgaaagag atcacaggct ttctgctgat tcaggcctgg  4320
cccgagaacc ggacagacct gcacgccttc gagaacctgg aaatcatcag aggccggacc  4380
aagcagcacg gccagttttc tctggccgtg gtgtccctga acatcaccag cctgggcctg  4440
cggagcctga aagaaatcag cgacggcgac gtgatcatct ccggcaacaa gaacctgtgc  4500
tacgccaaca ccatcaattg gaagaagctg ttcggcacct ccggccagaa aacaaagatc  4560
atctctaacc ggggcgagaa cagctgcaaa gccaccggac aagtgtgcca cgccctgtgt  4620
agccctgagg gctgttgggg acccgagccc agagattgcg tgtcctgccg gaatgtgtcc  4680
agaggccgcg agtgcgtgga caagtgcaac ctgctggaag gcgagccccg cgagtttgtg  4740
gaaaacagcg agtgcatcca gtgccacccc gagtgtctgc cccaggccat gaacattacc  4800
tgcaccggca gaggccccga caactgtatc cagtgcgccc actacatcga cggcccccac  4860
tgcgtgaaaa cctgtccagc tggcgtgatg ggagagaaca acaccctcgt gtggaagtac  4920
gccgacgccg gccatgtgtg ccacctgtgt caccccaatt gcacctacgg ctgtaccggc  4980
cctggcctgg aaggctgtcc taccaacggc cccaagatcc cttctaaaga tcccaaattt  5040
tgggtgctgg tggtggttgg tggagtcctg gcttgctata gcttgctagt aacagtggcc  5100
tttattattt tctgggtgag gagtaagagg agcaggctcc tgcacagtga ctacatgaac  5160
atgactcccc gccgccccgg gcccacccgc aagcattacc agccctatgc cccaccacgc  5220
gacttcgcag cctatcgctc cagagtgaag ttcagcagga gcgcagacgc ccccgcgtac  5280
cagcagggcc agaaccagct ctataacgag ctcaatctag gacgaagaga ggagtacgat  5340
gttttggaca agagacgtgg ccgggaccct gagatggggg gaaagccgag aaggaagaac  5400
cctcaggaag gcctgtacaa tgaactgcag aaagataaga tggcggaggc ctacagtgag  5460
attgggatga aaggcgagcg ccggaggggc aaggggcacg atggccttta ccagggtctc  5520
agtacagcca ccaaggacac ctacgacgcc cttcacatgc aggccctgcc ccctcgcgga  5580
ccgcagtgta ctaattatgc tctcttgaaa ttggctggag atgttgagag caatcccggg  5640
cccatgcgga tcagcaagcc ccacctgcgg agcatcagca tccagtgcta cctgtgcctg  5700
ctgctgaaca gccacttcct gaccgaggcc ggcatccacg tgttcatcct gggctgcttc  5760
agcgccggac tgcccaagac cgaggccaac tgggtgaacg tgatcagcga cctgaagaag  5820
atcgaggacc tgatccagag catgcacatc gacgccaccc tgtacaccga gagcgacgtg  5880
caccccagct gcaaggtgac cgccatgaag tgctttctgc tggaactgca ggtgatcagc  5940
ctggaaagcg gcgacgccag catccacgac accgtggaga acctgatcat cctggccaac  6000
aacagcctga gcagcaacgg caacgtgacc gagagcggct gcaaagagtg cgaggaactg  6060
gaagagaaga acatcaaaga gtttctgcag agcttcgtgc acatcgtgca gatgttcatc  6120
aacaccagct gacgcgtcat catcgatccg gattagtcca atttgttaaa gacaggatat  6180
cagtggtcca ggctctagtt ttgactcaac aatatcacca gctgaagcct atagagtacg  6240
agccatagat aaaataaaag attttattta gtctccagaa aaagggggga atgaaagacc  6300
ccacctgtag gtttggcaag ctagcttaag taacgccatt ttgcaaggca tggaaaaata  6360
cataactgag aatagagaag ttcagatcaa ggtcaggaac agatggaaca gctgaatatg  6420
ggccaaacag gatatctgtg gtaagcagtt cctgccccgg ctcagggcca agaacagatg  6480
gaacagctga atatgggcca aacaggatat ctgtggtaag cagttcctgc cccggctcag  6540
ggccaagaac agatggtccc cagatgcggt ccagccctca gcagtttcta gagaaccatc  6600
agatgtttcc agggtgcccc aaggacctga aatgaccctg tgccttattt gaactaacca  6660
atcagttcgc ttctcgcttc tgttcgcgcg cttctgctcc ccgagctcaa taaaagagcc  6720
cacaacccct cactcggggc gccagtcctc cgattgactg agtcgcccgg gtacccgtgt  6780
atccaataaa ccctcttgca gttgcatccg acttgtggtc tcgctgttcc ttgggagggt  6840
ctcctctgag tgattgacta cccgtcagcg ggggtctttc acacatgcag catgtatcaa  6900
aattaatttg gttttttttc ttaagtattt acattaaatg gccatagtac ttaaagttac  6960
attggcttcc ttgaaataaa catggagtat tcagaatgtg tcataaatat ttctaatttt  7020
aagatagtat ctccattggc tttctacttt ttcttttatt ttttttgtc ctctgtcttc  7080
catttgttgt tgttgttgtt tgtttgtttg tttgttggtt ggttggttaa ttttttttta  7140
aagatcctac actatagttc aagctagact attagctact ctgtaaccca gggtgacctt  7200
gaagtcatgg gtagcctgct gttttagcct tcccacatct aagattacag gtatgagcta  7260
tcatttttgg tatattgatt gattgattga ttgatgtgtg tgtgtgtgat tgtgtttgtg  7320
tgtgtgactg tgaaaatgtg tgtatgggtg tgtgtgaatg tgtgtatgta tgtgtgtgtg  7380
tgagtgtgtg tgtgtgtgtg tgcatgtgtg tgtgtgtgac tgtgtctatg tgtatgactg  7440
```

```
tgtgtgtgtg tgtgtgtgtg tgtgtgtgtg tgtgtgtgtg tgtgttgtga aaaaatattc  7500
tatggtagtg agagccaacg ctccggctca ggtgtcaggt tggtttttga gacagagtct  7560
ttcacttagc ttggaattca ctggccgtcg ttttacaacg tcgtgactgg gaaaaccctg  7620
gcgttaccca acttaatcgc cttgcagcac atcccccttt cgccagctgg cgtaatagcg  7680
aagaggcccg caccgatcgc ccttcccaac agttgcgcag cctgaatggc gaatggcgcc  7740
tgatgcggta ttttctcctt acgcatctgt gcggtatttc acaccgcata tggtgcactc  7800
tcagtacaat ctgctctgat gccgcatagt taagccagcc ccgacacccg ccaacacccg  7860
ctgacgcgcc ctgacgggct tgtctgctcc cggcatccgc ttacagacaa gctgtgaccg  7920
tctccgggag ctgcatgtgt cagaggtttt caccgtcatc accgaaacgc gcgagacgaa  7980
agggcctcgt gatacgccta tttttatagg ttaatgtcat gataataatg gtttcttaga  8040
cgtcaggtgg cacttttcgg ggaaatgtgc gcggaacccc tatttgttta tttttctaaa  8100
tacattcaaa tatgtatccg ctcatgagac aataaccctg ataaatgctt caataatatt  8160
gaaaaaggaa gagtatgagt attcaacatt tccgtgtcgc ccttattccc ttttttgcgg  8220
cattttgcct tcctgttttt gctcacccag aaacgctggt gaaagtaaaa gatgctgaag  8280
atcagttggg tgcacgagtg ggttacatcg aactggatct caacagcggt aagatccttg  8340
agagttttcg ccccgaagaa cgttttccaa tgatgagcac ttttaaagtt ctgctatgtg  8400
gcgcggtatt atcccgtatt gacgccgggc aagagcaact cggtcgccgc atacactatt  8460
ctcagaatga cttggttgag tactcaccag tcacagaaaa gcatcttacg gatggcatga  8520
cagtaagaga attatgcagt gctgccataa ccatgagtga taacactgcg gccaacttac  8580
ttctgacaac gatcggagga ccgaaggagc taaccgcttt tttgcacaac atgggggatc  8640
atgtaactcg ccttgatcgt tgggaaccgg agctgaatga agccatacca aacgacgagc  8700
gtgacaccac gatgcctgta gcaatggcaa caacgttgcg caaactatta actggcgaac  8760
tacttactct agcttcccgg caacaattaa tagactggat ggaggcggat aaagttgcag  8820
gaccacttct gcgctcggcc cttccggctg gctggtttat tgctgataaa tctggagccg  8880
gtgagcgtgg gtctcgcggt atcattgcag cactggggcc agatggtaag ccctcccgta  8940
tcgtagttat ctacacgacg gggagtcagg caactatgga tgaacgaaat agacagatcg  9000
ctgagatagg tgcctcactg attaagcatt ggtaactgtc agaccaagtt tactcatata  9060
tactttagat tgatttaaaa cttcattttt aatttaaaag gatctaggtg aagatccttt  9120
ttgataatct catgaccaaa atcccttaac gtgagttttc gttccactga gcgtcagacc  9180
ccgtagaaaa gatcaaagga tcttcttgag atcctttttt tctgcgcgta atctgctgct  9240
tgcaaacaaa aaaaccaccg ctaccagcgg tggtttgttt gccggatcaa gagctaccaa  9300
ctctttttcc gaaggtaact ggcttcagca gagcgcagat accaaatact gttcttctag  9360
tgtagccgta gttaggccac cacttcaaga actctgtagc accgcctaca tacctcgctc  9420
tgctaatcct gttaccagtg gctgctgcca gtggcgataa gtcgtgtctt accgggttgg  9480
actcaagacg atagttaccg gataaggcgc agcggtcggg ctgaacgggg ggttcgtgca  9540
cacagcccag cttggagcga acgacctaca ccgaactgag atacctacag cgtgagctat  9600
gagaaagcgc cacgcttccc gaagggagaa aggcggacag gtatccggta agcggcaggg  9660
tcggaacagg agagcgcacg agggagcttc caggggggaaa cgcctggtat ctttatagtc  9720
ctgtcgggtt tcgccacctc tgacttgagc gtcgattttt gtgatgctcg tcaggggggc  9780
ggagcctatg gaaaaacgcc agcaacgcgg cctttttacg gttcctggcc ttttgctggc  9840
cttttgctca catgttcttt cctgcgttat cccctgattc tgtggataac cgtattaccg  9900
cctttgagtg agctgatacc gctcgccgca gccgaacgac cgagcgcagc gagtcagtga  9960
gcgaggaagc ggaagagcgc ccaatacgca aaccgcctct ccccgcgcgt tggccgattc  10020
attaatgcag ctggcacgac aggtttcccg actggaaagc gggcagtgag cgcaacgcaa  10080
ttaatgtgag ttagctcact cattaggcac cccaggcttt acactttatg cttccggctc  10140
gtatgttgtg tggaattgtg agcggataac aatttcacac aggaaacagc tatgaccatg  10200
attacgccaa gctttgctct taggagtttc ctaatacatc ccaaactcaa atatataaag  10260
catttgactt gttctatgcc ctagggggcg gggggaagct aagccagctt tttttaacat  10320
ttaaaatgtt aattccattt taaatgcaca gatgttttta tttcataagg gtttcaatgt  10380
gcatgaatgc tgcaatattc ctgttaccaa agctagtata aataaaaata gataaacgtg  10440
gaaattactt agagtttctg tcattaacgt ttccttcctc agttgacaac ataaatgcgc  10500
tgctgagcaa gccagtttgc atctgtcagg atcaatttcc cattatgcca gtcatattaa  10560
ttactagtca attagttgat ttttattttt gacatataca tgtg                  10604

SEQ ID NO: 41           moltype = DNA  length = 10604
FEATURE                 Location/Qualifiers
misc_feature            1..10604
                        note = pSFG4-hCD123-Ev3-CAR
source                  1..10604
                        mol_type = other DNA
                        organism = synthetic construct
SEQUENCE: 41
aatgaaagac cccacctgta ggtttggcaa gctagcttaa gtaacgccat tttgcaaggc  60
atggaaaaat acataactga gaatagaaaa gttcagatca aggtcaggaa cagatggaac  120
agctgaatat gggccaaaca ggatatctgt ggtaagcagt tcctgccccg gctcagggcc  180
aagaacagat ggaacagctg aatatgggcc aaacaggata tctgtggtaa gcagttcctg  240
ccccggctca gggccaagaa cagatggtcc ccagatgcgg tccagccctc agcagtttct  300
agagaaccat cagatgtttc cagggtgccc caaggacctg aaatgaccct gtgccttatt  360
tgaactaacc aatcagttcg cttctcgctt ctgttcgcgc gcttatgctc cccgagctca  420
ataaaagagc ccacaacccc tcactcgggg cgccagtcct ccgattgact gagtcgcccg  480
ggtacccgtg tatccaataa accctcttgc agttgcatcc gacttgtggt ctcgctgttc  540
cttgggaggg tctcctctga gtgattgact acccgtcagc gggggtcttt catttggggg  600
ctcgtccggg atcgggagac ccctgcccag ggaccaccga cccaccaccg ggaggtaagc  660
tggccagcaa cttatctgtg tctgtccgat tgtctagtgt ctatgactga ttttatgcgc  720
ctgcgtcggt actagttagc taactagctc tgtatctggc ggacccgtgg tggaactgac  780
gagttcggaa cacccggccg caaccctggg agacgtccca gggacttcgg gggccgtttt  840
tgtggcccga cctgagtcct aaaatcccga tcgtttagga ctctttggtg cacccccctt  900
agaggaggga tatgtggttc tggtaggaga cgagaaccta aaacagttcc cgcctccgtc  960
tgaatttttg ctttcggttt gggaccgaag ccgcgccgcg cgtcttgtct gctgcagcat  1020
```

-continued

```
cgttctgtgt tgtctctgtc tgactgtgtt tctgtatttg tctgaaaata tgggcccggg  1080
ctagcctgtt accactccct taagtttgac cttaggtcac tggaaagatg tcgagcggat  1140
cgctcacaac cagtcggtag atgtcaagaa gagacgttgg gttaccttct gctctgcaga  1200
atggccaacc tttaacgtcg gatggccgcg agacggcacc tttaaccgag acctcatcac  1260
ccaggttaag atcaaggtct tttcacctgg cccgcatgga cacccagacc aggtggggta  1320
catcgtgacc tgggaagcct tggcttttga ccccctccc tgggtcaagc cctttgtaca  1380
ccctaagcct ccgcctcctc ttcctccatc cgccccgtct ctccccttg aacctcctcg  1440
ttcgaccccg cctcgatcct ccctttatcc agccctcact ccttctctag gcgcccccat  1500
atggccatat gagatcttat atggggcacc cccgcccctt gtaaacttcc ctgaccctga  1560
catgacaaga gttactaaca gcccctctct ccaagctcac ttacaggctc tctacttagt  1620
ccagcacgaa gtctggagac ctctggcggc agcctaccaa gaacaactgg accgaccggt  1680
ggtacctcac ccttaccgag tcggcgacac agtgtgggtc cgccgacacc agactaagaa  1740
cctagaacct cgctggaaag gaccttacac agtcctgctg accacccca ccgccctcaa  1800
agtagacggc atcgcagctt ggatacacgc cgcccacgtg aaggctgccg accccggggg  1860
tggaccatcc tctagactgc catgctcgag ggagtgcagg tggaaaccat ctccccagga  1920
gacgggcgca ccttccccaa gcgcggccag acctgcgtgg tgcactacac cgggatgctt  1980
gaagatggaa agaaagttga ttcctcccgg gacagaaaca agccctttaa gtttatgcta  2040
ggcaagcagg aggtgatccg aggctgggaa gaaggggttg cccagatgag tgtgggtcag  2100
agagccaaac tgactatatc tccagattat gcctatggtg ccactgggca cccaggcatc  2160
atcccaccac atgccactct cgtcttcgat gtggagcttc taaaactgga atctggcggt  2220
ggatccggag tcgacggatt tggtgatgtc ggtgctcttg agagtttgag gggaaatgca  2280
gatttggctt acatcctgag catggagccc tgtggccact gcctcattat caacaatgtg  2340
aacttctgcc gtgagtccgg gctccgcacc cgcactggct ccaacatcga ctgtgagaag  2400
ttgcggcgtc gcttctcctc gctgcatttc atggtggagg tgaagggcga cctgactgcc  2460
aagaaaatgg tgctggcttt gctggagctg gcgcagcagg accacggtgc tctggactgc  2520
tgcgtggtgg tcattctctc tcacggctgt caggccagcc acctgcagtt cccaggggct  2580
gtctacggca cagatggatg ccctgtgtcg gtcgagaaga ttgtgaacat cttcaatggg  2640
accagctgcc ccagcctggg agggaagccc aagctctttt tcatccaggc ctgtggtggg  2700
gagcagaaag accatgggtt tgaggtggcc tccacttccc ctgaagacga gtcccctggc  2760
agtaaccccg agccagatgc caccccgttc caggaaggtt tgaggacctt cgaccagctg  2820
gacgccatat ctagtttgcc cacacccagt gacatctttg tgtcctactc tactttccca  2880
ggttttgttt cctggaggga ccccaagagt ggctcctggt acgttgagac cctggacgac  2940
atctttgagc agtgggctca ctctgaagac ctgcagtccc tcctgcttag ggtcgctaat  3000
gctgtttcgg tgaaagggat ttataaacag atgcctggtt gctttaattt cctccggaaa  3060
aaacttttct ttaaaacatc agctagcaga gccgagggca ggggaagtct tctaacatgc  3120
ggggacgtgg aggaaaatcc cgggcccatg gaattcgggc tttcatggtt gttcctcgtt  3180
gcgatactta aaggcgttca gtgcagtaga gacattcaga tgacccaaag ccctagtagc  3240
ctctccgcca gtgtgggtga ccgcgtgact attacgtgcc gagcaagcaa gagtattagc  3300
aaagatttgg catggtacca gcagaaacca ggcaaggtcc ctaagttgct tatatatagc  3360
gggtctacac tccaatctgg agtgccggat cgcttctcag gttccggatc aggaaccgat  3420
ttcactctta caatttcctc tctgcaaccg gaggacgtgg caacatacta ttgccagcag  3480
cataacaaat atccctatac tttcggtcaa ggtacaaaag tagaaataaa acgaggttcc  3540
acctccggga gtgggaagcc cggctccggc gaaggatcca ccaaaggcga ggtacagctc  3600
gttgaaagcg gggcggtct cgtccaacca ggagggtctc ttcgactttc ttgtgctgca  3660
agtgggtaca cgtttacttc ctattggatg aattgggttc ggcaagcccc cggtaaaggg  3720
cttgaatgga tagggaggat agacccctac gattctgaga cgcattataa tcagaaattc  3780
aaagataagt tcataataag cagagacaat gcaaaaaata gtttgtacct ccagatgaat  3840
agtcttcggg cagaagacac agcggtatat tactgtgctc ggggtaactg ggatgattac  3900
tggggtcagg gaactctggt tactgtgtct agctacgtca ccgtctcttc acaggatccc  3960
gccctggaag agaagaaagg caattacgtc gtgaccgacc acggcagctg tgtgcgggct  4020
tgtggcgccg atagctacga gatggaagag gacggcgtgc ggaagtgcaa gaagtgcgag  4080
ggcccctgca gaaaagtgtg caacggcatc ggcatcggag agttcaagga tagcctgagc  4140
atcaacgcca ccaacatcaa gcacttcaag aactgcacca gcatcagcgg cgacctgcac  4200
atcctgcccg tggcctttag aggcgacagc ttcacccaca cccccccact ggatccccag  4260
gaactggaca tcctgaaaac cgtgaaagag atcacaggct ttctgctgat tcaggcctgg  4320
cccgagaacc ggacagacct gcacgccttc gagaacctgg aaatcatcag aggccggacc  4380
aagcagcacg gccagttttc tctggccgtg gtgtccctga acatcaccag cctgggcctg  4440
cggagcctga aagaaatcag cgacggcgac gtgatcatct ccggcaacaa gaacctgtgc  4500
tacgccaaca ccatcaattg gaagaagctg ttcggcacct ccggccagaa aacaaagatc  4560
atctctaacc ggggcgagaa cagctgcaaa gccaccggac aagtgtgcca cgccctgtgt  4620
agccctgagg gctgttgggg acccgagccc agagattgcg tgtcctgccg gaatgtgtcc  4680
agaggccgcg agtgcgtgga caagtgcaac ctgctggaag gcgagccccg cgagtttgtg  4740
gaaaacagcg agtgcatcca gtgccacccc gagtgtctgc cccaggccat gaacattacc  4800
tgcaccggca gaggccccga caactgtatc cagtgcgccc actacatcga cggcccccac  4860
tgcgtgaaaa cctgtccagc tggcgtgatg ggagagaaca acaccctcgt gtggaagtac  4920
gccgacgccg gccatgtgtg ccacctgtgt caccccaatt gcacctacgg ctgtaccggc  4980
cctggcctgg aaggctgtcc taccaacggc cccaagatcc cttctaaaga tcccaaattt  5040
tgggtgctgg tggtggttgg tggagtcctg gcttgctata gcttgctagt aacagtggcc  5100
tttattattt tctgggtgag gagtaagagg agcaggctcc tgcacagtga ctacatgaac  5160
atgactcccc gccgccccgg gcccacccgc aagcattacc agccctatgc cccaccacgc  5220
gacttcgcag cctatcgctc cagagtgaag ttcagcagga gcgcagacgc ccccgcgtac  5280
cagcagggcc agaaccagct ctataacgag ctcaatctag gacgaagaga ggagtacgat  5340
gttttggaca agagacgtgg ccgggaccct gagatggggg gaaagccgag aaggaagaac  5400
cctcaggaag gcctgtacaa tgaactgcag aaagataaga tggcggaggc ctacagtgag  5460
attgggatga aaggcgagcg ccggaggggc aaggggcacg atggccttta ccagggtctc  5520
agtacagcca ccaaggacac ctacgacgcc cttcacatgc aggccctgcc ccctcgcgga  5580
ccgcagtgta ctaattatgc tctcttgaaa ttggctggag atgttgagag caatcccggg  5640
cccatgcgga tcagcaagcc ccacctgcgg agcatcagca tccagtgcta cctgtgcctg  5700
ctgctgaaca gccacttcct gaccgaggcc ggcatccacg tgttcatcct gggctgcttc  5760
```

```
agcgccggac tgcccaagac cgaggccaac tgggtgaacg tgatcagcga cctgaagaag  5820
atcgaggacc tgatccagag catgcacatc gacgccaccc tgtacaccga gagcgacgtg  5880
caccccagct gcaaggtgac cgccatgaag tgctttctgc tggaactgca ggtgatcagc  5940
ctggaaagcg gcgacgccag catccacgac accgtggaga acctgatcat cctggccaac  6000
aacagcctga gcagcaacgg caacgtgacc gagagcggct gcaaagagtg cgaggaactg  6060
gaagagaaga acatcaaaga gtttctgcag agcttcgtgc acatcgtgca gatgttcatc  6120
aacaccagct gacgcgtcat catcgatccg gattagtcca atttgttaaa gacaggatat  6180
cagtggtcca ggctctagtt ttgactcaac aatatcacca gctgaagcct atagagtacg  6240
agccatagat aaaataaaag attttattta gtctccagaa aaagggggga atgaaagacc  6300
ccacctgtag gtttggcaag ctagcttaag taacgccatt ttgcaaggca tggaaaaata  6360
cataactgag aatagagaag ttcagatcaa ggtcaggaac agatggaaca gctgaatatg  6420
ggccaaacag gatatctgtg gtaagcagtt cctgccccgg ctcagggcca agaacagatg  6480
gaacagctga atatgggcca aacaggatat ctgtggtaag cagttcctgc cccggctcag  6540
ggccaagaac agatggtccc cagatgcggt ccagccctca gcagtttcta gagaaccatc  6600
agatgtttcc agggtgcccc aaggacctga aatgaccctg tgccttattt gaactaacca  6660
atcagttcgc ttctcgcttc tgttcgcgcg cttctgctcc ccgagctcaa taaaagagcc  6720
cacaacccct cactcggggc gccagtcctc cgattgactg agtcgcccgg gtacccgtgt  6780
atccaataaa ccctcttgca gttgcatccg acttgtggtc tcgctgttcc ttgggagggt  6840
ctcctctgag tgattgacta cccgtcagcg ggggtctttc acacatgcag catgtatcaa  6900
aattaatttg gttttttttc ttaagtattt acattaaatg gccatagtac ttaaagttac  6960
attggcttcc ttgaaataaa catggagtat tcagaatgtg tcataaatat ttctaatttt  7020
aagatagtat ctccattggc tttctacttt ttcttttatt tttttttgtc ctctgtcttc  7080
catttgttgt tgttgttgtt tgtttgtttg tttgttggtt ggttggttaa tttttttta  7140
aagatcctac actatagttc aagctagact attagctact ctgtaaccca gggtgacctt  7200
gaagtcatgg gtagcctgct gttttagcct tcccacatct aagattacag gtatgagcta  7260
tcatttttgg tatattgatt gattgattga ttgatgtgtg tgtgtgtgat tgtgtttgtg  7320
tgtgtgactg tgaaaatgtg tgtatgggtg tgtgtgaatg tgtgtatgta tgtgtgtgtg  7380
tgagtgtgtg tgtgtgtgtg tgcatgtgtg tgtgtgtgac tgtgtctatg tgtatgactg  7440
tgtgtgtgtg tgtgtgtgtg tgtgtgtgtg tgtgtgtgtg tgtgttgtga aaaaatattc  7500
tatggtagtg agagccaacg ctccggctca ggtgtcaggt tggtttttga gacagagtct  7560
ttcacttagc ttggaattca ctggccgtcg ttttacaacg tcgtgactgg gaaaaccctg  7620
gcgttaccca acttaatcgc cttgcagcac atcccccttt cgccagctgg cgtaatagcg  7680
aagaggcccg caccgatcgc ccttcccaac agttgcgcag cctgaatggc gaatggcgcc  7740
tgatgcggta ttttctcctt acgcatctgt gcggtatttc acaccgcata tggtgcactc  7800
tcagtacaat ctgctctgat gccgcatagt taagccagcc ccgacacccg ccaacacccg  7860
ctgacgcgcc ctgacgggct tgtctgctcc cggcatccgc ttacagacaa gctgtgaccg  7920
tctccgggag ctgcatgtgt cagaggtttt caccgtcatc accgaaacgc gcgagacgaa  7980
agggcctcgt gatacgccta tttttatagg ttaatgtcat gataataatg gtttcttaga  8040
cgtcaggtgg cacttttcgg ggaaatgtgc gcggaacccc tatttgttta tttttctaaa  8100
tacattcaaa tatgtatccg ctcatgagac aataaccctg ataaatgctt caataatatt  8160
gaaaaaggaa gagtatgagt attcaacatt tccgtgtcgc ccttattccc ttttttgcgg  8220
cattttgcct tcctgttttt gctcacccag aaacgctggt gaaagtaaaa gatgctgaag  8280
atcagttggg tgcacgagtg ggttacatcg aactggatct caacagcggt aagatccttg  8340
agagttttcg ccccgaagaa cgttttccaa tgatgagcac ttttaaagtt ctgctatgtg  8400
gcgcggtatt atcccgtatt gacgccgggc aagagcaact cggtcgccgc atacactatt  8460
ctcagaatga cttggttgag tactcaccag tcacagaaaa gcatcttacg gatggcatga  8520
cagtaagaga attatgcagt gctgccataa ccatgagtga taacactgcg gccaacttac  8580
ttctgacaac gatcggagga ccgaaggagc taaccgcttt tttgcacaac atgggggatc  8640
atgtaactcg ccttgatcgt tgggaaccgg agctgaatga agccatacca aacgacgagc  8700
gtgacaccac gatgcctgta gcaatggcaa caacgttgcg caaactatta actggcgaac  8760
tacttactct agcttcccgg caacaattaa tagactggat ggaggcggat aaagttgcag  8820
gaccacttct gcgctcggcc cttccggctg gctggtttat tgctgataaa tctggagccg  8880
gtgagcgtgg gtctcgcggt atcattgcag cactggggcc agatggtaag ccctcccgta  8940
tcgtagttat ctacacgacg gggagtcagg caactatgga tgaacgaaat agacagatcg  9000
ctgagatagg tgcctcactg attaagcatt ggtaactgtc agaccaagtt tactcatata  9060
tactttagat tgatttaaaa cttcattttt aatttaaaag gatctaggtg aagatccttt  9120
ttgataatct catgaccaaa atcccttaac gtgagttttc gttccactga gcgtcagacc  9180
ccgtagaaaa gatcaaagga tcttcttgag atcctttttt tctgcgcgta atctgctgct  9240
tgcaaacaaa aaaaccaccg ctaccagcgg tggtttgttt gccggatcaa gagctaccaa  9300
ctctttttcc gaaggtaact ggcttcagca gagcgcagat accaaatact gttcttctag  9360
tgtagccgta gttaggccac cacttcaaga actctgtagc accgcctaca tacctcgctc  9420
tgctaatcct gttaccagtg gctgctgcca gtggcgataa gtcgtgtctt accgggttgg  9480
actcaagacg atagttaccg gataaggcgc agcggtcggg ctgaacgggg ggttcgtgca  9540
cacagcccag cttggagcga acgacctaca ccgaactgag atacctacag cgtgagctat  9600
gagaaagcgc cacgcttccc gaagggagaa aggcggacag gtatccggta agcggcaggg  9660
tcggaacagg agagcgcacg agggagcttc caggggggaaa cgcctggtat ctttatagtc  9720
ctgtcgggtt tcgccacctc tgacttgagc gtcgattttt gtgatgctcg tcaggggggc  9780
ggagcctatg gaaaaacgcc agcaacgcgg cctttttacg gttcctggcc ttttgctggc  9840
cttttgctca catgttcttt cctgcgttat cccctgattc tgtggataac cgtattaccg  9900
cctttgagtg agctgatacc gctcgccgca gccgaacgac cgagcgcagc gagtcagtga  9960
gcgaggaagc ggaagagcgc ccaatacgca aaccgcctct ccccgcgcgt tggccgattc  10020
attaatgcag ctggcacgac aggtttcccg actggaaagc gggcagtgag cgcaacgcaa  10080
ttaatgtgag ttagctcact cattaggcac cccaggcttt acactttatg cttccggctc  10140
gtatgttgtg tggaattgtg agcggataac aatttcacac aggaaacagc tatgaccatg  10200
attacgccaa gctttgctct taggagtttc ctaatacatc ccaaactcaa atatataaag  10260
catttgactt gttctatgcc ctagggggcg gggggaagct aagccagctt tttttaacat  10320
ttaaaatgtt aattccattt taaatgcaca gatgttttta tttcataagg gtttcaatgt  10380
gcatgaatgc tgcaatattc ctgttaccaa agctagtata aataaaaata gataaacgtg  10440
gaaattactt agagtttctg tcattaacgt ttccttcctc agttgacaac ataaatgcgc  10500
```

```
tgctgagcaa gccagtttgc atctgtcagg atcaatttcc cattatgcca gtcatattaa  10560
ttactagtca attagttgat tttattttt gacatataca tgtg                    10604

SEQ ID NO: 42           moltype = DNA  length = 10610
FEATURE                 Location/Qualifiers
misc_feature            1..10610
                        note = pSFG4-Meso-Ev3-CAR
source                  1..10610
                        mol_type = other DNA
                        organism = synthetic construct
SEQUENCE: 42
aatgaaagac cccacctgta ggtttggcaa gctagcttaa gtaacgccat tttgcaaggc  60
atggaaaaat acataactga gaatagaaaa gttcagatca aggtcaggaa cagatggaac  120
agctgaatat gggccaaaca ggatatctgt ggtaagcagt tcctgccccg gctcagggcc  180
aagaacagat ggaacagctg aatatgggcc aaacaggata tctgtggtaa gcagttcctg  240
ccccggctca gggccaagaa cagatggtcc ccagatgcgg tccagccctc agcagtttct  300
agagaaccat cagatgtttc cagggtgccc caaggacctg aaatgaccct gtgccttatt  360
tgaactaacc aatcagttcg cttctcgctt ctgttcgcgc gcttatgctc cccgagctca  420
ataaaagagc ccacaacccc tcactcgggg cgccagtcct ccgattgact gagtcgcccg  480
ggtacccgtg tatccaataa accctcttgc agttgcatcc gacttgtggt ctcgctgttc  540
cttgggaggg tctcctctga gtgattgact acccgtcagc gggggtcttt catttggggg  600
ctcgtccggg atcgggagac ccctgcccag ggaccaccga cccaccaccg ggaggtaagc  660
tggccagcaa cttatctgtg tctgtccgat tgtctagtgt ctatgactga ttttatgcgc  720
ctgcgtcggt actagttagc taactagctc tgtatctggc ggacccgtgg tggaactgac  780
gagttcggaa cacccggccg caaccctggg agacgtccca gggacttcgg gggccgtttt  840
tgtggcccga cctgagtcct aaaatcccga tcgtttagga ctctttggtg caccccctt  900
agaggaggga tatgtggttc tggtaggaga cgagaaccta aaacagttcc cgcctccgtc  960
tgaattttg ctttcggttt gggaccgaag ccgcgccgcg cgtcttgtct gctgcagcat  1020
cgttctgtgt tgtctctgtc tgactgtgtt tctgtatttg tctgaaaata tgggcccggg  1080
ctagcctgtt accactccct taagtttgac cttaggtcac tggaaagatg tcgagcggat  1140
cgctcacaac cagtcggtag atgtcaagaa gagacgttgg gttaccttct gctctgcaga  1200
atggccaacc tttaacgtcg gatggccgcg agacggcacc tttaaccgag acctcatcac  1260
ccaggttaag atcaaggtct tttcacctgg cccgcatgga cacccagacc aggtggggta  1320
catcgtgacc tgggaagcct tggcttttga cccccctccc tgggtcaagc cctttgtaca  1380
ccctaagcct ccgcctcctc ttcctccatc cgccccgtct ctcccccttg aacctcctcg  1440
ttcgaccccg cctcgatcct ccctttatcc agccctcact ccttctctag gcgcccccat  1500
atggccatat gagatcttat atggggcacc cccgcccctt gtaaacttcc ctgaccctga  1560
catgacaaga gttactaaca gcccctctct ccaagctcac ttacaggctc tctacttagt  1620
ccagcacgaa gtctggagac ctctggcggc agcctaccaa gaacaactgg accgaccggt  1680
ggtacctcac ccttaccgag tcggcgacac agtgtgggtc cgccgacacc agactaagaa  1740
cctagaacct cgctggaaag gaccttacac agtcctgctg accaccccca ccgccctcaa  1800
agtagacggc atcgcagctt ggatacacgc cgcccacgtg aaggctgccg accccggggg  1860
tggaccatcc tctagactgc catgctcgag ggagtgcagg tggaaaccat ctccccagga  1920
gacgggcgca ccttccccaa gcgcggccag acctgcgtgg tgcactacac cgggatgctt  1980
gaagatggaa agaaagttga ttcctcccgg gacagaaaca agccctttaa gtttatgcta  2040
ggcaagcagg aggtgatccg aggctgggaa gaaggggttg cccagatgag tgtgggtcag  2100
agagccaaac tgactatatc tccagattat gcctatggtg ccactgggca cccaggcatc  2160
atcccaccac atgccactct cgtcttcgat gtggagcttc taaaactgga atctggcggt  2220
ggatccggag tcgacggatt tggtgatgtc ggtgctcttg agagtttgag gggaaatgca  2280
gatttggctt acatcctgag catggagccc tgtggccact gcctcattat caacaatgtg  2340
aacttctgcc gtgagtccgg gctccgcacc cgcactggct ccaacatcga ctgtgagaag  2400
ttgcggcgtc gcttctcctc gctgcatttc atggtggagg tgaagggcga cctgactgcc  2460
aagaaaatgg tgctggcttt gctggagctg gcgcagcagg accacggtgc tctggactgc  2520
tgcgtggtgg tcattctctc tcacggctgt caggccagcc acctgcagtt cccaggggct  2580
gtctacggca cagatggatg ccctgtgtcg gtcgagaaga ttgtgaacat cttcaatggg  2640
accagctgcc ccagcctggg agggaagccc aagctctttt tcatccaggc ctgtggtggg  2700
gagcagaaag accatgggtt tgaggtggcc tccacttccc ctgaagacga gtcccctggc  2760
agtaaccccg agccagatgc caccccgttc caggaaggtt tgaggacctt cgaccagctg  2820
gacgccatat ctagtttgcc cacacccagt gacatctttg tgtcctactc tactttccca  2880
ggttttgttt cctggaggga ccccaagagt ggctcctggt acgttgagac cctggacgac  2940
atctttgagc agtgggctca ctctgaagac ctgcagtccc tcctgcttag ggtcgctaat  3000
gctgtttcgg tgaaagggat ttataaacag atgcctggtt gctttaattt cctccggaaa  3060
aaacttttct ttaaaacatc agctagcaga gccgagggca ggggaagtct tctaacatgc  3120
ggggacgtgg aggaaaatcc cgggcccatg gagttcggcc ttagctggct gttccttgtg  3180
gccatactca agggcgtcca gtgtagtcgc gatatagagc tgacgcaaag cccggcaatt  3240
atgtcagcaa gtccaggaga aaaggtgact atgacttgtt ccgcaagcag ttctgtaagt  3300
tacatgcact ggtaccagca aaaaagtgga actagcccta agcggtggat ctatgacacg  3360
tctaaattgg cctctggtgt ccccggacga ttttcaggtt caggaagtgg aaacagttac  3420
tctcttacta taagtagcgt cgaggcggag gatgacgcca cctactactg ccagcagtgg  3480
agcgggtacc ccctcacctt cggggccggg accaagttgg agattaaagg atcaacatcc  3540
gggagcggaa agccggggtc aggtgagggc tcaacaaaag ggcaggtaca gctccagcaa  3600
agtgggcccg agctggaaaa accgggtgcg agtgtcaaac tttcttgtaa ggccagcggt  3660
tactctttca cgggttatac aatgaattgg gtgaaacagt cccacggcaa gagcctcgaa  3720
tggataggtc tcatcacacc atacaacgga gcttcctcct ataatcagaa gttccgggga  3780
aaggcaaccc tcactgtaga caagtcttcc tcaacagcat atatggatct cctgtcactc  3840
acgtccgaag acagcgcggt ttatttttgt gcgagagggg gttatgacgg gcgcgggttc  3900
gactactggg gtcaaggcac tacagtaacg gtaagcagct acgtcaccgt ctcttcacag  3960
gatcccgccc tggaagagaa gaaaggcaat tacgtcgtga ccgaccacgg cagctgtgtg  4020
cgggcttgtg gcgccgatag ctacgagatg gaagaggacg gcgtgcggaa gtgcaagaag  4080
```

```
tgcgagggcc cctgcagaaa agtgtgcaac ggcatcggca tcggagagtt caaggatagc  4140
ctgagcatca acgccaccaa catcaagcac ttcaagaact gcaccagcat cagcggcgac  4200
ctgcacatcc tgcccgtggc ctttagaggc gacagcttca cccacacccc cccactggat  4260
ccccaggaac tggacatcct gaaaaccgtg aaagagatca caggctttct gctgattcag  4320
gcctggcccg agaaccggac agacctgcac gccttcgaga acctggaaat catcagaggc  4380
cggaccaagc agcacggcca gttttctctg gccgtggtgt ccctgaacat caccagcctg  4440
ggcctgcgga gcctgaaaga aatcagcgac ggcgacgtga tcatctccgg caacaagaac  4500
ctgtgctacg ccaacaccat caattggaag aagctgttcg gcacctccgg ccagaaaaca  4560
aagatcatct ctaaccgggg cgagaacagc tgcaaagcca ccggacaagt gtgccacgcc  4620
ctgtgtagcc ctgagggctg ttggggaccc gagcccagag attgcgtgtc ctgccggaat  4680
gtgtccagag gccgcgagtg cgtggacaag tgcaacctgc tggaaggcga gccccgcgag  4740
tttgtggaaa acagcgagtg catccagtgc caccccgagt gtctgcccca ggccatgaac  4800
attacctgca ccggcagagg ccccgacaac tgtatccagt gcgcccacta catcgacggc  4860
ccccactgcg tgaaaacctg tccagctggc gtgatgggag agaacaacac cctcgtgtgg  4920
aagtacgccg acgccggcca tgtgtgccac ctgtgtcacc ccaattgcac ctacggctgt  4980
accggccctg gcctggaagg ctgtcctacc aacggcccca agatcccttc taaagatccc  5040
aaattttggg tgctggtggt ggttggtgga gtcctggctt gctatagctt gctagtaaca  5100
gtggccttta ttattttctg ggtgaggagt aagaggagca ggctcctgca cagtgactac  5160
atgaacatga ctccccgccg ccccgggccc acccgcaagc attaccagcc ctatgcccca  5220
ccacgcgact tcgcagccta tcgctccaga gtgaagttca gcaggagcgc agacgccccc  5280
gcgtaccagc agggccagaa ccagctctat aacgagctca atctaggacg aagagaggag  5340
tacgatgttt tggacaagag acgtggccgg gaccctgaga tggggggaaa gccgagaagg  5400
aagaaccctc aggaaggcct gtacaatgaa ctgcagaaag ataagatggc ggaggcctac  5460
agtgagattg ggatgaaagg cgagcgccgg aggggcaagg ggcacgatgg cctttaccag  5520
ggtctcagta cagccaccaa ggacacctac gacgcccttc acatgcaggc cctgcccccct  5580
cgcggaccgc agtgtactaa ttatgctctc ttgaaattgg ctggagatgt tgagagcaat  5640
cccgggccca tgcggatcag caagccccac ctgcggagca tcagcatcca gtgctacctg  5700
tgcctgctgc tgaacagcca cttcctgacc gaggccggca tccacgtgtt catcctgggc  5760
tgcttcagcg ccggactgcc caagaccgag gccaactggg tgaacgtgat cagcgacctg  5820
aagaagatcg aggacctgat ccagagcatg cacatcgacg ccaccctgta caccgagagc  5880
gacgtgcacc ccagctgcaa ggtgaccgcc atgaagtgct ttctgctgga actgcaggtg  5940
atcagcctgg aaagcggcga cgccagcatc cacgacaccg tggagaacct gatcatcctg  6000
gccaacaaca gcctgagcag caacggcaac gtgaccgaga gcggctgcaa agagtgcgag  6060
gaactggaag agaagaacat caaagagttt ctgcagagct tcgtgcacat cgtgcagatg  6120
ttcatcaaca ccagctgacg cgtcatcatc gatccggatt agtccaattt gttaaagaca  6180
ggatatcagt ggtccaggct ctagttttga ctcaacaata tcaccagctg aagcctatag  6240
agtacgagcc atagataaaa taaaagattt tatttagtct ccagaaaaag gggggaatga  6300
aagaccccac ctgtaggttt ggcaagctag cttaagtaac gccattttgc aaggcatgga  6360
aaaatacata actgagaata gagaagttca gatcaaggtc aggaacagat ggaacagctg  6420
aatatgggcc aaacaggata tctgtggtaa gcagttcctg ccccggctca gggccaagaa  6480
cagatggaac agctgaatat gggccaaaca ggatatctgt ggtaagcagt tcctgccccg  6540
gctcagggcc aagaacagat ggtccccaga tgcggtccag ccctcagcag tttctagaga  6600
accatcagat gtttccaggg tgccccaagg acctgaaatg accctgtgcc ttatttgaac  6660
taaccaatca gttcgcttct cgcttctgtt cgcgcgcttc tgctccccga gctcaataaa  6720
agagcccaca acccctcact cggggcgcca gtcctccgat tgactgagtc gcccgggtac  6780
ccgtgtatcc aataaaccct cttgcagttg catccgactt gtggtctcgc tgttccttgg  6840
gagggtctcc tctgagtgat tgactacccg tcagcggggg tctttcacac atgcagcatg  6900
tatcaaaatt aatttggttt tttttcttaa gtatttacat taaatggcca tagtacttaa  6960
agttacattg gcttccttga aataaacatg gagtattcag aatgtgtcat aaatatttct  7020
aattttaaga tagtatctcc attggctttc tacttttttct tttatttttt tttgtcctct  7080
gtcttccatt tgttgttgtt gttgtttgtt tgtttgtttg ttggttggtt ggttaatttt  7140
tttttaaaga tcctacacta tagttcaagc tagactatta gctactctgt aacccagggt  7200
gaccttgaag tcatgggtag cctgctgttt tagccttccc acatctaaga ttacaggtat  7260
gagctatcat ttttggtata ttgattgatt gattgattga tgtgtgtgtg tgtgattgtg  7320
tttgtgtgtg tgactgtgaa aatgtgtgta tgggtgtgtg tgaatgtgtg tatgtatgtg  7380
tgtgtgtgag tgtgtgtgtg tgtgtgtgca tgtgtgtgtg tgtgactgtg tctatgtgta  7440
tgactgtgtg tgtgtgtgtg tgtgtgtgtg tgtgtgtgtg tgtgtgtgtg ttgtgaaaaa  7500
atattctatg gtagtgagag ccaacgctcc ggctcaggtg tcaggttggt ttttgagaca  7560
gagtctttca cttagcttgg aattcactgg ccgtcgtttt acaacgtcgt gactgggaaa  7620
accctggcgt tacccaactt aatcgccttg cagcacatcc ccctttcgcc agctggcgta  7680
atagcgaaga ggcccgcacc gatcgccctt cccaacagtt gcgcagcctg aatggcgaat  7740
ggcgcctgat gcggtatttt ctccttacgc atctgtgcgg tatttcacac cgcatatggt  7800
gcactctcag tacaatctgc tctgatgccg catagttaag ccagccccga cacccgccaa  7860
cacccgctga cgcgccctga cgggcttgtc tgctcccggc atccgcttac agacaagctg  7920
tgaccgtctc cgggagctgc atgtgtcaga ggttttcacc gtcatcaccg aaacgcgcga  7980
gacgaaaggg cctcgtgata cgcctatttt tataggttaa tgtcatgata ataatggttt  8040
cttagacgtc aggtggcact tttcggggaa atgtgcgcgg aacccctatt tgtttatttt  8100
tctaaataca ttcaaatatg tatccgctca tgagacaata accctgataa atgcttcaat  8160
aatattgaaa aaggaagagt atgagtattc aacatttccg tgtcgccctt attccctttt  8220
ttgcggcatt ttgccttcct gtttttgctc acccagaaac gctggtgaaa gtaaaagatg  8280
ctgaagatca gttgggtgca cgagtgggtt acatcgaact ggatctcaac agcggtaaga  8340
tccttgagag ttttcgcccc gaagaacgtt ttccaatgat gagcactttt aaagttctgc  8400
tatgtggcgc ggtattatcc cgtattgacg ccgggcaaga gcaactcggt cgccgcatac  8460
actattctca gaatgacttg gttgagtact caccagtcac agaaaagcat cttacggatg  8520
gcatgacagt aagagaatta tgcagtgctg ccataaccat gagtgataac actgcggcca  8580
acttacttct gacaacgatc ggaggaccga aggagctaac cgcttttttg cacaacatgg  8640
gggatcatgt aactcgcctt gatcgttggg aaccggagct gaatgaagcc ataccaaacg  8700
acgagcgtga caccacgatg cctgtagcaa tggcaacaac gttgcgcaaa ctattaactg  8760
gcgaactact tactctagct tcccggcaac aattaataga ctggatggag gcggataaag  8820
```

```
ttgcaggacc acttctgcgc tcggcccttc cggctggctg gtttattgct gataaatctg  8880
gagccggtga gcgtgggtct cgcggtatca ttgcagcact ggggccagat ggtaagccct  8940
cccgtatcgt agttatctac acgacgggga gtcaggcaac tatggatgaa cgaaatagac  9000
agatcgctga gataggtgcc tcactgatta agcattggta actgtcagac caagtttact  9060
catatatact ttagattgat ttaaaacttc atttttaatt taaaaggatc taggtgaaga  9120
tcctttttga taatctcatg accaaaatcc cttaacgtga gttttcgttc cactgagcgt  9180
cagaccccgt agaaaagatc aaaggatctt cttgagatcc tttttttctg cgcgtaatct  9240
gctgcttgca aacaaaaaaa ccaccgctac cagcggtggt ttgtttgccg gatcaagagc  9300
taccaactct ttttccgaag gtaactggct tcagcagagc gcagatacca aatactgttc  9360
ttctagtgta gccgtagtta ggccaccact tcaagaactc tgtagcaccg cctacatacc  9420
tcgctctgct aatcctgtta ccagtggctg ctgccagtgg cgataagtcg tgtcttaccg  9480
ggttggactc aagacgatag ttaccggata aggcgcagcg gtcgggctga acggggggtt  9540
cgtgcacaca gcccagcttg gagcgaacga cctacaccga actgagatac ctacagcgtg  9600
agctatgaga aagcgccacg cttcccgaag ggagaaaggc ggacaggtat ccggtaagcg  9660
gcagggtcgg aacaggagag cgcacgaggg agcttccagg gggaaacgcc tggtatcttt  9720
atagtcctgt cgggtttcgc cacctctgac ttgagcgtcg atttttgtga tgctcgtcag  9780
gggggcggag cctatggaaa aacgccagca acgcggcctt tttacggttc ctggcctttt  9840
gctggccttt tgctcacatg ttctttcctg cgttatcccc tgattctgtg gataaccgta  9900
ttaccgcctt tgagtgagct gataccgctc gccgcagccg aacgaccgag cgcagcgagt  9960
cagtgagcga ggaagcggaa gagcgcccaa tacgcaaacc gcctctcccc gcgcgttggc  10020
cgattcatta atgcagctgg cacgacaggt ttcccgactg gaaagcgggc agtgagcgca  10080
acgcaattaa tgtgagttag ctcactcatt aggcacccca ggctttacac tttatgcttc  10140
cggctcgtat gttgtgtgga attgtgagcg gataacaatt tcacacagga aacagctatg  10200
accatgatta cgccaagctt tgctcttagg agtttcctaa tacatcccaa actcaaatat  10260
ataaagcatt tgacttgttc tatgccctag gggcggggg gaagctaagc cagcttttt  10320
taacatttaa aatgttaatt ccattttaaa tgcacagatg tttttatttc ataagggttt  10380
caatgtgcat gaatgctgca atattcctgt taccaaagct agtataaata aaaatagata  10440
aacgtggaaa ttacttagag tttctgtcat taacgtttcc ttcctcagtt gacaacataa  10500
atgcgctgct gagcaagcca gtttgcatct gtcaggatca atttcccatt atgccagtca  10560
tattaattac tagtcaatta gttgattttt atttttgaca tatacatgtg             10610
```

```
SEQ ID NO: 43           moltype = DNA  length = 10595
FEATURE                 Location/Qualifiers
misc_feature            1..10595
                        note = pSFG4-hMeso-Ev3-CAR
source                  1..10595
                        mol_type = other DNA
                        organism = synthetic construct
SEQUENCE: 43
aatgaaagac cccacctgta ggtttggcaa gctagcttaa gtaacgccat tttgcaaggc  60
atggaaaaat acataactga gaatagaaaa gttcagatca aggtcaggaa cagatggaac  120
agctgaatat gggccaaaca ggatatctgt ggtaagcagt tcctgccccg gctcagggcc  180
aagaacagat ggaacagctg aatatgggcc aaacaggata tctgtggtaa gcagttcctg  240
ccccggctca gggccaagaa cagatggtcc ccagatgcgg tccagccctc agcagtttct  300
agagaaccat cagatgtttc cagggtgccc caaggacctg aaatgaccct gtgccttatt  360
tgaactaacc aatcagttcg cttctcgctt ctgttcgcgc gcttatgctc cccgagctca  420
ataaaagagc ccacaacccc tcactcgggg cgccagtcct ccgattgact gagtcgcccg  480
ggtacccgtg tatccaataa accctcttgc agttgcatcc gacttgtggt ctcgctgttc  540
cttgggaggg tctcctctga gtgattgact acccgtcagc gggggtcttt catttggggg  600
ctcgtccggg atcgggagac ccctgcccag ggaccaccga cccaccaccg ggaggtaagc  660
tggccagcaa cttatctgtg tctgtccgat tgtctagtgt ctatgactga ttttatgcgc  720
ctgcgtcggt actagttagc taactagctc tgtatctggc ggacccgtgg tggaactgac  780
gagttcggaa cacccggccg caaccctggg agacgtccca gggacttcgg gggccgtttt  840
tgtggcccga cctgagtcct aaaatcccga tcgtttagga ctctttggtg cacccccctt  900
agaggaggga tatgtggttc tggtaggaga cgagaaccta aaacagttcc cgcctccgtc  960
tgaatttttg ctttcggttt gggaccgaag ccgcgccgcg cgtcttgtct gctgcagcat  1020
cgttctgtgt tgtctctgtc tgactgtgtt tctgtatttg tctgaaaata tgggcccggg  1080
ctagcctgtt accactccct taagtttgac cttaggtcac tggaaagatg tcgagcggat  1140
cgctcacaac cagtcggtag atgtcaagaa gagacgttgg gttaccttct gctctgcaga  1200
atggccaacc tttaacgtcg gatggccgcg agacggcacc tttaaccgag acctcatcac  1260
ccaggttaag atcaaggtct tttcacctgg cccgcatgga cacccagacc aggtggggta  1320
catcgtgacc tgggaagcct tggcttttga cccccctccc tgggtcaagc cctttgtaca  1380
ccctaagcct ccgcctcctc ttcctccatc cgccccgtct ctcccccttg aacctcctcg  1440
ttcgaccccg cctcgatcct ccctttatcc agccctcact ccttctctag gcgcccccat  1500
atggccatat gagatcttat atggggcacc cccgcccctt gtaaacttcc ctgaccctga  1560
catgacaaga gttactaaca gcccctctct ccaagctcac ttacaggctc tctacttagt  1620
ccagcacgaa gtctggagac ctctggcggc agcctaccaa gaacaactgg accgaccggt  1680
ggtacctcac ccttaccgag tcggcgacac agtgtgggtc cgccgacacc agactaagaa  1740
cctagaacct cgctggaaag gaccttacac agtcctgctg accaccccca ccgccctcaa  1800
agtagacggc atcgcagctt ggatacacgc cgcccacgtg aaggctgccg accccggggg  1860
tggaccatcc tctagactgc catgctcgag ggagtgcagg tggaaaccat ctccccagga  1920
gacgggcgca ccttccccaa gcgcggccag acctgcgtgg tgcactacac cgggatgctt  1980
gaagatggaa agaaagttga ttcctcccgg gacagaaaca agccctttaa gtttatgcta  2040
ggcaagcagg aggtgatccg aggctgggaa gaaggggttg cccagatgag tgtgggtcag  2100
agagccaaac tgactatatc tccagattat gcctatggtg ccactgggca cccaggcatc  2160
atcccaccac atgccactct cgtcttcgat gtggagcttc taaaactgga atctggcggt  2220
ggatccggag tcgacggatt tggtgatgtc ggtgctcttg agagtttgag gggaaatgca  2280
gatttggctt acatcctgag catggagccc tgtggccact gcctcattat caacaatgtg  2340
aacttctgcc gtgagtccgg gctccgcacc cgcactggct ccaacatcga ctgtgagaag  2400
```

```
ttgcggcgtc gcttctcctc gctgcatttc atggtggagg tgaagggcga cctgactgcc  2460
aagaaaatgg tgctggcttt gctggagctg gcgcagcagg accacggtgc tctggactgc  2520
tgcgtggtgg tcattctctc tcacggctgt caggccagcc acctgcagtt cccaggggct  2580
gtctacggca cagatggatg ccctgtgtcg gtcgagaaga ttgtgaacat cttcaatggg  2640
accagctgcc ccagcctggg agggaagccc aagctctttt tcatccaggc ctgtggtggg  2700
gagcagaaag accatgggtt tgaggtggcc tccacttccc ctgaagacga gtcccctggc  2760
agtaaccccg agccagatgc caccccgttc caggaaggtt tgaggacctt cgaccagctg  2820
gacgccatat ctagtttgcc cacacccagt gacatctttg tgtcctactc tactttccca  2880
ggttttgttt cctggaggga ccccaagagt ggctcctggt acgttgagac cctggacgac  2940
atctttgagc agtgggctca ctctgaagac ctgcagtccc tcctgcttag ggtcgctaat  3000
gctgtttcgg tgaaagggat ttataaacag atgcctggtt gctttaattt cctccggaaa  3060
aaactttttct ttaaaacatc agctagcaga gccgagggca ggggaagtct tctaacatgc  3120
ggggacgtgg aggaaaatcc cgggcccatg gagttcggcc tttcttggct gtttttggtc  3180
gcaatattga agggcgttca gtgttcaagg gacatacaga tgacgcagtc acctagctct  3240
ctttcagcct ctgtgggaga ccgcgttaca attacgtgtt ctgcttctag ttcagtgtct  3300
tacatgcatt ggtaccagca aaaacccggc aaggttccaa agctccttat atacgatacg  3360
tccaaactgg cttcaggcgt gccagacagg tttagtggat ctgggagcgg cactgacttc  3420
acacttacaa tatccagtct gcaacccgaa gatgttgcga catactattg tcagcaatgg  3480
agcggctatc cgctcaccgg acaggggaca aaagtggaga taaagcgggg ctccaccagt  3540
ggttccggga agcctggtag tggtgagggt tctacgaaag gcgaagtgca gttggtggag  3600
tctggtggcg ggcttgttca acccggtggt tctctcaggc ttagctgtgc agcctctggg  3660
tacacaatga attgggtaag gcaagcgcct ggaaagggcc ttgagtggat cggtttgata  3720
accccataca acggagcttc aagttacaac caaaagttcc gcgggaagtt tattataagc  3780
agggataacg caaagaacag cctctatctt caaatgaact cactccgggc tgaagacaca  3840
gccgtctatt attgtgcccg ggggggctac gacggacgag ggttcgatta ctggggtcag  3900
ggcacactcg tgaccgtgtc aagctacgtc accgtctctt cacaggatcc cgccctggaa  3960
gagaagaaag gcaattacgt cgtgaccgac cacggcagct gtgtgcgggc ttgtggcgcc  4020
gatagctacg agatggaaga ggacggcgtg cggaagtgca agaagtgcga gggcccctgc  4080
agaaaagtgt gcaacggcat cggcatcgga gagttcaagg atagcctgag catcaacgcc  4140
accaacatca agcacttcaa gaactgcacc agcatcagcg gcgacctgca catcctgccc  4200
gtggccttta gaggcgacag cttcacccac accccccccac tggatcccca ggaactggac  4260
atcctgaaaa ccgtgaaaga gatcacaggc tttctgctga ttcaggcctg gcccgagaac  4320
cggacagacc tgcacgcctt cgagaacctg gaaatcatca gaggccggac caagcagcac  4380
ggccagtttt ctctggccgt ggtgtccctg aacatcacca gcctgggcct gcggagcctg  4440
aaagaaatca gcgacggcga cgtgatcatc tccggcaaca agaacctgtg ctacgccaac  4500
accatcaatt ggaagaagct gttcggcacc tccggccaga aaacaaagat catctctaac  4560
cggggcgaga acagctgcaa agccaccgga caagtgtgcc acgccctgtg tagccctgag  4620
ggctgttggg gacccgagcc cagagattgc gtgtcctgcc ggaatgtgtc cagaggccgc  4680
gagtgcgtgg acaagtgcaa cctgctggaa ggcgagcccc gcgagtttgt ggaaaacagc  4740
gagtgcatcc agtgccaccc cgagtgtctg ccccaggcca tgaacattac ctgcaccggc  4800
agaggccccg acaactgtat ccagtgcgcc cactacatcg acggccccca ctgcgtgaaa  4860
acctgtccag ctggcgtgat gggagagaac aacaccctcg tgtggaagta cgccgacgcc  4920
ggccatgtgt gccacctgtg tcaccccaat tgcacctacg gctgtaccgg ccctggcctg  4980
gaaggctgtc ctaccaacgg ccccaagatc ccttctaaag atcccaaatt ttgggtgctg  5040
gtggtggttg gtggagtcct ggcttgctat agcttgctag taacagtggc ctttattatt  5100
ttctgggtga ggagtaagag gagcaggctc ctgcacagtg actacatgaa catgactccc  5160
cgccgccccg ggcccacccg caagcattac cagccctatg ccccaccacg cgacttcgca  5220
gcctatcgct ccagagtgaa gttcagcagg agcgcagacg cccccgcgta ccagcagggc  5280
cagaaccagc tctataacga gctcaatcta ggacgaagag aggagtacga tgttttggac  5340
aagagacgtg gccgggaccc tgagatgggg ggaaagccga gaaggaagaa ccctcaggaa  5400
ggcctgtaca atgaactgca gaaagataag atggcggagg cctacagtga gattgggatg  5460
aaaggcgagc gccggagggg caaggggcac gatggccttt accagggtct cagtacagcc  5520
accaaggaca cctacgacgc ccttcacatg caggccctgc cccctcgcgg accgcagtgt  5580
actaattatg ctctcttgaa attggctgga gatgttgaga gcaatcccgg gcccatgcgg  5640
atcagcaagc cccacctgcg gagcatcagc atccagtgct acctgtgcct gctgctgaac  5700
agccacttcc tgaccgaggc cggcatccac gtgttcatcc tgggctgctt cagcgccgga  5760
ctgcccaaga ccgaggccaa ctgggtgaac gtgatcagcg acctgaagaa gatcgaggac  5820
ctgatccaga gcatgcacat cgacgccacc ctgtacaccg agagcgacgt gcaccccagc  5880
tgcaaggtga ccgccatgaa gtgctttctg ctggaactgc aggtgatcag cctggaaagc  5940
ggcgacgcca gcatccacga caccgtggag aacctgatca tcctggccaa caacagcctg  6000
agcagcaacg gcaacgtgac cgagagcggc tgcaaagagt gcgaggaact ggaagagaag  6060
aacatcaaag agtttctgca gagcttcgtg cacatcgtgc agatgttcat caacaccagc  6120
tgacgcgtca tcatcgatcc ggattagtcc aatttgttaa agacaggata tcagtggtcc  6180
aggctctagt tttgactcaa caatatcacc agctgaagcc tatagagtac gagccataga  6240
taaaataaaa gattttattt agtctccaga aaaagggggg aatgaaagac cccacctgta  6300
ggtttggcaa gctagcttaa gtaacgccat tttgcaaggc atggaaaaat acataactga  6360
gaatagagaa gttcagatca aggtcaggaa cagatggaac agctgaatat gggccaaaca  6420
ggatatctgt ggtaagcagt tcctgccccg gctcagggcc aagaacagat ggaacagctg  6480
aatatgggcc aaacaggata tctgtggtaa gcagttcctg ccccggctca gggccaagaa  6540
cagatggtcc ccagatgcgg tccagccctc agcagtttct agagaaccat cagatgtttc  6600
cagggtgccc caaggacctg aaatgaccct gtgccttatt tgaactaacc aatcagttcg  6660
cttctcgctt ctgttcgcgc gcttctgctc cccgagctca ataaaagagc ccacaacccc  6720
tcactcgggg cgccagtcct ccgattgact gagtcgcccg ggtacccgtg tatccaataa  6780
accctcttgc agttgcatcc gacttgtggt ctcgctgttc cttgggaggg tctcctctga  6840
gtgattgact acccgtcagc gggggtcttt cacacatgca gcatgtatca aaattaattt  6900
ggtttttttt cttaagtatt tacattaaat ggccatagta cttaaagtta cattggcttc  6960
cttgaaataa acatggagta ttcagaatgt gtcataaata tttctaattt taagatagta  7020
tctccattgg ctttctactt tttcttttat tttttttttgt cctctgtctt ccatttgttg  7080
ttgttgttgt ttgtttgttt gtttgttggt tggttggtta attttttttt aaagatccta  7140
```

```
cactatagtt caagctagac tattagctac tctgtaaccc agggtgacct tgaagtcatg  7200
ggtagcctgc tgttttagcc ttcccacatc taagattaca ggtatgagct atcatttttg  7260
gtatattgat tgattgattg attgatgtgt gtgtgtgtga ttgtgtttgt gtgtgtgact  7320
gtgaaaatgt gtgtatgggt gtgtgtgaat gtgtgtatgt atgtgtgtgt gtgagtgtgt  7380
gtgtgtgtgt gtgcatgtgt gtgtgtgtga ctgtgtctat gtgtatgact gtgtgtgtgt  7440
gtgtgtgtgt gtgtgtgtgt gtgtgtgtgt gtgtgttgtg aaaaaatatt ctatggtagt  7500
gagagccaac gctccggctc aggtgtcagg ttggtttttg agacagagtc tttcacttag  7560
cttggaattc actggccgtc gttttacaac gtcgtgactg ggaaaaccct ggcgttaccc  7620
aacttaatcg ccttgcagca catcccccct tcgccagctg gcgtaatagc gaagaggccc  7680
gcaccgatcg cccttcccaa cagttgcgca gcctgaatgg cgaatggcgc ctgatgcggt  7740
attttctcct tacgcatctg tgcggtattt cacaccgcat atggtgcact ctcagtacaa  7800
tctgctctga tgccgcatag ttaagccagc cccgacaccc gccaacaccc gctgacgcgc  7860
cctgacgggc ttgtctgctc ccggcatccg cttacagaca agctgtgacc gtctccggga  7920
gctgcatgtg tcagaggttt tcaccgtcat caccgaaacg cgcgagacga aagggcctcg  7980
tgatacgcct atttttatag gttaatgtca tgataataat ggtttcttag acgtcaggtg  8040
gcacttttcg gggaaatgtg cgcggaaccc ctatttgttt atttttctaa atacattcaa  8100
atatgtatcc gctcatgaga caataaccct gataaatgct tcaataatat tgaaaaagga  8160
agagtatgag tattcaacat ttccgtgtcg cccttattcc cttttttgcg gcattttgcc  8220
ttcctgtttt tgctcaccca gaaacgctgg tgaaagtaaa agatgctgaa gatcagttgg  8280
gtgcacgagt gggttacatc gaactggatc tcaacagcgg taagatcctt gagagttttc  8340
gccccgaaga acgttttcca atgatgagca cttttaaagt tctgctatgt ggcgcggtat  8400
tatcccgtat tgacgccggg caagagcaac tcggtcgccg catacactat tctcagaatg  8460
acttggttga gtactcacca gtcacagaaa agcatcttac ggatggcatg acagtaagag  8520
aattatgcag tgctgccata accatgagtg ataacactgc ggccaactta cttctgacaa  8580
cgatcggagg accgaaggag ctaaccgctt ttttgcacaa catgggggat catgtaactc  8640
gccttgatcg ttgggaaccg gagctgaatg aagccatacc aaacgacgag cgtgacacca  8700
cgatgcctgt agcaatggca acaacgttgc gcaaactatt aactggcgaa ctacttactc  8760
tagcttcccg gcaacaatta atagactgga tggaggcgga taaagttgca ggaccacttc  8820
tgcgctcggc ccttccggct ggctggttta ttgctgataa atctggagcc ggtgagcgtg  8880
ggtctcgcgg tatcattgca gcactggggc cagatggtaa gccctcccgt atcgtagtta  8940
tctacacgac ggggagtcag gcaactatgg atgaacgaaa tagacagatc gctgagatag  9000
gtgcctcact gattaagcat tggtaactgt cagaccaagt ttactcatat atactttaga  9060
ttgatttaaa acttcatttt taatttaaaa ggatctaggt gaagatcctt tttgataatc  9120
tcatgaccaa aatcccttaa cgtgagtttt cgttccactg agcgtcagac cccgtagaaa  9180
agatcaaagg atcttcttga gatccttttt ttctgcgcgt aatctgctgc ttgcaaacaa  9240
aaaaaccacc gctaccagcg gtggtttgtt tgccggatca agagctacca actctttttc  9300
cgaaggtaac tggcttcagc agagcgcaga taccaaatac tgttcttcta gtgtagccgt  9360
agttaggcca ccacttcaag aactctgtag caccgcctac atacctcgct ctgctaatcc  9420
tgttaccagt ggctgctgcc agtggcgata agtcgtgtct taccgggttg gactcaagac  9480
gatagttacc ggataaggcg cagcggtcgg gctgaacggg gggttcgtgc acacagccca  9540
gcttggagcg aacgacctac accgaactga gatacctaca gcgtgagcta tgagaaagcg  9600
ccacgcttcc cgaagggaga aaggcggaca ggtatccggt aagcggcagg gtcggaacag  9660
gagagcgcac gagggagctt ccagggggaa acgcctggta tctttatagt cctgtcgggt  9720
ttcgccacct ctgacttgag cgtcgatttt tgtgatgctc gtcagggggg cggagcctat  9780
ggaaaaacgc cagcaacgcg gcctttttac ggttcctggc cttttgctgg ccttttgctc  9840
acatgttctt tcctgcgtta tcccctgatt ctgtggataa ccgtattacc gcctttgagt  9900
gagctgatac cgctcgccgc agccgaacga ccgagcgcag cgagtcagtg agcgaggaag  9960
cggaagagcg cccaatacgc aaaccgcctc tccccgcgcg ttggccgatt cattaatgca  10020
gctggcacga caggtttccc gactggaaag cgggcagtga gcgcaacgca attaatgtga  10080
gttagctcac tcattaggca ccccaggctt tacactttat gcttccggct cgtatgttgt  10140
gtggaattgt gagcggataa caatttcaca caggaaacag ctatgaccat gattacgcca  10200
agctttgctc ttaggagttt cctaatacat cccaaactca aatatataaa gcatttgact  10260
tgttctatgc cctagggggc gggggaagc taagccagct ttttttaaca tttaaaatgt  10320
taattccatt ttaaatgcac agatgtttt atttcataag ggtttcaatg tgcatgaatg  10380
ctgcaatatt cctgttacca aagctagtat aaataaaaat agataaacgt ggaaattact  10440
tagagtttct gtcattaacg tttccttcct cagttgacaa cataaatgcg ctgctgagca  10500
agccagtttg catctgtcag gatcaatttc ccattatgcc agtcatatta attactagtc  10560
aattagttga tttttatttt tgacatatac atgtg                              10595

SEQ ID NO: 44          moltype = DNA  length = 10613
FEATURE                Location/Qualifiers
misc_feature           1..10613
                       note = pSFG4-ROR1-Ev3-CAR
source                 1..10613
                       mol_type = other DNA
                       organism = synthetic construct
SEQUENCE: 44
aatgaaagac cccacctgta ggtttggcaa gctagcttaa gtaacgccat tttgcaaggc  60
atggaaaaat acataactga gaatagaaaa gttcagatca aggtcaggaa cagatggaac  120
agctgaatat gggccaaaca ggatatctgt ggtaagcagt tcctgccccg gctcagggcc  180
aagaacagat ggaacagctg aatatgggcc aaacaggata tctgtggtaa gcagttcctg  240
ccccggctca gggccaagaa cagatggtcc ccagatgcgg tccagccctc agcagtttct  300
agagaaccat cagatgtttc cagggtgccc caaggacctg aaatgaccct gtgccttatt  360
tgaactaacc aatcagttcg cttctcgctt ctgttcgcgc gcttatgctc cccgagctca  420
ataaaagagc ccacaacccc tcactcgggg cgccagtcct ccgattgact gagtcgcccg  480
ggtacccgtg tatccaataa accctcttgc agttgcatcc gacttgtggt ctcgctgttc  540
cttgggaggg tctcctctga gtgattgact acccgtcagc gggggtcttt catttggggg  600
ctcgtccggg atcgggagac ccctgcccag ggaccaccga cccaccaccg ggaggtaagc  660
tggccagcaa cttatctgtg tctgtccgat tgtctagtgt ctatgactga ttttatgcgc  720
```

```
ctgcgtcggt actagttagc taactagctc tgtatctggc ggacccgtgg tggaactgac  780
gagttcggaa cacccggccg caaccctggg agacgtccca gggacttcgg gggccgtttt  840
tgtggcccga cctgagtcct aaaatcccga tcgtttagga ctctttggtg cacccccctt  900
agaggaggga tatgtggttc tggtaggaga cgagaaccta aaacagttcc cgcctccgtc  960
tgaatttttg ctttcggttt gggaccgaag ccgcgccgcg cgtcttgtct gctgcagcat  1020
cgttctgtgt tgtctctgtc tgactgtgtt tctgtatttg tctgaaaata tgggcccggg  1080
ctagcctgtt accactccct taagtttgac cttaggtcac tggaaagatg tcgagcggat  1140
cgctcacaac cagtcggtag atgtcaagaa gagacgttgg gttaccttct gctctgcaga  1200
atggccaacc tttaacgtcg gatggccgcg agacggcacc tttaaccgag acctcatcac  1260
ccaggttaag atcaaggtct tttcacctgg cccgcatgga cacccagacc aggtggggta  1320
catcgtgacc tgggaagcct tggcttttga cccccctccc tgggtcaagc cctttgtaca  1380
ccctaagcct ccgcctcctc ttcctccatc cgccccgtct ctcccccttg aacctcctcg  1440
ttcgaccccg cctcgatcct ccctttatcc agccctcact ccttctctag gcgcccccat  1500
atggccatat gagatcttat atggggcacc cccgcccctt gtaaacttcc ctgaccctga  1560
catgacaaga gttactaaca gcccctctct ccaagctcac ttacaggctc tctacttagt  1620
ccagcacgaa gtctggagac ctctggcggc agcctaccaa gaacaactgg accgaccggt  1680
ggtacctcac ccttaccgag tcggcgacac agtgtgggtc cgccgacacc agactaagaa  1740
cctagaacct cgctggaaag gaccttacac agtcctgctg accaccccca ccgccctcaa  1800
agtagacggc atcgcagctt ggatacacgc cgcccacgtg aaggctgccg accccggggg  1860
tggaccatcc tctagactgc catgctcgag ggagtgcagg tggaaaccat ctccccagga  1920
gacgggcgca ccttccccaa gcgcggccag acctgcgtgg tgcactacac cgggatgctt  1980
gaagatggaa agaaagttga ttcctcccgg gacagaaaca agccctttaa gtttatgcta  2040
ggcaagcagg aggtgatccg aggctgggaa gaaggggttg cccagatgag tgtgggtcag  2100
agagccaaac tgactatatc tccagattat gcctatggtg ccactgggca cccaggcatc  2160
atcccaccac atgccactct cgtcttcgat gtggagcttc taaaactgga atctggcggt  2220
ggatccggag tcgacggatt tggtgatgtc ggtgctcttg agagtttgag gggaaatgca  2280
gatttggctt acatcctgag catggagccc tgtggccact gcctcattat caacaatgtg  2340
aacttctgcc gtgagtccgg gctccgcacc cgcactggct ccaacatcga ctgtgagaag  2400
ttgcggcgtc gcttctcctc gctgcatttc atggtggagg tgaagggcga cctgactgcc  2460
aagaaaatgg tgctggcttt gctggagctg gcgcagcagg accacggtgc tctggactgc  2520
tgcgtggtgg tcattctctc tcacggctgt caggccagcc acctgcagtt cccaggggct  2580
gtctacggca cagatggatg ccctgtgtcg gtcgagaaga ttgtgaacat cttcaatggg  2640
accagctgcc ccagcctggg agggaagccc aagctctttt tcatccaggc ctgtggtggg  2700
gagcagaaag accatgggtt tgaggtggcc tccacttccc ctgaagacga gtcccctggc  2760
agtaaccccg agccagatgc caccccgttc caggaaggtt tgaggacctt cgaccagctg  2820
gacgccatat ctagtttgcc cacacccagt gacatctttg tgtcctactc tactttccca  2880
ggttttgttt cctggaggga ccccaagagt ggctcctggt acgttgagac cctggacgac  2940
atctttgagc agtgggctca ctctgaagac ctgcagtccc tcctgcttag ggtcgctaat  3000
gctgtttcgg tgaaagggat ttataaacag atgcctggtt gctttaattt cctccggaaa  3060
aaactttttct ttaaaacatc agctagcaga gccgagggca ggggaagtct tctaacatgc  3120
ggggacgtgg aggaaaatcc cgggcccatg gagttcggtc ttagctggct gttcctcgtg  3180
gcaatcctca agggagtaca atgcagcaga gatattaaga tgacgcagtc cccctcttct  3240
atgtacgcga gtctgggaga gagggtaacc attacatgta aggcgtctcc cgatataaac  3300
tcatatctga gctggtttca acaaaagccg ggcaagagtc cgaagacact catttaccga  3360
gcaaaccgcc tggtagacgg tgtgccttcc agattctctg gcggtggcag cgggcaagac  3420
tactcactca ccataaattc acttgaatac gaggatatgg gtatatacta ctgcttgcaa  3480
tatgatgagt ttccatatac ttttggcggc ggaactaaac ttgaaatgaa agggagcacg  3540
tctggttccg gcaagcctgg ttcaggagag ggtagcacca aggggaaagt caaactcgtc  3600
gaaagtggtg gtggcttggt gaaacccggc ggatctctga aactcagttg tgccgcttct  3660
ggttttacat ttagctccta cgcgatgagt tgggtcaggc aaataccaga gaagagactt  3720
gagtgggtcg ctagtattag caggggaggg accacctact atccagactc tgtgaaaggt  3780
agattcacta tctctagaga caacgtacgc aatatcctgt atctccaaat gagctcattg  3840
aggagcgagg atacggctat gtactattgt ggccgatacg actatgatgg atactatgcg  3900
atggattact ggggccaagg cacttctgta acagtttcta gctacgtcac cgtctcttca  3960
caggatcccg ccctggaaga gaagaaaggc aattacgtcg tgaccgacca cggcagctgt  4020
gtgcgggctt gtggcgccga tagctacgag atggaagagg acggcgtgcg gaagtgcaag  4080
aagtgcgagg gcccctgcag aaaagtgtgc aacggcatcg gcatcggaga gttcaaggat  4140
agcctgagca tcaacgccac caacatcaag cacttcaaga actgcaccag catcagcggc  4200
gacctgcaca tcctgcccgt ggcctttaga ggcgacagct tcacccacac cccccccactg  4260
gatccccagg aactggacat cctgaaaacc gtgaaagaga tcacaggctt tctgctgatt  4320
caggcctggc ccgagaaccg gacagacctg cacgccttcg agaacctgga aatcatcaga  4380
ggccggacca agcagcacgg ccagttttct ctggccgtgg tgtccctgaa catcaccagc  4440
ctgggcctgc ggagcctgaa agaaatcagc gacggcgacg tgatcatctc cggcaacaag  4500
aacctgtgct acgccaacac catcaattgg aagaagctgt tcggcacctc cggccagaaa  4560
acaaagatca tctctaaccg gggcgagaac agctgcaaag ccaccggaca agtgtgccac  4620
gccctgtgta gccctgaggg ctgttgggga cccgagccca gagattgcgt gtcctgccgg  4680
aatgtgtcca gaggccgcga gtgcgtggac aagtgcaacc tgctggaagg cgagccccgc  4740
gagtttgtgg aaaacagcga gtgcatccag tgccaccccg agtgtctgcc ccaggccatg  4800
aacattacct gcaccggcag aggccccgac aactgtatcc agtgcgccca ctacatcgac  4860
ggcccccact gcgtgaaaac ctgtccagct ggcgtgatgg gagagaacaa caccctcgtg  4920
tggaagtacg ccgacgccgg ccatgtgtgc cacctgtgtc accccaattg cacctacggc  4980
tgtaccggcc ctggcctgga aggctgtcct accaacggcc ccaagatccc ttctaaagat  5040
cccaaatttt gggtgctggt ggtggttggt ggagtcctgg cttgctatag cttgctagta  5100
acagtggcct ttattatttt ctgggtgagg agtaagagga gcaggctcct gcacagtgac  5160
tacatgaaca tgactccccg ccgccccggg cccacccgca agcattacca gccctatgcc  5220
ccaccacgcg acttcgcagc ctatcgctcc agagtgaagt tcagcaggag cgcagacgcc  5280
cccgcgtacc agcagggcca gaaccagctc tataacgagc tcaatctagg acgaagagag  5340
gagtacgatg ttttggacaa gagacgtggc cgggaccctg agatgggggg aaagccgaga  5400
aggaagaacc ctcaggaagg cctgtacaat gaactgcaga aagataagat ggcggaggcc  5460
```

```
tacagtgaga ttgggatgaa aggcgagcgc cggaggggca aggggcacga tggcctttac  5520
cagggtctca gtacagccac caaggacacc tacgacgccc ttcacatgca ggccctgccc  5580
cctcgcggac cgcagtgtac taattatgct ctcttgaaat tggctggaga tgttgagagc  5640
aatcccgggc ccatgcggat cagcaagccc cacctgcgga gcatcagcat ccagtgctac  5700
ctgtgcctgc tgctgaacag ccacttcctg accgaggccg gcatccacgt gttcatcctg  5760
ggctgcttca gcgccggact gcccaagacc gaggccaact gggtgaacgt gatcagcgac  5820
ctgaagaaga tcgaggacct gatccagagc atgcacatcg acgccaccct gtacaccgag  5880
agcgacgtgc accccagctg caaggtgacc gccatgaagt gctttctgct ggaactgcag  5940
gtgatcagcc tggaaagcgg cgacgccagc atccacgaca ccgtggagaa cctgatcatc  6000
ctggccaaca acagcctgag cagcaacggc aacgtgaccg agagcggctg caaagagtgc  6060
gaggaactgg aagagaagaa catcaaagag tttctgcaga gcttcgtgca catcgtgcag  6120
atgttcatca acaccagctg acgcgtcatc atcgatccgg attagtccaa tttgttaaag  6180
acaggatatc agtggtccag gctctagttt tgactcaaca atatcaccag ctgaagccta  6240
tagagtacga gccatagata aaataaaaga ttttatttag tctccagaaa aaggggggaa  6300
tgaaagaccc cacctgtagg tttggcaagc tagcttaagt aacgccattt tgcaaggcat  6360
ggaaaaatac ataactgaga atagagaagt tcagatcaag gtcaggaaca gatggaacag  6420
ctgaatatgg gccaaacagg atatctgtgg taagcagttc ctgccccggc tcagggccaa  6480
gaacagatgg aacagctgaa tatgggccaa acaggatatc tgtggtaagc agttcctgcc  6540
ccggctcagg gccaagaaca gatggtcccc agatgcggtc cagccctcag cagtttctag  6600
agaaccatca gatgtttcca gggtgcccca aggacctgaa atgaccctgt gccttatttg  6660
aactaaccaa tcagttcgct tctcgcttct gttcgcgcgc ttctgctccc cgagctcaat  6720
aaaagagccc acaacccctc actcggggcg ccagtcctcc gattgactga gtcgcccggg  6780
tacccgtgta tccaataaac cctcttgcag ttgcatccga cttgtggtct cgctgttcct  6840
tgggagggtc tcctctgagt gattgactac ccgtcagcgg gggtctttca cacatgcagc  6900
atgtatcaaa attaatttgg tttttttttct taagtattta cattaaatgg ccatagtact  6960
taaagttaca ttggcttcct tgaaataaac atggagtatt cagaatgtgt cataaatatt  7020
tctaatttta agatagtatc tccattggct ttctactttt tcttttattt tttttgtcc  7080
tctgtcttcc atttgttgtt gttgttgttt gtttgtttgt ttgttggttg gttggttaat  7140
tttttttaa agatcctaca ctatagttca agctagacta ttagctactc tgtaacccag  7200
ggtgaccttg aagtcatggg tagcctgctg ttttagcctt cccacatcta agattacagg  7260
tatgagctat catttttggt atattgattg attgattgat tgatgtgtgt gtgtgtgatt  7320
gtgtttgtgt gtgtgactgt gaaaatgtgt gtatgggtgt gtgtgaatgt gtgtatgtat  7380
gtgtgtgtgt gagtgtgtgt gtgtgtgtgt gcatgtgtgt gtgtgtgact gtgtctatgt  7440
gtatgactgt gtgtgtgtgt gtgtgtgtgt gtgtgtgtgt gtgtgtgtgt gtgttgtgaa  7500
aaaatattct atggtagtga gagccaacgc tccggctcag gtgtcaggtt ggtttttgag  7560
acagagtctt tcacttagct tggaattcac tggccgtcgt tttacaacgt cgtgactggg  7620
aaaaccctgg cgttacccaa cttaatcgcc ttgcagcaca tccccctttc gccagctggc  7680
gtaatagcga agaggcccgc accgatcgcc cttcccaaca gttgcgcagc ctgaatggcg  7740
aatggcgcct gatgcggtat tttctcctta cgcatctgtg cggtatttca caccgcatat  7800
ggtgcactct cagtacaatc tgctctgatg ccgcatagtt aagccagccc cgacacccgc  7860
caacacccgc tgacgcgccc tgacgggctt gtctgctccc ggcatccgct tacagacaag  7920
ctgtgaccgt ctccgggagc tgcatgtgtc agaggttttc accgtcatca ccgaaacgcg  7980
cgagacgaaa gggcctcgtg atacgcctat ttttataggt taatgtcatg ataataatgg  8040
tttcttagac gtcaggtggc acttttcggg gaaatgtgcg cggaacccct atttgtttat  8100
ttttctaaat acattcaaat atgtatccgc tcatgagaca ataaccctga taaatgcttc  8160
aataatattg aaaaaggaag agtatgagta ttcaacattt ccgtgtcgcc cttattccct  8220
tttttgcggc attttgcctt cctgtttttg ctcacccaga aacgctggtg aaagtaaaag  8280
atgctgaaga tcagttgggt gcacgagtgg gttacatcga actggatctc aacagcggta  8340
agatccttga gagttttcgc cccgaagaac gttttccaat gatgagcact tttaaagttc  8400
tgctatgtgg cgcggtatta tcccgtattg acgccgggca agagcaactc ggtcgccgca  8460
tacactattc tcagaatgac ttggttgagt actcaccagt cacagaaaag catcttacgg  8520
atggcatgac agtaagagaa ttatgcagtg ctgccataac catgagtgat aacactgcgg  8580
ccaacttact tctgacaacg atcggaggac cgaaggagct aaccgctttt ttgcacaaca  8640
tgggggatca tgtaactcgc cttgatcgtt gggaaccgga gctgaatgaa gccataccaa  8700
acgacgagcg tgacaccacg atgcctgtag caatggcaac aacgttgcgc aaactattaa  8760
ctggcgaact acttactcta gcttcccggc aacaattaat agactggatg gaggcggata  8820
aagttgcagg accacttctg cgctcggccc ttccggctgg ctggtttatt gctgataaat  8880
ctggagccgg tgagcgtggg tctcgcggta tcattgcagc actggggcca gatggtaagc  8940
cctcccgtat cgtagttatc tacacgacgg ggagtcaggc aactatggat gaacgaaata  9000
gacagatcgc tgagataggt gcctcactga ttaagcattg gtaactgtca gaccaagttt  9060
actcatatat actttagatt gatttaaaac ttcattttta atttaaaagg atctaggtga  9120
agatcctttt tgataatctc atgaccaaaa tcccttaacg tgagttttcg ttccactgag  9180
cgtcagaccc cgtagaaaag atcaaaggat cttcttgaga tccttttttt ctgcgcgtaa  9240
tctgctgctt gcaaacaaaa aaaccaccgc taccagcggt ggtttgtttg ccggatcaag  9300
agctaccaac tctttttccg aaggtaactg gcttcagcag agcgcagata ccaaatactg  9360
ttcttctagt gtagccgtag ttaggccacc acttcaagaa ctctgtagca ccgcctacat  9420
acctcgctct gctaatcctg ttaccagtgg ctgctgccag tggcgataag tcgtgtctta  9480
ccgggttgga ctcaagacga tagttaccgg ataaggcgca gcggtcgggc tgaacggggg  9540
gttcgtgcac acagcccagc ttggagcgaa cgacctacac cgaactgaga tacctacagc  9600
gtgagctatg agaaagcgcc acgcttcccg aagggagaaa ggcggacagg tatccggtaa  9660
gcggcagggt cggaacagga gagcgcacga gggagcttcc agggggaaac gcctggtatc  9720
tttatagtcc tgtcgggttt cgccacctct gacttgagcg tcgatttttg tgatgctcgt  9780
caggggggcg gagcctatgg aaaaacgcca gcaacgcggc ctttttacgg ttcctggcct  9840
tttgctggcc ttttgctcac atgttctttc ctgcgttatc ccctgattct gtggataacc  9900
gtattaccgc ctttgagtga gctgataccg ctcgccgcag ccgaacgacc gagcgcagcg  9960
agtcagtgag cgaggaagcg gaagagcgcc caatacgcaa accgcctctc cccgcgcgtt  10020
ggccgattca ttaatgcagc tggcacgaca ggtttcccga ctggaaagcg ggcagtgagc  10080
gcaacgcaat taatgtgagt tagctcactc attaggcacc ccaggcttta cactttatgc  10140
ttccggctcg tatgttgtgt ggaattgtga gcggataaca atttcacaca ggaaacagct  10200
```

```
atgaccatga ttacgccaag ctttgctctt aggagtttcc taatacatcc caaactcaaa  10260
tatataaagc atttgacttg ttctatgccc tagggggcgg ggggaagcta agccagcttt  10320
ttttaacatt taaaatgtta attccatttt aaatgcacag atgtttttat ttcataaggg  10380
tttcaatgtg catgaatgct gcaatattcc tgttaccaaa gctagtataa ataaaaatag  10440
ataaacgtgg aaattactta gagtttctgt cattaacgtt tccttcctca gttgacaaca  10500
taaatgcgct gctgagcaag ccagtttgca tctgtcagga tcaatttccc attatgccag  10560
tcatattaat tactagtcaa ttagttgatt tttatttttg acatatacat gtg         10613

SEQ ID NO: 45          moltype = DNA  length = 10616
FEATURE                Location/Qualifiers
misc_feature           1..10616
                       note = pSFG4-hROR1-Ev3-CAR
source                 1..10616
                       mol_type = other DNA
                       organism = synthetic construct
SEQUENCE: 45
aatgaaagac cccacctgta ggtttggcaa gctagcttaa gtaacgccat tttgcaaggc  60
atggaaaaat acataactga gaatagaaaa gttcagatca aggtcaggaa cagatggaac  120
agctgaatat gggccaaaca ggatatctgt ggtaagcagt tcctgccccg gctcagggcc  180
aagaacagat ggaacagctg aatatgggcc aaacaggata tctgtggtaa gcagttcctg  240
ccccggctca gggccaagaa cagatggtcc ccagatgcgg tccagccctc agcagtttct  300
agagaaccat cagatgtttc cagggtgccc caaggacctg aaatgaccct gtgccttatt  360
tgaactaacc aatcagttcg cttctcgctt ctgttcgcgc gcttatgctc cccgagctca  420
ataaaagagc ccacaacccc tcactcgggg cgccagtcct ccgattgact gagtcgcccg  480
ggtacccgtg tatccaataa accctcttgc agttgcatcc gacttgtggt ctcgctgttc  540
cttgggaggg tctcctctga gtgattgact acccgtcagc gggggtcttt catttggggg  600
ctcgtccggg atcgggagac ccctgcccag ggaccaccga cccaccaccg ggaggtaagc  660
tggccagcaa cttatctgtg tctgtccgat tgtctagtgt ctatgactga ttttatgcgc  720
ctgcgtcggt actagttagc taactagctc tgtatctggc ggacccgtgg tggaactgac  780
gagttcggaa cacccggccg caaccctggg agacgtccca gggacttcgg gggccgtttt  840
tgtggcccga cctgagtcct aaaatcccga tcgtttagga ctctttggtg cacccccctt  900
agaggaggga tatgtggttc tggtaggaga cgagaaccta aaacagttcc cgcctccgtc  960
tgaatttttg ctttcggttt gggaccgaag ccgcgccgcg cgtcttgtct gctgcagcat  1020
cgttctgtgt tgtctctgtc tgactgtgtt tctgtatttg tctgaaaata tgggcccggg  1080
ctagcctgtt accactccct taagtttgac cttaggtcac tggaaagatg tcgagcggat  1140
cgctcacaac cagtcggtag atgtcaagaa gagacgttgg gttaccttct gctctgcaga  1200
atggccaacc tttaacgtcg gatggccgcg agacggcacc tttaaccgag acctcatcac  1260
ccaggttaag atcaaggtct tttcacctgg cccgcatgga cacccagacc aggtggggta  1320
catcgtgacc tgggaagcct tggcttttga cccccctccc tgggtcaagc cctttgtaca  1380
ccctaagcct ccgcctcctc ttcctccatc cgccccgtct ctcccccttg aacctcctcg  1440
ttcgaccccg cctcgatcct ccctttatcc agccctcact ccttctctag gcgcccccat  1500
atggccatat gagatcttat atggggcacc cccgcccctt gtaaacttcc ctgaccctga  1560
catgacaaga gttactaaca gcccctctct ccaagctcac ttacaggctc tctacttagt  1620
ccagcacgaa gtctggagac ctctggcggc agcctaccaa gaacaactgg accgaccggt  1680
ggtacctcac ccttaccgag tcggcgacac agtgtgggtc cgccgacacc agactaagaa  1740
cctagaacct cgctggaaag gaccttacac agtcctgctg accaccccca ccgccctcaa  1800
agtagacggc atcgcagctt ggatacacgc cgcccacgtg aaggctgccg accccggggg  1860
tggaccatcc tctagactgc catgctcgag ggagtgcagg tggaaaccat ctccccagga  1920
gacgggcgca ccttccccaa gcgcggccag acctgcgtgg tgcactacac cgggatgctt  1980
gaagatggaa agaaagttga ttcctcccgg gacagaaaca agccctttaa gtttatgcta  2040
ggcaagcagg aggtgatccg aggctgggaa gaaggggttg cccagatgag tgtgggtcag  2100
agagccaaac tgactatatc tccagattat gcctatggtg ccactgggca cccaggcatc  2160
atcccaccac atgccactct cgtcttcgat gtggagcttc taaaactgga atctggcggt  2220
ggatccggag tcgacggatt tggtgatgtc ggtgctcttg agagtttgag gggaaatgca  2280
gatttggctt acatcctgag catggagccc tgtggccact gcctcattat caacaatgtg  2340
aacttctgcc gtgagtccgg gctccgcacc cgcactggct ccaacatcga ctgtgagaag  2400
ttgcggcgtc gcttctcctc gctgcatttc atggtggagg tgaagggcga cctgactgcc  2460
aagaaaatgg tgctggcttt gctggagctg gcgcagcagg accacggtgc tctggactgc  2520
tgcgtggtgg tcattctctc tcacggctgt caggccagcc acctgcagtt cccaggggct  2580
gtctacggca cagatggatg ccctgtgtcg gtcgagaaga ttgtgaacat cttcaatggg  2640
accagctgcc ccagcctggg agggaagccc aagctctttt tcatccaggc ctgtggtggg  2700
gagcagaaag accatgggtt tgaggtggcc tccacttccc ctgaagacga gtcccctggc  2760
agtaaccccg agccagatgc caccccgttc caggaaggtt tgaggacctt cgaccagctg  2820
gacgccatat ctagtttgcc cacacccagt gacatctttg tgtcctactc tactttccca  2880
ggttttgttt cctggaggga ccccaagagt ggctcctggt acgttgagac cctggacgac  2940
atctttgagc agtgggctca ctctgaagac ctgcagtccc tcctgcttag ggtcgctaat  3000
gctgtttcgg tgaaagggat ttataaacag atgcctggtt gctttaattt cctccggaaa  3060
aaacttttct ttaaaacatc agctagcaga gccgagggca ggggaagtct tctaacatgc  3120
ggggacgtgg aggaaaatcc cgggcccatg gagttcggac ttagttggct tttcctcgtc  3180
gccatactca aaggtgtaca atgctcacgc gatatacaaa tgacgcagag tccatcctca  3240
ctgtctgcct cagtaggcga cagggtcaca ataacctgta aagcaagccc ggatatcaac  3300
tcttacctca gttggttcca acagaaacca ggaaaggtgc cgaagttgtt gatttaccgc  3360
gcaaaccgcc tcgttgacgg cgtgccagat aggttttctg gcagcgggag cggcactgac  3420
tttacgctca ctatatcaag cctgcagccg gaggacgtag caacttacta ttgcctccaa  3480
tacgacgaat tcccttacac gttcgggcaa ggaactaaag ttgaaataaa aagaggaagc  3540
acaagtggtt ctggaaaacc cggttccggt gagggcagta ccaaaggaga ggtgcagttg  3600
gtagagtctg gtgggggttt ggtgcaaccc ggagggtctc tgaggttgtc ttgcgcggca  3660
tccggcttta ctttttcctc atatgcgatg tcatgggtac gacaggcccc aggcaaggga  3720
ctggagtgga tcgcatctat ttcacgagga gggacgacat attacccgga ttcagtgaag  3780
```

```
ggcaaattca taatttcacg cgataacgcc aagaactccc tctacctgca aatgaacagt  3840
cttagagcgg aagatacggc tgtgtattac tgtgcgcgat atgactacga tggatattac  3900
gcgatggatt attggggaca aggtacactg gtaaccgttt ccagctacgt caccgtctct  3960
tcacaggatc ccgccctgga agagaagaaa ggcaattacg tcgtgaccga ccacggcagc  4020
tgtgtgcggg cttgtggcgc cgatagctac gagatggaag aggacggcgt gcggaagtgc  4080
aagaagtgcg agggcccctg cagaaaagtg tgcaacggca tcggcatcgg agagttcaag  4140
gatagcctga gcatcaacgc caccaacatc aagcacttca agaactgcac cagcatcagc  4200
ggcgacctgc acatcctgcc cgtggccttt agaggcgaca gcttcaccca cacccccccca  4260
ctggatcccc aggaactgga catcctgaaa accgtgaaag agatcacagg ctttctgctg  4320
attcaggcct ggcccgagaa ccggacagac ctgcacgcct tcgagaacct ggaaatcatc  4380
agaggccgga ccaagcagca cggccagttt tctctggccg tggtgtccct gaacatcacc  4440
agcctgggcc tgcggagcct gaaagaaatc agcgacggcg acgtgatcat ctccggcaac  4500
aagaacctgt gctacgccaa caccatcaat tggaagaagc tgttcggcac ctccggccag  4560
aaaacaaaga tcatctctaa ccggggcgag aacagctgca aagccaccgg acaagtgtgc  4620
cacgccctgt gtagccctga gggctgttgg ggacccgagc ccagagattg cgtgtcctgc  4680
cggaatgtgt ccagaggccg cgagtgcgtg gacaagtgca acctgctgga aggcgagccc  4740
cgcgagtttg tggaaaacag cgagtgcatc cagtgccacc ccgagtgtct gccccaggcc  4800
atgaacatta cctgcaccgg cagaggcccc gacaactgta tccagtgcgc ccactacatc  4860
gacggccccc actgcgtgaa aacctgtcca gctggcgtga tgggagagaa caacaccctc  4920
gtgtggaagt acgccgacgc cggccatgtg tgccacctgt gtcaccccaa ttgcacctac  4980
ggctgtaccg gccctggcct ggaaggctgt cctaccaacg gccccaagat cccttctaaa  5040
gatcccaaat tttgggtgct ggtggtggtt ggtggagtcc tggcttgcta tagcttgcta  5100
gtaacagtgg cctttattat tttctgggtg aggagtaaga ggagcaggct cctgcacagt  5160
gactacatga acatgactcc ccgccgcccc gggcccaccc gcaagcatta ccagccctat  5220
gccccaccac gcgacttcgc agcctatcgc tccagagtga agttcagcag gagcgcagac  5280
gcccccgcgt accagcaggg ccagaaccag ctctataacg agctcaatct aggacgaaga  5340
gaggagtacg atgttttgga caagagacgt ggccgggacc ctgagatggg gggaaagccg  5400
agaaggaaga accctcagga aggcctgtac aatgaactgc agaaagataa gatggcggag  5460
gcctacagtg agattgggat gaaaggcgag cgccggaggg gcaaggggca cgatggcctt  5520
taccagggtc tcagtacagc caccaaggac acctacgacg cccttcacat gcaggccctg  5580
ccccctcgcg gaccgcagtg tactaattat gctctcttga aattggctgg agatgttgag  5640
agcaatcccg ggcccatgcg gatcagcaag ccccacctgc ggagcatcag catccagtgc  5700
tacctgtgcc tgctgctgaa cagccacttc ctgaccgagg ccggcatcca cgtgttcatc  5760
ctgggctgct tcagcgccgg actgcccaag accgaggcca actgggtgaa cgtgatcagc  5820
gacctgaaga agatcgagga cctgatccag agcatgcaca tcgacgccac cctgtacacc  5880
gagagcgacg tgcaccccag ctgcaaggtg accgccatga agtgctttct gctggaactg  5940
caggtgatca gcctggaaag cggcgacgcc agcatccacg acaccgtgga gaacctgatc  6000
atcctggcca acaacagcct gagcagcaac ggcaacgtga ccgagagcgg ctgcaaagag  6060
tgcgaggaac tggaagagaa gaacatcaaa gagtttctgc agagcttcgt gcacatcgtg  6120
cagatgttca tcaacaccag ctgacgcgtc atcatcgatc cggattagtc caatttgtta  6180
aagacaggat atcagtggtc caggctctag ttttgactca acaatatcac cagctgaagc  6240
ctatagagta cgagccatag ataaaataaa agattttatt tagtctccag aaaaaggggg  6300
gaatgaaaga ccccacctgt aggtttggca agctagctta agtaacgcca ttttgcaagg  6360
catggaaaaa tacataactg agaatagaga agttcagatc aaggtcagga acagatggaa  6420
cagctgaata tgggccaaac aggatatctg tggtaagcag ttcctgcccc ggctcagggc  6480
caagaacaga tggaacagct gaatatgggc caaacaggat atctgtggta agcagttcct  6540
gccccggctc agggccaaga acagatggtc cccagatgcg gtccagccct cagcagtttc  6600
tagagaacca tcagatgttt ccagggtgcc ccaaggacct gaaatgaccc tgtgccttat  6660
ttgaactaac caatcagttc gcttctcgct tctgttcgcg cgcttctgct ccccgagctc  6720
aataaaagag cccacaaccc ctcactcggg gcgccagtcc tccgattgac tgagtcgccc  6780
gggtacccgt gtatccaata aaccctcttg cagttgcatc cgacttgtgg tctcgctgtt  6840
ccttgggagg gtctcctctg agtgattgac tacccgtcag cgggggtctt tcacacatgc  6900
agcatgtatc aaaattaatt tggttttttt tcttaagtat ttacattaaa tggccatagt  6960
acttaaagtt acattggctt ccttgaaata aacatggagt attcagaatg tgtcataaat  7020
atttctaatt ttaagatagt atctccattg gctttctact tttctttta ttttttttg  7080
tcctctgtct tccatttgtt gttgttgttg tttgtttgtt tgtttgttgg ttggttggtt  7140
aattttttt taaagatcct acactatagt tcaagctaga ctattagcta ctctgtaacc  7200
cagggtgacc ttgaagtcat gggtagcctg ctgttttagc cttcccacat ctaagattac  7260
aggtatgagc tatcattttt ggtatattga ttgattgatt gattgatgtg tgtgtgtgtg  7320
attgtgtttg tgtgtgtgac tgtgaaaatg tgtgtatggg tgtgtgtgaa tgtgtgtatg  7380
tatgtgtgtg tgtgagtgtg tgtgtgtgtg tgtgcatgtg tgtgtgtgtg actgtgtcta  7440
tgtgtatgac tgtgtgtgtg tgtgtgtgtg tgtgtgtgtg tgtgtgtgtg tgtgtgttgt  7500
gaaaaaatat tctatggtag tgagagccaa cgctccggct caggtgtcag gttggttttt  7560
gagacagagt ctttcactta gcttggaatt cactggccgt cgttttacaa cgtcgtgact  7620
gggaaaaccc tggcgttacc caacttaatc gccttgcagc acatccccct ttcgccagct  7680
ggcgtaatag cgaagaggcc cgcaccgatc gcccttccca acagttgcgc agcctgaatg  7740
gcgaatggcg cctgatgcgg tattttctcc ttacgcatct gtgcggtatt tcacaccgca  7800
tatggtgcac tctcagtaca atctgctctg atgccgcata gttaagccag ccccgacacc  7860
cgccaacacc cgctgacgcg ccctgacggg cttgtctgct cccggcatcc gcttacagac  7920
aagctgtgac cgtctccggg agctgcatgt gtcagaggtt ttcaccgtca tcaccgaaac  7980
gcgcgagacg aaagggcctc gtgatacgcc tatttttata ggttaatgtc atgataataa  8040
tggtttctta gacgtcaggt ggcacttttc ggggaaatgt gcgcggaacc cctatttgtt  8100
tatttttcta aatacattca aatatgtatc cgctcatgag acaataaccc tgataaatgc  8160
ttcaataata ttgaaaaagg aagagtatga gtattcaaca tttccgtgtc gcccttattc  8220
ccttttttgc ggcattttgc cttcctgttt ttgctcaccc agaaacgctg gtgaaagtaa  8280
aagatgctga agatcagttg ggtgcacgag tgggttacat cgaactggat ctcaacagcg  8340
gtaagatcct tgagagtttt cgccccgaag aacgttttcc aatgatgagc acttttaaag  8400
ttctgctatg tggcgcggta ttatcccgta ttgacgccgg gcaagagcaa ctcggtcgcc  8460
gcatacacta ttctcagaat gacttggttg agtactcacc agtcacagaa aagcatctta  8520
```

```
cggatggcat gacagtaaga gaattatgca gtgctgccat aaccatgagt gataacactg  8580
cggccaactt acttctgaca acgatcggag gaccgaagga gctaaccgct tttttgcaca  8640
acatggggga tcatgtaact cgccttgatc gttgggaacc ggagctgaat gaagccatac  8700
caaacgacga gcgtgacacc acgatgcctg tagcaatggc aacaacgttg cgcaaactat  8760
taactggcga actacttact ctagcttccc ggcaacaatt aatagactgg atggaggcgg  8820
ataaagttgc aggaccactt ctgcgctcgg cccttccggc tggctggttt attgctgata  8880
aatctggagc cggtgagcgt gggtctcgcg gtatcattgc agcactgggg ccagatggta  8940
agccctcccg tatcgtagtt atctacacga cggggagtca ggcaactatg gatgaacgaa  9000
atagacagat cgctgagata ggtgcctcac tgattaagca ttggtaactg tcagaccaag  9060
tttactcata tatactttag attgatttaa aacttcattt ttaatttaaa aggatctagg  9120
tgaagatcct ttttgataat ctcatgacca aaatccctta acgtgagttt tcgttccact  9180
gagcgtcaga ccccgtagaa aagatcaaag gatcttcttg agatcctttt tttctgcgcg  9240
taatctgctg cttgcaaaca aaaaaaccac cgctaccagc ggtggtttgt ttgccggatc  9300
aagagctacc aactcttttt ccgaaggtaa ctggcttcag cagagcgcag ataccaaata  9360
ctgttcttct agtgtagccg tagttaggcc accacttcaa gaactctgta gcaccgccta  9420
catacctcgc tctgctaatc ctgttaccag tggctgctgc cagtggcgat aagtcgtgtc  9480
ttaccgggtt ggactcaaga cgatagttac cggataaggc gcagcggtcg ggctgaacgg  9540
ggggttcgtg cacacagccc agcttggagc gaacgaccta caccgaactg agatacctac  9600
agcgtgagct atgagaaagc gccacgcttc ccgaagggag aaaggcggac aggtatccgg  9660
taagcggcag ggtcggaaca ggagagcgca cgagggagct tccaggggga aacgcctggt  9720
atctttatag tcctgtcggg tttcgccacc tctgacttga gcgtcgattt ttgtgatgct  9780
cgtcaggggg gcggagccta tggaaaaacg ccagcaacgc ggccttttta cggttcctgg  9840
ccttttgctg gccttttgct cacatgttct ttcctgcgtt atcccctgat tctgtggata  9900
accgtattac cgcctttgag tgagctgata ccgctcgccg cagccgaacg accgagcgca  9960
gcgagtcagt gagcgaggaa gcggaagagc gcccaatacg caaaccgcct ctccccgcgc  10020
gttggccgat tcattaatgc agctggcacg acaggtttcc cgactggaaa gcgggcagtg  10080
agcgcaacgc aattaatgtg agttagctca ctcattaggc accccaggct ttacacttta  10140
tgcttccggc tcgtatgttg tgtggaattg tgagcggata acaatttcac acaggaaaca  10200
gctatgacca tgattacgcc aagctttgct cttaggagtt tcctaataca tcccaaactc  10260
aaatatataa agcatttgac ttgttctatg ccctaggggg cgggggggaag ctaagccagc  10320
tttttttaac atttaaaatg ttaattccat tttaaatgca cagatgtttt tatttcataa  10380
gggtttcaat gtgcatgaat gctgcaatat tcctgttacc aaagctagta taaataaaaa  10440
tagataaacg tggaaattac ttagagtttc tgtcattaac gtttccttcc tcagttgaca  10500
acataaatgc gctgctgagc aagccagttt gcatctgtca ggatcaattt cccattatgc  10560
cagtcatatt aattactagt caattagttg atttttattt ttgacatata catgtg      10616

SEQ ID NO: 46          moltype = DNA  length = 10610
FEATURE                Location/Qualifiers
misc_feature           1..10610
                       note = pSFG4-CD5-Ev3-CAR
source                 1..10610
                       mol_type = other DNA
                       organism = synthetic construct
SEQUENCE: 46
aatgaaagac cccacctgta ggtttggcaa gctagcttaa gtaacgccat tttgcaaggc  60
atggaaaaat acataactga gaatagaaaa gttcagatca aggtcaggaa cagatggaac  120
agctgaatat gggccaaaca ggatatctgt ggtaagcagt tcctgccccg gctcagggcc  180
aagaacagat ggaacagctg aatatgggcc aaacaggata tctgtggtaa gcagttcctg  240
ccccggctca gggccaagaa cagatggtcc ccagatgcgg tccagccctc agcagtttct  300
agagaaccat cagatgtttc cagggtgccc caaggacctg aaatgaccct gtgccttatt  360
tgaactaacc aatcagttcg cttctcgctt ctgttcgcgc gcttatgctc cccgagctca  420
ataaaagagc ccacaacccc tcactcgggg cgccagtcct ccgattgact gagtcgcccg  480
ggtacccgtg tatccaataa accctcttgc agttgcatcc gacttgtggt ctcgctgttc  540
cttgggaggg tctcctctga gtgattgact acccgtcagc gggggtcttt catttggggg  600
ctcgtccggg atcgggagac ccctgcccag ggaccaccga cccaccaccg ggaggtaagc  660
tggccagcaa cttatctgtg tctgtccgat tgtctagtgt ctatgactga ttttatgcgc  720
ctgcgtcggt actagttagc taactagctc tgtatctggc ggacccgtgg tggaactgac  780
gagttcggaa cacccggccg caaccctggg agacgtccca gggacttcgg gggccgtttt  840
tgtggcccga cctgagtcct aaaatcccga tcgtttagga ctctttggtg cacccccctt  900
agaggaggga tatgtggttc tggtaggaga cgagaaccta aaacagttcc cgcctccgtc  960
tgaatttttg ctttcggttt gggaccgaag ccgcgccgcg cgtcttgtct gctgcagcat  1020
cgttctgtgt tgtctctgtc tgactgtgtt tctgtatttg tctgaaaata tgggcccggg  1080
ctagcctgtt accactccct taagtttgac cttaggtcac tggaaagatg tcgagcggat  1140
cgctcacaac cagtcggtag atgtcaagaa gagacgttgg gttaccttct gctctgcaga  1200
atggccaacc tttaacgtcg gatggccgcg agacggcacc tttaaccgag acctcatcac  1260
ccaggttaag atcaaggtct tttcacctgg cccgcatgga cacccagacc aggtggggta  1320
catcgtgacc tgggaagcct tggcttttga cccccctccc tgggtcaagc cctttgtaca  1380
ccctaagcct ccgcctcctc ttcctccatc cgccccgtct ctcccccttg aacctcctcg  1440
ttcgaccccg cctcgatcct ccctttatcc agccctcact ccttctctag gcgcccccat  1500
atggccatat gagatcttat atggggcacc cccgcccctt gtaaacttcc ctgaccctga  1560
catgacaaga gttactaaca gcccctctct ccaagctcac ttacaggctc tctacttagt  1620
ccagcacgaa gtctggagac ctctggcggc agcctaccaa gaacaactgg accgaccggt  1680
ggtacctcac ccttaccgag tcggcgacac agtgtgggtc cgccgacacc agactaagaa  1740
cctagaacct cgctggaaag gaccttacac agtcctgctg accacccccca ccgccctcaa  1800
agtagacggc atcgcagctt ggatacacgc cgcccacgtg aaggctgccg accccggggg  1860
tggaccatcc tctagactgc catgctcgag ggagtgcagg tggaaaccat ctccccagga  1920
gacgggcgca ccttccccaa gcgcggccag acctgcgtgg tgcactacac cgggatgctt  1980
gaagatggaa agaaagttga ttcctcccgg gacagaaaca agccctttaa gtttatgcta  2040
ggcaagcagg aggtgatccg aggctgggaa gaaggggttg cccagatgag tgtgggtcag  2100
```

```
agagccaaac tgactatatc tccagattat gcctatggtg ccactgggca cccaggcatc 2160
atcccaccac atgccactct cgtcttcgat gtggagcttc taaaactgga atctggcggt 2220
ggatccggag tcgacggatt tggtgatgtc ggtgctcttg agagtttgag gggaaatgca 2280
gatttggctt acatcctgag catggagccc tgtggccact gcctcattat caacaatgtg 2340
aacttctgcc gtgagtccgg gctccgcacc cgcactggct ccaacatcga ctgtgagaag 2400
ttgcggcgtc gcttctcctc gctgcatttc atggtggagg tgaagggcga cctgactgcc 2460
aagaaaatgg tgctggcttt gctggagctg gcgcagcagg accacggtgc tctggactgc 2520
tgcgtggtgg tcattctctc tcacggctgt caggccagcc acctgcagtt cccaggggct 2580
gtctacggca cagatggatg ccctgtgtcg gtcgagaaga ttgtgaacat cttcaatggg 2640
accagctgcc ccagcctggg agggaagccc aagctctttt tcatccaggc ctgtggtggg 2700
gagcagaaag accatgggtt tgaggtggcc tccacttccc ctgaagacga gtcccctggc 2760
agtaaccccg agccagatgc caccccgttc caggaaggtt tgaggacctt cgaccagctg 2820
gacgccatat ctagtttgcc cacacccagt gacatctttg tgtcctactc tactttccca 2880
ggttttgttt cctggaggga ccccaagagt ggctcctggt acgttgagac cctggacgac 2940
atctttgagc agtgggctca ctctgaagac ctgcagtccc tcctgcttag ggtcgctaat 3000
gctgtttcgg tgaaagggat ttataaacag atgcctggtt gctttaattt cctccggaaa 3060
aaactttttct ttaaaacatc agctagcaga gccgagggca ggggaagtct tctaacatgc 3120
ggggacgtgg aggaaaatcc cgggcccatg gagttcggct tgagttggtt gttccttgtg 3180
gcgatactca aaggcgttca atgtagccga gacataaaaa tgacccagtc tccgtcatct 3240
atgtatgcaa gcctcggcga gcgagtgacc atcacgtgca aggcgagtca agatataaac 3300
agctacttgt catggttcca acaaaaacca gggaaatcac ctaagaccct gatctataga 3360
gccaatcgcc tggttgacgg tgtcccctcc cgctttagcg gctccggaag cggtcaagat 3420
tactctctca caatttcttc cttggattat gaagacatgg ggatctacta ttgtcaacag 3480
tatgacgaat ccccgtggac tttcggtggc ggtaccaaat tggaaataaa gggctctaca 3540
agcggctcag gaaaacctgg atcaggcgaa gggtctacga agggccagat acaactcgtt 3600
caaagtgggc cagaactcaa aaaaccggga gaaacagtga aaatttcttg taaggcatca 3660
ggatacacat tcacaaacta cgggatgaat tgggtcaaac aagcacccgg aaaggggctg 3720
cgctggatgg ggtggatcaa cacacatact ggggaaccta cttacgcaga cgatttcaag 3780
ggcagattcg ccttttcttt ggagacctcc gcctctactg catacttgca gataaacaac 3840
ctgaagaatg aagataccgc cacctacttc tgtacgcgca ggggctacga ttggtatttt 3900
gatgtatggg ggcaggcac cactgttact gtgtcaagct acgtcaccgt ctcttcacag 3960
gatcccgccc tggaagagaa gaaaggcaat tacgtcgtga ccgaccacgg cagctgtgtg 4020
cgggcttgtg gcgccgatag ctacgagatg gaagaggacg gcgtgcggaa gtgcaagaag 4080
tgcgagggcc cctgcagaaa agtgtgcaac ggcatcggca tcggagagtt caaggatagc 4140
ctgagcatca acgccaccaa catcaagcac ttcaagaact gcaccagcat cagcggcgac 4200
ctgcacatcc tgcccgtggc ctttagaggc gacagcttca cccacacccc cccactggat 4260
ccccaggaac tggacatcct gaaaaccgtg aaagagatca caggctttct gctgattcag 4320
gcctggcccg agaaccggac agacctgcac gccttcgaga acctggaaat catcagaggc 4380
cggaccaagc agcacggcca gttttctctg gccgtggtgt ccctgaacat caccagcctg 4440
ggcctgcgga gcctgaaaga aatcagcgac ggcgacgtga tcatctccgg caacaagaac 4500
ctgtgctacg ccaacaccat caattggaag aagctgttcg gcacctccgg ccagaaaaca 4560
aagatcatct ctaaccgggg cgagaacagc tgcaaagcca ccggacaagt gtgccacgcc 4620
ctgtgtagcc ctgagggctg ttggggaccc gagcccagag attgcgtgtc ctgccggaat 4680
gtgtccagag gccgcgagtg cgtggacaag tgcaacctgc tggaaggcga gccccgcgag 4740
tttgtggaaa acagcgagtg catccagtgc caccccgagt gtctgcccca ggccatgaac 4800
attacctgca ccggcagagg ccccgacaac tgtatccagt gcgcccacta catcgacggc 4860
ccccactgcg tgaaaacctg tccagctggc gtgatgggag agaacaacac cctcgtgtgg 4920
aagtacgccg acgccggcca tgtgtgccac ctgtgtcacc ccaattgcac ctacggctgt 4980
accggccctg gcctggaagg ctgtcctacc aacggcccca agatcccttc taaagatccc 5040
aaattttggg tgctggtggt ggttggtgga gtcctggctt gctatagctt gctagtaaca 5100
gtggccttta ttattttctg ggtgaggagt aagaggagca ggctcctgca cagtgactac 5160
atgaacatga ctccccgccg ccccgggccc acccgcaagc attaccagcc ctatgcccca 5220
ccacgcgact tcgcagccta tcgctccaga gtgaagttca gcaggagcgc agacgccccc 5280
gcgtaccagc agggccagaa ccagctctat aacgagctca atctaggacg aagagaggag 5340
tacgatgttt tggacaagag acgtggccgg gaccctgaga tggggggaaa gccgagaagg 5400
aagaaccctc aggaaggcct gtacaatgaa ctgcagaaag ataagatggc ggaggcctac 5460
agtgagattg ggatgaaagg cgagcgccgg aggggcaagg ggcacgatgg cctttaccag 5520
ggtctcagta cagccaccaa ggacacctac gacgcccttc acatgcaggc cctgcccccct 5580
cgcggaccgc agtgtactaa ttatgctctc ttgaaattgg ctggagatgt tgagagcaat 5640
cccgggccca tgcggatcag caagccccac ctgcggagca tcagcatcca gtgctacctg 5700
tgcctgctgc tgaacagcca cttcctgacc gaggccggca tccacgtgtt catcctgggc 5760
tgcttcagcg ccggactgcc caagaccgag gccaactggg tgaacgtgat cagcgacctg 5820
aagaagatcg aggacctgat ccagagcatg cacatcgacg ccaccctgta caccgagagc 5880
gacgtgcacc ccagctgcaa ggtgaccgcc atgaagtgct ttctgctgga actgcaggtg 5940
atcagcctgg aaagcggcga cgccagcatc cacgacaccg tggagaacct gatcatcctg 6000
gccaacaaca gcctgagcag caacggcaac gtgaccgaga gcggctgcaa agagtgcgag 6060
gaactggaag agaagaacat caaagagttt ctgcagagct tcgtgcacat cgtgcagatg 6120
ttcatcaaca ccagctgacg cgtcatcatc gatccggatt agtccaattt gttaaagaca 6180
ggatatcagt ggtccaggct ctagttttga ctcaacaata tcaccagctg aagcctatag 6240
agtacgagcc atagataaaa taaaagattt tatttagtct ccagaaaaag gggggaatga 6300
aagaccccac ctgtaggttt ggcaagctag cttaagtaac gccattttgc aaggcatgga 6360
aaaatacata actgagaata gagaagttca gatcaaggtc aggaacagat ggaacagctg 6420
aatatgggcc aaacaggata tctgtggtaa gcagttcctg ccccggctca gggccaagaa 6480
cagatggaac agctgaatat gggccaaaca ggatatctgt ggtaagcagt tcctgccccg 6540
gctcagggcc aagaacagat ggtccccaga tgcggtccag ccctcagcag tttctagaga 6600
accatcagat gtttccaggg tgccccaagg acctgaaatg accctgtgcc ttatttgaac 6660
taaccaatca gttcgcttct cgcttctgtt cgcgcgcttc tgctccccga gctcaataaa 6720
agagcccaca acccctcact cggggcgcca gtcctccgat tgactgagtc gcccgggtac 6780
ccgtgtatcc aataaaccct cttgcagttg catccgactt gtggtctcgc tgttccttgg 6840
```

```
gagggtctcc tctgagtgat tgactacccg tcagcggggg tctttcacac atgcagcatg  6900
tatcaaaatt aatttggttt tttttcttaa gtatttacat taaatggcca tagtacttaa  6960
agttacattg gcttccttga aataaacatg gagtattcag aatgtgtcat aaatatttct  7020
aattttaaga tagtatctcc attggctttc tactttttct tttatttttt tttgtcctct  7080
gtcttccatt tgttgttgtt gttgtttgtt tgtttgtttg ttggttggtt ggttaatttt  7140
tttttaaaga tcctacacta tagttcaagc tagactatta gctactctgt aacccagggt  7200
gaccttgaag tcatgggtag cctgctgttt tagccttccc acatctaaga ttacaggtat  7260
gagctatcat ttttggtata ttgattgatt gattgattga tgtgtgtgtg tgtgattgtg  7320
tttgtgtgtg tgactgtgaa aatgtgtgta tgggtgtgtg tgaatgtgtg tatgtatgtg  7380
tgtgtgtgag tgtgtgtgtg tgtgtgtgca tgtgtgtgtg tgtgactgtg tctatgtgta  7440
tgactgtgtg tgtgtgtgtg tgtgtgtgtg tgtgtgtgtg tgtgtgtgtg ttgtgaaaaa  7500
atattctatg gtagtgagag ccaacgctcc ggctcaggtg tcaggttggt tttgagaca   7560
gagtctttca cttagcttgg aattcactgg ccgtcgtttt acaacgtcgt gactgggaaa  7620
accctggcgt tacccaactt aatcgccttg cagcacatcc ccctttcgcc agctggcgta  7680
atagcgaaga ggcccgcacc gatcgccctt cccaacagtt gcgcagcctg aatggcgaat  7740
ggcgcctgat gcggtatttt ctccttacgc atctgtgcgg tatttcacac cgcatatggt  7800
gcactctcag tacaatctgc tctgatgccg catagttaag ccagccccga cacccgccaa  7860
cacccgctga cgcgccctga cgggcttgtc tgctcccggc atccgcttac agacaagctg  7920
tgaccgtctc cgggagctgc atgtgtcaga ggttttcacc gtcatcaccg aaacgcgcga  7980
gacgaaaggg cctcgtgata cgcctatttt tataggttaa tgtcatgata ataatggttt  8040
cttagacgtc aggtggcact tttcggggaa atgtgcgcgg aacccctatt tgtttatttt  8100
tctaaataca ttcaaatatg tatccgctca tgagacaata accctgataa atgcttcaat  8160
aatattgaaa aaggaagagt atgagtattc aacatttccg tgtcgccctt attccctttt  8220
ttgcggcatt ttgccttcct gtttttgctc acccagaaac gctggtgaaa gtaaaagatg  8280
ctgaagatca gttgggtgca cgagtgggtt acatcgaact ggatctcaac agcggtaaga  8340
tccttgagag ttttcgcccc gaagaacgtt ttccaatgat gagcactttt aaagttctgc  8400
tatgtggcgc ggtattatcc cgtattgacg ccgggcaaga gcaactcggt cgccgcatac  8460
actattctca gaatgacttg gttgagtact caccagtcac agaaaagcat cttacggatg  8520
gcatgacagt aagagaatta tgcagtgctg ccataaccat gagtgataac actgcggcca  8580
acttacttct gacaacgatc ggaggaccga aggagctaac cgcttttttg cacaacatgg  8640
gggatcatgt aactcgcctt gatcgttggg aaccggagct gaatgaagcc ataccaaacg  8700
acgagcgtga caccacgatg cctgtagcaa tggcaacaac gttgcgcaaa ctattaactg  8760
gcgaactact tactctagct tcccggcaac aattaataga ctggatggag gcggataaag  8820
ttgcaggacc acttctgcgc tcggcccttc cggctggctg gtttattgct gataaatctg  8880
gagccggtga gcgtgggtct cgcggtatca ttgcagcact ggggccagat ggtaagccct  8940
cccgtatcgt agttatctac acgacgggga gtcaggcaac tatggatgaa cgaaatagac  9000
agatcgctga gataggtgcc tcactgatta agcattggta actgtcagac caagtttact  9060
catatatact ttagattgat ttaaaacttc atttttaatt taaaaggatc taggtgaaga  9120
tcctttttga taatctcatg accaaaatcc cttaacgtga gttttcgttc cactgagcgt  9180
cagaccccgt agaaaagatc aaaggatctt cttgagatcc tttttttctg cgcgtaatct  9240
gctgcttgca aacaaaaaaa ccaccgctac cagcggtggt ttgtttgccg gatcaagagc  9300
taccaactct ttttccgaag gtaactggct tcagcagagc gcagatacca aatactgttc  9360
ttctagtgta gccgtagtta ggccaccact tcaagaactc tgtagcaccg cctacatacc  9420
tcgctctgct aatcctgtta ccagtggctg ctgccagtgg cgataagtcg tgtcttaccg  9480
ggttggactc aagacgatag ttaccggata aggcgcagcg gtcgggctga acggggggtt  9540
cgtgcacaca gcccagcttg gagcgaacga cctacaccga actgagatac ctacagcgtg  9600
agctatgaga aagcgccacg cttcccgaag ggagaaaggc ggacaggtat ccggtaagcg  9660
gcagggtcgg aacaggagag cgcacgaggg agcttccagg gggaaacgcc tggtatcttt  9720
atagtcctgt cgggtttcgc cacctctgac ttgagcgtcg atttttgtga tgctcgtcag  9780
gggggcggag cctatggaaa aacgccagca acgcggcctt tttacggttc ctggcctttt  9840
gctggccttt tgctcacatg ttctttcctg cgttatcccc tgattctgtg gataaccgta  9900
ttaccgcctt tgagtgagct gataccgctc gccgcagccg aacgaccgag cgcagcgagt  9960
cagtgagcga ggaagcggaa gagcgcccaa tacgcaaacc gcctctcccc gcgcgttggc  10020
cgattcatta atgcagctgg cacgacaggt ttcccgactg gaaagcgggc agtgagcgca  10080
acgcaattaa tgtgagttag ctcactcatt aggcacccca ggctttacac tttatgcttc  10140
cggctcgtat gttgtgtgga attgtgagcg gataacaatt tcacacagga aacagctatg  10200
accatgatta cgccaagctt tgctcttagg agtttcctaa tacatcccaa actcaaatat  10260
ataaagcatt tgacttgttc tatgccctag ggggcggggg gaagctaagc cagcttttt   10320
taacatttaa aatgttaatt ccattttaaa tgcacagatg tttttatttc ataagggttt  10380
caatgtgcat gaatgctgca atattcctgt taccaaagct agtataaata aaaatagata  10440
aacgtggaaa ttacttagag tttctgtcat taacgtttcc ttcctcagtt gacaacataa  10500
atgcgctgct gagcaagcca gtttgcatct gtcaggatca atttcccatt atgccagtca  10560
tattaattac tagtcaatta gttgattttt atttttgaca tatacatgtg             10610
```

```
SEQ ID NO: 47          moltype = DNA  length = 10610
FEATURE                Location/Qualifiers
misc_feature           1..10610
                       note = pSFG4-hCD5-Ev3-CAR
source                 1..10610
                       mol_type = other DNA
                       organism = synthetic construct
SEQUENCE: 47
aatgaaagac cccacctgta ggtttggcaa gctagcttaa gtaacgccat tttgcaaggc  60
atggaaaaat acataactga gaatagaaaa gttcagatca aggtcaggaa cagatggaac  120
agctgaatat gggccaaaca ggatatctgt ggtaagcagt tcctgccccg gctcagggcc  180
aagaacagat ggaacagctg aatatgggcc aaacaggata tctgtggtaa gcagttcctg  240
ccccggctca gggccaagaa cagatggtcc ccagatgcgg tccagccctc agcagtttct  300
agagaaccat cagatgtttc cagggtgccc caaggacctg aaatgaccct gtgccttatt  360
tgaactaacc aatcagttcg cttctcgctt ctgttcgcgc gcttatgctc cccgagctca  420
```

```
ataaaagagc ccacaacccc tcactcgggg cgccagtcct ccgattgact gagtcgcccg  480
ggtacccgtg tatccaataa accctcttgc agttgcatcc gacttgtggt ctcgctgttc  540
cttgggaggg tctcctctga gtgattgact acccgtcagc gggggtcttt catttggggg  600
ctcgtccggg atcgggagac ccctgcccag ggaccaccga cccaccaccg ggaggtaagc  660
tggccagcaa cttatctgtg tctgtccgat tgtctagtgt ctatgactga ttttatgcgc  720
ctgcgtcggt actagttagc taactagctc tgtatctggc ggacccgtgg tggaactgac  780
gagttcggaa cacccggccg caaccctggg agacgtccca gggacttcgg gggccgtttt  840
tgtggcccga cctgagtcct aaaatcccga tcgtttagga ctctttggtg cacccccctt  900
agaggaggga tatgtggttc tggtaggaga cgagaaccta aaacagttcc cgcctccgtc  960
tgaatttttg ctttcggttt gggaccgaag ccgcgccgcg cgtcttgtct gctgcagcat  1020
cgttctgtgt tgtctctgtc tgactgtgtt tctgtatttg tctgaaaata tgggcccggg  1080
ctagcctgtt accactccct taagtttgac cttaggtcac tggaaagatg tcgagcggat  1140
cgctcacaac cagtcggtag atgtcaagaa gagacgttgg gttaccttct gctctgcaga  1200
atggccaacc tttaacgtcg gatggccgcg agacggcacc tttaaccgag acctcatcac  1260
ccaggttaag atcaaggtct tttcacctgg cccgcatgga cacccagacc aggtggggta  1320
catcgtgacc tgggaagcct tggcttttga cccccctccc tgggtcaagc cctttgtaca  1380
ccctaagcct ccgcctcctc ttcctccatc cgccccgtct ctcccccttg aacctcctcg  1440
ttcgaccccg cctcgatcct ccctttatcc agccctcact ccttctctag gcgcccccat  1500
atggccatat gagatcttat atggggcacc cccgcccctt gtaaacttcc ctgaccctga  1560
catgacaaga gttactaaca gcccctctct ccaagctcac ttacaggctc tctacttagt  1620
ccagcacgaa gtctggagac ctctggcggc agcctaccaa gaacaactgg accgaccggt  1680
ggtacctcac ccttaccgag tcggcgacac agtgtgggtc cgccgacacc agactaagaa  1740
cctagaacct cgctggaaag gaccttacac agtcctgctg accaccccca ccgccctcaa  1800
agtagacggc atcgcagctt ggatacacgc cgcccacgtg aaggctgccg accccggggg  1860
tggaccatcc tctagactgc catgctcgag ggagtgcagg tggaaaccat ctccccagga  1920
gacgggcgca ccttccccaa gcgcggccag acctgcgtgg tgcactacac cgggatgctt  1980
gaagatggaa agaaagttga ttcctcccgg gacagaaaca agccctttaa gtttatgcta  2040
ggcaagcagg aggtgatccg aggctgggaa gaaggggttg cccagatgag tgtgggtcag  2100
agagccaaac tgactatatc tccagattat gcctatggtg ccactgggca cccaggcatc  2160
atcccaccac atgccactct cgtcttcgat gtggagcttc taaaactgga atctggcggt  2220
ggatccggag tcgacggatt tggtgatgtc ggtgctcttg agagtttgag gggaaatgca  2280
gatttggctt acatcctgag catggagccc tgtggccact gcctcattat caacaatgtg  2340
aacttctgcc gtgagtccgg gctccgcacc cgcactggct ccaacatcga ctgtgagaag  2400
ttgcggcgtc gcttctcctc gctgcatttc atggtggagg tgaagggcga cctgactgcc  2460
aagaaaatgg tgctggcttt gctggagctg gcgcagcagg accacggtgc tctggactgc  2520
tgcgtggtgg tcattctctc tcacggctgt caggccagcc acctgcagtt cccaggggct  2580
gtctacggca cagatggatg ccctgtgtcg gtcgagaaga ttgtgaacat cttcaatggg  2640
accagctgcc ccagcctggg agggaagccc aagctctttt tcatccaggc ctgtggtggg  2700
gagcagaaag accatgggtt tgaggtggcc tccacttccc ctgaagacga gtcccctggc  2760
agtaaccccg agccagatgc caccccgttc caggaaggtt tgaggacctt cgaccagctg  2820
gacgccatat ctagtttgcc cacacccagt gacatctttg tgtcctactc tactttccca  2880
ggttttgttt cctggaggga ccccaagagt ggctcctggt acgttgagac cctggacgac  2940
atctttgagc agtgggctca ctctgaagac ctgcagtccc tcctgcttag ggtcgctaat  3000
gctgtttcgg tgaaagggat ttataaacag atgcctggtt gctttaattt cctccggaaa  3060
aaacttttct ttaaaacatc agctagcaga gccgagggca ggggaagtct tctaacatgc  3120
ggggacgtgg aggaaaatcc cggcccatg gagttcggtc tcagttggct gtttttggtt  3180
gctatcttga agggcgtcca atgcagccgg gacatccaga tgacccagtc tccctctagc  3240
atgtcagcga gtcttggtga tcgagtgacg attacctgca gagcctctca agatataaac  3300
agctatcttt catggttcca acagaagccg gggaagtccc caaaaactct catatacagg  3360
gcgaatcgac tcgtagacgg tgtgccttca aggttttccg ggagtggtag tggcacagat  3420
tacacactta caatctcttc attgcagtat gaggatttcg ggatctacta ctgtcaacag  3480
tacgacgaat ccccatggac gtttggggc gggaccaaac ttgagataaa agggagcaca  3540
tctggaagtg gtaaacctgg gtcaggggag ggttccacaa aggacaaat tcaacttgtc  3600
caaagcggtc ctggtcttaa gaagcctgga gggtctgtca ggataagttg tgcggcatcc  3660
ggctacacct tcaccaacta tgggatgaac tgggtgaaac aagcgcctgg gaaaggtctt  3720
cgatggatgg gctggattaa tacccacact ggagagccca cttacgctga tgatttcaaa  3780
ggacgattta ccttctcctt ggatacttcc aagagtaccg cgtacttgca aatcaacagt  3840
ctccgggctg aagacacggc cacatacttc tgtacgcgga gagggtatga ctggtatttt  3900
gatgtgtggg gtcagggaac aaccgtgact gtttcaagct acgtcaccgt ctcttcacag  3960
gatcccgccc tggaagagaa gaaaggcaat tacgtcgtga ccgaccacgg cagctgtgtg  4020
cgggcttgtg gcgccgatag ctacgagatg gaagaggacg gcgtgcggaa gtgcaagaag  4080
tgcgagggcc cctgcagaaa agtgtgcaac ggcatcggca tcggagagtt caaggatagc  4140
ctgagcatca acgccaccaa catcaagcac ttcaagaact gcaccagcat cagcggcgac  4200
ctgcacatcc tgcccgtggc ctttagaggc gacagcttca cccacacccc cccactggat  4260
ccccaggaac tggacatcct gaaaaccgtg aaagagatca caggctttct gctgattcag  4320
gcctggcccg agaaccggac agacctgcac gccttcgaga acctggaaat catcagaggc  4380
cggaccaagc agcacggcca gttttctctg gccgtggtgt ccctgaacat caccagcctg  4440
ggcctgcgga gcctgaaaga aatcagcgac ggcgacgtga tcatctccgg caacaagaac  4500
ctgtgctacg ccaacaccat caattggaag aagctgttcg gcacctccgg ccagaaaaca  4560
aagatcatct ctaaccgggg cgagaacagc tgcaaagcca ccggacaagt gtgccacgcc  4620
ctgtgtagcc ctgagggctg ttggggaccc gagcccagag attgcgtgtc ctgccggaat  4680
gtgtccagag gccgcgagtg cgtggacaag tgcaacctgc tggaaggcga gccccgcgag  4740
tttgtggaaa acagcgagtg catccagtgc caccccgagt gtctgcccca ggccatgaac  4800
attacctgca ccggcagagg ccccgacaac tgtatccagt gcgcccacta catcgacggc  4860
cccactgcg tgaaaacctg tccagctggc gtgatgggag agaacaacac cctcgtgtgg  4920
aagtacgccg acgccggcca tgtgtgccac ctgtgtcacc ccaattgcac ctacggctgt  4980
accggccctg gcctggaagg ctgtcctacc aacggcccca agatcccttc taaagatccc  5040
aaatttgggg tgctggtggt ggttggtgga gtcctggctt gctatagctt gctagtaaca  5100
gtggccttta ttattttctg ggtgaggagt aagaggagca ggctcctgca cagtgactac  5160
```

atgaacatga ctccccgccg ccccgggccc acccgcaagc attaccagcc ctatgcccca 5220
ccacgcgact tcgcagccta tcgctccaga gtgaagttca gcaggagcgc agacgccccc 5280
gcgtaccagc agggccagaa ccagctctat aacgagctca atctaggacg aagagaggag 5340
tacgatgttt tggacaagag acgtggccgg gaccctgaga tggggggaaa gccgagaagg 5400
aagaaccctc aggaaggcct gtacaatgaa ctgcagaaag ataagatggc ggaggcctac 5460
agtgagattg ggatgaaagg cgagcgccgg aggggcaagg ggcacgatgg cctttaccag 5520
ggtctcagta cagccaccaa ggacacctac gacgcccttc acatgcaggc cctgcccccct 5580
cgcggaccgc agtgtactaa ttatgctctc ttgaaattgg ctggagatgt tgagagcaat 5640
cccgggccca tgcggatcag caagccccac ctgcggagca tcagcatcca gtgctacctg 5700
tgcctgctgc tgaacagcca cttcctgacc gaggccggca tccacgtgtt catcctgggc 5760
tgcttcagcg ccggactgcc caagaccgag gccaactggg tgaacgtgat cagcgacctg 5820
aagaagatcg aggacctgat ccagagcatg cacatcgacg ccaccctgta caccgagagc 5880
gacgtgcacc ccagctgcaa ggtgaccgcc atgaagtgct ttctgctgga actgcaggtg 5940
atcagcctgg aaagcggcga cgccagcatc cacgacaccg tggagaacct gatcatcctg 6000
gccaacaaca gcctgagcag caacggcaac gtgaccgaga gcggctgcaa agagtgcgag 6060
gaactggaag agaagaacat caaagagttt ctgcagagct tcgtgcacat cgtgcagatg 6120
ttcatcaaca ccagctgacg cgtcatcatc gatccggatt agtccaattt gttaaagaca 6180
ggatatcagt ggtccaggct ctagttttga ctcaacaata tcaccagctg aagcctatag 6240
agtacgagcc atagataaaa taaaagattt tatttagtct ccagaaaaag gggggaatga 6300
aagaccccac ctgtaggttt ggcaagctag cttaagtaac gccattttgc aaggcatgga 6360
aaaatacata actgagaata gagaagttca gatcaaggtc aggaacagat ggaacagctg 6420
aatatgggcc aaacaggata tctgtggtaa gcagttcctg ccccggctca gggccaagaa 6480
cagatggaac agctgaatat gggccaaaca ggatatctgt ggtaagcagt tcctgccccg 6540
gctcagggcc aagaacagat ggtccccaga tgcggtccag ccctcagcag tttctagaga 6600
accatcagat gtttccaggg tgccccaagg acctgaaatg accctgtgcc ttatttgaac 6660
taaccaatca gttcgcttct cgcttctgtt cgcgcgcttc tgctccccga gctcaataaa 6720
agagcccaca acccctcact cggggcgcca gtcctccgat tgactgagtc gcccgggtac 6780
ccgtgtatcc aataaaccct cttgcagttg catccgactt gtggtctcgc tgttccttgg 6840
gagggtctcc tctgagtgat tgactacccg tcagcggggg tctttcacac atgcagcatg 6900
tatcaaaatt aatttggttt tttttcttaa gtatttacat taaatggcca tagtacttaa 6960
agttacattg gcttccttga aataaacatg gagtattcag aatgtgtcat aaatatttct 7020
aattttaaga tagtatctcc attggctttc tactttttct tttatttttt tttgtcctct 7080
gtcttccatt tgttgttgtt gttgtttgtt tgtttgtttg ttggttggtt ggttaatttt 7140
tttttaaaga tcctacacta tagttcaagc tagactatta gctactctgt aacccagggt 7200
gaccttgaag tcatgggtag cctgctgttt tagccttccc acatctaaga ttacaggtat 7260
gagctatcat ttttggtata ttgattgatt gattgattga tgtgtgtgtg tgtgattgtg 7320
tttgtgtgtg tgactgtgaa aatgtgtgta tgggtgtgtg tgaatgtgtg tatgtatgtg 7380
tgtgtgtgag tgtgtgtgtg tgtgtgtgca tgtgtgtgtg tgtgactgtg tctatgtgta 7440
tgactgtgtg tgtgtgtgtg tgtgtgtgtg tgtgtgtgtg tgtgtgtgtg ttgtgaaaaa 7500
atattctatg gtagtgagag ccaacgctcc ggctcaggtg tcaggttggt ttttgagaca 7560
gagtctttca cttagcttgg aattcactgg ccgtcgtttt acaacgtcgt gactgggaaa 7620
accctggcgt tacccaactt aatcgccttg cagcacatcc ccctttcgcc agctggcgta 7680
atagcgaaga ggcccgcacc gatcgccctt cccaacagtt gcgcagcctg aatggcgaat 7740
ggcgcctgat gcggtatttt ctccttacgc atctgtgcgg tatttcacac cgcatatggt 7800
gcactctcag tacaatctgc tctgatgccg catagttaag ccagccccga cacccgccaa 7860
cacccgctga cgcgccctga cgggcttgtc tgctcccggc atccgcttac agacaagctg 7920
tgaccgtctc cgggagctgc atgtgtcaga ggttttcacc gtcatcaccg aaacgcgcga 7980
gacgaaaggg cctcgtgata cgcctatttt tataggttaa tgtcatgata ataatggttt 8040
cttagacgtc aggtggcact tttcggggaa atgtgcgcgg aacccctatt tgtttatttt 8100
tctaaataca ttcaaatatg tatccgctca tgagacaata accctgataa atgcttcaat 8160
aatattgaaa aaggaagagt atgagtattc aacatttccg tgtcgccctt attccctttt 8220
ttgcggcatt ttgccttcct gtttttgctc acccagaaac gctggtgaaa gtaaaagatg 8280
ctgaagatca gttgggtgca cgagtgggtt acatcgaact ggatctcaac agcggtaaga 8340
tccttgagag ttttcgcccc gaagaacgtt ttccaatgat gagcactttt aaagttctgc 8400
tatgtggcgc ggtattatcc cgtattgacg ccgggcaaga gcaactcggt cgccgcatac 8460
actattctca gaatgacttg gttgagtact caccagtcac agaaaagcat cttacggatg 8520
gcatgacagt aagagaatta tgcagtgctg ccataaccat gagtgataac actgcggcca 8580
acttacttct gacaacgatc ggaggaccga aggagctaac cgcttttttg cacaacatgg 8640
gggatcatgt aactcgcctt gatcgttggg aaccggagct gaatgaagcc ataccaaacg 8700
acgagcgtga caccacgatg cctgtagcaa tggcaacaac gttgcgcaaa ctattaactg 8760
gcgaactact tactctagct tcccggcaac aattaataga ctggatggag gcggataaag 8820
ttgcaggacc acttctgcgc tcggcccttc cggctggctg gtttattgct gataaatctg 8880
gagccggtga gcgtgggtct cgcggtatca ttgcagcact ggggccagat ggtaagccct 8940
cccgtatcgt agttatctac acgacgggga gtcaggcaac tatggatgaa cgaaatagac 9000
agatcgctga gataggtgcc tcactgatta agcattggta actgtcagac caagtttact 9060
catatatact ttagattgat ttaaaacttc atttttaatt taaaaggatc taggtgaaga 9120
tcctttttga taatctcatg accaaaatcc cttaacgtga gttttcgttc cactgagcgt 9180
cagaccccgt agaaaagatc aaaggatctt cttgagatcc tttttttctg cgcgtaatct 9240
gctgcttgca aacaaaaaaa ccaccgctac cagcggtggt ttgtttgccg gatcaagagc 9300
taccaactct ttttccgaag gtaactggct tcagcagagc gcagatacca aatactgttc 9360
ttctagtgta gccgtagtta ggccaccact tcaagaactc tgtagcaccg cctacatacc 9420
tcgctctgct aatcctgtta ccagtggctg ctgccagtgg cgataagtcg tgtcttaccg 9480
ggttggactc aagacgatag ttaccggata aggcgcagcg gtcgggctga acggggggtt 9540
cgtgcacaca gcccagcttg gagcgaacga cctacaccga actgagatac ctacagcgtg 9600
agctatgaga aagcgccacg cttcccgaag ggagaaaggc ggacaggtat ccggtaagcg 9660
gcagggtcgg aacaggagag cgcacgaggg agcttccagg gggaaacgcc tggtatcttt 9720
atagtcctgt cgggtttcgc cacctctgac ttgagcgtcg atttttgtga tgctcgtcag 9780
gggggcggag cctatggaaa aacgccagca acgcggcctt tttacggttc ctggcctttt 9840
gctggccttt tgctcacatg ttctttcctg cgttatcccc tgattctgtg gataaccgta 9900

```
ttaccgcctt tgagtgagct gataccgctc gccgcagccg aacgaccgag cgcagcgagt  9960
cagtgagcga ggaagcggaa gagcgcccaa tacgcaaacc gcctctcccc gcgcgttggc  10020
cgattcatta atgcagctgg cacgacaggt ttcccgactg gaaagcgggc agtgagcgca  10080
acgcaattaa tgtgagttag ctcactcatt aggcacccca ggctttacac tttatgcttc  10140
cggctcgtat gttgtgtgga attgtgagcg gataacaatt tcacacagga aacagctatg  10200
accatgatta cgccaagctt tgctcttagg agtttcctaa tacatcccaa actcaaatat  10260
ataaagcatt tgacttgttc tatgccctag gggcggggg gaagctaagc cagcttttt  10320
taacatttaa aatgttaatt ccattttaaa tgcacagatg tttttatttc ataagggttt  10380
caatgtgcat gaatgctgca atattcctgt taccaaagct agtataaata aaaatagata  10440
aacgtggaaa ttacttagag tttctgtcat taacgtttcc ttcctcagtt gacaacataa  10500
atgcgctgct gagcaagcca gtttgcatct gtcaggatca atttcccatt atgccagtca  10560
tattaattac tagtcaatta gttgattttt atttttgaca tatacatgtg            10610

SEQ ID NO: 48          moltype = DNA  length = 10274
FEATURE                Location/Qualifiers
misc_feature           1..10274
                       note = pSFG4-CD19-DAP12-CAR
source                 1..10274
                       mol_type = other DNA
                       organism = synthetic construct
SEQUENCE: 48
aatgaaagac cccacctgta ggtttggcaa gctagcttaa gtaacgccat tttgcaaggc  60
atggaaaaat acataactga gaatagaaaa gttcagatca aggtcaggaa cagatggaac  120
agctgaatat gggccaaaca ggatatctgt ggtaagcagt tcctgccccg gctcagggcc  180
aagaacagat ggaacagctg aatatgggcc aaacaggata tctgtggtaa gcagttcctg  240
ccccggctca gggccaagaa cagatggtcc ccagatgcgg tccagccctc agcagtttct  300
agagaaccat cagatgtttc cagggtgccc caaggacctg aaatgaccct gtgccttatt  360
tgaactaacc aatcagttcg cttctcgctt ctgttcgcgc gcttatgctc cccgagctca  420
ataaaagagc ccacaacccc tcactcgggg cgccagtcct ccgattgact gagtcgcccg  480
ggtacccgtg tatccaataa accctcttgc agttgcatcc gacttgtggt ctcgctgttc  540
cttgggaggg tctcctctga gtgattgact acccgtcagc gggggtcttt catttggggg  600
ctcgtccggg atcgggagac ccctgcccag ggaccaccga cccaccaccg ggaggtaagc  660
tggccagcaa cttatctgtg tctgtccgat tgtctagtgt ctatgactga ttttatgcgc  720
ctgcgtcggt actagttagc taactagctc tgtatctggc ggacccgtgg tggaactgac  780
gagttcggaa cacccggccg caaccctggg agacgtccca gggacttcgg gggccgtttt  840
tgtggcccga cctgagtcct aaaatcccga tcgtttagga ctctttggtg cacccccctt  900
agaggaggga tatgtggttc tggtaggaga cgagaaccta aaacagttcc cgcctccgtc  960
tgaatttttg ctttcggttt gggaccgaag ccgcgccgcg cgtcttgtct gctgcagcat  1020
cgttctgtgt tgtctctgtc tgactgtgtt tctgtatttg tctgaaaata tgggcccggg  1080
ctagcctgtt accactccct taagtttgac cttaggtcac tggaaagatg tcgagcggat  1140
cgctcacaac cagtcggtag atgtcaagaa gagacgttgg gttaccttct gctctgcaga  1200
atggccaacc tttaacgtcg gatggccgcg agacggcacc tttaaccgag acctcatcac  1260
ccaggttaag atcaaggtct tttcacctgg cccgcatgga cacccagacc aggtggggta  1320
catcgtgacc tgggaagcct tggcttttga cccccctccc tgggtcaagc cctttgtaca  1380
ccctaagcct ccgcctcctc ttcctccatc cgccccgtct ctcccccttg aacctcctcg  1440
ttcgaccccg cctcgatcct ccctttatcc agccctcact ccttctctag gcgcccccat  1500
atggccatat gagatcttat atggggcacc cccgcccctt gtaaacttcc ctgaccctga  1560
catgacaaga gttactaaca gcccctctct ccaagctcac ttacaggctc tctacttagt  1620
ccagcacgaa gtctggagac ctctggcggc agcctaccaa gaacaactgg accgaccggt  1680
ggtacctcac ccttaccgag tcggcgacac agtgtgggtc cgccgacacc agactaagaa  1740
cctagaacct cgctggaaag gaccttacac agtcctgctg accaccccca ccgccctcaa  1800
agtagacggc atcgcagctt ggatacacgc cgcccacgtg aaggctgccg accccggggg  1860
tggaccatcc tctagactgc catgctcgag ggagtgcagg tggaaaccat ctccccagga  1920
gacgggcgca ccttccccaa gcgcggccag acctgcgtgg tgcactacac cgggatgctt  1980
gaagatggaa agaaagttga ttcctcccgg gacagaaaca agccctttaa gtttatgcta  2040
ggcaagcagg aggtgatccg aggctgggaa gaaggggttg cccagatgag tgtgggtcag  2100
agagccaaac tgactatatc tccagattat gcctatggtg ccactgggca cccaggcatc  2160
atcccaccac atgccactct cgtcttcgat gtggagcttc taaaactgga atctggcggt  2220
ggatccggag tcgacggatt tggtgatgtc ggtgctcttg agagtttgag gggaaatgca  2280
gatttggctt acatcctgag catggagccc tgtggccact gcctcattat caacaatgtg  2340
aacttctgcc gtgagtccgg gctccgcacc cgcactggct ccaacatcga ctgtgagaag  2400
ttgcggcgtc gcttctcctc gctgcatttc atggtggagg tgaagggcga cctgactgcc  2460
aagaaaatgg tgctggcttt gctggagctg gcgcagcagg accacggtgc tctggactgc  2520
tgcgtggtgg tcattctctc tcacggctgt caggccagcc acctgcagtt cccaggggct  2580
gtctacggca cagatggatg ccctgtgtcg gtcgagaaga ttgtgaacat cttcaatggg  2640
accagctgcc ccagcctggg agggaagccc aagctctttt tcatccaggc ctgtggtggg  2700
gagcagaaag accatgggtt tgaggtggcc tccacttccc ctgaagacga gtcccctggc  2760
agtaaccccg agccagatgc caccccgttc caggaaggtt tgaggacctt cgaccagctg  2820
gacgccatat ctagtttgcc cacacccagt gacatctttg tgtcctactc tactttccca  2880
ggttttgttt cctggaggga ccccaagagt ggctcctggt acgttgagac cctggacgac  2940
atctttgagc agtgggctca ctctgaagac ctgcagtccc tcctgcttag ggtcgctaat  3000
gctgtttcgg tgaaagggat ttataaacag atgcctggtt gctttaattt cctccggaaa  3060
aaacttttct ttaaaacatc agctagcaga gccgagggca ggggaagtct tctaacatgc  3120
ggggacgtgg aggaaaatcc cgggcccatg gagtttgggc tgagctggct tttcttgtg  3180
gctattttaa aaggtgtcca gtgctctaga gacatccaga tgacacagac tacatcctcc  3240
ctgtctgcct ctctgggaga cagagtcacc atcagttgca gggcaagtca ggacattagt  3300
aaatatttaa attggtatca gcagaaacca gatggaactg ttaaactcct gatctaccat  3360
acatcaagat tacactcagg agtcccatca aggttcagtg gcagtgggtc tggaacagat  3420
tattctctca ccattagcaa cctggagcaa gaagatattg ccacttactt ttgccaacag  3480
```

-continued

```
ggtaatacgc ttccgtacac gttcggaggg gggaccaagc tggagctgaa acgtggtggt  3540
ggtggttctg gtggtggtgg ttctggcggc ggcggctccg gtggtggtgg atccgaggtg  3600
cagctgcagc agtctggacc tggcctggtg gcgccctcac agagcctgtc cgtcacatgc  3660
actgtctcag ggtctcatt acccgactat ggtgtaagct ggattcgcca gcctccacga  3720
aagggtctgg agtggctggg agtaatatgg ggtagtgaaa ccacatacta taattcagct  3780
ctcaaatcca gactgaccat catcaaggac aactccaaga gccaagtttt cttaaaaatg  3840
aacagtctgc aaactgatga cacagccatt tactactgtg ccaaacatta ttactacggt  3900
ggtagctatg ctatggacta ctggggccaa gggaccacgg tcaccgtctc ctcgtacgtc  3960
accgtctctt cacaggatcc cgccgagccc aaatctcctg acaaaactca cacatgccca  4020
ccgtgcccag cacctgaact cctgggggga ccgtcagtct tcctcttccc cccaaaaccc  4080
aaggacaccc tcatgatctc ccggacccct gaggtcacat gcgtggtggt ggacgtgagc  4140
cacgaagacc ctgaggtcaa gttcaactgg tacgtggacg gcgtggaggt gcataatgcc  4200
aagacaaagc cgcgggagga gcagtacaac agcacgtacc gtgtggtcag cgtcctcacc  4260
gtcctgcacc aggactggct gaatggcaag gagtacaagt gcaaggtctc caacaaagcc  4320
ctcccagccc ccatcgagaa aaccatctcc aaagccaaag ggcagccccg agaaccacag  4380
gtgtacaccc tgcccccatc ccgggatgag ctgaccaaga accaggtcag cctgacctgc  4440
ctggtcaaag gcttctatcc cagcgacatc gccgtggagt gggagagcaa tgggcaaccg  4500
gagaacaact acaagaccac gcctcccgtg ctggactccg acggctcctt cttcctctac  4560
agcaagctca ccgtggacaa gagcaggtgg cagcagggga acgtcttctc atgctccgtg  4620
atgcatgagg ctctgcacaa ccactacacg cagaagagcc tctccctgtc tccgggtaaa  4680
aaagatccca aaggcgtgct ggccggaatc gtgatgggcg acctggtgct gacagtgctg  4740
atcgccctgg ctgtgtactt cctgggcaga ctggtgccca gaggaagagg cgctgccgaa  4800
gccgccaccc ggaagcagag aatcaccgag acagagagcc cctatcagga actgcagggc  4860
cagcggagcg acgtgtacag cgacctgaat acccagcggc cctactacaa gagagtgaag  4920
ttcagcagga gcgcagacgc ccccgcgtac cagcagggcc agaaccagct ctataacgag  4980
ctcaatctag gacgaagaga ggagtacgat gttttggaca agagacgtgg ccgggaccct  5040
gagatggggg gaaagccgag aaggaagaac cctcaggaag gcctgtacaa tgaactgcag  5100
aaagataaga tggcggaggc ctacagtgag attgggatga aaggcgagcg ccggaggggc  5160
aaggggcacg atggccttta ccagggtctc agtacagcca ccaaggacac ctacgacgcc  5220
cttcacatgc aggccctgcc ccctcgcgga ccgcagtgta ctaattatgc tctcttgaaa  5280
ttggctggag atgttgagag caatcccggg cccatgcgga tcagcaagcc ccacctgcgg  5340
agcatcagca tccagtgcta cctgtgcctg ctgctgaaca gccacttcct gaccgaggcc  5400
ggcatccacg tgttcatcct gggctgcttc agcgccggac tgcccaagac cgaggccaac  5460
tgggtgaacg tgatcagcga cctgaagaag atcgaggacc tgatccagag catgcacatc  5520
gacgccaccc tgtacaccga gagcgacgtg caccccagct gcaaggtgac cgccatgaag  5580
tgctttctgc tggaactgca ggtgatcagc ctggaaagcg gcgacgccag catccacgac  5640
accgtggaga acctgatcat cctggccaac aacagcctga gcagcaacgg caacgtgacc  5700
gagagcggct gcaaagagtg cgaggaactg gaagagaaga acatcaaaga gtttctgcag  5760
agcttcgtgc acatcgtgca gatgttcatc aacaccagct gacgcgtcat catcgatccg  5820
gattagtcca atttgttaaa gacaggatat cagtggtcca ggctctagtt ttgactcaac  5880
aatatcacca gctgaagcct atagagtacg agccatagat aaaataaaag attttattta  5940
gtctccagaa aaagggggga atgaaagacc ccacctgtag gtttggcaag ctagcttaag  6000
taacgccatt ttgcaaggca tggaaaaata cataactgag aatagagaag ttcagatcaa  6060
ggtcaggaac agatggaaca gctgaatatg ggccaaacag gatatctgtg gtaagcagtt  6120
cctgccccgg ctcagggcca agaacagatg gaacagctga atatgggcca aacaggatat  6180
ctgtggtaag cagttcctgc cccggctcag ggccaagaac agatggtccc cagatgcggt  6240
ccagccctca gcagtttcta gagaaccatc agatgtttcc agggtgcccc aaggacctga  6300
aatgaccctg tgccttattt gaactaacca atcagttcgc ttctcgcttc tgttcgcgcg  6360
cttctgctcc ccgagctcaa taaaagagcc cacaacccct cactcggggc gccagtcctc  6420
cgattgactg agtcgcccgg gtacccgtgt atccaataaa ccctcttgca gttgcatccg  6480
acttgtggtc tcgctgttcc ttgggagggt ctcctctgag tgattgacta cccgtcagcg  6540
ggggtctttc acacatgcag catgtatcaa aattaatttg gtttttttc ttaagtattt  6600
acattaaatg gccatagtac ttaaagttac attggcttcc ttgaaataaa catggagtat  6660
tcagaatgtg tcataaatat ttctaatttt aagatagtat ctccattggc tttctacttt  6720
ttcttttatt tttttttgtc ctctgtcttc catttgttgt tgttgttgtt tgtttgtttg  6780
tttgttggtt ggttggttaa ttttttttta aagatcctac actatagttc aagctagact  6840
attagctact ctgtaaccca gggtgacctt gaagtcatgg gtagcctgct gttttagcct  6900
tcccacatct aagattacag gtatgagcta tcatttttgg tatattgatt gattgattga  6960
ttgatgtgtg tgtgtgtgat tgtgtttgtg tgtgtgactg tgaaaatgtg tgtatgggtg  7020
tgtgtgaatg tgtgtatgta tgtgtgtgtg tgagtgtgtg tgtgtgtgtg tgcatgtgtg  7080
tgtgtgtgac tgtgtctatg tgtatgactg tgtgtgtgtg tgtgtgtgtg tgtgtgtgtg  7140
tgtgtgtgtg tgtgttgtga aaaaatattc tatggtagtg agagccaacg ctccggctca  7200
ggtgtcaggt tggtttttga gacagagtct ttcacttagc ttggaattca ctggccgtcg  7260
ttttacaacg tcgtgactgg gaaaaccctg gcgttaccca acttaatcgc cttgcagcac  7320
atccccctt cgccagctgg cgtaatagcg aagaggcccg caccgatcgc ccttcccaac  7380
agttgcgcag cctgaatggc gaatggcgcc tgatgcggta ttttctcctt acgcatctgt  7440
gcggtatttc acaccgcata tggtgcactc tcagtacaat ctgctctgat gccgcatagt  7500
taagccagcc ccgacacccg ccaacacccg ctgacgcgcc ctgacgggct tgtctgctcc  7560
cggcatccgc ttacagacaa gctgtgaccg tctccgggag ctgcatgtgt cagaggtttt  7620
caccgtcatc accgaaacgc gcgagacgaa agggcctcgt gatacgccta tttttatagg  7680
ttaatgtcat gataataatg gtttcttaga cgtcaggtgg cacttttcgg ggaaatgtgc  7740
gcggaacccc tatttgttta tttttctaaa tacattcaaa tatgtatccg ctcatgagac  7800
aataaccctg ataaatgctt caataatatt gaaaaaggaa gagtatgagt attcaacatt  7860
tccgtgtcgc ccttattccc ttttttgcgg cattttgcct tcctgttttt gctcacccag  7920
aaacgctggt gaaagtaaaa gatgctgaag atcagttggg tgcacgagtg ggttacatcg  7980
aactggatct caacagcggt aagatccttg agagttttcg ccccgaagaa cgttttccaa  8040
tgatgagcac ttttaaagtt ctgctatgtg gcgcggtatt atcccgtatt gacgccgggc  8100
aagagcaact cggtcgccgc atacactatt ctcagaatga cttggttgag tactcaccag  8160
tcacagaaaa gcatcttacg gatggcatga cagtaagaga attatgcagt gctgccataa  8220
```

```
ccatgagtga taacactgcg gccaacttac ttctgacaac gatcggagga ccgaaggagc  8280
taaccgcttt tttgcacaac atgggggatc atgtaactcg ccttgatcgt tgggaaccgg  8340
agctgaatga agccatacca aacgacgagc gtgacaccac gatgcctgta gcaatggcaa  8400
caacgttgcg caaactatta actggcgaac tacttactct agcttcccgg caacaattaa  8460
tagactggat ggaggcggat aaagttgcag gaccacttct gcgctcggcc cttccggctg  8520
gctggtttat tgctgataaa tctggagccg gtgagcgtgg gtctcgcggt atcattgcag  8580
cactggggcc agatggtaag ccctcccgta tcgtagttat ctacacgacg gggagtcagg  8640
caactatgga tgaacgaaat agacagatcg ctgagatagg tgcctcactg attaagcatt  8700
ggtaactgtc agaccaagtt tactcatata tactttagat tgatttaaaa cttcattttt  8760
aatttaaaag gatctaggtg aagatccttt ttgataatct catgaccaaa atcccttaac  8820
gtgagttttc gttccactga gcgtcagacc ccgtagaaaa gatcaaagga tcttcttgag  8880
atcctttttt tctgcgcgta atctgctgct tgcaaacaaa aaaaccaccg ctaccagcgg  8940
tggtttgttt gccggatcaa gagctaccaa ctctttttcc gaaggtaact ggcttcagca  9000
gagcgcagat accaaatact gttcttctag tgtagccgta gttaggccac cacttcaaga  9060
actctgtagc accgcctaca tacctcgctc tgctaatcct gttaccagtg gctgctgcca  9120
gtggcgataa gtcgtgtctt accgggttgg actcaagacg atagttaccg gataaggcgc  9180
agcggtcggg ctgaacgggg ggttcgtgca cacagcccag cttggagcga acgacctaca  9240
ccgaactgag atacctacag cgtgagctat gagaaagcgc cacgcttccc gaagggagaa  9300
aggcggacag gtatccggta agcggcaggg tcggaacagg agagcgcacg agggagcttc  9360
caggggggaaa cgcctggtat ctttatagtc ctgtcgggtt tcgccacctc tgacttgagc  9420
gtcgattttt gtgatgctcg tcaggggggc ggagcctatg gaaaaacgcc agcaacgcgg  9480
cctttttacg gttcctggcc ttttgctggc cttttgctca catgttcttt cctgcgttat  9540
cccctgattc tgtggataac cgtattaccg cctttgagtg agctgatacc gctcgccgca  9600
gccgaacgac cgagcgcagc gagtcagtga gcgaggaagc ggaagagcgc ccaatacgca  9660
aaccgcctct ccccgcgcgt tggccgattc attaatgcag ctggcacgac aggtttcccg  9720
actggaaagc gggcagtgag cgcaacgcaa ttaatgtgag ttagctcact cattaggcac  9780
cccaggcttt acactttatg cttccggctc gtatgttgtg tggaattgtg agcggataac  9840
aatttcacac aggaaacagc tatgaccatg attacgccaa gctttgctct taggagtttc  9900
ctaatacatc ccaaactcaa atatataaag catttgactt gttctatgcc ctagggggcg  9960
gggggaagct aagccagctt tttttaacat ttaaaatgtt aattccattt taaatgcaca  10020
gatgttttta tttcataagg gtttcaatgt gcatgaatgc tgcaatattc ctgttaccaa  10080
agctagtata aataaaaata gataaacgtg gaaattactt agagtttctg tcattaacgt  10140
ttccttcctc agttgacaac ataaatgcgc tgctgagcaa gccagtttgc atctgtcagg  10200
atcaatttcc cattatgcca gtcatattaa ttactagtca attagttgat ttttattttt  10260
gacatataca tgtg                                                   10274
```

```
SEQ ID NO: 49          moltype = DNA  length = 9374
FEATURE                Location/Qualifiers
misc_feature           1..9374
                       note = pSFG4-CD19-DAP12-Ev3-CAR 2.0
source                 1..9374
                       mol_type = other DNA
                       organism = synthetic construct
SEQUENCE: 49
aatgaaagac cccacctgta ggtttggcaa gctagcttaa gtaacgccat tttgcaaggc  60
atggaaaaat acataactga gaatagaaaa gttcagatca aggtcaggaa cagatggaac  120
agctgaatat gggccaaaca ggatatctgt ggtaagcagt tcctgccccg gctcagggcc  180
aagaacagat ggaacagctg aatatgggcc aaacaggata tctgtggtaa gcagttcctg  240
ccccggctca gggccaagaa cagatggtcc ccagatgcgg tccagccctc agcagtttct  300
agagaaccat cagatgtttc cagggtgccc caaggacctg aaatgaccct gtgccttatt  360
tgaactaacc aatcagttcg cttctcgctt ctgttcgcgc gcttatgctc cccgagctca  420
ataaaagagc ccacaacccc tcactcgggg cgccagtcct ccgattgact gagtcgcccg  480
ggtacccgtg tatccaataa accctcttgc agttgcatcc gacttgtggt ctcgctgttc  540
cttgggaggg tctcctctga gtgattgact acccgtcagc gggggtcttt catttggggg  600
ctcgtccggg atcgggagac ccctgcccag ggaccaccga cccaccaccg ggaggtaagc  660
tggccagcaa cttatctgtg tctgtccgat tgtctagtgt ctatgactga ttttatgcgc  720
ctgcgtcggt actagttagc taactagctc tgtatctggc ggacccgtgg tggaactgac  780
gagttcggaa cacccggccg caaccctggg agacgtccca gggacttcgg gggccgtttt  840
tgtggcccga cctgagtcct aaaatcccga tcgtttagga ctctttggtg cacccccctt  900
agaggaggga tatgtggttc tggtaggaga cgagaaccta aaacagttcc cgcctccgtc  960
tgaatttttg ctttcggttt gggaccgaag ccgcgccgcg cgtcttgtct gctgcagcat  1020
cgttctgtgt tgtctctgtc tgactgtgtt tctgtatttg tctgaaaata tgggcccggg  1080
ctagcctgtt accactccct taagtttgac cttaggtcac tggaaagatg tcgagcggat  1140
cgctcacaac cagtcggtag atgtcaagaa gagacgttgg gttaccttct gctctgcaga  1200
atggccaacc tttaacgtcg gatggccgcg agacggcacc tttaaccgag acctcatcac  1260
ccaggttaag atcaaggtct tttcacctgg cccgcatgga cacccagacc aggtggggta  1320
catcgtgacc tgggaagcct tggcttttga cccccctccc tgggtcaagc cctttgtaca  1380
ccctaagcct ccgcctcctc ttcctccatc cgccccgtct ctcccccttg aacctcctcg  1440
ttcgaccccg cctcgatcct ccctttatcc agccctcact ccttctctag gcgcccccat  1500
atggccatat gagatcttat atggggcacc cccgcccctt gtaaacttcc ctgaccctga  1560
catgacaaga gttactaaca gcccctctct ccaagctcac ttacaggctc tctacttagt  1620
ccagcacgaa gtctggagac ctctggcggc agcctaccaa gaacaactgg accgaccggt  1680
ggtacctcac ccttaccgag tcggcgacac agtgtgggtc cgccgacacc agactaagaa  1740
cctagaacct cgctggaaag gaccttacac agtcctgctg accacccccca ccgccctcaa  1800
agtagacggc atcgcagctt ggatacacgc cgcccacgtg aaggctgccg accccggggg  1860
tggaccatcc tctagactgc catggagttt gggctgagct ggctttttct tgtggctatt  1920
ttaaaaggtg tccagtgctc tagagacatc cagatgacac agactacatc ctccctgtct  1980
gcctctctgg gagacagagt caccatcagt tgcagggcaa gtcaggacat tagtaaatat  2040
ttaaattggt atcagcagaa accagatgga actgttaaac tcctgatcta ccatacatca  2100
```

```
agattacact caggagtccc atcaaggttc agtggcagtg ggtctggaac agattattct  2160
ctcaccatta gcaacctgga gcaagaagat attgccactt acttttgcca acagggtaat  2220
acgcttccgt acacgttcgg aggggggacc aagctggagc tgaaacgtgg tggtggtggt  2280
tctggtggtg gtggttctgg cggcggcggc tccggtggtg gtggatccga ggtgcagctg  2340
cagcagtctg gacctggcct ggtggcgccc tcacagagcc tgtccgtcac atgcactgtc  2400
tcaggggtct cattacccga ctatggtgta agctggattc gccagcctcc acgaaagggt  2460
ctggagtggc tgggagtaat atggggtagt gaaaccacat actataattc agctctcaaa  2520
tccagactga ccatcatcaa ggacaactcc aagagccaag ttttcttaaa aatgaacagt  2580
ctgcaaactg atgacacagc catttactac tgtgccaaac attattacta cggtggtagc  2640
tatgctatgg actactgggg ccaagggacc acggtcaccg tctcctcgta cgtcaccgtc  2700
tcttcacagg atcccgccct ggaagagaag aaaggcaatt acgtcgtgac cgaccacggc  2760
agctgtgtgc gggcttgtgg cgccgatagc tacgagatgg aagaggacgg cgtgcggaag  2820
tgcaagaagt gcgagggccc ctgcagaaaa gtgtgcaacg gcatcggcat cggagagttc  2880
aaggatagcc tgagcatcaa cgccaccaac atcaagcact tcaagaactg caccagcatc  2940
agcggcgacc tgcacatcct gcccgtggcc tttagaggcg acagcttcac ccacaccccc  3000
ccactggatc cccaggaact ggacatcctg aaaaccgtga aagagatcac aggctttctg  3060
ctgattcagg cctggcccga gaaccggaca gacctgcacg ccttcgagaa cctggaaatc  3120
atcagaggcc ggaccaagca gcacggccag ttttctctgg ccgtggtgtc cctgaacatc  3180
accagcctgg gcctgcggag cctgaaagaa atcagcgacg gcgacgtgat catctccggc  3240
aacaagaacc tgtgctacgc caacaccatc aattggaaga agctgttcgg cacctccggc  3300
cagaaaacaa agatcatctc taaccggggc gagaacagct gcaaagccac cggacaagtg  3360
tgccacgccc tgtgtagccc tgagggctgt tggggacccg agcccagaga ttgcgtgtcc  3420
tgccggaatg tgtccagagg ccgcgagtgc gtggacaagt gcaacctgct ggaaggcgag  3480
ccccgcgagt ttgtggaaaa cagcgagtgc atccagtgcc accccgagtg tctgccccag  3540
gccatgaaca ttacctgcac cggcagaggc cccgacaact gtatccagtg cgcccactac  3600
atcgacggcc cccactgcgt gaaaacctgt ccagctggcg tgatgggaga gaacaacacc  3660
ctcgtgtgga agtacgccga cgccggccat gtgtgccacc tgtgtcaccc caattgcacc  3720
tacggctgta ccggccctgg cctggaaggc tgtcctacca acggccccaa gatccctagc  3780
aaggatccta agggagtgct ggccggaatc gtgatgggcg acctggtgct gacagtgctg  3840
atcgccctgg ctgtgtactt cctgggcaga ctggtgccca gaggaagagg cgctgccgaa  3900
gccgccaccc ggaagcagag aatcaccgag acagagagcc cctatcagga actgcagggc  3960
cagcggagcg acgtgtacag cgacctgaat acccagcggc cctactacaa gagagtgaag  4020
ttcagcagga gcgcagacgc ccccgcgtac cagcagggcc agaaccagct ctataacgag  4080
ctcaatctag gacgaagaga ggagtacgat gttttggaca agagacgtgg ccgggaccct  4140
gagatggggg gaaagccgag aaggaagaac cctcaggaag gcctgtacaa tgaactgcag  4200
aaagataaga tggcggaggc ctacagtgag attgggatga aaggcgagcg ccggaggggc  4260
aaggggcacg atggccttta ccagggtctc agtacagcca ccaaggacac ctacgacgcc  4320
cttcacatgc aggccctgcc ccctcgcgga ccgcagtgta ctaattatgc tctcttgaaa  4380
ttggctggag atgttgagag caatcccggg cccatgcgga tcagcaagcc ccacctgcgg  4440
agcatcagca tccagtgcta cctgtgcctg ctgctgaaca gccacttcct gaccgaggcc  4500
ggcatccacg tgttcatcct gggctgcttc agcgccggac tgcccaagac cgaggccaac  4560
tgggtgaacg tgatcagcga cctgaagaag atcgaggacc tgatccagag catgcacatc  4620
gacgccaccc tgtacaccga gagcgacgtg caccccagct gcaaggtgac cgccatgaag  4680
tgctttctgc tggaactgca ggtgatcagc ctggaaagcg gcgacgccag catccacgac  4740
accgtggaga acctgatcat cctggccaac aacagcctga gcagcaacgg caacgtgacc  4800
gagagcggct gcaaagagtg cgaggaactg gaagagaaga acatcaaaga gtttctgcag  4860
agcttcgtgc acatcgtgca gatgttcatc aacaccagct gacgcgtcat catcgatccg  4920
gattagtcca atttgttaaa gacaggatat cagtggtcca ggctctagtt ttgactcaac  4980
aatatcacca gctgaagcct atagagtacg agccatagat aaaataaaag attttattta  5040
gtctccagaa aaagggggga atgaaagacc ccacctgtag gtttggcaag ctagcttaag  5100
taacgccatt ttgcaaggca tggaaaaata cataactgag aatagagaag ttcagatcaa  5160
ggtcaggaac agatggaaca gctgaatatg ggccaaacag gatatctgtg gtaagcagtt  5220
cctgccccgg ctcagggcca agaacagatg gaacagctga atatgggcca aacaggatat  5280
ctgtggtaag cagttcctgc cccggctcag ggccaagaac agatggtccc cagatgcggt  5340
ccagccctca gcagtttcta gagaaccatc agatgtttcc agggtgcccc aaggacctga  5400
aatgaccctg tgccttattt gaactaacca atcagttcgc ttctcgcttc tgttcgcgcg  5460
cttctgctcc ccgagctcaa taaaagagcc cacaacccct cactcggggc gccagtcctc  5520
cgattgactg agtcgcccgg gtacccgtgt atccaataaa ccctcttgca gttgcatccg  5580
acttgtggtc tcgctgttcc ttgggagggt ctcctctgag tgattgacta cccgtcagcg  5640
ggggtctttc acacatgcag catgtatcaa aattaatttg gttttttttc ttaagtattt  5700
acattaaatg gccatagtac ttaaagttac attggcttcc ttgaaataaa catggagtat  5760
tcagaatgtg tcataaatat ttctaatttt aagatagtat ctccattggc tttctacttt  5820
ttcttttatt tttttttgtc ctctgtcttc catttgttgt tgttgttgtt tgtttgtttg  5880
tttgttggtt ggttggttaa tttttttta aagatcctac actatagttc aagctagact  5940
attagctact ctgtaaccca gggtgacctt gaagtcatgg gtagcctgct gttttagcct  6000
tcccacatct aagattacag gtatgagcta tcatttttgg tatattgatt gattgattga  6060
ttgatgtgtg tgtgtgtgat tgtgtttgtg tgtgtgactg tgaaaatgtg tgtatgggtg  6120
tgtgtgaatg tgtgtatgta tgtgtgtgtg tgagtgtgtg tgtgtgtgtg tgcatgtgtg  6180
tgtgtgtgac tgtgtctatg tgtatgactg tgtgtgtgtg tgtgtgtgtg tgtgtgtgtg  6240
tgtgtgtgtg tgtgttgtga aaaaatattc tatggtagtg agagccaacg ctccggctca  6300
ggtgtcaggt tggtttttga gacagagtct ttcacttagc ttggaattca ctggccgtcg  6360
ttttacaacg tcgtgactgg gaaaaccctg gcgttaccca acttaatcgc cttgcagcac  6420
atccccctttt cgccagctgg cgtaatagcg aagaggcccg caccgatcgc ccttcccaac  6480
agttgcgcag cctgaatggc gaatggcgcc tgatgcggta ttttctcctt acgcatctgt  6540
gcggtatttc acaccgcata tggtgcactc tcagtacaat ctgctctgat gccgcatagt  6600
taagccagcc ccgacacccg ccaacacccg ctgacgcgcc ctgacgggct tgtctgctcc  6660
cggcatccgc ttacagacaa gctgtgaccg tctccgggag ctgcatgtgt cagaggtttt  6720
caccgtcatc accgaaacgc gcgagacgaa agggcctcgt gatacgccta tttttatagg  6780
ttaatgtcat gataataatg gtttcttaga cgtcaggtgg cacttttcgg ggaaatgtgc  6840
```

```
gcggaacccc tatttgttta tttttctaaa tacattcaaa tatgtatccg ctcatgagac  6900
aataaccctg ataaatgctt caataatatt gaaaaaggaa gagtatgagt attcaacatt  6960
tccgtgtcgc ccttattccc ttttttgcgg cattttgcct tcctgttttt gctcacccag  7020
aaacgctggt gaaagtaaaa gatgctgaag atcagttggg tgcacgagtg ggttacatcg  7080
aactggatct caacagcggt aagatccttg agagttttcg ccccgaagaa cgttttccaa  7140
tgatgagcac ttttaaagtt ctgctatgtg gcgcggtatt atcccgtatt gacgccgggc  7200
aagagcaact cggtcgccgc atacactatt ctcagaatga cttggttgag tactcaccag  7260
tcacagaaaa gcatcttacg gatggcatga cagtaagaga attatgcagt gctgccataa  7320
ccatgagtga taacactgcg gccaacttac ttctgacaac gatcggagga ccgaaggagc  7380
taaccgcttt tttgcacaac atgggggatc atgtaactcg ccttgatcgt tgggaaccgg  7440
agctgaatga agccatacca aacgacgagc gtgacaccac gatgcctgta gcaatggcaa  7500
caacgttgcg caaactatta actggcgaac tacttactct agcttcccgg caacaattaa  7560
tagactggat ggaggcggat aaagttgcag gaccacttct gcgctcggcc cttccggctg  7620
gctggtttat tgctgataaa tctggagccg gtgagcgtgg gtctcgcggt atcattgcag  7680
cactggggcc agatggtaag ccctcccgta tcgtagttat ctacacgacg gggagtcagg  7740
caactatgga tgaacgaaat agacagatcg ctgagatagg tgcctcactg attaagcatt  7800
ggtaactgtc agaccaagtt tactcatata tactttagat tgatttaaaa cttcattttt  7860
aatttaaaag gatctaggtg aagatccttt ttgataatct catgaccaaa atcccttaac  7920
gtgagttttc gttccactga gcgtcagacc ccgtagaaaa gatcaaagga tcttcttgag  7980
atcctttttt tctgcgcgta atctgctgct tgcaaacaaa aaaaccaccg ctaccagcgg  8040
tggtttgttt gccggatcaa gagctaccaa ctctttttcc gaaggtaact ggcttcagca  8100
gagcgcagat accaaatact gttcttctag tgtagccgta gttaggccac cacttcaaga  8160
actctgtagc accgcctaca tacctcgctc tgctaatcct gttaccagtg gctgctgcca  8220
gtggcgataa gtcgtgtctt accgggttgg actcaagacg atagttaccg gataaggcgc  8280
agcggtcggg ctgaacgggg ggttcgtgca cacagcccag cttggagcga acgacctaca  8340
ccgaactgag atacctacag cgtgagctat gagaaagcgc cacgcttccc gaagggagaa  8400
aggcggacag gtatccggta agcggcaggg tcggaacagg agagcgcacg agggagcttc  8460
caggggggaaa cgcctggtat ctttatagtc ctgtcgggtt tcgccacctc tgacttgagc  8520
gtcgattttt gtgatgctcg tcaggggggc ggagcctatg gaaaaacgcc agcaacgcgg  8580
cctttttacg gttcctggcc ttttgctggc cttttgctca catgttcttt cctgcgttat  8640
cccctgattc tgtggataac cgtattaccg cctttgagtg agctgatacc gctcgccgca  8700
gccgaacgac cgagcgcagc gagtcagtga gcgaggaagc ggaagagcgc ccaatacgca  8760
aaccgcctct ccccgcgcgt tggccgattc attaatgcag ctggcacgac aggtttcccg  8820
actggaaagc gggcagtgag cgcaacgcaa ttaatgtgag ttagctcact cattaggcac  8880
cccaggcttt acactttatg cttccggctc gtatgttgtg tggaattgtg agcggataac  8940
aatttcacac aggaaacagc tatgaccatg attacgccaa gctttgctct taggagtttc  9000
ctaatacatc ccaaactcaa atatataaag catttgactt gttctatgcc ctagggggcg  9060
gggggaagct aagccagctt tttttaacat ttaaaatgtt aattccattt taaatgcaca  9120
gatgttttta tttcataagg gtttcaatgt gcatgaatgc tgcaatattc ctgttaccaa  9180
agctagtata aataaaaata gataaacgtg gaaattactt agagtttctg tcattaacgt  9240
ttccttcctc agttgacaac ataaatgcgc tgctgagcaa gccagtttgc atctgtcagg  9300
atcaatttcc cattatgcca gtcatattaa ttactagtca attagttgat ttttattttt  9360
gacatataca tgtg                                                    9374
```

```
SEQ ID NO: 50           moltype = AA  length = 1006
FEATURE                 Location/Qualifiers
REGION                  1..1006
                        note = pSFG4-CD19-DAP12-Ev3-CAR 2.0
source                  1..1006
                        mol_type = protein
                        organism = synthetic construct
SEQUENCE: 50
MEFGLSWLFL VAILKGVQCS RDIQMTQTTS SLSASLGDRV TISCRASQDI SKYLNWYQQK  60
PDGTVKLLIY HTSRLHSGVP SRFSGSGSGT DYSLTISNLE QEDIATYFCQ QGNTLPYTFG  120
GGTKLELKRG GGGSGGGGSG GGGSGGGGSE VQLQQSGPGL VAPSQSLSVT CTVSGVSLPD  180
YGVSWIRQPP RKGLEWLGVI WGSETTYYNS ALKSRLTIIK DNSKSQVFLK MNSLQTDDTA  240
IYYCAKHYYY GGSYAMDYWG QGTTVTVSSY VTVSSQDPAL EEKKGNYVVT DHGSCVRACG  300
ADSYEMEEDG VRKCKKCEGP CRKVCNGIGI GEFKDSLSIN ATNIKHFKNC TSISGDLHIL  360
PVAFRGDSFT HTPPLDPQEL DILKTVKEIT GFLLIQAWPE NRTDLHAFEN LEIIRGRTKQ  420
HGQFSLAVVS LNITSLGLRS LKEISDGDVI ISGNKNLCYA NTINWKKLFG TSGQKTKIIS  480
NRGENSCKAT GQVCHALCSP EGCWGPEPRD CVSCRNVSRG RECVDKCNLL EGEPREFVEN  540
SECIQCHPEC LPQAMNITCT GRGPDNCIQC AHYIDGPHCV KTCPAGVMGE NNTLVWKYAD  600
AGHVCHLCHP NCTYGCTGPG LEGCPTNGPK IPSKDPKGVL AGIVMGDLVL TVLIALAVYF  660
LGRLVPRGRG AAEAATRKQR ITETESPYQE LQGQRSDVYS DLNTQRPYYK RVKFSRSADA  720
PAYQQGQNQL YNELNLGRRE EYDVLDKRRG RDPEMGGKPR RKNPQEGLYN ELQKDKMAEA  780
YSEIGMKGER RRGKGHDGLY QGLSTATKDT YDALHMQALP PRGPQCTNYA LLKLAGDVES  840
NPGPMRISKP HLRSISIQCY LCLLLNSHFL TEAGIHVFIL GCFSAGLPKT EANWVNVISD  900
LKKIEDLIQS MHIDATLYTE SDVHPSCKVT AMKCFLLELQ VISLESGDAS IHDTVENLII  960
LANNSLSSNG NVTESGCKEC EELEEKNIKE FLQSFVHIVQ MFINTS                 1006
```

```
SEQ ID NO: 51           moltype = DNA  length = 219
FEATURE                 Location/Qualifiers
misc_feature            1..219
                        note = DAP12
source                  1..219
                        mol_type = other DNA
                        organism = synthetic construct
```

```
SEQUENCE: 51
ggcgtgctgg ccggaatcgt gatgggcgac ctggtgctga cagtgctgat cgccctggct  60
gtgtacttcc tgggcagact ggtgcccaga ggaagaggcg ctgccgaagc cgccacccgg  120
aagcagagaa tcaccgagac agagagcccc tatcaggaac tgcagggcca gcggagcgac  180
gtgtacagcg acctgaatac ccagcggccc tactacaag                         219

SEQ ID NO: 52          moltype = AA  length = 73
FEATURE                Location/Qualifiers
REGION                 1..73
                       note = DAP12
source                 1..73
                       mol_type = protein
                       organism = synthetic construct
SEQUENCE: 52
GVLAGIVMGD LVLTVLIALA VYFLGRLVPR GRGAAEAATR KQRITETESP YQELQGQRSD  60
VYSDLNTQRP YYK                                                     73

SEQ ID NO: 53          moltype = DNA  length = 342
FEATURE                Location/Qualifiers
misc_feature           1..342
                       note = CD3zeta
source                 1..342
                       mol_type = other DNA
                       organism = synthetic construct
SEQUENCE: 53
agagtgaagt tcagcaggag cgcagacgcc cccgcgtacc agcagggcca gaaccagctc  60
tataacgagc tcaatctagg acgaagagag gagtacgatg ttttggacaa gagacgtggc  120
cgggaccctg agatgggggg aaagccgaga aggaagaacc ctcaggaagg cctgtacaat  180
gaactgcaga aagataagat ggcggaggcc tacagtgaga ttgggatgaa aggcgagcgc  240
cggaggggca aggggcacga tggcctttac cagggtctca gtacagccac caaggacacc  300
tacgacgccc ttcacatgca ggccctgccc cctcgcggac cg                     342

SEQ ID NO: 54          moltype = AA  length = 114
FEATURE                Location/Qualifiers
REGION                 1..114
                       note = CD3zeta
source                 1..114
                       mol_type = protein
                       organism = synthetic construct
SEQUENCE: 54
RVKFSRSADA PAYQQGQNQL YNELNLGRRE EYDVLDKRRG RDPEMGGKPR RKNPQEGLYN  60
ELQKDKMAEA YSEIGMKGER RRGKGHDGLY QGLSTATKDT YDALHMQALP PRGP        114

SEQ ID NO: 55          moltype = DNA  length = 489
FEATURE                Location/Qualifiers
misc_feature           1..489
                       note = IL15
source                 1..489
                       mol_type = other DNA
                       organism = synthetic construct
SEQUENCE: 55
atgcggatca gcaagcccca cctgcggagc atcagcatcc agtgctacct gtgcctgctg  60
ctgaacagcc acttcctgac cgaggccggc atccacgtgt tcatcctggg ctgcttcagc  120
gccggactgc ccaagaccga ggccaactgg gtgaacgtga tcagcgacct gaagaagatc  180
gaggacctga tccagagcat gcacatcgac gccaccctgt acaccgagag cgacgtgcac  240
cccagctgca aggtgaccgc catgaagtgc tttctgctgg aactgcaggt gatcagcctg  300
gaaagcggcg acgccagcat ccacgacacc gtggagaacc tgatcatcct ggccaacaac  360
agcctgagca gcaacggcaa cgtgaccgag agcggctgca aagagtgcga ggaactggaa  420
gagaagaaca tcaaagagtt tctgcagagc ttcgtgcaca tcgtgcagat gttcatcaac  480
accagctga                                                          489

SEQ ID NO: 56          moltype = AA  length = 162
FEATURE                Location/Qualifiers
REGION                 1..162
                       note = IL15
source                 1..162
                       mol_type = protein
                       organism = synthetic construct
SEQUENCE: 56
MRISKPHLRS ISIQCYLCLL LNSHFLTEAG IHVFILGCFS AGLPKTEANW VNVISDLKKI  60
EDLIQSMHID ATLYTESDVH PSCKVTAMKC FLLELQVISL ESGDASIHDT VENLIILANN  120
SLSSNGNVTE SGCKECEELE EKNIKEFLQS FVHIVQMFIN TS                     162

SEQ ID NO: 57          moltype = DNA  length = 819
FEATURE                Location/Qualifiers
misc_feature           1..819
                       note = hCLL-1 scFv
```

```
source                  1..819
                        mol_type = other DNA
                        organism = synthetic construct
SEQUENCE: 57
atggagtttg ggctgagctg gctttttctt gtggctattt taaaaggtgt ccagtgctcg  60
cgagacatcc agatgaccca gagccccagc agcctgagcg ccagcgtggg cgacagagtg  120
accatcacct gcagagccag cagcaacgtg atcagcagct acgtgcactg gtaccagcag  180
aagcccggca aggcccccaa gctgctgatc tacagcacca gcaacctggc cagcggcgtg  240
cccagcagat tcagcggcag cagaagcggc accgacttca ccctgaccat cagcagcctg  300
cagcccgagg acttcgccac ctactactgc cagcagtaca gcggctaccc cctgaccttc  360
ggccagggca ccaaggtgga gatcaagaga ggtggtggtg gttctggtgg tggtggttct  420
ggcggcggcg gctccggtgg tggtggatcc gaggtgcagc tggtggagag cggcggcggc  480
ctggtgcagc ccggcggcag cctgagactg agctgcgccg ccagcggcta cagcatcacc  540
agcgcctact actggaactg ggtgagacag gcccccggca agggcctgga gtgggtggcc  600
tacatcagct acgacggcag aaacaactac aaccccagcc tgaagaacag attcaccatc  660
agcgccgaca ccagcaagaa caccgcctac ctgcagatga acagcctgag agccgaggac  720
accgccgtgt actactgcag cagagagggc gactacgacg tgggcaacta ctacgccatg  780
gactactggg gccagggcac cctggtgacc gtgagctcg                         819

SEQ ID NO: 58           moltype = AA  length = 273
FEATURE                 Location/Qualifiers
REGION                  1..273
                        note = hCLL-1 scFv
source                  1..273
                        mol_type = protein
                        organism = synthetic construct
SEQUENCE: 58
MEFGLSWLFL VAILKGVQCS RDIQMTQSPS SLSASVGDRV TITCRASSNV ISSYVHWYQQ  60
KPGKAPKLLI YSTSNLASGV PSRFSGSRSG TDFTLTISSL QPEDFATYYC QQYSGYPLTF  120
GQGTKVEIKR GGGGSGGGGS GGGGSGGGGS EVQLVESGGG LVQPGGSLRL SCAASGYSIT  180
SAYYWNWVRQ APGKGLEWVA YISYDGRNNY NPSLKNRFTI SADTSKNTAY LQMNSLRAED  240
TAVYYCSREG DYDVGNYYAM DYWGQGTLVT VSS                                273

SEQ ID NO: 59           moltype = AA  length = 109
FEATURE                 Location/Qualifiers
REGION                  1..109
                        note = hCLL1 VH
source                  1..109
                        mol_type = protein
                        organism = synthetic construct
SEQUENCE: 59
DIQMTQSPSS LSASVGDRVT ITCRASSNVI SSYVHWYQQK PGKAPKLLIY STSNLASGVP  60
SRFSGSRSGT DFTLTISSLQ PEDFATYYCQ QYSGYPLTFG QGTKVEIKR              109

SEQ ID NO: 60           moltype = AA  length = 123
FEATURE                 Location/Qualifiers
REGION                  1..123
                        note = hCLL1 VL
source                  1..123
                        mol_type = protein
                        organism = synthetic construct
SEQUENCE: 60
EVQLVESGGG LVQPGGSLRL SCAASGYSIT SAYYWNWVRQ APGKGLEWVA YISYDGRNNY  60
NPSLKNRFTI SADTSKNTAY LQMNSLRAED TAVYYCSREG DYDVGNYYAM DYWGQGTLVT  120
VSS                                                                123

SEQ ID NO: 61           moltype = DNA  length = 804
FEATURE                 Location/Qualifiers
misc_feature            1..804
                        note = CD99 scFv
source                  1..804
                        mol_type = other DNA
                        organism = synthetic construct
SEQUENCE: 61
atggagtttg ggctgagctg gctttttctt gtggctattt taaaaggtgt ccagtgctct  60
agaagcagcg agctgaccca ggaccccgcc gtgagcgtgg ccctgggcca gaccgtgaga  120
atcacctgcc agggcgacag cctgagaagc tactacgcca gctggtacca gcagaagccc  180
ggccaggccc ccgtgctggt gatctacggc aagaacaaca gacccagcgg catccccgac  240
agattcagcg gcagcagcag cggcaacacc gccagcctga ccatcaccgg cgcccaggcc  300
gaggacgagg ccgactacta ctgcaacagc agcttcccca gaaccagcag cgtggtgttc  360
ggcggcggca ccaagctgac cgtgctgggc ggtggtggtg gttctggtgg tggtggttct  420
ggcggcggcg gctccggtgg tggtggatcc atggccgagg tgcagctggt ggagagcggc  480
ggcggcctgg tgagacccgg cggcagcctg agactgagct gcgccgccag cggcttcacc  540
ttcagcagct acgccatgag ctgggtgaga caggcccccg gcaagggcct ggagtgggtg  600
agcgccatca gcggcagcgg cggcagcacc tactacgccg acagcgtgaa gggcagattc  660
accatcagca gagacaacag caagaacacc ctgtacctgc agatgaacag cctgagagcc  720
gaggacaccg ccgtgtacta ctgcgccaag agccacaaga gattcgacta ctggggccag  780
ggcaccctgg tgaccgtgag caga                                         804
```

```
SEQ ID NO: 62          moltype = AA  length = 268
FEATURE                Location/Qualifiers
REGION                 1..268
                       note = CD99 scFv
source                 1..268
                       mol_type = protein
                       organism = synthetic construct
SEQUENCE: 62
MEFGLSWLFL VAILKGVQCS RSSELTQDPA VSVALGQTVR ITCQGDSLRS YYASWYQQKP  60
GQAPVLVIYG KNNRPSGIPD RFSGSSSGNT ASLTITGAQA EDEADYYCNS SFPRTSSVVF  120
GGGTKLTVLG GGGGSGGGGS GGGGSGGGGS MAEVQLVESG GGLVRPGGSL RLSCAASGFT  180
FSSYAMSWVR QAPGKGLEWV SAISGSGGST YYADSVKGRF TISRDNSKNT LYLQMNSLRA  240
EDTAVYYCAK SHKRFDYWGQ GTLVTVSR                                    268

SEQ ID NO: 63          moltype = AA  length = 108
FEATURE                Location/Qualifiers
REGION                 1..108
                       note = CD99 VH
source                 1..108
                       mol_type = protein
                       organism = synthetic construct
SEQUENCE: 63
SSELTQDPAV SVALGQTVRI TCQGDSLRSY YASWYQQKPG QAPVLVIYGK NNRPSGIPDR  60
FSGSSSGNTA SLTITGAQAE DEADYYCNSS FPRTSSVVFG GGTKLTVL              108

SEQ ID NO: 64          moltype = AA  length = 118
FEATURE                Location/Qualifiers
REGION                 1..118
                       note = CD99 VL
source                 1..118
                       mol_type = protein
                       organism = synthetic construct
SEQUENCE: 64
MAEVQLVESG GGLVRPGGSL RLSCAASGFT FSSYAMSWVR QAPGKGLEWV SAISGSGGST  60
YYADSVKGRF TISRDNSKNT LYLQMNSLRA EDTAVYYCAK SHKRFDYWGQ GTLVTVSR    118

SEQ ID NO: 65          moltype = AA  length = 383
FEATURE                Location/Qualifiers
REGION                 1..383
                       note = Ev3
source                 1..383
                       mol_type = protein
                       organism = synthetic construct
SEQUENCE: 65
MRPSGTAGAA LLALLAALCP ASRALEEKKG NYVVTDHGSC VRACGADSYE MEEDGVRKCK  60
KCEGPCRKVC NGIGIGEFKD SLSINATNIK HFKNCTSISG DLHILPVAFR GDSFTHTPPL  120
DPQELDILKT VKEITGFLLI QAWPENRTDL HAFENLEIIR GRTKQHGQFS LAVVSLNITS  180
LGLRSLKEIS DGDVIISGNK NLCYANTINW KKLFGTSGQK TKIISNRGEN SCKATGQVCH  240
ALCSPEGCWG PEPRDCVSCR NVSRGRECVD KCNLLEGEPR EFVENSECIQ CHPECLPQAM  300
NITCTGRGPD NCIQCAHYID GPHCVKTCPA GVMGENNTLV WKYADAGHVC HLCHPNCTYG  360
CTGPGLEGCP TNGPKIPSIA TGM                                         383

SEQ ID NO: 66          moltype = AA  length = 108
FEATURE                Location/Qualifiers
REGION                 1..108
                       note = hCD19 scFv
source                 1..108
                       mol_type = protein
                       organism = synthetic construct
SEQUENCE: 66
DIQMTQTTSS LSASLGDRVT ISCRASQDIS KYLNWYQQKP DGTVKLLIYH TSRLHSGVPS  60
RFSGSGSGTD YSLTISNLEQ EDIATYFCQQ GNTLPYTFGG GTKLELKR              108

SEQ ID NO: 67          moltype = AA  length = 120
FEATURE                Location/Qualifiers
REGION                 1..120
                       note = mCD19 scFv
source                 1..120
                       mol_type = protein
                       organism = synthetic construct
SEQUENCE: 67
EVQLQQSGPG LVAPSQSLSV TCTVSGVSLP DYGVSWIRQP PRKGLEWLGV IWGSETTYYN  60
SALKSRLTII KDNSKSQVFL KMNSLQTDDT AIYYCAKHYY YGGSYAMDYW GQGTTVTVSS  120

SEQ ID NO: 68          moltype = AA  length = 89
FEATURE                Location/Qualifiers
REGION                 1..89
                       note = Synthetic peptide
```

-continued

```
source                  1..89
                        mol_type = protein
                        organism = synthetic construct
SEQUENCE: 68
DIQMTQSPSS LSASVGDRVT ITCRASQDIN NYLNWYQQKP GKAPKLLIYY TSTLHSSSLQ  60
PEDFATYYCQ QGNTLPPTFG QGTKVEIKR                                    89

SEQ ID NO: 69           moltype = AA  length = 122
FEATURE                 Location/Qualifiers
REGION                  1..122
                        note = Synthetic peptide
source                  1..122
                        mol_type = protein
                        organism = synthetic construct
SEQUENCE: 69
EVQLVESGGG VVQPGGSLRL SCAASGFTFS DYDMSWIRQA PGKGLEWVSG ILGGSERSYY  60
RDSVKGRFTI SRDNSRKTLY LQMNSLRAED TAVYYCARHG SPGYTLYAWD YWGQGTTVTV  120
SS                                                                 122
```

What is claimed is:

1. A polynucleotide, encoding:

a) a chimeric antigen receptor (CAR) comprising a CD5-specific single chain variable fragment (scFv) comprising a light chain variable region ($V_L$) and a heavy chain variable region ($V_H$), wherein the $V_L$ comprises an amino acid sequence having at least 90% sequence identity to SEQ ID NO:31 and the $V_H$ comprises an amino acid sequence having at least 90% sequence identity to SEQ ID NO:32, and wherein the CAR comprises (1) a CD28 transmembrane domain and (2) a CD28 intracellular signaling domain or a DAP10 intracellular signaling domain; and b) IL-15, wherein the IL-15 comprises the amino acid sequence set forth in SEQ ID NO:56 or an amino acid sequence having at least 90% sequence identity thereto.

2. The polynucleotide of claim 1, wherein the scFv is murine.

3. The polynucleotide of claim 1 wherein the CAR comprises the CD28 intracellular signaling domain.

4. The polynucleotide of claim 1, wherein the CAR further comprises a CD3zeta domain.

5. The polynucleotide of claim 4, wherein the CD3zeta domain comprises the amino acid sequence set forth in SEQ ID NO:54 or an amino acid sequence having at least 90% sequence identity thereto.

6. The polynucleotide of claim 5, wherein the CD3zeta domain comprises the amino acid sequence set forth in SEQ ID NO:54.

7. The polynucleotide of claim 1, wherein the polynucleotide further encodes a suicide gene.

8. The polynucleotide of claim 7, wherein the suicide gene is inducible caspase 9.

9. The polynucleotide of claim 1, wherein the polynucleotide is expressed in an immune cell.

10. The polynucleotide of claim 9, wherein the immune cell is an NK cell.

11. A host cell comprising the polynucleotide of claim 1.

12. The host cell of claim 11, wherein the host cell is an immune cell.

13. The host cell of claim 12, wherein the immune cell is an NK cell.

* * * * *